United States Patent
Kim et al.

(10) Patent No.: US 9,994,812 B2
(45) Date of Patent: Jun. 12, 2018

(54) SYSTEMS AND METHOD FOR ENGINEERING MUSCLE TISSUE

(71) Applicant: UNIVERSITY OF WASHINGTON THROUGH ITS CENTER FOR COMMERCIALIZATION, Seattle, WA (US)

(72) Inventors: Deok-Ho Kim, Seattle, WA (US); Michael Laflamme, Seattle, WA (US); Charles Murry, Seattle, WA (US); Kshitiz Gupta, Seattle, WA (US); Hyok Yoo, Shoreline, WA (US); Alex Jiao, Seattle, WA (US)

(73) Assignee: University of Washington through Its Center For Commercialization, Seattle, WA (US)

( * ) Notice: Subject to any disclaimer, the term of this patent is extended or adjusted under 35 U.S.C. 154(b) by 0 days. days.

(21) Appl. No.: 14/390,490

(22) PCT Filed: Mar. 15, 2013

(86) PCT No.: PCT/US2013/032237
§ 371 (c)(1),
(2) Date: Oct. 3, 2014

(87) PCT Pub. No.: WO2013/151755
PCT Pub. Date: Oct. 10, 2013

(65) Prior Publication Data
US 2015/0125952 A1    May 7, 2015

Related U.S. Application Data

(60) Provisional application No. 61/620,301, filed on Apr. 4, 2012.

(51) Int. Cl.

| | |
|---|---|
| *A61K 48/00* | (2006.01) |
| *C12N 5/0735* | (2010.01) |
| *A61L 27/14* | (2006.01) |
| *C12M 3/00* | (2006.01) |
| *C12M 1/12* | (2006.01) |
| *A61L 27/18* | (2006.01) |
| *A61L 27/38* | (2006.01) |
| *A61L 27/50* | (2006.01) |
| *B01L 3/00* | (2006.01) |
| *C12N 5/077* | (2010.01) |
| *C12N 5/074* | (2010.01) |

(52) U.S. Cl.
CPC ............ *C12N 5/0606* (2013.01); *A61L 27/14* (2013.01); *A61L 27/18* (2013.01); *A61L 27/3826* (2013.01); *A61L 27/3834* (2013.01); *A61L 27/3873* (2013.01); *A61L 27/50* (2013.01); *B01L 3/5085* (2013.01); *C12M 21/08* (2013.01); *C12M 25/14* (2013.01); *C12N 5/0657* (2013.01); *C12N 5/0658* (2013.01); *C12N 5/0696* (2013.01); *A61K 48/00* (2013.01); *A61L 2400/12* (2013.01); *A61L 2400/18* (2013.01); *B01L 2300/0851* (2013.01); *B01L 2300/0896* (2013.01); *B01L 2400/086* (2013.01); *C12N 2503/02* (2013.01); *C12N 2533/30* (2013.01); *C12N 2533/40* (2013.01); *C12N 2535/00* (2013.01)

(58) Field of Classification Search
USPC ....................................................... 435/366
See application file for complete search history.

(56) References Cited

U.S. PATENT DOCUMENTS

| | | |
|---|---|---|
| 4,789,601 A | 12/1988 | Banes |
| 5,733,538 A | 3/1998 | Riffle |
| | (Continued) | |

FOREIGN PATENT DOCUMENTS

| | | |
|---|---|---|
| EP | 0689051 A2 | 12/1995 |
| WO | 00/34454 A2 | 6/2000 |
| | (Continued) | |

OTHER PUBLICATIONS

Vunjak-Novakovic et al. Challenges in cardiac tissue engineering. Tissue Engineering: Part B. 2010;16(2):169-187.*
Dvir et al. Nanotechnological strategies for engineering complex tissues. Nature Nanotechnology. 2011;6:13-22.*
Goumans et al. TGF-beta1 induces efficient differentiation of human cardiomyocyte progenitor cells into functional cardiomyocytes in vitro. Stem Cell Research. 2008;1:138-149.*
Janmey et al. Mechanisms of mechanical signaling in development and disease. J Cell Sci. 2011;124(1):9-18.*
Zhang et al. Functional cardiomyocytes derived from human induced pluripotent stem cells. Circ Res. 2009;104(4):e30-41.*
Plates. Multiwell culture plates. Sigma-Aldrich. 2010;1-2.*

(Continued)

*Primary Examiner* — Lynn Y Fan
(74) *Attorney, Agent, or Firm* — Nixon Peabody LLP

(57) ABSTRACT

The present invention generally relates to the field of cell growth and tissue engineering, in particular, tissue engineered compositions comprising a nanotextured substrate which is structurally configured for growth of cells in an anatomically correct adult phenotype in vitro. In particular, described herein are nanotextured substrates which are structurally configured for the anisotropic organization, maturation, and growth of in vitro-differentiated muscle cells, such as cardiomyocytes, and methods for the production and use thereof in varying sizes, nanotextures and substrate rigidities. In vitro-differentiated cardiomyocytes grown on the nanotextured substrates described herein are better-differentiated and more closely mimic adult cardiac tissue than the same cells grown on a non-textured substrate of the same composition. The nanotextured substrate/cell constructs provide a platform for screening to predict the effect of test agents or drugs on, for example, human cardiac tissue, including patient-derived tissue, or for the identification of agents that effect various cardiac functional parameters.

14 Claims, 58 Drawing Sheets

(56) References Cited

U.S. PATENT DOCUMENTS

| | | | |
|---|---|---|---|
| 7,695,967 | B1 | 4/2010 | Russell et al. |
| 7,698,967 | B2 | 4/2010 | Ording et al. |
| 2003/0022367 | A1 | 1/2003 | Xu |
| 2006/0085063 | A1 | 4/2006 | Shastri |
| 2008/0187995 | A1 | 8/2008 | Murphy et al. |
| 2008/0195229 | A1 | 8/2008 | Quijano et al. |
| 2009/0108503 | A1 | 4/2009 | Scott-Carnell |
| 2010/0158979 | A1 | 6/2010 | Russell et al. |
| 2010/0196432 | A1 | 8/2010 | Feinberg et al. |
| 2011/0008397 | A1 | 1/2011 | Cohen |
| 2011/0085968 | A1 | 4/2011 | Jin et al. |
| 2011/0142806 | A1 | 6/2011 | Scott-Carnell et al. |
| 2011/0160869 | A1 | 6/2011 | Duch et al. |
| 2011/0262958 | A1 | 10/2011 | Yashuda |
| 2012/0004716 | A1 | 1/2012 | Langhammer |
| 2012/0027807 | A1 | 2/2012 | Chien et al. |

FOREIGN PATENT DOCUMENTS

| | | | |
|---|---|---|---|
| WO | 2003/050266 | A2 | 6/2003 |
| WO | 2003050266 | A3 | 6/2003 |
| WO | 2008054819 | A2 | 5/2008 |
| WO | 2010/108025 | A2 | 9/2010 |
| WO | 2011028579 | A3 | 3/2011 |
| WO | 2011/028579 | A2 | 10/2011 |
| WO | 2013/151755 | A1 | 10/2013 |

OTHER PUBLICATIONS

Kim et al., Proc Natl Acad Sci U S A., 107(2):565-570, (2010). "Nanoscale cues regulate the structure and function of macroscopic cardiac tissue constructs."
Abrams et al., "Ultrastructural basement membrane topography of the bladder epithelium", Urol Res, 2003, 31:341-346.
Baxter et al., "Adaptive changes in cardiac fibroblast morphology and collagen organization as a result of mechanical environment", Cell Biochem Biophys., 2008, 51(1):33-44.
Bursac et al., "Cardiac muscle tissue engineering: Toward an in vitro model for electrophysiological studies", Am J Physiol,1999, 277:H433-444.
Cavalcanti-Adam et al., "Cell spreading and focal adhesion dynamics are regulated by spacing of integrin ligands", Biophys J, 2007, 92:2964-2974.
Costa et al., "Creating alignment and anisotropy in engineered heart tissue: role of boundary conditions in a model three-dimensional culture system",Tissue Eng., 2003, 9(4):567-77.
Dreyer et al., "The chemistry of graphene oxide", Chem Soc Rev, 2010, 39(1): p. 228-40.
Geiger et al., "Transmembrane Extracellular Matrix-cytoskeleton Crosstalk", Nat Rev Mol Cell Biol, 2001, 2:793-805.
Gibson, "Reading and writing with electron beams", Physics Today, 1997, 50:56-61.
Jiang et al., "Nanoparticle-mediated cellular response is size-dependent", Nat Nanotechnol, 2008, 3:145-150.
Joshi-Mukherjee et al., "Evidence for the presence of a free C-terminal fragment of cx43 in cultured cells", Cell Commun Adhes., 2007, 14(2-3):75-84.
Joshi-Mukherjee et al., "Structural and functional plasticity in long-term cultures of adult ventricular myocytes", J Mol Cell Cardiol., 2013, 65:76-87.
Khademhosseini et al., "Microfluidic patterning for fabrication of contractile cardiac organoids", Biomed Microdevices, 2007, 9:149-157.
Kim et al., "Guided three-dimensional growth of functional cardiomyocytes on polyethylene glycol nanostructures", Langmuir, 2006, 22(12): p. 5419-5426.
Kim et al., "Guided Cell Migration on Microtextured Substrates with Variable Local Density and Anisotropy", Advanced Functional Materials, 2009, 19(10): p. 1579-1586.
Kim et al., "Nanopatterned cardiac cell patches promote stem cell niche formation and myocardial regeneration", Integr Biol (Camb), 2012, 4(9): p. 1019-33.
Karuri et al., "Biological length scale topography enhances cell-substratum adhesion of human corneal epithelial cells", J Cell Sci, 2004, 117:3153-3164.
Mahdavi et al., "A biodegradable and biocompatible gecko-inspired tissue adhesive", Proc Natl Acad Sci USA, 2008,105:2307-2312.
Mkhoyan et al., "Atomic and electronic structure of graphene-oxide", Nano Lett, 2009, 9(3): p. 1058-63.
Nayar et al., "Macrocompression and Nanoindentation of Soft Viscoelastic Biological Materials", Tissue Engineering Part C: Methods, 2012, 18(12): 968-975.
Oh et al. "Stem cell fate dictated solely by altered nanotube dimension", Proc Natl Acad Sci USA, 2009, 106:2130-2135.
Ohashi et al., "Engineering functional two- and three-dimensional liver systems in vivo using hepatic tissue sheets", Nat Med, 2007, 13:880-885.
Ott et al., "Perfusion-decellularized matrix: using nature's platform to engineer a bioartificial heart", Nature Medicine, 2008, 14, 213-221.
Park et al., "Nanofabrication and Microfabrication of Functional Materials for Tissue Engineering", Tissue Eng, 2007, 13:1867-1877.
Perumal et al., "Collagen fibril architecture, domain organization, and triple-helical conformation govern its proteolysis", Proc Natl Acad Sci U S A, 2008, 105(8): p. 2824-9.
Salaita et al., "Applications of dip-pen nanolithography", Nat Nanotechnol, 2007, 2:145-155.
Silverman, "Challenges and progress in x-ray lithography", J Vac Sci Technol B, 1998, 16:3137-3141.
Stevens et al., "Exploring and Engineering the Cell Surface Interface", Science, 2005, 310:1135-1138.1.
Teixeira et al., "Epithelial contact guidance on well-defined micro- and nanostructured substrates", J Cell Sci, 2003, 116:1881-1892.
Tohama et al., "Distinct Metabolic Flow Enables Large-Scale Purification of Mouse and Human Pluripotent Stem Cell-Derived Cardiomyocytes", Cell Stem Cell, 2013,12; 127-137.
Vandenburgh et al., "Computer-aided mechanogenesis of skeletal muscle organs from single cells in vitro", FASEB J. 5, 1991, 2860-2867.
Watkins et al., "Investigation of molecular transport and distributions in poly(ethylene glycol) hydrogels with confocal laser scanning microscopy", Macromolecules, 2005, 38:1326-1334.25-53.
Yang, K., et al., The influence of surface chemistry and size of nanoscale graphene oxide on photothermal therapy of cancer using ultra-low laser power. Biomaterials, 2012. 33(7): p. 2206-14.
Yeoh and Holtzer, Experimental Cell Research, 104(1):63-78, 1977.
You, M.H., et al., Synergistically Enhanced Osteogenic Differentiation of Human Mesenchymal Stem Cells by Culture on Nanostructured Surfaces with Induction Media. Biomacromolecules, 2010 11(7): p. 1856-1862.
Supplementary Partial European Search Report from corresponding EP Application No. EP13771865 dated Mar. 16, 2015.
Supplementary European Search Report from corresponding EP Application No. EP13771865 dated May 27, 2015.
Mercola et al., "iPSCs in Cardiovascular Drug Discovery" Circ Res. 112(3):534-548 (2013).
Yang et al., "Engineering Adolescence; Maturation of Human Pluripotent Stem Cell-Derived Cardiomyocytes" Circ Res. 114:511-523 (2014).
Louch et al., "Methods in Cardiomyocyte Isolation, Culture, and Gene Transfer" J Mol Cell Cardiol. 51(3):288-298 (2011).
Abbaspour-Tamijani et al., "A miniature fully-passive microwave back-scattering device for short-range telemetry of neural potentials", Conf Proc IEEE Eng Med Biol Soc 2008: 129-132 (2008).
Bershadsky et al., "Adhesion-mediated mechanosensitivity: a time to experiment, and a time to theorize", Curr Opin Cell Biol 18(5) 472-481 (2006).
Choi et al., "A microfluidic biosensor based on competitive protein adsorption for thyroglobulin detection", Biosenc Bioelectron 25(1) 118-123 (2009).

(56) References Cited

OTHER PUBLICATIONS

Choi et al., "Surface plasmon resonance protein sensor using Vroman effect", Biosens Bioelectron 24(4) 899-905 (2008).
Choi et al., "Using competitive protein adsorption to measure fibrinogen in undiluted human serum", Applied Physics Letters 97(25) 253701-253703 (2010).
Chu et al., "Articular cartilage repair using allogeneic perichondrocyte-seeded biodegradable porous polylactic acid (PLA): a tissue-engineering study", J Biomed Mater Res 29(9) 1147-1154 (1995).
Farooqui et al., "An experimental verification of a microwave backscatter tag for recording neural signals", Antennas and Propagation Society International Symposium IEEE AP-S 2008 (2008).
Garzon-Muvdi et al., "Regulation of brain tumor dispersal by NKCC1 through a novel role in focal adhesion regulation", PLoS Biol 10(5) e1001320 (2012).
Hendrickson et al., "Chondrocyte-fibrin matrix transplants for resurfacing extensive articular cartilage defects", J Orthop Res 12(4) 485-497 (1994).
Himmel, "Drug-induced functional cardiotoxicity screening in stem cell-derived human and mouse cardiomyocytes: effects of reference compounds", J Pharmacol Toxicol Methods 68(1) 97-111 (2013).
Hur et al., "Engineering neuronal growth cones to promote axon regeneration over inhibitory molecules", Proc Natl Acad Sci USA 108(12) 5057-5062 (2011).
Je et al., "An electromagnetically actuated microspeaker with fully-integrated wax-bonded Nd—Fe—B micromagnets for hearing aid applications", Solid-State Sensors, Acutators and Microsystems Conference, Tranducers, International IEEE (2009).
Je et al., "In situ tuning of a MEMS microphone using electrodeposited nanostructures", Journal of Micromechanics and Microengineering 19(3) 035015 (2009).
Je et al., "In situ tuning of omnidirectional microelectromechanical-systems microphones to improve performance fit in hearing aids", Applied Physics Letters 93(12) 123501 (2008).
Jones et al., "The potential of microelectrode arrays and microelectronics for biomedical research and diagnostics", Anal Bioanal Chem 399(7) 2313-2129 (2011).
Kim et al., "Fabrication of nanostructures of polyethylene glycol for applications to protein adsorption and cell adhesion", Nanotechnology 16(10) 2420-2426 (2005).
Kim et al., "Mechanosensitivity of fibroblast cell shape and movement to anisotropic substratum topography gradients", Biomaterials 30(29) 5433-5444 (2009).
Kshitiz et al., "Matrix rigidity controls endothelial differentiation and morphogenesis of cardiac precursors", Sci Signal 5(227) ra41 (2012).
M64-GLx "Planar Electrode Arrays", Axion Biosystems 2010 http://www.axionbiosystems.com/wp-content/uploads/2012/05/Singlewell-M64-GLx_datasheet.pdf (Web).
MEA-System, "Extracellular recording with microelectrode arrays for all applications", Multi Channel Systems MCS GmbH, Harvard Bioscience, Inc. Sep. 2015 http://www.multichannelsystems.com/downloads/documentation (Web).
MED64 System, "MED Probe for Basic/Plex System", Alpha MED Scientific, Inc. http://www.med64.com/products/med-probe-mea/med-probe-basic-plex/ (Web).
Perka et al., "Matrix-mixed culture: new methodology for chondrocyte culture and preparation of cartilage transplants", J Biomed Mater Res 49(3) 305-311 (2000).
Qwane Biosciences MEA60 Biochip Products MH Aug. 2011 (Web).
Rehfeldt et al., "Cell responses to the mechanochemical microenvironment—implications for regenerative medicine and drug delivery", Adv Drug Deliv Rev 59(13) 1329-1339 (2007).
Schwerdt et al., "A Fully Passive Wireless Backscattering Neurorecording Microsystem Embedded in Dispersive Human-Head Phantom Medium", IEEE Electron Device Letter 33(6) 908-910 (2012).
Schwerdt et al., "A Fully-Passive Wireless Microsystem for Recording of Neuropotentials using RF Backscattering Methods", J Microelectromech Syst 20(5) 1119-1130 (2011).
Sechriest et al., "GAG-augmented polysaccharide hydrogel: a novel biocompatible and biodegradable material to support chondrogenesis", J Biomed Mater Res 49(4) 534-541 (2000).
Stett et al., "Biological application of microelectrode arrays in drug discovery and basic research", Anal Bioanal Chem 377(3) 486-495 (2003).
Suh et al., "Capillarity-assisted fabrication of nanostructures using a less permeable mold for nanotribological applications", Journal of Applies Physics 100(3) 034303 (2006).
Thomas et al., "A miniature microelectrode array to monitor the bioelectric activity of cultured cells", Exp Cell Res 74 (1) 61-66 (1972).
Xu et al., "In-liquid quality factor improvement for film bulk acoustic resonators by integration of microfluidic channels", IEEE Electron Device Letters 30(6) 647-649 (2009).
Yang et al., "An *Escherichia coli* Concentrator Using Magnetic Particles in a Microfluidic Channgel for the Urinary Tract Infection (UTI) Application", Solid-State Sensors, Acutators, and Microsystems Workshop, 162-165 (2010).
Yang et al. "Design of high-speed serial links in CMOS", Technical Report No. CSL-TR-98-775 (1998).
Yoon et al., "Tribological properties of bio-mimetic nano-patterned polymeric surfaces on silicon wafer", Tribology Letters 21(1) 31-37 (2006).
Zhang et al., "Passive wireless monitoring of wafer cleanliness during rinsing of semiconductor wafers", IEEE Sensors Journal 10(6) 1048-1055 (2010).
Zhang et al., "Working distance comparison of inductive and electromagnetic couplings for wireless and passive underwater monitoring system of rinsing process in semiconductor facilities", IEEE Sensors Journal 11(11) 2932-2939 (2011).

\* cited by examiner

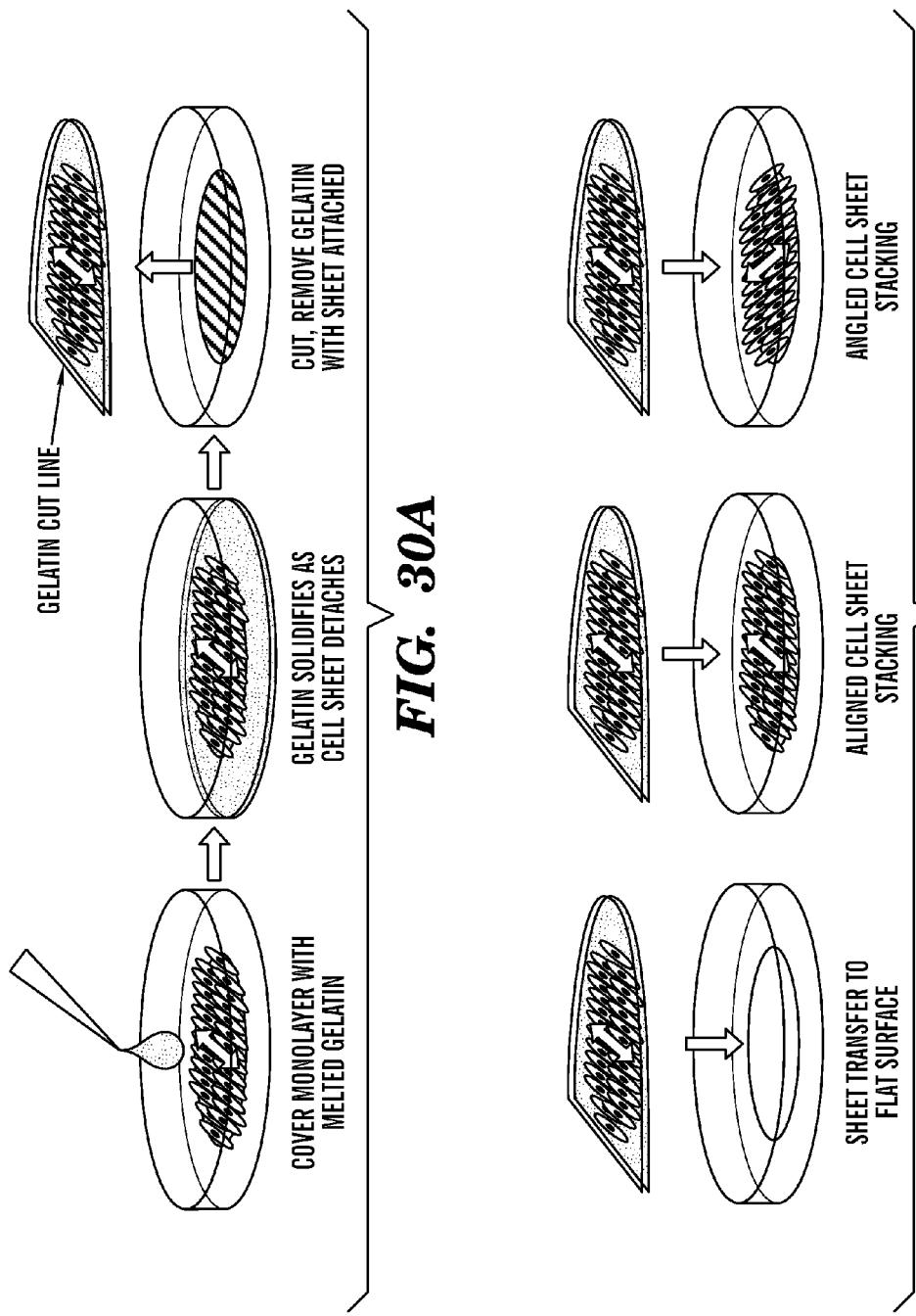

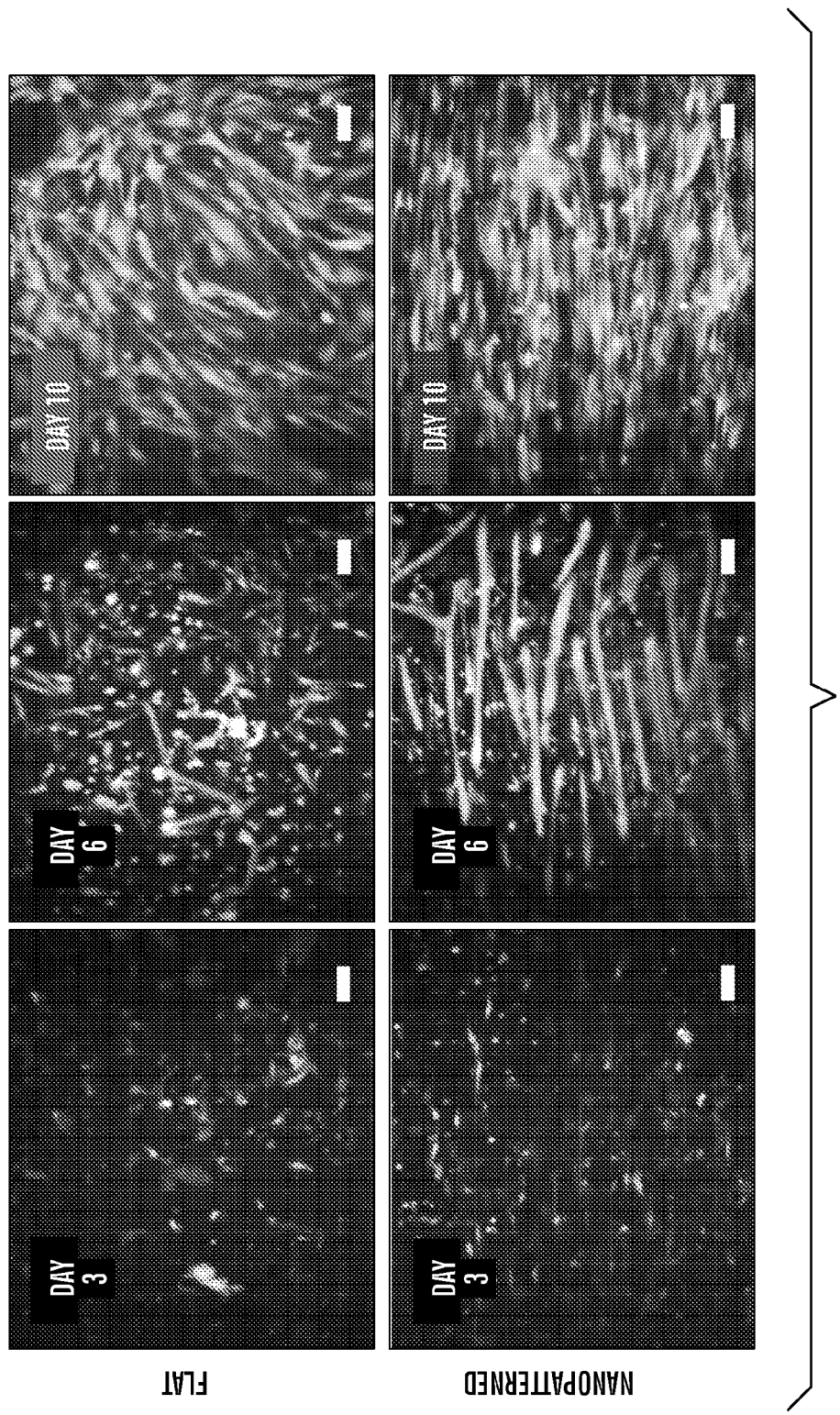

SYSTEMS AND METHOD FOR ENGINEERING MUSCLE TISSUE

CROSS REFERENCE TO RELATED APPLICATIONS

This application is a 35 U.S.C. § 371 National Phase Entry Application of International Application No. PCT/US2013/032237 filed Mar. 15, 2013, which designates the U.S., and which claims benefit under 35 U.S.C. 119(e) of U.S. Provisional Patent Application Ser. No. 61/620,301, filed on Apr. 4, 2012, the contents of which is incorporated herein in its entireties by reference.

FIELD OF THE INVENTION

The present invention generally relates to the field of cell growth and tissue engineering, in particular, a tissue engineered composition comprising a nanotextured platform which is structurally configured for growth of cells in an anatomically correct adult phenotype in vitro.

BACKGROUND OF THE INVENTION

Living cells and tissues can display high sensitivity to local micro- and nanoscale molecular and topographic patterns, including those provided in vivo by complex and well-defined structures of extracellular matrix (ECM) (Stevens M et al., (2005) Science 310:1135-1138.1). However, given the small scale of the underlying interactions, their effect on cell and tissue function is far from completely understood. Studies of engineered cell-biomaterial interactions at the subcellular, nanoscale levels are providing evidence for potential importance of submicrometer cues for cell signaling, adhesion, growth, and differentiation. However, these initial attempts at engineering control of cell function have frequently not been bioinspired or biomimetic and have failed to reproduce the multiscale effects of complex ECM structures (e.g., networks of fibers and components of the basement membrane) and associated chemical ligands, which control integrated multicellular ensembles on scales ranging from a few nanometers to hundreds of micrometers (Geiger B, et al., (2001) Nat Rev Mol Cell Biol 2:793-805, Abrams et al., (2003) Urol Res 31:341-3469, 10). Recent advances in nanofabrication techniques can enable the design and fabrication of scalable scaffolding materials mimicking the structural and mechanical cues present in the in vivo ECM environment (Park H, et al. (2007) Tissue Eng 13:1867-1877).

Heart tissue possesses complex structural organization on multiple scales, from macro- to nano-, but nanoscale control of cardiac function has not been extensively analyzed. The myocardium is an ensemble of different cell types embedded in the complex and well-defined structures of the ECM and arranged in nanoscale topographical and molecular patterns. Although the structure of cardiac tissue is highly organized in vivo, cardiomyocyte ensembles lose their native organization and adopt random distribution when cultured in vitro by using common culturing techniques, potentially compromising many of their physiological properties. A variety of methods such as mechanical stretching, microcontact printing, and electrical stimulation have been used to engineer better organized cardiomyocyte cultures. Both 2D and 3D substrata with the ~10 μm feature size have been employed to direct cardiomyocytes into anisotropic arrangements for electrophysiological and mechanical characterization. However, it is likely that the structure and function of the in vivo cardiac tissue are regulated by much smaller, nanoscale cues provided by the ECM, which might exercise complex, multiscale control of cell and tissue function. Thus, it is important to investigate whether finer control over the cell-material interface on the nanoscale facilitates the creation of truly biomimetic cardiac tissue constructs that recapitulate the structural and functional aspects of the in vivo ventricular myocardial phenotype. In addition, the ability to robustly and reproducibly generate uniformly controlled (both structurally and functionally) and precisely defined engineered cardiac tissue will likely be necessary for eventual therapeutic products.

In this regard, the inability to direct the differentiation of multipotent progenitors specifically to mature muscle cells remains a major obstacle for optimal in vivo cardiac myogenesis during cardiac repair following injury. Furthermore, while methods of cell based therapy using cells on scaffolds exist, their use is limited benefit to the extent to which they support growth, differentiation and function of cells for a functional engineered cardiac tissue.

SUMMARY

The present technology described herein generally relates to a nanotextured platform composition comprising a polymer substrate which has a nanotextured array of parallel grooves and ridges that is structurally configured to enhance the maturation of immature muscle cells or myocytes to a more mature phenotype, thus producing a functional engineered tissue myocardium construct which is capable of conducting action potentials and has superior muscle function over existing engineered tissue constructs. In particular, a nanotextured platform as described herein comprises an array of substantially parallel grooves and ridges that is structurally configured to organize immature muscle cells or myocytes (e.g., immature cardiomyocytes or immature skeletal muscle myocytes), in an anisotropic manner, such that when they are cultured on the nanotextured platform, the cells are matured and have more a differentiated phenotype. That is, myocytes cultured on the nanostructure substrates described herein have a tissue phenotype more closely similar to adult cardiac or skeletal muscle than the same cells cultured on a substrate lacking the nanotextured described herein. Such nanotextured platforms (e.g., comprising the myocytes) can be referred to herein as anisotropically nanotextured platforms (ANP), and can be nanofabricated from scalable biocompatible polymers, including but not limited to polyethene glycol (PEG), polyethene glycol-gelatin methacrylate (PEG-GelMA) and chemical variants thereof and hydrogel arrays.

In some embodiments, the immature myocytes are in vitro differentiated myocytes, such as in vitro-differentiated cardiomyocytes. In some embodiments, the immature cardiomyocytes are cardiomyocyte precursors. In some embodiments, the cardiomyocytes are derived from stem cells, such as embryonic stem (ES) cells, adult stem cells, or induced pluripotent stem cells (iPSCs). In some embodiments, a population of stem cells, such as ESCs or iPSCs can be in vitro differentiated into immature cardiomyocytes for use in the compositions and methods disclosed herein, while in other embodiments, the differentiation of iPSC or ESCs into immature cardiomyocytes can be done prior to coating the cells on the nanotextured platform, or can be done while they are coated on, or present on, the nanotextured platform. In some embodiments, the iPSCs are cells which have been reprogrammed from somatic cells obtained from a subject, e.g., a human subject. In some embodiments, the human subject is a healthy subject, while in other embodiments, the subject can have a cardiovascular condition, disease or disorder as disclosed herein, including but not limited to, arrhythmia.

In particular, the inventors have developed a nanotextured polymer platform that is configured to have the rigidity, flexibility and topography for the enhanced maturation of myogenic cells in an anisotropically and anatomically correct manner to mature these into an adult phenotype in vitro. In particular, the inventors demonstrate the mechanical and electrophysiological function of engineered cardiac tissue constructs, demonstrating that they faithfully mimic the highly organized function seen in normal heart tissue in vivo. Moreover, strikingly, the inventors demonstrate that the engineered tissue structure and function were highly sensitive to variation of the nanoscale topographic features of the platform, revealing an unexpected level of mechanical regulation.

Mutual cell alignment in two-dimensional cell cultures was primarily achieved on the basis of ad hoc applications of various patterning techniques with micro- rather than nanofeatures, not explicitly mimicking the organizing principles of the native heart tissue, and relying on non-physiological "cell constraining" methods to achieve cardiac anisotropy which reduces the amount of cell-cell contacts and overall degree of alignment of generated tissue. Thus, although these attempts have been made to organize the cardiomyocytes into anisotropic arrays, the controllability, scalability and bio-mimetic properties of such efforts remain uncertain and uncontrolled. In addition, the structural and mechanical properties and the degree of biocompatibility of the materials commonly used as the cell substrata have limited both the therapeutic potential of the designed tissues and their ability to provide a fundamental understanding of the principles of cardiac tissue self-organization.

To address these drawbacks, the inventors have employed a bio-inspired design of a model cardiac tissue with structural and functional anisotropy, more rationally based on ultrastructural analysis of the native cardiac tissue environment using nanofabricated anisotropic culture scaffolds. Importantly, the inventors have demonstrated that nanotextured scaffold surfaces organize and allow the maturation of cardiomyocytes in an anisotropic manner than microtextured scaffold surfaces, and such nano-textured surfaces are able to anisotropically organize cardiomyocytes to mimic the functional and phenotypic characteristics of cardiomyocytes present in native cardiac tissue. In some embodiments, the inventors have demonstrated the ability to generate sheets of in vitro differentiated cardiomyocytes with physical and functional phenotypes which are characteristic to cardiomyocytes in native cardiac tissue, using varying anisotropy and rigidities, which is characteristic of many myocardial disease states. Accordingly, the present invention represents a robust approach which provides flexibility and specificity to producing an in vitro myocardial model which can used as the screening platforms. Additionally, in some embodiments, the ANP polymer substrate is transparent, thus allowing optical methods to allow large amounts of parameter data to be collected rapidly and efficiently.

While other investigators have contemplated the use of hiPSC-derived cardiomyocytes in in vitro drug screens for both efficacy and safety, the present invention allows the hiPSCs-derived cardiomyocytes to be matured and organized in manner which resembles native or endogenous cardiomyocytes, thus producing a much more relevant cardiac tissue mimetic. Additionally, in some embodiments, the nanotextured platform enables mid-high throughput screening multiplex or a multi-well plate system, in which it is possible to simultaneously vary nanotopography and the substrate stiffness, two biomimetic cues that regulate the alignment and organization of cardiomyocytes. By varying these two parameters, it two important goals are accomplished: 1) the optimal set of conditions for promoting the structural and functional maturation of hiPSC-derived cardiomyocytes can be identified and optimized, and 2) the nanotextures can be altered to make available a diverse array of alternative conditions and alternative nanotextured ANPs to model the extracellular matrix (ECM) and structural environment of cardiomyocytes in diseased states (e.g. the fibrotic heart).

As disclosed herein, the nanopatterned texture and mechanical stiffness of the ANP can be separately tuned, creating optimal mimicry of native myocardial conditions in the in vitro differentiated cardiomyocytes and to confer tissue-like anisotropy to sheets of specifically oriented cells. Additionally, the nanotextured platform can also be coupled with other devices which may improve cardiomyocyte maturity, such as an electrical pacing system which could use coupled excitation-contraction conditioning to further mature anisotropic cardiac tissues.

In some embodiments, this present disclosure relates to a device or a composition comprising a anisotropically nanotextured platform (ANP) which is able to generate aligned, anisotropic cultures of mature cardiomyocytes from in vitro-differentiated cardiomyocytes through the use of cell culture scaffolds which contain nanotopographical surface cues and tunable rigidities. Accordingly, the nanotextured platform can be used to generate more faithful models of human cardiac tissue for disease modeling and in vitro drug screens, using hiPSC-derived cardiomyocytes and other immature cardiomyocyte types. These anisotropic cultures of cardiomyocytes will more accurately recapitulate adult human cardiac tissue due to their incorporation of human cardiomyocytes and inherent organization mimicking that of physiological heart tissue. In some embodiments, the nanotextured platform can be specifically applied to human pluripotent-stem cell derived cardiomyocytes as a method to align and mature these immature cell lines into a more mature model of the adult human myocardium. These organized tissues can be then used for various other purposes, such as generation of functional, organized tissue for the clinical setting, generation of physiologically relevant tissues for use in drug or pharmacological characterization by screening cellular effects of differing drugs, or use in patient specific disease modeling by culturing organized tissues derived directly from the patient. Alternatively, cardiomyocytes derived from hiPSCs from normal or diseased subjects can be cultured under conditions of nanopatterning or mechanical stiffness intended to recapitulate those in the diseased heart (e.g. the foci of cardiomyocyte disarray and fibrosis encountered in hypertrophic cardiomyopathy).

Accordingly, in some embodiments, the nanotextured platform as disclosed herein is a nanofabricated polymer cell culture scaffold or substrate with tunable topographies, topopgraphical dimensions and scaffold rigidities. These scaffold or substrates are scalable and can be used individually in a dish or incorporated for multiplex analysis, e.g., in a multiwell format. More specific to the application of mature anisotropic cardiac tissue, in some embodiments, the nanogratings (e.g., ridges and grooves of nano-diameter widths) of varying dimensions to mimic the extracellular matrix (ECM) of heart tissue. Accordingly, the nanopatterned platform as disclosed herein is different from previous devices in that the textures are on a nano-scale and can be independently varied with respect to topography and rigidity in a scalable and high throughput format.

In some embodiments, the myocytes, e.g., cardiomyocytes are derived from human induced pluripotent stem cells (hiPSCs), which are generated by reprogramming adult somatic cells (e.g. fibroblasts) that can be subsequently expanded and differentiated into cardiomyocytes. While other researchers have contemplated the use of hiPSC-derived cardiomyocytes (hiPSC-CMs) in drug screens, the key innovation as disclosed herein is the use of largescale, nanotextured cell culture surfaces that act as biomimetic cues. In some embodiments, the ANP can be specifically tuned to comprise a nanopatterned texture and mechanical stiffness, to closely mimic native myocardial conditions and confer tissue-like anisotropy to sheets of hiPSC-CMs. By varying the patient origin of the input human cardiomyocytes, the anisotropy of the cultures and the substrate rigidity, one can model both healthy and diseased heart tissue. When combined with available high-throughput optical methods for assessing cardiac phenotype and function, the ANP comprising cardiomyocytes can be used for drug screening for both safety and efficacy.

Accordingly, the present disclosure has important health and commercial implications. It will facilitate the development of new life saving and improve medical treatments, as well as help identify potentially dangerous drugs at an earlier point in the drug developmental pipeline, and perhaps even spur the development of a new regulatory scheme that will allow for more innovation.

Accordingly, the inventors have demonstrated herein a scalable, nanotopographically controlled model of myocardium which mimics in vivo ventricular organization and maturation of cardiomyocytes. Guided by nanoscale mechanical cues provided by an underlying hydrogel, the tissue constructs displayed anisotropic action potential propagation and contractility characteristic of the native tissue. Surprisingly, cell geometry, action potential conduction velocity, and the expression of a cell-cell coupling protein were exquisitely sensitive to differences in the substratum nanoscale features of the surrounding extracellular matrix. Accordingly, the inventors have discovered that by controlling cell-material interactions of cardiomyocytes on the nanotextured substrate, one can stipulate structure and function on the tissue level and yield novel insights into in vivo tissue physiology, while providing materials for tissue repair. Accordingly, the ANP is scalable to produce large scale tissue generation and can be used in high-throughput screening assays.

Accordingly, another aspect of the technology described relates to the use of the nanotextured platforms as disclosed herein comprising matured myocytes in methods and assays to screen for agents that affect the action potentials and other functional properties of the myocytes. In some embodiments, the assays can be used to identify agents which adversely affect the action potential and functional properties of normal myocytes, e.g., cardiomyocytes, for example, in a toxicity screen. In alternative embodiments, the assays can be used to identify agents which beneficially affect the action potential and functional properties of myocytes, e.g., cardiomyocytes, for example, where the cardiomyocytes are differentiated from cells, such as iPSCs originally obtained from a subject with a cardiovascular condition, disease or disorder as disclosed herein, or where the subject has arrhythmia.

One aspect of the present invention relates to a nanotextured platform composition comprising a polymer substrate comprising: a nanotextured array of parallel grooves and ridges that organizes cultured cardiomyocytes in an anisotropic manner; and in vitro-differentiated cardiomyocytes cultured on said nanotextured array, wherein said cardiomyocytes have a more differentiated, mature and adult-like phenotype on said nanotextured array than said in vitro-differentiated cardiomyocytes when cultured on a polymer substrate of the same composition but substantially lacking said array of parallel grooves and ridges.

In some embodiments, the matured cardiomyocytes have the characteristics of adult mature cardiomyocytes, for example, they have an increased expression of cardiac specific transcription factors, cardiac specific proteins expressed in adult human heart, expression of ion and voltage channels more similar to adult heart tissue pattern as compared to cardiomyocytes cultured on control textures, hypertrophy or increased size of cells, increased Z-disk, higher expression of gap junction proteins, increased cell-cell connection, increased cell-contraction, anisotropic arrangement of cells, anisotropic/directional propagation of an induced electrical impulse across the cultured tissue on nanotextured platform, as compared to immature cardiomyocytes, or cardiomyocytes which have not been cultured on the nanotextured platform. In some embodiments, increased size of cells and/or increase in Z-disc can be detected using microscope analysis after staining with F-actin. In some embodiments, an increase in cell-cell connection can be assessed by microscope analysis after immunostaining for connexin-43 and electrical propagation using optical mapping. In some embodiments, increased cell contraction can be assessed by contractile analysis using video microscopy, and mathematical analysis. In some embodiments, the anisotropic arrangement of cells can be assessed by microscopy and mathematical analysis after immunostaining with analysis F-actin and a-actinin. In some embodiments, anisotropic/directional propagation of induced electrical impulse, and/or increased cell-cell electrical conductivity can be assessed by optical mapping. In some embodiments, an increased syncytial nature of cells can be assessed by optical mapping using voltage sensitive dye after point stimulation by electrodes. In some embodiments, increased wave speed and/or decreased excitation threshold can be assessed by optical mapping, and/or patch clamping. In some embodiments, a measure of ridgidity can be assessed by nanoidentation, as disclosed in Timothy Nayar, et al., Tissue Engineering Part C: Methods. December 2012, 18(12): 968-975, which is incorporated herein in its entirety by reference.

Accordingly, in vitro differentiated cardiomyocytes from hESC and hiPSC cultures tend to have more fetal phenotype than adult cardiomyocyte phenotype. The nanotextured platform as disclosed herein allows further maturation of the cells in a multi-cellular format mimicking cardiac like anisotropic structure and expressing increased adult-like phenotypes.

In some embodiments, markers which indicate increased maturity of a cardiomyocyte include, but are not limited to, an increased expression of α-actinin, c-TnT and/or b-MHC, increased anisotropy, cellular alignment, anisotropic arrangement of gap junctions & cadherins between cells, increased T-tubule formation and caveolin expression. In some embodiments, the matured cardiomyocytes have an increased conversion of ssTnI to ctTnI, N2BA to N2B, and appropriate increase or decrease in expression of ion channels as expressed in adult cardiac tissue (voltage gated K+ channels, Na+ channels, voltage dependent Ca2+ channels, cyclic nucleotide dependent K+ channels, and other ion channels). In some embodiments, the matured cardiomyocytes have an increased contraction at single cell and multi-cellular level measured by contraction mapping aided by microscopy, increased strength of contraction. In some embodiments, the matured cardiomyocytes have an increased cell-cell electrical conductivity, increased syncytial nature of 2D in vitro culture in large area (cm$^2$) allowing electrical action potential to propagate from one point to another, increased wave speed and decreased excitation threshold, increased Ca2+ transient current.

Another aspect of the present invention relates to a nanotextured platform composition comprising a polymer substrate comprising: a nanotextured array of parallel grooves and ridges that organizes cultured cardiomyocytes in an anisotropic manner; and embryonic or induced pluripotent stem cells, e.g., human stem cells, cultured on said nanotextured array.

In some embodiments, the stem cells differentiate to cardiomyocytes with a more differentiated phenotype on said nanotextured array than said stem cells when cultured on a polymer substrate of the same composition but substantially lacking said array of parallel grooves and ridges.

In all aspects as disclosed herein, the in vitro-differentiated cardiomyocytes are human. In some embodiments, the cardiomyocytes or stem cells are derived from a patient diagnosed with a cardiac disease or disorder, or cardiovascular disease or disorder, e.g., arrhythmia.

In some embodiments, an nanotextured platform comprises an agent that promotes differentiation and/or the maturation of cardiomyocytes into more adult-like cells.

In all aspects of the present invention, a nanotextured platform as disclosed herein comprises grooves which have a depth of about 10 nm-1000 nm, and a width of about 5-1000 nm, where ridges, between the grooves, have a width of about 5-1000 nm. In some embodiments, the width of the groove and/or ridge is between the range of 200-800 nm, and the depth of the groove (or height of the ridge) is between about 20-100 nm. In some embodiments, the nanotextured array of parallel grooves and ridges be fabricated with large surface area with high fidelity and, in some embodiments, can cover a surface area greater than (>1 cm2). In some embodiments, the array of parallel grooves and ridges has a precision of texture of at least 90% fidelity, as evidenced by atomic force microscopy, and electron microscopy.

In some embodiments, the cardiomyocytes form a monolayer on the ANP substrate as disclosed herein with anisotropic and polarized cell arrangement in the direction of the nanotextures. This can be evidenced by, for example, a high spindle shape factor or major axis of cells aligned in parallel to nanotextured arrays, as detected for example, using fluorescent or other microscopy.

In some embodiments, the array of parallel grooves and ridges is generated using a process selected from the group consisting of capillary force lithography, nanoindentation, e-beam lithography, and electrospinning or any other method known to persons of ordinary skill in the art. In some embodiments, capillary force lithography is used.

In all aspects of the present invention, the ANP as disclosed herein can be coated with, or where the substrate comprises within its polymer matrix, at least one of: a biocompatible extracellular matrix polypeptide, an engineered matrix polypeptides, or engineered polypeptides. In some embodiments, the ANP as disclosed herein can be coated with, or where the substrate comprises within its polymer matrix, at least one or a combination of electroconductive materials selected from the group consisting of charcoal, graphene, graphene oxide, reduced graphene oxide, nanotubes, e.g., carbon nanotubes, titanium and gold, whereby one or more functional parameters of the substrate, selected from adsorption of proteins to surface, or electrical conductivity, or other physico-chemical property. In embodiments, the substrate can be coated with a single-later, a few layers or multi-layers of the electroconductive material e.g. graphene, e.g., at least one layer, or at least 2 layers, or at least 3 layers, or at least 4 layers, or at least 5 layers or more than 5 layers. In some embodiments, the physio-chemical properties modulated by the coating as disclosed herein, include, but are not limited to surface topography, surface mechanics surface chemistry, adsorption, conductivity, hydrophobicity, biochemical ligand availability that increase interaction with surface receptors expressed in cells surface membranes of the cultured myocytes. In some embodiments, the measurements of such physio-chemical properties can be done by, for example, but not limited to, the following methods: AFM, nanoindentation, X-ray photoelectron spectroscopy (XPS), FTIR, Raman Spectroscopy, immunostaining, water contact angle measurements, Surface Plasomon Resonance (SPS), ELISA respectively. Accordingly, the coatings on the substrate can be modulate the properties of the surface in a manner that influences the phenotype of said cardiac cells.

In some embodiments, the substrate of an ANP comprises a polymer hydrogel comprising, within the matrix, a biocompatible extracellular matrix protein, a synthetic or engineered matrix polypeptide, or engineered polypeptides. In some embodiments, a biocompatible extracellular matrix protein can be selected from the group consisting of, for example, a poly-L-lysine, poly-D-lysine, poly-orinithine, vitronectin, erythronectin. In some embodiments, the engineered polypeptides can be, for example, peptide segments including CS1, RGD, domains in extracellular matrix proteins that bind to integrin receptors, and others commonly known to person of ordinary skill in the art.

In some embodiments, the substrate of the ANP can comprise, within the substrate polymer, coating of one or more of gelatin, collagen type I, collagen type IV, fibronectin, fibronectin domains, laminin, engineered extracellular matrix proteins or peptides.

In some embodiments, the cardiomyocytes cultured on the nanotextured polymer (ANP) substrate express at least one marker from the group consisting of Nkx2.5, GATA4, connexin-43, a-myosin heavy chain, cTNT, sarcomere expression, sarcomere length, contractility, beat rate, or electrical propagation in a manner more similar to adult cardiomyocytes than in vitro-differentiated cardiomyocytes cultured on a polymer of the same composition but substantially lacking said nanotextured array.

In some embodiments, the polymer substrate comprises, either coated on its surface or within its polymer matrix, one or more agents selected from the group consisting of sphingosine phosphate or an analog thereof, fluric acid, zFAD-vmk, cardiotropin, or a growth factor selected from the group consisting of FGF, HGF, IGF1, SDF1a, EGF, VEGF, AM, HGF, Angiopoietin, BMPs, BDNF, Erythropoietin, GDNF, G-CSF, GDF9, HDNF, GDF, Thrombopoietin, TGF-alpha, TGF-beta, TNF-alpha, PIGF, PDGF, and interleukins IL1 to IL7, or any other growth factor known to one of ordinary skill in the art which may be beneficial to the cardiomyocytes to enhance their maturity and/or survival on the ANP substrate. In some embodiments, the agent can be used which functions to do any one or combination of the following; enhances the maturation of a cardiomyocyte on the ANP, or enhances the survival of a cardiomyocyte on the ANP, or enhances the survival of a cardiomyocyte in response to toxic stimuli, or enhances cardiomyocyte adherence to the ANP substrate, or enhances action potential wave propagation across the cardiomyocytes.

In some embodiments, the polymer substrate is optically transparent. In some embodiments, the polymer substrate has rigidity in the range of 5 to 200 kPa, for example, in the range of 5 to 40 kPa, which is characteristic of the rigidity of normal heart, or in the range of 30 to 200 kPa, which is characteristic of the rigidity of a diseased heart or an aged heart. In some embodiments, a measure of ridgidity can be assessed by nanoidentation, as disclosed in Timothy Nayar, et al., Tissue Engineering Part C: Methods. December 2012, 18(12): 968-975, which is incorporated herein in its entirety by reference.

In some embodiments, the polymer substrate is composed of a biocompatible hydrogel compatible with thermal or UV based curing methods to fabricate and/or capillary force lithography. In some embodiments, the polymer substrate is composed of PEG or a chemical variant thereof, such as, for example, PUA, PLGA, PMMA, PUA-PGMA and chemical variant thereof. In some embodiments, the polymer substrate comprises a UV curable hydrogel polymer, a thermosensitive hydrogel polymer or a polymer produced by solvent evaporation. In some embodiments, the thermosensitive polymer is PNIPAM.

In some embodiments, the polymer substrate comprises a nanotextured array of parallel grooves and ridges that organizes cultured cardiomyocytes on one or both sides of a substantially planar substrate. In some embodiments, the cardiomyocytes or stem cells can be present on one or both sides of an ANP substrate.

Another aspect of the present invention relates to a multiwell culture plate comprising a plurality of polymer substrate compositions, each in a substrate in a separate well of said multiwell plate and comprising a nanotextured array of parallel grooves and ridges that organizes cultured cardiomyocytes in an anisotropic manner, wherein individual members of said plurality have different rigidities, or topography, or coating. In some embodiments, the different rigidities range from 5 to 200 kPA. In some embodiments, the nanoarrays comprise in vitro differentiated cardiomyocytes cultured on them, for example, human cardiomyocytes. In some embodiments, the in vitro-differentiated cardiomyocytes are derived from stem cells, e.g., ESC and/or iPSCs. In some embodiments, the stem cells, e.g., iPSCs are derived from a subject with a cardiovascular disease or disorder, a cardiac disease or a subject who has arrhythmia.

In some embodiments, the ANP in a multiwall culture can have grooves with a depth in the range of 10-1000 nm and width in the range of 5-1000 nm, with the ridges between the grooves, having a width of between 5-1000 nm. In some embodiments, the ridgidity of the ANP in the multiwall culture is varied by varying polymer substrate curing time, UV intensity, or relative co-polymer concentration.

Another aspect of the present invention relates to nanotextured platform composition comprising a polymer substrate comprising: a nanotextured array of parallel grooves and ridges that organizes cultured skeletal muscle cells in an anisotropic manner; and in vitro-differentiated skeletal muscle cells cultured on said nanotextured array, wherein said skeletal muscle cells have a more differentiated phenotype on said nanotextured array than said in vitro-differentiated skeletal muscle cells when cultured on a polymer substrate of the same composition but substantially lacking said array of parallel grooves and ridges.

In some embodiments, the in vitro-differentiated skeletal muscle cells seeded on the ANP are less as mature than isolated adult skeletal muscle cells, and when they are cultured on the nanotextured surface for a predetermined time, they undergo maturation and develop a similar phenotype to mature skeletal muscle myocytes, as demonstrated herein in Example 4.

Another aspect of the present invention relates to a method of making a tissue composition, the method comprising: contacting a plurality of polymer substrates, each comprising a nanotextured array of parallel grooves and ridges that organizes cultured cardiomyocytes, e.g., human cardiomyocytes, in an anisotropic manner, with cultured cardiomyocytes to generate on each of said plurality of polymer substrates, a layer of anisotropically arranged cardiomyocytes; removing a plurality of said layers from their respective substrates by thermal alteration of adhesion of cell-substrate; and contacting said plurality of layers of anisotropically arranged cardiomyocytes with each other such that they are stacked one upon the other, and culturing the stacked layers in arbitrary direction such that a tissue composition is formed with desired anisotropy at individual layer levels.

In some embodiments, the cardiomyocytes in each layer are arranged substantially parallel to cardiomyocytes in the other layers, such that the direction of contraction of the cells is substantially the same in each layer. In alternate embodiments, the cardiomyocytes in each layer are arranged slightly rotated (e.g., at an angle) as compared to layer of cardiomyocytes above and/or below (e.g., See FIGS. 30C and 30D). In some embodiments, a non-cardiomyocyte layer can be placed between two myocyte layers, for example, a cell layer to assist with vascularization, e.g., epithelial cells, endothelial cells, mesenchymal cells or fibroblasts, as disclosed herein in Example 5. In some embodiments, the non-myocyte cells are cardiac fibroblasts, cardiac endothelial cells or mesenchymal cells. In some embodiments, a layer between each myocytes is made by culturing the myocytes on a layer of non-myocyte cells, e.g., fibroblasts, as discussed in Example 5.

In some embodiments, the cardiomyocytes are differentiated in a culture prior to contacting the cardiomyocytes on the ANP polymer substrates.

In some embodiments, the layers are removed from said substrates by and/or alteration of hydrophobicity or adhesiveness of said substrates, for example, by a change in temperature, where for example, the polymer comprises a thermal responsive polymer such as PNIPAM as disclosed herein.

Another aspect of the present invention relates to a tissue composition formed by layers of cardiomyocytes being stacked, for example, to generate tissue engineered myocardium as disclosed herein.

Another aspect of the present invention relates to a method of making a tissue composition, the method comprising: contacting in vitro-differentiated cardiomyocytes with a polymer substrate comprising a nanotextured array of parallel grooves and ridges that organizes cultured cardiomyocytes in an anisotropic manner; and culturing said cardiomyocytes on said substrate, wherein said cardiomyocytes arrange anisotropically on said substrate and have a more differentiated cardiomyocyte phenotype than said cardiomyocytes prior to said contacting and culturing steps.

In some embodiments, stem cells, e.g., ESCs and/or iPSCs are differentiated into a cardiomyocyte phenotype, e.g., an immature cardiomyocyte phenotype, prior to seeding the cardiomyocytes on the ANP substrate. In some embodiments, the ESCs and/or iPSCs is a human stem cell, for example, originally derived from a healthy human subject, or a human subject who has a cardiac disease or cardiovascular disease or disorder or arrhythmia.

Another aspect of the present invention relates to a method of making a tissue composition, the method comprising: contacting a stem cell with a polymer substrate comprising a nanotextured array of parallel grooves and ridges that organizes cultured cardiomyocytes in an anisotropic manner; and culturing said stem cell on said substrate in the presence of one or more agents that induces cardiomyocyte differentiation, wherein said culturing generates cardiomyocytes arranged anisotropically on said substrate, and wherein said cardiomyocytes have a more mature cardiomyocyte phenotype than cardiomyocytes differentiated from said stem cells with the same one or more agents but in the absence of said polymer substrate.

Another aspect of the present invention relates to a method of enhancing the maturity [defined by biochemical expression of adult-cardiac specific proteins and ion channels, anisotropic structural organization of individual cells mimicking adult heart cell, adult-heart like functional activity of individual cell and multicellular organized ensemble as evidenced by their mechanical contraction, Ca2+ transient activity, and electrical response individually and in collective] of in vitro differentiated cardiomyocytes, the method comprising contacting in vitro-differentiated cardiomyocytes with a polymer substrate comprising a nanotextured array of parallel grooves and ridges that organizes cultured cardiomyocytes in an anisotropic manner, wherein said contacting results in anisotropic arrangement and enhanced maturity of said cardiomyocytes.

In some embodiments, the anisotropically-arranged cardiomyocytes express one or more of the following markers of cardiomyocyte maturity in a manner more similar to cardiomyocytes in cardiac tissue than said in vitro differentiated cardiomyocytes prior to contacting with said polymer substrate.

Another aspect of the present invention relates to a method of differentiating stem cells to cardiomyocytes, the method comprising: contacting a population of stem cells with a polymer substrate comprising a nanotextured array of parallel grooves and ridges that organizes cultured cardiomyocytes in an anisotropic manner; and contacting said population of stem cells with an agent that promotes cardiomyocyte differentiation, wherein said stem cells differentiate to a cardiomyocyte phenotype. In some embodiments, the stem cells are human stem cell, e.g., ESCs and/or iPSCs, for example, ESCs and/or iPSCs originally derived from a healthy human subject, or a human subject who has a cardiac disease or cardiovascular disease or disorder or arrhythmia.

In some embodiments, the method of differentiation of stem cells to cardiomyocytes involves using ANP's with electroconductive carbon-based materials, e.g, graphene, graphene oxide, carbon nanotubes and the like. Such carbon based electroconductive materials include but are not limited to graphene, graphene oxide, reduced graphene oxide. The changes oxidation state of graphene based materials can result in variable surface conductivity of ANPs. Further, the electroconductive coating can be used as an electrode.

In some embodiments, the method of differentiating stem cells to cardiomyocytes results in cardiomyocytes with a more mature phenotype than the differentiation of said stem cells achieved by contacting said stem cells with agent that promotes cardiomyocyte differentiation on a polymer substrate of the same composition but substantially lacking said nanotextured array of parallel grooves and ridges.

Another aspect of the present invention relates to a method of screening for agents that cause cardiac arrhythmia or irregularity in action potential generation and/or propagation, the method comprising: contacting cardiomyocytes differentiated in vitro with a polymer substrate comprising a nanotextured array of parallel grooves and ridges that organizes cultured cardiomyocytes in an anisotropic manner, such that a monolayer of cardiomyocytes is arranged anisotropically on said substrate; measuring one or more parameters indicative of cardiac rhythm, and/or action potential generation or propagation in said monolayer; contacting said cardiomyocytes with a test agent; and measuring said one or more parameters after test agent contacting, wherein a difference in said one or more parameters is indicative that said agent may cause cardiac arrhythmia or irregularity in action potential generation and/or propagation.

In some embodiments, measuring one or more parameters comprises use of a calcium-sensitive or voltage-sensitive dye, confocal microscopy, optical mapping, or other fluorescent detection system.

Another aspect of the present invention relates to a method of screening for anti-arrythmogenic agents, the method comprising: contacting cardiomyocytes differentiated in vitro with a polymer substrate comprising a nano-textured array of parallel grooves and ridges that organizes cultured cardiomyocytes in an anisotropic manner, such that a monolayer of cardiomyocytes is arranged anisotropically on said substrate; contacting said monolayer with an arrythmogenic agent such that one or more parameters indicative of cardiac rhythm and/or action potential is perturbed relative to a parallel culture lacking said arrythmogenic agent; contacting said cardiomyocytes with a test agent; and measuring said one or more parameters after test agent contacting, wherein detection of a shift in said one or more parameters to a value more closely similar to the value for that parameter in the absence of the arrythmogenic agent is indicative that said test agent is a candidate anti-arrythmogenic agent.

Another aspect of the present invention relates to a method of screening for anti-arrythmogenic agents, the method comprising: contacting cardiomyocytes differentiated in vitro from a stem cell derived from an individual with cardiomyopathy and/or arrhythmia with a polymer substrate comprising a nanotextured array of parallel grooves and ridges that organizes cultured cardiomyocytes in an anisotropic manner, such that a monolayer of cardiomyocytes is arranged anisotropically on said substrate; measuring one or more parameters indicative of cardiac rhythm, and/or action potential generation or propagation in said monolayer, wherein at least one of said parameters indicates an abnormal cardiac cell rhythm; contacting said cardiomyocytes with a test agent; and measuring said one or more parameters after test agent contacting, wherein detection of a shift in said one or more parameters to a value more closely similar to the value for that parameter in cells derived from an individual with normal cardiac rhythm is indicative that said test agent is a candidate anti-arrythmogenic agent.

Another aspect of the technology described relates to use of the nanotextured platform as disclosed herein to enhance the maturation of immature myocytes, e.g., cardiomyocytes in vitro to produce an engineered myocardial tissue. In some embodiments, after a predetermined time of culturing the myocytes on the nanotextured platform, the myocytes, e.g., cardiomyocytes are removed from the nanotextured platform and multiple layers of two-dimensional myocyte monolayers or sheets can be stacked upon each other to generate a three-dimensional engineered tissue muscle tissue, e.g., engineered tissue myocardium. Such engineered tissue muscle tissue, e.g., engineered tissue myocardium can be used in methods for the treatment of subject, for example, as "muscle patches" for repair of skeletal muscle and/or cardiac muscle in subject in need thereof.

For example, another embodiment relates to use for the nanotextured substrate to align, elongate and mature skeletal muscle cells derived from animals and humans, for example, cells differentiated from stem cells (e.g., iPSC), or muscle cell lines (e.g. C2C12). In some embodiments, the nanotextured substrate comprises additional features, e.g., components of the extracellular matrix fibers found in a given muscle tissue, which can increase cell maturation, and allow more effective transplantation and integration with the host tissue.

In some embodiments, any number of maturation markers can be used to identify the enhanced maturity of myocytes into skeletal muscle myocytes, for example, including, but not limited to an increase in any number of the following as compared to myocytes cultured on a non-textured substrate: (a) Higher metabolic output, (b) More elongated and anisotropic morphology, (b) Higher expression of Pax7, Myf5, MyoG, MyoD, and dystrophin genes. In some embodiments, a higher or increased level of any one of these parameters is an increase of at least 10% as compared to the same parameter of myocytes cultured on non-textured substrates.

In some embodiments, nanotextured substrates which are used to culture skeletal muscle cells can be made from any polymer that is biocompatible, for example, a biodegradable material, and can be conjugated with a multitudes of factors that are known to promote angiogenesis, myogenesis, and nerve cell migration, including but not limited to, S1P, growth factors, laminin and other factors known to persons of ordinary skill in the art In some embodiments, the nanotextured substrates with skeletal muscle cells can be transplanted into a subject at the site of muscle injury, or diseased muscle and promote cell maturation, cell integration when the direction of patch is parallel to the host muscle fibers. In some embodiments, the subject has a muscle injury, or other wound (e.g., burn). In some embodiments, the subject has a myogenic disease or muscle wasting disease or disorder, for example, but not limited to muscular dystrophy, amylolateral sclerosis (ALS) and other such diseases.

In some embodiments, the nanotextured substrates can be coated with a thermoresponsive polymers (e.g. NIPAAm) as discussed herein, which can be used to create detachable skeletal muscle sheets that can be stacked to form 3D muscle grafts with anisotropy maintained at individual sheet level. Monolayer or multiple layer muscle patches with or without scaffold when transplanted promote cell integration, and maturation as defined by increased calcium transient, increased force generation, increase metabolic activity, increased expression of muscle-specific markers. These characteristics can be measured by of immunostaining, or live cell imaging of a reporter gene (e.g. calcium reporter in transplanted cells). Force generation can be measured by myography, and animal motor control measurements.

Accordingly, the present disclosure relates to an ANP substrate which is able to generate aligned, anisotropic cultures of mature cardiomyocytes through the use of nanotextured cell culture substrates/scaffolds which contain nanotopographical surface cues and tunable rigidities. Its purpose is to generate more faithful models of human cardiac tissue for disease modeling and in vitro drug screens, using hiPSC-derived cardiomyocytes and other immature cardiomyocyte types. These anisotropic cultures of cardiomyocytes will more accurately recapitulate adult human cardiac tissue due to their incorporation of human cardiomyocytes and inherent organization mimicking that of physiological heart tissue.

In some embodiments, the ANP substrate can be specifically applied to human pluripotent-stem cell derived cardiomyocytes as a method to align and mature these immature cell lines into a more mature model of the adult human myocardium. These organized tissues can be then used for various other purposes, such as generation of functional, organized tissue for the clinical setting, generation of physiologically relevant tissues for use in drug or pharmacological characterization by screening cellular effects of differing drugs, or use in patient specific disease modeling by culturing organized tissues derived directly from the patient. The ANP substrate as disclosed herein is a nanofabricated polymer cell culture scaffold with tunable topographies, topopgraphical dimensions and scaffold rigidities. These scaffolds are scalable and can be used individually in a dish or incorporated into a multiwell format. More specific to the application of mature anisotropic cardiac tissue, nanogratings of varying dimensions can be used to mimic the extracellular matrix (ECM) of heart tissue. Accordingly, the present invention is especially unique in its ability to independently vary scaffold topography and rigidity in a scalable and high throughput format.

The present disclosure also includes data and information that can be found in Kim et al. "Nanoscale cues regulate the structure and function of macroscopic cardiac tissue constructs," PNAS, Jan. 12, 2010 vol. 107 no. 2 565-570; the entirety of which is incorporated by reference herein.

The present invention also relates to kits comprising the nanotextured platform polymer substrate as disclosed herein. In some embodiments, the kit also comprises reagents and agents for coating the nanotextured platform with immature myocytes, e.g., cardiomyocytes. In some embodiments, the kit can optionally comprise the nanotextured platform polymer substrate organized a multi-well culture plate for use in the assays and methods as disclosed herein, for example, in toxicity screening assays or for screening to identify agents which beneficially affect the action potential and functional properties of myocytes, e.g., cardiomyocytes with irregular action potentials, e.g., where the cells, such as iPSCs are originally obtained from a subject with a cardiovascular condition, disease or disorder as disclosed herein, or where the subject has arrhythmia.

BRIEF DESCRIPTION OF THE DRAWINGS

FIG. 1A shows an embodiment of a multi-well cell culture device integrated with large area nanotopographic substrates for parallel screening of cellular response to variable substrate topography and rigidity. FIG. 1B shows electron microscopy (SEM) images of the fabricated patterns with representative examples showing that nanopatterns are highly tunable, and can be formed in any arbitrary feature sizes.

FIG. 2A is an example of an embodiment of a nanopatterned coverglass. FIG. 2B shows an example of nanotextured substrates in a multiwell plate, allowing the comparison of cardiomyocytes cultured on a nanotextured substrate or a non-textured substrate in different wells on the multiwell plate. The panels on the right show the nanotagraphy of the surface of the non-textured substrate (top) and the nanotextured substrate (bottom). Scale bar=10 µm.

FIG. 3A shows the wide scan spectra of PLGA (black), and S1P-PLGA (red) nanostructured substrate showing high amount of Nitrogen and Phosphorus in S1P-PLGA. FIG. 3B shows the narrow scan substrate of C1s for PLGA (left), and S1P-PLGA (right) showing decrease in peaks assigned to COOH group.

FIG. 4A shows SEM images of ex vivo myocardium of adult rat heart, showing that well-aligned myocardium (middle) correlates with matrix fibers aligned in parallel beneath (bottom). FIG. 4B shows a photograph of a large-area (3.5 cm$^2$) nanopatterned substrate (top) and its cross-sectional SEM image (bottom). FIG. 4C shows the formation of confluent neonatal rat ventricular myocytes (NRVMs) on the unpatterned and nanopatterned substrates. Immunofluorescent images of sarcomeric α-actinin and cell nuclei are shown. FIG. 4D shows the action potential propagation across monolayers cultured on unpatterned and nanopatterned substrates.

FIG. 6A shows that the nanogrooves promote alignment of hiPSC-derived cardiomyocytes (right) as compared to hiPSC-derived cardiomyocytes cultured on non-patterned substrate. FIG. 6B shows the nanogrooves promotes the elongation of hiPSC-derived cardiomyces as compared to hiPSC-derived cardiomyocytes grown on the non-patterned substrate and the increase in elongation as a result of culturing on the nanopattened substrate continues over 2 weeks of culture. FIG. 6C shows a computational image analysis of F-actin fiber angle in Kebs hiPSC-derived cardiomyocytes cultured on flat and nanotextured platform show a highly directional arrangements of F-actin in cells cultured on nanotextured platforms. Immunostaining for a-actinin, and F-actin, and DAPI (nuclei) are shown. *p<0.01

FIG. 7A shows that the nanotopography promotes maturation of hESC/hiPSC-derived cardiomyocytes. FIG. 7B shows that both sarcomere length and Z-band width are increased in patterned hESC-derived cardiomyocyte cultures. Increased sarcomere length and Z-band width are correlated with enhanced force generation during development. FIG. 7C shows results from qRT-PCR which demonstrates that nanotopography enhances expression of contractile MYH7 protein in hESC-derived cardiomyocytes, as compared to hESC-derived cardiomyocytes not cultured on a nanotextured substrate. FIG. 7D shows results from qRT-PCR which demonstrates that nanotopography enhances expression of the calcium channel protein CACNA1C in hESC-derived cardiomyocytes, as compared to hESC-derived cardiomyocytes not cultured on a nanotextured substrate. *p<0.05, **p<0.01.

FIG. 8A shows the expression of TNNT2 (cTnT), and FIG. 8B shows the expression of NPPB (BNP). Significance was determined by single-factor analysis of variance followed by Student t test in comparison with unpatterned substrate. *P<0.05. Error bar represent standard error. FIG. 8C shows the binucleation rate of cells on each substrate at 1 week after cell seeding. P=0.05.

FIG. 9A is a heat maps from representative movies showing that cells on non-textured flat substrates. FIG. 9B shows a heat map of a representative move from cardiomyocytes cultured on a nanopatterned substrate, showing that these myocytes have much larger areas of high magnitude contractions as compared to cells on flat substrates. FIG. 9C shows the average contraction units of cell cultured on nanotextured substrates as compared to non-textured (e.g., smooth) substrates, and shows that the magnitude of cellular contraction was significantly greater in cells on nanopatterned substrates as compared to myocytes cultured on the non-textured substrates. *P<0.001. Error bar represent standard error.

FIG. 11A shows the magnitude of Ca2+ signal is greater for hESC-CMs on nanopatterned substrates as compared to non-textured substrates. FIG. 11B shows the Ca$^{2+}$ rise time was decreased in hESC-CMs cultured on nanotextured substrates as compared to non-textured substrates. FIG. 11C shows the Ca$^{2+}$ decay time was decreased in hESC-CMs cultured on nanotextured substrates as compared to non-textured substrates. FIG. 11D shows FWHM was also decreased in hESC-CMs cultured on nanotextured substrates as compared to non-textured substrates.

FIG. 12A shows each spot represents the fluorescent voltage detected at a particular location in the hiPSC-CM monolayer cultured on the nanogrooved surface. Specific voltage intensities can be determined using the scale to the right. FIG. 12B shows each of the variously colored tracess represents the changing voltage over time at a different location in the culture. Stimuli (15 V for 10 ms) were applied from the edge of the culture every 500 ms.

FIG. 13A shows the synergistic effects of the nanotopography (e.g., array of substantially parallel nanogrooves and nanoridges) and electrical stimulation increases cardiomyocyte hypertrophy as compared to cardiomyocytes cultured on substrates with perpendicular nanotopography. FIG. 13B shows the synergistic effects of the nanotopography (e.g., array of substantially parallel nanogrooves and nanoridges) and electrical stimulation increases the maturation as measured by increasing sarcomere length of cardiomyocytes as compared to cardiomyocytes cultured on substrates with perpendicular nanotopography. *$P<0.01$.

FIG. 14A shows that the ANP polymer substrate allows hESC/hiPSC-CMs to mature and be electrically responsive and shows the electrical response as measured by optical mapping using MiCAM Ultima Camera in hESC-CMs cultured over nanoengineered platform for 7 days. FIG. 14B shows the conduction velocity vectors of action potential propagation in nanoengineered platform seeded with hESC-CMs for 7 days.

FIG. 15A is a representative image of optical activation map showing syncytial electrical activity of a hES-hiPS-derived cardiac monolayer cultured on the nanotextured substrate upon stimulation, and responds in a wave like fashion with the direction of wave parallel to underlying nanotopography. FIG. 15B is a representative image of conduction velocity vectors which show anistropic conduction velocity in hES/hiPSC-derived cardiomyocyte monolayer.

FIG. 16A shows live cells stained with Calcein-AM, and dead cells with EtBr. FIG. 16B shows that, as expected for this known cardiotoxic drug, doxorubicin (10 mm) induced a statistically significant increase in the percentage of dead hESC-CMs.

FIG. 17A shows the effect on action potential profile without and with the addition of cisapride for 2 minutes. FIG. 17B shows the effect of cisapride addition on paced cells. FIG. 17C shows that cisapride results in prolongation of action potential in a significant manner. FIG. 17D shows a representative trace of action potential profile without and in the presence of cisapride.

FIG. 13 shows the addition of Verapamil, a L type Ca2+ channel inhibitor causes distortions in AP profile.

FIG. 20A shows conduction velocity vectors identified by optical mapping of paced hiPSC-derived cardiomyocytes monolayer in the presence of 0 μM carboxelone, and FIG. 20B shows the conduction velocity vectors of paced hiPSC-derived cardiomyocytes in the presence of 40 μM carboxelone, showing a decrease in conduction across the tissue. FIG. 20C shows a spatial activation map of electrical activity of paced hiPSC-derived cardiomyocytes monolayer in the presence of 0 μM carboxelone, and FIG. 20D shows a spatial activation map of electrical activity of paced hiPSC-derived cardiomyocytes monolayer in the presence of 40 μM carboxelone, showing a decrease in electrical activity of the monolayer.

FIG. 21 shows an AFM (atomic force microscopy) image of nanopatterned PEG substrate with 50-1000 nm ridge-groove dimensions coated with few-layered graphene shows successful coating of graphene onto PEG nanotextured platforms.

FIG. 22A shows AFM topography map of single-layer graphene coated PEG nanopattern and shows successful transfer of single-layer graphene on PEG ANP. FIG. 22B shows the conductive AFM (c-AFM) image showing the current map of the same sample collected with 20 mV bias voltage shows that nanotextured platform of polymers can be rendered conductive by graphene coating.

FIG. 23A shows the Raman spectra of single-layer graphene coated PEG nanopattern (bottom trace), single-layer graphene coated PEG nanopattern oxidized for 1 second (middle trace) and single-layer graphene coated PEG nanopattern oxidized for 2 seconds (top trace) showing D, G and G' bands. FIG. 23B shows I-V curve for single-layer-graphene covered PEG nanopattern, 1 second oxidation and 2 second oxidation. The graphene coated ANP is the most conductive with its conductivity reaching values close to pristine single layer graphene and further controlled oxidation can reduce the surface conductivity, denoted by the slop of I-V curve.

FIG. 24A shows that RUES2 (human ESC cell line obtained from Rockefeller University) derived cardiomyocytes cultured for 21 days on PEG nanopattern, and FIG. 24B shows a single-layer graphene oxide (GO) show increased and more pronounced expression of a-actinin, and increased confluency. FIG. 24C shows high magnification images of RUES2-derived cardiomyocyte cultures on control PEG nanopatterns, and FIG. 24D shows GO-coated nanopatterns (D) show more coupling among the cells and more developed structures of carcomeres and z-bands of hES/hiPSC-derived cardiomyocytes cultured on graphene coated electroconductive PEG ANP vs. bare PEG ANP.

FIG. 26A-26 B shows graphene coated ANPs promote long range coupling of cardiac cells. FIG. 26A shows action potential curve for RUES2-derived cardiomyocytes cultured on graphene coated nanotextured substrates. The monolayer is field stimulated with 1 Hz. The potential curve shows efficient pacing of the cardiac cells under stimulation.

FIG. 27A shows a scanning electron microscopy of the nanotextured substrate, and FIG. 27B shows the atomic force microscopy confirm nanopattern fidelity and dimensions. FIG. 27C shows results from X-ray photoelectron spectroscopy confirms an increase in nitrogen content when amine-functionalized PNIPAm is grafted to nanotextured scaffolds. FIG. 27D shows PNIPAm incorporation allows for temperature-dependent change from a hydrophilic to hydrophobic surface. Lower critical solution temperature=32° C.

FIG. 28A shows a schematic drawing showing the capillary force lithography-based nanofabrication of PUA-PGMA scaffolds. Incorporation of GMA monomers allows for epoxy group functionalization of the scaffold. FIG. 28B shows a schematic showing the reaction between surface epoxy groups and amine-functionalized PNIPAM, allowing for PNIPAM surface grafting.

FIG. 29A shows a brightfield microscope image of cell attachment and alignment of C2C12 mouse myoblasts. FIG. 29B shows a brightfield microscope image of cell attachment and alignment of neonatal rat ventricular myocytes. FIG. 29C shows a brightfield microscope image of cell attachment and alignment of RUES2 human embryonic stem cell-derived cardiomyocytes. FIG. 29D shows a brightfield microscope image of cell attachment and alignment of IMR90 human induced pluripotent stem cell-derived cardiomyocytes.

FIGS. 30A-30D shows a generic method of creating multiple layers of arbitrarily aligned scaffold free aligned sheets using thermoresponsive polymer coated ANP. Gel casting method to transfer sheets or fabricate 3D tissues with controllable layer structure. FIG. 30A shows that a gel casting method can be utilized to detach anisotropic cardiac sheets. FIG. 30B shows that detached sheets of anisotropically organized cardiomyocytes can be transferred to a new surface or stacked onto additional cell sheets on thermoresponsive scaffolds. FIG. 30C shows a schematic of orientation key to control individual layer orientation while stacking. FIG. 30D shows a stacked bilayer of myoblast tissue with differing layer orientation (e.g., each layer is rotated at a slight angle as compared to the above or below layer). Confocal microscope image of immunostaining for F-actin demonstrates retained individual layer anisotropy of bilayer tissue (arrows indicate the different directions of the cells in each biolayer).

FIG. 31A shows a confocal microscope image of transferred anisotropic neonatal rat ventricular myocytes (NRVM) sheets. FIG. 31D shows a confocal microscope image of transferred anisotropic hiPSC-derived cardiomyocyte (RUES2-CM) sheets after 6 days of culture on flat glass. Immunostaining for F-actin, α-sarcomeric actinin and nuclei demonstrate maintained anisotropic cell morphology and tissue alignment. Arrows indicate the alignment direction. FIG. 31B shows MATLAB analysis of confocal images quantified F-actin orientation and confirmed maintained tissue anisotropy of NRVM sheet. FIG. 31E shows MATLAB analysis of confocal images quantified F-actin orientation and confirmed maintained tissue anisotropy of RUES2-CM sheet. FIG. 31C shows MATLAB movie analysis of transferred sheet contraction direction and magnitude also demonstrates anisotropic beating after transfer of a NRVM sheet. FIG. 31F shows MATLAB movie analysis of transferred sheet contraction direction and magnitude also demonstrates anisotropic beating after transfer of a RUES2-CM sheet.

FIG. 32A shows the average magnitude of contraction displacement of the cardiomyocyte monolayer. FIG. 32B shows the average magnitude of contraction displacement of a cardiomyocyte bilayer. FIG. 32C relative contractions averaged over each contractile pixel. *P<0.01.

FIG. 33A shows cardiomyocytes derived from MHF2 (fetal fibroblast derived hiPSCs) cultured on non-textured substrates, and FIG. 33B shows cardiomyocytes derived from a patient with cardiomyopathy due to mutation in MHY7 gene on non-textured substrates show poorly organized sarcomeric structures. FIG. 33C show MHF2-derived cardiomyocytes cultured on nanotextured scaffolds allow highly organized sarcomeric structures. FIG. 33D shows patient-derived cardiomyocytes cultured on nanotextured scaffolds also have a highly organized sarcomeric structures. Arrows in C, D show the direction of nanotextured grooves.

FIG. 34A shows cardiomyocytes derived from IMR90 hiPSCs show well defined sarcomeres when cultured on nanotextured platforms. FIG. 334B shows cardiomyocytes derived from a patient with cardiomyopathy due to mutation in MHY7 gene cultured on nanotextured scaffolds also have highly organized sarcomeric structures. FIG. 34C shows the addition of isoproterenol, a β1 and β2 agonist does not result in loss of sarcmeric organization in control IMR90 cells. FIG. 34D shows that addition of isoproterenol results in loss of sarcomere organization in MHY7 mutated iPSC-derived CMs. Since nanotextures allow physiological organization of sarcomeres, it serves as a disease model to test the effect of a drug on a diseased cardiomyocyte.

FIG. 35A shows a schematic illustration of nano-patterned PLGA. FIG. 35B shows SEM images of flat and nano-patterned PLGA. The scale bars indicated 10 µm. FIG. 35C shows an illustration of muscle cell patch transplantation on mdx mouse quadriceps muscle.

FIGS. 36A-36D depict attachment, growth and alignment of muscle cell on the flat and nano-patterned PLGA. FIG. 36A shows fluorescent images of GFP+ cells cultured on flat and nano-patterned PLGA substrate. The scale bars indicated 100 µm. FIG. 36A shows SEM images of muscle cells attached to two types of patches and cultured at 10 days. The scale bars indicated 50 µm. FIGS. 36C-36D show quantitative analysis of the morphology of muscle cell on the flat PLGA and nano-patterned PLGA after 3, 6, and 10 days of culture: (FIG. 36C) Elongation, and (FIG. 36D) Orientation. Error bars represent ±SEM. Student's t-test *P<0.05.

FIG. 37A shows mitochondrial metabolic activity of muscle cells cultured on two types of patches, as determined by MTT assay (n=3). FIG. 37B demonstrates that X-gal staining reveals expressing of the nuclear localized MLC3F-nLacZ reporter in myonuclei of cultured myotubes as indicated. Scale bars indicated 100 µm. FIG. 37C shows quantification of β-galactosidase positive nuclei per mm$^2$. FIG. 37D shows q-RT-PCR of muscle cells indicated muscle maturation gene express to two types of patches at day 6. Error bars represent ±SEM. Student's t-test *P<0.05.

FIG. 38A shows a photograph of muscle cell patch transplants over mdx mouse quadriceps muscle. FIG. 38B shows muscle sections stained with x-gal display numerous β-galactosidase positive events, some localized within the myofibers. FIG. 38C shows staining with laminin (red) reveals β-galactosidase positive/DAPI negative myonuclei under the basal lamina. Arrow indicated x-gal positive staining with basal lamina. FIG. 38D shows staining for dystrophin (red) reveals numerous dystrophin positive muscle fibers (marked by asterisks) only in muscles transplanted with nano-patterned patches. Scale bars indicate 100 µm. Quantification of dystrophin positive fibers reveals a significant difference between flat and nanopatterned transplants. Error bars represent ±SEM. Student's t-test *P<0.05, **P<0.001.

FIG. 39B shows Confocal images showing actin phalloidin in unaligned and aligned aGPFs at 10 and 40× magnification. Note global alignment of aGPFs in both magnifications.

FIG. 40A shows confocal images showing actin phalloid (green), α-sarcomeric actinin (red) in unaligned and aligned coverslips. DAPI (blue) shows the nuclear counterstain. Blue arrow shows the direction of grooves. Note the alignment of actin, sarcomeric actinin, and even nuclei along the grooves. FIG. 40B shows α-sarcomeric actinin (red) images of different regions within one unaligned (left) and aligned (right) coverslip. Blue arrow shows the direction of grooves. Although there is some local alignment on the unaligned monolayer, images from different regions show no global alignment. However, on the aligned monolayer, there is global alignment in the direction of the grooves.

FIG. 41A shows AP trace of each monolayer, averaged over different waves. FIG. 41B shows an AP trace of aligned versus unaligned monolayers, averaged over monolayers. Note the different waveforms. FIG. 41C shows P-value of difference in voltage between aligned and unaligned monolayers over time. FIG. 41D shows APD of each monolayer at different levels of repolarization, averaged over different waves. FIG. 41E shows APD of aligned versus unaligned monolayers at different levels of repolarization, averaged over monolayers. Note the difference in APD between aligned and unaligned monolayers over a wide range of repolarization levels. FIG. 41F shows P-value of difference in APD between aligned and unaligned monolayers over levels of repolarization. Note that aligned and unaligned APDs are statistically significant at almost every stage of repolarization.

FIG. 42A shows the aligned monolayers had increased functional anisotropy over unaligned monolayers. FIG. 42A: Activation maps for unaligned and aligned monolayers, respectively. Note the generally circular activation isochrones in the unaligned monolayer, indicating isotropic propagation, as opposed to the highly elliptical isochrones for the aligned monolayer, indicating anisotropic propagation. FIG. 42B shows activation maps were mapped onto a surface in x,y,t space, and fit to an elliptical cone. By looking at the ratio of the slope parameters on the major and minor axes, anisotropy could be calculated. Calculated anisotropy ratios for aligned and unaligned coverslips. Error bars are SD. Note the statistically significantly increased functional anisotropy of aligned monolayers.

DETAILED DESCRIPTION

Figure 1A:
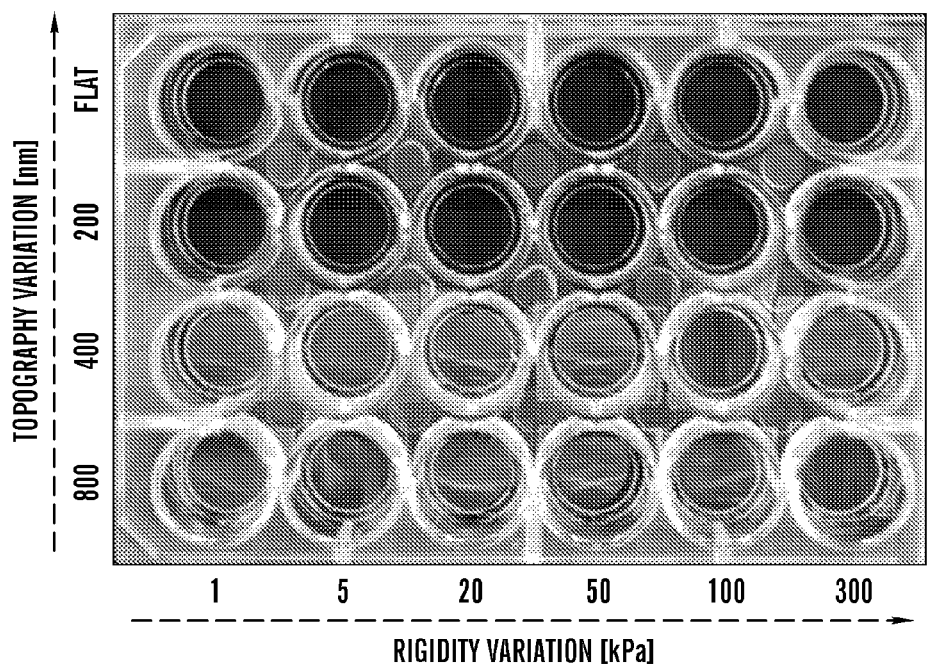
FIG. 1A-1B shows an example use of a nanotextured platform polymer substrate in multi-well cell culture device format. Nanostructures can be fabricated in multi-well plates (6, 12, 24, 48, and 96 well plates) with control over individual well nanotopography features, and rigidity.

As disclosed herein, the inventors have discovered that a nanotextured polymer platform, referred to herein as an "anisotropically nanotextured platform" or "ANP", fabricated to comprise a nanotextured array of parallel grooves and ridges can organize immature muscle cells or myocytes (e.g., immature cardiomyocytes or immature skeletal muscle myocytes) in an anisotropic manner, and the nanotextured platform promotes a more adult-like phenotypes in anisotropically arranged myocytes relative to the same cells cultured on a substrate lacking the nanostructures. Accordingly, the nanotextured polymer platform as disclosed herein can be used to enhance the maturation of immature myocytes, e.g., cardiomyocytes to produce a functional tissue engineered muscle tissue construct, e.g., engineered myocardium construct. Accordingly, the inventors have discovered a method to produce functional tissue engineered myocardium which is capable of action potential propagation and has vastly superior cardiac muscle function as compared to existing tissue engineered cardiac tissue.

One aspect of the present invention relates to a composition comprising an nanotextured platform composition comprising a polymer substrate which has a nanotextured array of parallel grooves and ridges that is structurally configured to enhance the maturation of immature muscle cells or myocytes to more mature phenotype, thus producing a functional engineered tissue myocardium construct which is capable of conducting action potentials and has superior muscle function over existing engineered tissue constructs. In particular, a nanotextured platform of as described herein comprises an array of nanoscale parallel grooves and ridges that is structurally configured to organize immature muscle cells or myocytes (e.g., immature cardiomyocytes or immature skeletal muscle myocytes), in an anisotropic manner, such that when immature myocytes are cultured on the nanotextured platform, they are matured and have more differentiated phenotype, relative to the same cells cultured on a substrate lacking the nanotextured grooves and ridges.

In some embodiments, the immature myocytes are in vitro differentiated myocytes, such as in vitro-differentiated cardiomyocytes. In some embodiments, the immature cardiomyocytes are cardiomyocyte precursors. In some embodiments, the cardiomyocytes are derived from stem cells, such as embryonic stem (ES) cells, adult stem cells, or induced pluripotent stem cells (iPSCs). In some embodiments, a population of stem cells, such as ESCs or iPSCs can be in vitro differentiated into immature cardiomyocytes for use in the compositions and methods disclosed herein, and in some embodiments, the differentiation of iPSC or ESCs into immature cardiomyocytes can be done prior to coating the cells on the nanotextured platform, or can be done while they are coated on, or present on, the nanotextured platform. In some embodiments, the iPSCs are cells which have been reprogrammed from somatic cells obtained from a subject, e.g., a human subject. In some embodiments, the human subject is a healthy subject, and in some embodiments, the subject has a cardiovascular condition, disease or disorder as disclosed herein, including, but not limited to arrhythmia.

The inventors have developed a nanotextured polymer platform that is configured to have the rigidity, flexibility and topography for the enhanced maturation of myogenic cells in an anisotropically and anatomically correct manner to mature these into an adult phenotype in vitro. Furthermore, the nanotextured polymer platform is scalable to permit large scale tissue generation and can be used in high-throughput screening assays.

Accordingly, another aspect of the present invention relates to the use of the nanotextured platform as disclosed herein comprising immature myocytes in methods and assays to screen for agents that affect the action potentials and other functional properties of the myocytes. In some embodiments, the assays can be used to identify agents which adversely affect the action potential and functional properties of normal myocytes, e.g., cardiomyocytes, for example, in a toxicity screen. In alternative embodiments, the assays can be used to identify agents which beneficially affect the action potential and functional properties of myocytes, e.g., cardiomyocytes, for example, where the cardiomyocytes are differentiated from cells, such as iPSCs originally obtained from a subject with a cardiovascular condition, disease or disorder as disclosed herein, including but not limited to arrhythmia.

Another aspect of the technology described herein relates to use of the nanotextured platform as disclosed herein to enhance the maturation of immature myocytes, e.g., cardiomyocytes, in vitro to produce an engineered myocardial tissue. In some embodiments, after a predetermined time of culturing the myocytes on the nanotextured platform, the myocytes, e.g., cardiomyocytes can be removed from the nanotextured platform and multiple layers of two-dimensional myocyte monolayers or sheets can be stacked upon each other to generate a three-dimensional engineered muscle tissue, e.g., engineered tissue myocardium. Such engineered muscle tissue, e.g., engineered myocardium can be used in methods for the treatment of a subject, for example, as "muscle patches" for repair of skeletal muscle and/or cardiac muscle in a subject in need thereof. Alternatively, or in addition to, such three-dimensional tissue constructs can also be used as screening methods to evaluate the effect of drugs on the myocardium.

The technology described herein also relates to kits comprising a nanotextured polymer substrate as disclosed herein. In some embodiments, the kit also comprises reagents and agents for coating the nanotextured platform with immature myocytes, e.g., cardiomyocytes. In some embodiments, the kit can optionally comprise the nanotextured polymer substrate organized in a multi-well culture plate format for use in the assays and methods as disclosed herein. For example, nanotextured polymer substrates organized in a multi-well culture plate can be used in toxicity screening assays and/or for screening to identify agents which beneficially affect the action potential and functional properties of myocytes, e.g., cardiomyocytes with irregular function, e.g., where the cells, such as iPSCs are originally obtained from a subject with a cardiovascular condition, disease or disorder as disclosed herein, e.g., arrhythmia.

In vitro differentiated cardiomyocytes tend to have a less mature phenotype than, for example, cardiomyocytes isolated from adult cardiac tissue. While it had been demonstrated that nanotextured grooves and ridges in a substrate promoted anisotropic arrangement of cardiomyocytes isolated from adult tissue (Kim et al., entitled "Nanoscale cues regulate the structure and function of macroscopic cardiac tissue constructs", PNAS (2010) 107(2); 565-570, which is incorporated herein in its entirety by reference), it was unexpected that a similar nanotextured substrate could actually enhance the maturation of in vitro differentiated myocytes or cardiomyocytes to a more mature phenotype.

One aspect of the technology described herein relates to the use of in vitro-differentiated cardiomyocytes in combination with a nanotextured platform for controlled maturation of the in vitro-differentiated cardiomyocytes into mature cardiomyocytes resulting in the generation of functional cardiac tissue.

In some embodiments, the nanotextured platform as disclosed herein can be used to generate the functional muscle tissue, e.g., functional engineered myocardium, as the nanotextured platform is patterned, so that the cellular environment at multiple spatial scales (nanometer to meter) is modified in order to direct the maturation of in vitro differentiated myocytes, e.g., cardiomyocytes and to subsequently organize the in vitro differentiated myocytes into two-dimensional (2D) and three-dimensional (3D) myocardial tissue structures. In some embodiments, the nanotextured platform can be coated with agents, such as differentiation factors, which promote the differentiation of the myocytes, e.g., cardiomyocytes along a more differentiated phenotype, and/or the culture media can also comprise similar differentiating factors.

In some embodiments, the inventors demonstrate by using a population of human iPS-derived cardiomyocytes, the methodology to mature in vitro-differentiated cardiomyocytes into mature cardiomyocytes, e.g., ventricular cardiomyocytes and the formation of engineered cardiac muscle, such as engineered myocardium. The inventors demonstrate that the functional performance of tissue generated from iPSC-derived in vitro-differentiated cardiomyocytes is comparable to myocardial tissue constructed from rat adult cardiomyocytes, as disclosed in Kim et al., entitled "*Nanoscale cues regulate the structure and function of macroscopic cardiac tissue constructs*", PNAS (2010) 107 (2); 565-570, which is incorporated herein in its entirety by reference.

This invention represents a key advancement in the strategy for large-scale engineering of functional myocardium from a stem cell source, e.g., ES cell and iPSC source. In particular, one key advance is the ability to mature in vitro-differentiated cardiomyocytes into a functional tissue, as prior efforts to produce mature cardiomyocytes from cardiomyocyte precursors or progenitors is highly inefficient and does not produce functional cardiomyocytes which resemble mature adult cardiomyocytes. This is because the myocardium is an ensemble of different cell types embedded in the complex=structures of the extracellular matrix (ECM) arranged in nanoscale topographical and molecular patterns. Although the structure of cardiac tissue is highly organized in vivo, common culturing techniques for in vitro-differentiated cardiomyocytes lack their native organization, resulting in random distribution when cultured in vitro, compromising many of their physiological properties.

The cellular environment of the ANP is engineered on the nanometer scale to encompass lengths of macroscopic length cells, providing precise nanoscale cues to allow the organization of the differentiated cardiomyocytes to adopt a more mature organization. Factors that are engineered or manipulated to benefit include, but are not limited to, material mechanical properties, material solubility, spatial patterning of the topological features, e.g., ridges and grooves, soluble bioactive compounds, mechanical perturbation (cyclical or static strain, stress, shear, etc. . . . ), electrical stimulation, and thermal perturbation.

Accordingly, the ANP allows the in vitro-differentiated myocytes, e.g., cardiomyocytes, including those differentiated from ESCs and iPSCs to be driven towards a more differentiated and mature cell phenotype at an efficiency that surpasses all current methodologies. In particular, because of the nano-scale cues, the ANP is able to robustly and reproducibly generate uniformly controlled (both structurally and functionally) and precisely defined engineered cardiac tissue or myocardium that is necessary for controlled high-throughput screening assays as well as for therapeutic utility. Further, experimental results demonstrate unequivocally that the in-vitro differentiated cardiomyocytes which have been anisotropically organized on the ANP have structural and functional properties (e.g., action potential generation) comparable to myocardium from adult rat cardiomyocytes. Accordingly, any myocyte cell, e.g., cardiomyocytes, derived from an ES cell or other source, such as induced pluripotent stem (IPS) cells, or the reprogramming of somatic cells can be used to generate tissue engineered myocardium as disclosed herein. Accordingly, the technology described herein provides the capability to generate functional myocardium from a renewable cell source. In some embodiments, use of a population of in vitro-derived cardiomyocytes derived by some from some other renewable cell source, such as from reprogrammed cells such as iPS cells, permits the functional engineered cardiac tissue constructs, e.g., engineered myocardium constructs to be generated from patient-specific populations, e.g., having a cardiovascular disease or disorder, or having arrhythmia. Such patient-specific cardiac tissue constructs are valuable in the use of the cardiac tissue constructs for advanced assays for drug screening, as well as for therapeutic purposes such as regeneration and prognostication of disease states.

DEFINITIONS

For convenience, certain terms employed in the entire disclosure (including the specification, examples, and appended claims) are collected here. Unless defined otherwise, all technical and scientific terms used herein have the same meaning as commonly understood by one of ordinary skill in the art to which this invention belongs.

The term "nanotextured" as used herein refers to a repeating pattern of substantially parallel grooves and ridges where the heights and depths and width of the grooves and ridges are all of sub-micron scale.

The term "anisotropic" refers to items, such as cells, being spatially organized or arranged in a direction-related manner.

The term "myocytes" refer to a muscle cells. Sub-categories of myocytes include, for example, skeletal myocytes, smooth muscle myocytes, cardiomyocytes, as well as ESC- and iPSC-derived myocytes.

The term "cardiomyocyte" as used herein broadly refers to a muscle cell of the heart (e.g. a cardiac muscle cell). The term cardiomyocyte includes smooth muscle cells of the heart, as well as cardiac muscle cells, which also include striated muscle cells, as well as spontaneous beating muscle cells of the heart. A cardiomyocyte will generally express on its cell surface and/or in the cytoplasm one or more cardiac-specific marker. Suitable cardiomyocyte-specific markers include, but are not limited to, cardiac troponin I, cardiac troponin-C, tropomyosin, caveolin-3, GATA-4, myosin heavy chain, myosin light chain-2a, myosin light chain-2v, ryanodine receptor, and atrial natriuretic factor.

The term "myogenically committed" or "myogenic committed" refers to a cell, such as a progenitor cell, such as a myogenic progenitor cell, which differentiates into a substantially pure population of cardiac muscle cells such as cardiomyocytes.

The terms "cardiac progenitor cell" and "CPC" are used interchangeably herein to refer to a progenitor cell which is capable of proliferation and giving rise to more progenitor cells having the ability to generate a large number of mother cells that can in turn give rise to differentiated, or differentiable daughter cells which can eventually terminally differentiate primarily into cells of the heart tissue, including endothelial lineages and muscle lineages (smooth, cardiac and skeletal muscles).

The term "progenitor cell" is used herein to refers to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only.

The term "embryonic stem cell" is used to refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. As indicated above, stem cells have been found resident in virtually every tissue. Accordingly, the technology described herein appreciates that stem cell populations can be isolated from virtually any animal tissue.

As used herein, the term "adult cell" refers to a cell found throughout the body after embryonic development.

As used herein, the terms "iPS cell" and "induced pluripotent stem cell" are used interchangeably and refers to a pluripotent cell artificially derived (e.g., induced by complete or partial reversal) from a differentiated somatic cell (i.e. from a non-pluripotent cell). A pluripotent cell can differentiate to cells of all three developmental germ layers.

The term "derived from" used in the context of a cell derived from another cell means that a cell has stemmed from (e.g. changed from or was produced by) a cell which is a different cell type. In some instances, for example, a cell derived from an iPS cell refers to a cell which has differentiated from an iPS cell. Alternatively, a cell can be converted from one cell type to a different cell type by a process referred to as transdifferention or direct reprogramming. Alternatively, in the terms of iPS cells, a cell (e.g. an iPS cell) can be derived from a differentiated cell by a process referred to in the art as dedifferentiation or reprogramming.

The term "pluripotent" as used herein refers to a cell that can give rise to any type of cell in the body except germ line cells. The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages. Pluripotency is also evidenced by the expression of embryonic stem (ES) cell markers, although the preferred test for pluripotency is the demonstration of the capacity to differentiate into cells of all three germ layers, as detected using, for example, a nude mouse teratoma formation assay. iPS cells are pluripotent cells. Pluripotent cells undergo further differentiation into multipotent cells that are committed to give rise to cells that have a particular function. For example, multipotent cardiovascular stem cells give rise to the cells of the heart, including cardiomyocytes, as well as other cells involved in the vasculature of the heart. Cell useful for in vitro differentiation to myocytes or cardiomyocytes as disclosed herein include, for example, iPS cells as well as multipotent cardiovascular stem cells. A major benefit of the use of iPSC or other stem cells to generate myocytes or cardiomyocytes for the compositions and methods as disclosed herein is the ability to prepare large numbers of such cells and propagate them, e.g., from a specific human patient or subject. This is in contrast to methods, compositions that rely upon the isolation and use of adult cardiac cells.

The term "phenotype" refers to one or a number of total biological characteristics that define the cell or organism under a particular set of environmental conditions and factors, regardless of the actual genotype.

The term "contractibility" is used interchangeably herein with "cell contractility" and refers to the force (or contraction force) generated by unified coordinated contraction of a collection of cells. The contractility of a plurality of cells is measured by biophysical and biomechanical properties of the force transmission. Contractility is measured using phase-contrast microscopy of monolayers or multiple-layers of said cardiac cells and computational analysis, which is calibrated with direct force measurement using force transducers.

A "marker" as used herein describes the characteristics and/or phenotype of a cell. Markers can be used for selection of cells comprising characteristics of interest. Markers vary with specific cells. Markers are characteristics, whether morphological, functional or biochemical (enzymatic) characteristics particular to a cell type, or molecules expressed by the cell type. Preferably, such markers are proteins, and more preferably, possess an epitope for antibodies or other binding molecules available in the art. A marker may consist of any molecule found in, or on the surface of a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Functional markers or characteristics of myocytes also include, for example, contractibility, beat rate, action potential propagation and the like. Markers can be detected by any method commonly available to one of skill in the art.

The term "engineered" with respect to myocardium as used herein refers to the artificial creation (or de novo generation) of myocardial tissue. In the instant disclosure, engineered myocardium refers to the artificial creation of myocardial tissue from components of in vitro-differentiated cardiomyocytes which have been matured from a more immature phenotype using the nanotextured substrate as disclosed herein. Without being limited by theory, tissue engineering uses a combination of cells, optionally with other materials, e.g., matrix materials, and suitable biochemical and physio-chemical factors for the de novo generation of tissue or tissue structures. Such engineered tissue or tissue structures can be useful for therapeutic purposes to improve or replacement of biological functions. Engineered tissue covers a broad range of applications, including but not limited to utility in the repair or replace portions of, or whole tissues (e.g., heart, cardiac tissue, ventricular myocardium and other tissues such as bone, cartilage, blood vessels, bladder, etc.) or in assays for identifying agents which modify the function of parts of, or entire organs, without the need to obtain such organs from a subject. Engineered tissue that is generated typically has desired certain mechanical and structural properties for proper functioning.

The term "tissue engineered myocardium" refers to the artificial creation of myocardial tissue from in vitro-differentiated cardiomyocytes which have been matured from a more immature phenotype using the ANP as disclosed herein. In some embodiments, an engineered myocardium construct comprises the cells and the ANP and in alternative embodiments, an engineered myocardium construct comprises the matured cells without the ANP (e.g., the cells removed in 2D-monolayers and stacked together with other 2D-monolayers to form an 3D-engineered myocardium construct). Typically, a tissue engineered myocardium as disclosed herein is used in methods for therapeutic use or for screening purposes, as disclosed herein.

The term "biodegradable" as used herein within the context of a substrate denotes a composition that is not biologically harmful and can be chemically degraded or decomposed by natural effectors (e.g., weather, soil bacteria, plants, animals).

The term "bioresorbable" as used herein within the context of a substrate refers to the ability of a material to be reabsorbed over time in the body (e.g. in vivo) so that its original presence is no longer detected once it has been reabsorbed.

The term "bioreplaceable" as used herein within the context of a substrate as used herein, and when used in the context of an implant, refers to a process where de novo growth of the endogenous tissue replaces the implant material. A bioreplaceable material as disclosed herein does not provoke an immune or inflammatory response from the subject and does not induce fibrosis. A bioreplaceable material is distinguished from bioresorbable material in that bioresorbable material is not replaced by de novo growth by endogenous tissue.

The term "isolated" or "enriching" or "partially purified" as used herein refers, in the case of an in vitro-differentiated cardiomyocyte is separated from at least one other cell type. The term "enriching" is used synonymously with "isolating" cells, and means that the yield (fraction) of cells of one type is increased by at least 10% over the fraction of cells of that type in the starting culture or preparation.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a preparation of one or more partially and/or terminally differentiated cell types, such as immature cardiomyocytes, refer to a population of cells that contain fewer than about 20%, more preferably fewer than about 15%, 10%, 8%, 7%, most preferably fewer than about 5%, 4%, 3%, 2%, 1%, or less than 1%, of cells that are immature cardiomyocytes or immature cardiomyocytes progeny.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "lineages" as used herein refers to a term to describe cells with a common ancestry, for example cells that are derived from the same cardiovascular stem cell or other stem cell, or cells with a common developmental fate. By way of an example only, when referring to a cell that is of endoderm origin or is "endodermal linage," this means the cell was derived from an endodermal cell and can differentiate along the endodermal lineage restricted pathways, such as one or more developmental lineage pathways which give rise to definitive endoderm cells, which in turn can differentiate into liver cells, thymus, pancreas, lung and intestine.

The term "derived from" as applied to a cell being "derived from" another cell or from a tissue means the cell was either isolated from the tissue referred to, or was differentiated from the reference tissue or cell type. Thus, a cell "derived from" a particular individual's tissue was isolated from or differentiated from that individual's tissue. An individual can include an individual having a given condition. An induced pluripotent stem cell is derived from a somatic tissue of an individual, e.g., a post-partum human individual, frequently an adult. Similarly, and embryonic stem cell is derived from an embryo. A cell differentiated from an iPS cell or an ES cell is derived from that cell.

The term "contacting" or "contact" as used herein in connection with contacting a mature cardiomyocyte, either present on an ANP, or in the absence of a support, with an agent as described herein, includes subjecting the cell to a culture medium which comprises that agent. The term "modulate" is used consistently with its use in the art, e.g., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

The terms "decrease", "reduced", "reduction", or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) difference in the parameter of variable measurement. The term refers to statistical evidence that there is a difference. It is defined as the probability of making a decision to reject the null hypothesis when the null hypothesis is actually true. The decision is often made using the p-value.

The term "reprogramming" as used herein refers to the transition of a differentiated cell to become a pluripotent or multipotent progenitor cell. Stated another way, the term reprogramming refers to the transition of a differentiated cell to an earlier developmental phenotype or developmental stage. A "reprogrammed cell" is a cell that has reversed or retraced all, or part of its developmental differentiation pathway to become a progenitor cell. Thus, a differentiated cell (which can only produce daughter cells of a predetermined phenotype or cell linage) or a terminally differentiated cell can be reprogrammed to an earlier developmental stage and become a progenitor cell, which can both self renew and give rise to differentiated or undifferentiated daughter cells. The daughter cells themselves can be induced to proliferate and produce progeny that subsequently differentiate into one or more mature cell types, while also retaining one or more cells with parental developmental potential. The term reprogramming is also commonly referred to as retrodifferentiation or dedifferentiation in the art. A "reprogrammed cell" is also sometimes referred to in the art as an "induced pluripotent stem" (iPS) cell.

In the context of cell ontogeny, the term "differentiated", or "differentiating" is a relative term. A "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an atrial precursor), and then to an end-stage differentiated cell, such as atrial cardiomyocytes or smooth muscle cells, which play a characteristic role in a certain tissue type, and may or may not retain the capacity to proliferate further. The term "differentiated cell" refers to any primary cell that is not, in its native form, pluripotent as that term is defined herein. The term a "differentiated cell" also encompasses cells that are partially differentiated, such as multipotent cells, or cells that are stable non-pluripotent partially reprogrammed cells. In some embodiments, a differentiated cell is a cell that is a stable intermediate cell, such as a non-pluripotent partially reprogrammed cell. It should be noted that placing many primary cells in culture can lead to some loss of fully differentiated characteristics. However, simply culturing such primary cells, e.g., after removal or isolation from a tissue or organism does not render these cells non-differentiated cells (e.g. undifferentiated cells) or pluripotent cells. The transition of a differentiated cell (including stable non-pluripotent partially reprogrammed cell intermediates) to pluripotency requires a reprogramming stimulus beyond the stimuli that lead to partial loss of differentiated character in culture.

The term "differentiation" as referred to herein refers to the process whereby a cell moves further down the developmental pathway and begins expressing markers and phenotypic characteristics known to be associated with a cell that are more specialized and closer to becoming terminally differentiated cells. The pathway along which cells progress from a less committed cell to a cell that is increasingly committed to a particular cell type, and eventually to a terminally differentiated cell is referred to as progressive differentiation or progressive commitment. Cell which are more specialized (e.g., have begun to progress along a path of progressive differentiation) but not yet terminally differentiated are referred to as partially differentiated. Differentiation is a developmental process whereby cells assume a more specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, in the context of this specification, the terms "differentiation" or "differentiated" refer to cells that are more specialized in their fate or function than at one time in their development. For example in the context of this application, a differentiated cell includes a ventricular cardiomyocyte which has differentiated from cardiovascular progenitor cell, where such cardiovascular progenitor cell can in some instances be derived from the differentiation of an ES cell, or alternatively from the differentiation of an induced pluripotent stem (iPS) cell, or in some embodiments from a human ES cell line. Thus, while such a ventricular cardiomyocyte cell is more specialized than the time in which it had the phenotype of a cardiovascular progenitor cell, it can also be less specialized as compared to when the cell existed as a mature cell from which the iPS cell was derived (e.g. prior to the reprogramming of the cell to form the iPS cell).

A cell that is "differentiated" relative to a progenitor cell has one or more phenotypic differences relative to that progenitor cell and characteristic of a more mature or specialized cell type. Phenotypic differences include, but are not limited to morphologic differences and differences in gene expression and biological activity, including not only the presence or absence of an expressed marker, but also differences in the amount of a marker and differences in the co-expression patterns of a set of markers.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "tissue" refers to a group or layer of similarly specialized cells which together perform certain special functions. The term "tissue-specific" refers to a source or defining characteristic of cells from a specific tissue.

The term "genetically modified" as used herein refers to a cell or organism in which genetic information or material has been modified by human manipulation. Modification can be effectuated by chemical, physical, viral or stress-induced or other means, including introduction exogenous nucleic acid through any standard means, such as transfection, such that the cell or organism has acquired a new characteristic, phenotype, genotype, and/or gene expression product, including but not limited to a gene marker, a gene product, and/or an mRNA, to endow the original cell or organism, at a genetic level, with a function, characteristic, or genetic element not present in non-genetically modified, non-selected counterpart cells or entities.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied. The terms "peptide(s)", "protein(s)" and "polypeptide(s)" are used interchangeably herein.

The terms "subject" and "individual" are used interchangeably herein, and refer to an animal, for example a human, to whom treatment, including prophylactic treatment, with methods and compositions described herein, is or are provided, or from whom a sample, e.g., a cell or tissue sample, is taken. For treatment of those conditions or disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates.

The term "regeneration" means regrowth of a cell population, organ or tissue after disease or trauma.

As used herein, the phrase "cardiovascular condition, disease or disorder" is intended to include all disorders characterized by insufficient, undesired or abnormal cardiac function, e.g., arrhythmia, ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The term "disease" or "disorder" is used interchangeably herein, and refers to any alteration in state of the body or of some of the organs, interrupting or disturbing the performance of their functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affliction.

As used herein, the terms "treat" or "treatment" or "treating" refers to both therapeutic treatment and prophylactic or preventative measures, wherein the object is to prevent or slow the development of the disease, such as slow down the development of a cardiac disorder, or reducing at least one adverse effect or symptom of a cardiovascular condition, disease or disorder, e.g., any disorder characterized by insufficient or undesired cardiac function. Adverse effects or symptoms of cardiac disorders are well-known in the art and include, but are not limited to, dyspnea, chest pain, palpitations, dizziness, syncope, edema, cyanosis, pallor, fatigue and death. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

The term "effective amount" as used herein refers to the amount of therapeutic agent of pharmaceutical composition to reduce at least one or more symptom(s) of the disease or disorder, and relates to a sufficient amount of pharmacological composition to provide the desired effect. The phrase "therapeutically effective amount" as used herein, e.g., an engineered cardiomyocyte tissue preparation (e.g., tissue engineered myocardium) as disclosed herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylactically significant reduction in a symptom or clinical marker associated with a cardiac dysfunction or disorder when administered to a typical subject who has a cardiovascular condition, disease or disorder.

The term "drug" or "compound" as used herein refers to a chemical entity or biological product, or combination of chemical entities or biological products, administered or to be administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally not present or not present at the levels being administered to a cell, tissue or subject. An agent can be selected from a group comprising: chemicals; small molecules; nucleic acid molecules; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, including, but not limited to: mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An gent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "substantially" as used herein means for the most part, essentially the same as the character it is substantially a feature of. In some embodiments, for example, a feature which is "substantially parallel" refers to features which are at least about 60%, or preferably at least about 70% or at least about 80%, or at least about 90%, at least about 95%, at least about 97% or at least about 99% or more, or any integer between 70% and 100% similar to a parallel structure.

The articles "a" and "an" are used herein to refer to one or to more than one (e.g., to at least one) of the grammatical object of the article. By way of example, "an element" means one element or more than one element.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

The term "consisting essentially of" means "including principally, but not necessary solely at least one", and as such, is intended to mean a "selection of one or more, and in any combination." Stated another way, other elements can be included in the description of the composition, method or respective component thereof provided the other elements are limited to those that do not materially affect the basic and novel characteristic(s) of the invention ("consisting essentially of"). This applies equally to steps within a described method as well as compositions and components therein.

The term "consisting of" as used herein as used in reference to the inventions, compositions, methods, and respective components thereof, is intended to be exclusive of any element not deemed an essential element to the component, composition or method.

It should be understood that this invention is not limited to the particular methodology, protocols, and reagents, etc., described herein and as such can vary. The terminology used herein is for the purpose of describing particular embodiments only, and is not intended to limit the scope of the technology described herein, which is defined solely by the claims.

Anisotropically Nanotextured Platform (ANP).

As disclosed herein, the nanotextured platform, referred herein as an anisotropically nanotextured platform (ANP), has a nanotextured array of parallel grooves and ridges that is structurally configured to enhance the maturation of immature muscle cells or myocytes to a more mature phenotype. In particular, the ANP can be used to mature or enhance the differentiation of in vitro-differentiated cardiomyocytes, thus producing a functional engineered tissue myocardium construct which is capable of conducting action potentials, and closely mimics the functional features of adult myocardium. In particular, a nanotextured platform of the technology described herein comprises an array of parallel grooves and ridges that is structurally configured to organize immature muscle cells or myocytes (e.g., immature cardiomyocytes or immature skeletal muscle myocytes), in an anisotropic manner, such that when they are cultured on the nanotextured platform, they are matured and have a more differentiated phenotype than the same cells cultured on a substrate without the nanostructures.

In some embodiments, the ANP as disclosed herein is patterned, for example the scaffold is engineered so that the cellular environment at multiple spatial scales (e.g., nanometer scale) is modified in order to direct the immature cardiomyocytes along a more mature differentiation pathway and to subsequently organize the cardiomyocytes into two-dimensional (2D) myocardial tissue structures.

One advantage of the integration of these immature cardiomyocytes on an ANP such as the free-standing polymer structure as disclosed herein is that the free-standing polymer structure provides environmental cues to control and direct the differentiation of immature cardiomyocytes into a more mature or differentiated phenotype to generate a functional contracting tissue engineered myocardium construct. In some embodiments, the ANP is engineered on the nanometer scale to organize cells into structures of macroscopic length cells, and comprises factors such as, but are not limited to, material mechanical properties, material solubility, spatial patterning of bioactive compounds, spatial patterning of topological features, soluble bioactive compounds, mechanical perturbation (cyclical or static strain, stress, shear, etc. . . . ), electrical stimulation, and thermal perturbation.

The nanotextured pattern not only directs the anisotropic arrangement of in vitro-differentiated cardiomyocytes, but also promotes their further differentiation to a more mature cardiomyocyte phenotype. For example, one aspect of the cells have at least the structure, function and marker expression more similar to adult cardiomyocytes, As disclosed herein, an ANP for use in the generation of tissue engineered myocardium as disclosed herein can contain a flexible polymer scaffold (e.g., biologically derived) that is imprinted with a predetermined nanotextured pattern of parallel grooves and ridges as described herein, In some embodiments, an ANP is a polymer, e.g., a biopolymer, and can be created by providing a transitional polymer on a substrate; depositing a biopolymer on the transitional polymer; shaping the polymer into a structure having a selected pattern on the transitional polymer (e.g., poly(N-Isopropylacrylamide); and releasing the biopolymer from the transitional polymer with the polymer's structure and integrity intact. The polymer can be based upon, e.g., extracellular matrix protein, a biologically active carbohydrate, a biologically derived homopolymer, silks, polyprotein (e.g., poly(lysine)) or a combination thereof. For example, the polymer can be selected from the group consisting of fibronectin, vitronectin, laminin, collagen, fibrinogen, silk or silk fibrin. The polymer component of the structure can comprise a combination of two or more ECM proteins such as fibronectin, vitronectin, laminin, collagens, fibrinogen and structurally related protein (e.g. fibrin).

The polymer or biopolymer component can additionally include, either within the polymer or coated upon it, one or more growth factors, lipids, fatty acids, steroids, hormones, or nucleic acid molecules that further promote aggregation or function of myocyte, e.g., cardiomyocytes cultured on the polymer substrate.

The nanotextured ridges and grooves on the substrates described herein includes features with dimensions of less than 1 micrometer. The polymer can be deposited via soft lithography. For example, the polymer can be printed on the transitional polymer with a polydimethylsiloxane stamp. Optionally, the process includes printing multiple polymer structures with successive, stacked printings. For example, where each polymer is a protein, different proteins are printed in different (e.g., successive) printings. Alternatively, the polymer is deposited via self assembly on the transitional polymer. Exemplary self-assembly processes include assembly of collagen into fibrils, and assembly of actin into filaments, and assembly of DNA into double strands. In another approach, the polymer is deposited via vaporization of the polymer and deposition of the polymer through a mask onto the transitional polymer. For example, the polymer is deposited via patterned photo-cross-linking on the transitional polymer and patterned light photo-cross-links the polymer in the selected pattern. The method optionally includes the step of dissolving non-cross-linked polymer outside the selected pattern. The patterned light changes the reactivity of the polymer via release of a photoliable group or via a secondary photosensitive compound in the selected pattern.

The method of preparing a polymer substrate can include a step of allowing the polymer to bind together via a force selected from hydrophilic, hydrophobic, ionic, covalent, Van der Waals, and hydrogen bonding or via physical entanglement. The polymer structure is released by applying a solvent to the transitional polymer to dissolve the transitional polymer or to change the surface energy of the transitional polymer, wherein the polymer structure is released into the solvent as a freestanding structure. For example, the polymer is released by applying a positive charge bias to the transitional polymer, by allowing the transitional polymer to undergo hydrolysis, or by subjecting the transitional polymer to enzymatic action. The polymer is constructed in a pattern such as a mesh or net structure. Optionally, a plurality of structures are produced, e.g., the method includes a step of stacking a plurality polymer structures to produce a multi-layer scaffold.

Following construction of the polymer structure, living immature cardiomyocytes are integrated into or onto the scaffold to from the ANP. For example, immature cardiomyocytes are grown on the scaffold to produce three-dimensional, anisotropic myocardium. In various applications, the immature cardiomyocytes can be ES-derived cardiomyocytes or iPSC-derived cardiomyocytes, and cardiomyocyte tissue constructs are generated where the structure, composition, ECM type, growth factors and/or other cell types assist in differentiation and maturation of the immature cardiomyocytes into more differentiated and mature phenotype, e.g., ventricular cardiomyocytes. The cells form functional tissue engineered myocardium composition useful as a cardiac muscle replacement tissue, or as a tool for studying ventricular muscle development or to identify agents which modify the function of cardiac muscle (e.g. to identify cardiotoxic agents or agents with therapeutic benefit, e.g., to correct arrhythmia or other cardiac functional abnormality).

The resulting anisotropically (e.g. direction-related) organized tissue structure, facilitates efficient electrical and mechanical activity of the tissue engineered myocardium construct.

In some embodiments, the ANP is fabricated for ease of scalability. Capillary force lithography or nano-imprinting techniques are used to fabricate highly uniform nanopatterned substrates on a large area for large scale tissue generation; this robust technique can be used on a number of polymers with various chemical, physical and electrical properties. This technique is scalable, and scaffold size (surface area) can vary from extremely small for smaller or individual cell analyses to large constructs of macroscopic tissue, e.g., to examine tissue-level characteristics.

Furthermore, the ANP is configured for use in high throughput assays. In some embodiments, the ANP polymer substrates can be incorporated into a multiwell format owing to the ability to change the scale of individual scaffolds. Such a multiwell format permits one to examine multiple scaffold parameters at once, and thus analysis of multiple cardiac models in tandem (e.g., a multiplex assay). For example, a 24 well plate (4×6) could be used to examine the effects of varying rigidity and varying topography dimension on cardiomyocyte function by having 4 rows of different scaffold rigidities and 6 columns of varying scaffold topographical dimension (see FIG. 1A). This multiwell format is extremely helpful in rapidly characterizing the independent effects of nanotopography and rigidity on cardiomyocyte function. Additionally, a multiwell format could be used in patient specific modeling by utilizing one patient's own iPSC-CMs in different cardiac models or using different patients' iPSC-CMs to examine the same cardiac model.

Nanotopography:

As discussed herein, the ANP comprises a nanotextured array of substantially parallel grooves and ridges that promotes immature cardiomyocytes to organize themselves in an anisotropic manner and promotes their further differentiation. In particular, the ANP has a nanotextured with four independently tunable parameters: ridge width, groove width, ridge height and periodicity. These parameters can be easily tuned, for example, by the use of differing masters in capillary force lithography, and these masters can be custom generated through conventional nanofabrication techniques such as electron-beam lithography. By being able to vary these dimensions independently, cell function, morphology and alignment can be altered. These effects can also additionally impact cell maturity. This precise level of topographical tuning allows one to both faithfully recreate the topographical cues of the heart ECM, as well as alter the cardiac monolayer model as needed.

In some embodiments, the ANP has grooves with a depth of between 10 nm-10 μm, or between about 50 nm-500 nm, or at least about 10 nm, or at least about 20 nm, or at least about 30 nm, or at least about 40 nm, or at least about 50 nm, or at least about 75 nm, or at least about 100 nm, or at least about 150 nm, or at least about 200 nm, or at least about 250 nm or at least about 500 nm, or at least about 1000 nm, or at least about 2000 nm, or at least about 3000 nm, or at least about 4000 nm, or at least about 5000 nm, or at least about 6 μm, or at least about 7 μm, or at least about 8 μm, or at least about 9 μm or at least about 10 μm. In some embodiments, the depth is between about 300 nm, but is less than 1000 nm. In some embodiments, the depth of the groove is between 5 nm-1000 nm (1 μm), for example at least about 5 nm, at least about 10 nm, at least about 20 nm, at least about 30 nm, at least about 40 nm, at least about 50 nm, at least about 60 nm, at least about 70 nm, or at least about 80 nm, or at least about 90 nm, at least about 100 nm, at least about 200 nm, at least about 300 nm, at least about 400 nm, or at least about 500 nm, or at least about 600 nm, or at least about 700 nm, or at least about 800 nm, or at least about 900 nm, or at least about 1000 nm (1 μm), but not more than 1000 nm (1 μm) in depth. In some embodiments, the depth of the groove is between about 200-800 nm, or between about 100-200 nm, or between about 200-400 nm, or between about 400-600 nm, or between about 600-800 nm, or between about 800-1000 nm (1 μm). In some embodiments, the depth of the groove is 200 nm. In some embodiments, the depth of the groove is between 20-100 nm, or between about 20-50 nm, or between about 40-60 nm, or between about 50-75 nm, or between about 75-100 nm. In some embodiments, a preferred range for the groove depth for maturing cardiomyocytes is between about 50 nm-500 nm.

In some embodiments, the width of the groove is between 50 nm-10 μm, or between about 200 nm-1000 nm, or at least about 50 nm, or at least about 75 nm, or at least about 100 nm, or at least about 150 nm, or at least about 200 nm, or at least about 250 nm or at least about 500 nm, or at least about 1000 nm, or at least about 2000 nm, or at least about 3000 nm, or at least about 4000 nm, or at least about 5000 nm, or at least about 6 μm, or at least about 7 μm, or at least about 8 μm, or at least about 9 μm or at least about 10 μm. In some embodiments, the depth is between about 300 nm, but is less than 1000 nm. In some embodiments, a preferred range for the groove width for maturing cardiomyocytes is between about 200 nm-1000 nm.

In some embodiments, the width of the groove is between 10-100 nm, for example at least about 10 nm, or at least about 20 nm, or at least about 30 nm, or at least about 40 nm, or at least about 50 nm, or at least about 60 nm, or at least about 70 nm, or at least about 80 nm, or at least about 90 nm, or at least about 100 nm or more than 100 nm in width. In some embodiments, the width of the groove is between 5 nm-1 μm, for example at least about 5 nm, at least about 10 nm, at least about 20 nm, at least about 30 nm, at least about 40 nm, at least about 50 nm, at least about 60 nm, at least about 70 nm, or at least about 80 nm, or at least about 90 nm, at least about 100 nm, at least about 200 nm, at least about 300 nm, at least about 400 nm, or at least about 500 nm, or at least about 600 nm, or at least about 700 nm, or at least about 800 nm, or at least about 900 nm, or at least about 1000 nm (1 μm), but not more than 1000 nm (1 μm) in width. In some embodiments, the width of the groove is between about 200-800 nm, or between about 100-200 nm, or between about 200-400 nm, or between about 400-600 nm, or between about 600-800 nm, or between about 800-1000 nm (1 μm).

In some embodiments, the width of the ridge is between 50 nm-10 μm, or between about 200 nm-1000 nm, or at least about 50 nm, or at least about 75 nm, or at least about 100 nm, or at least about 150 nm, or at least about 200 nm, or at least about 250 nm or at least about 500 nm, or at least about 1000 nm, or at least about 2000 nm, or at least about 3000 nm, or at least about 4000 nm, or at least about 5000 nm, or at least about 6 μm, or at least about 7 μm, or at least about 8 μm, or at least about 9 μm or at least about 10 μm. In some embodiments, the depth is between about 300 nm, but is less than 1000 nm. In some embodiments, a preferred width of the ridge for maturing cardiomyocytes between about 200 nm-1000 nm.

In some embodiments, the ridges between the grooves have a width of about 50 nm-1 μm (1000 nm), for example, for example, at least about 50 nm, or at least about 60 nm, or at least about 70 nm, or at least about 80 nm, or at least about 90 nm, or at least about 100 nm, or at least about 125 nm, or at least about 150 nm, or at least about 175 nm, or at least about 200 nm, or at least about 250 nm, or at least about 300 nm, or at least about 400 nm, or at least about 500 nm, or at least about 600 nm, or at least about 700 nm, or at least about 800 nm, or at least about 900 nm, or at least about 50 nm or any integer between 50 nm and 1 µm (1000 nm), but not more than 1000 nm. In some embodiments, the width of the ridges is 150 nm. In some embodiments, the width of the ridge is between 5 nm-1 µm, for example at least about 5 nm, at least about 10 nm, at least about 20 nm, at least about 30 nm, at least about 40 nm, at least about 50 nm, at least about 60 nm, at least about 70 nm, or at least about 80 nm, or at least about 90 nm, at least about 100 nm, at least about 200 nm, at least about 300 nm, at least about 400 nm, or at least about 500 nm, or at least about 600 nm, or at least about 700 nm, or at least about 800 nm, or at least about 900 nm, or at least about 1000 nm (1 µm), but not more than 1000 nm (1 µm) in width. In some embodiments, the width of the groove is between about 200-800 nm, or between about 100-200 nm, or between about 200-400 nm, or between about 400-600 nm, or between about 600-800 nm, or between about 800-1000 nm (1 µm).

In some embodiments, the array of parallel grooves and ridges has a precision of texture of at least 90% fidelity, as evidenced by atomic force microscopy and/or electron microscopy. In some embodiments, the array of parallel grooves and ridges can be used to fabricate a large surface with high fidelity, for example, at least 1 cm².

In some embodiments, the width of the ridge and the width of the groove provide a repeatable unit, which determines the periodicity of the parallel grooves and ridges. In some embodiments, the width of the groove and the ridge are the same, and in some embodiments, the width of the ridge is greater than the width of the groove, and vice versa, the width of the groove is wider than the width of the ridge.

The nanotopagraphy can be of any conformation and geometry of parallel grooves and ridges that allows for anisotropic and polarized cell arrangement in the direction of the nanotextures. In some embodiments, the top or surface of the ridge is substantially planar, and in some embodiments it is convex, and in some embodiments, it is concave. In some embodiments, the ridge is pointed or angular. In some embodiments, the hollow or bottom of the groove is substantially planar, and in some embodiments, it is concave and in some embodiments, it is convex. Any combination of planar, convex or concave surfaces of the groves and ridges can occur, although it is generally preferred that the nanotextured are has a repeating unit of the same geometry. Thus, in some embodiments, the surface of the ridges and/or grooves all have the same geometry, e.g., they are all substantially planar. In alternative embodiments, the ridges and/or grooves have a variety of a combination of convex, concave or substantially planar surfaces. In some embodiments, the ridges and grooves are convex and concave respectively, to provide a corrugated cross-sectional appearance.

In some embodiments, the nanotextured array of parallel grooves and ridges covers a surface area greater than 1 cm². In some embodiments, the surface is at least about 0.25 cm², or is at least about 0.5 cm², or at least about 1.0 cm², or at least about 1.5 cm², or is at least about 2.5 cm², or is at least about 3 cm² or greater than 3 cm² in surface area.

The parallel array of grooves and ridges has a periodicity defined by the length of the shortest interval over which the structure repeats its shape. Thus, the groove, with its given width and depth is separated from the next by a ridge of a given width—the period is set by the width of the groove and the width of the separating ridge, which together, make up the repeating unit of the parallel array. The lateral dimension of the array are defined by the shortest interval over which the structure repeats its shape.

In some embodiments, the ANP comprises a nanotextured array of parallel grooves and ridges that organizes cultured cardiomyocytes on both sides of a substantially planar substrate, thus allowing the organization of cardiomyocytes or stem cells on both sides of said substantially planar substrate of ANP.

The ANP is a free-standing polymer structure. Such structures are free-standing or free-floating, e.g., they do not require a support or substrate to maintain their shape or structural integrity. Shape and integrity is maintained in the absence of a support substrate. For example, a free-standing polymer structure is characterized as having an integral pattern of the polymer with repeating features with a dimension of less than 1000 nm and without a supporting substrate.

Polymer Substrate Materials:

An important aspect of the ANP is its rigidity and the ability to modulate it. The ANP polymer substrates as disclosed herein allow for independent alteration of scaffold rigidity in addition to the tunability of the scaffold topography. ANP scaffold rigidity can be altered in several ways, most notably through polymer concentration, crosslinker concentration, and polymer composition/type. For example, the concentration of the polymer can be varied (such as weight percent in an aqueous or solvated solution), and these varying concentrations of polymer can be nanofabricated to incorporate the same topographical cues (such as linear nanogratings with fixed dimensions in the case of cardiac tissue engineering) but will also have varying rigidities. This enables the ANP to be used to separately characterize the effects of scaffold rigidity on cell function. Rigidity tuning allows modeling of differing cardiac states, such as healthy cardiac tissue or cardiac scar tissue, which have variable stiffness and can profoundly impact cell function.

The term "substrate" should be understood in this connection to mean any suitable carrier material to which the cells are able to attach or adhere in order to form the corresponding cell composite, e.g. the tissue engineered myocardium composition as disclosed herein. In some embodiments, the matrix or carrier material, respectively, is present already in a three-dimensional form desired for later application. For example, bovine pericardial tissue can be used as a matrix which is crosslinked with collagen, decellularized and photofixed.

While not critical to the uses in which the platform/cell composition will be used in the in vitro screening assay, in some embodiments, a substrate (which in some embodiments is a "biocompatible substrate" as that term is defined herein) is a material that is suitable for implantation into a subject. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate provides the supportive framework that allows cells to attach to it, and grow on it. Cultured populations of cells can then be grown on the biocompatible substrate, which includes the nanotextured substrate that provides the appropriate interstitial distances required for cell-cell interaction.

In some embodiments, an ANP substrate comprises a polymer hydrogel comprising, within the matrix of said polymer substrate, a biocompatible extracellular matrix protein, a synthetic or engineered matrix polypeptide, or other engineered polypeptide(s). In some embodiments, an engineered matrix polypeptide includes poly-L-lysine, poly-D-lysine, poly-orinithine, vitronectin or erythronectin. In some embodiments, an engineered polypeptide includes including CS1, RGD, domains in extracellular matrix proteins that bind to integrin receptors, domains in extracellular matrix proteins that bind to integrin receptors, and others well know to persons of ordinary skill in the art.

In some embodiments, the ANP can be nanofabricated from scalable biocompatible polymers, such as but not limited to polyethene glycol (PEG), polyethene glycol-gelatin methacrylate (PEG-GelMA) and chemical variants thereof and hydrogel arrays. Others include, for example, but not limited to PUA, PLGA, or PMMA.

In some embodiments, the ANP polymer substrate comprises at least one of polyglycolic acid (PGA), polylactic acid (PLA), poly(lactic-co-glycolic) acid (PLGA), polyanhydride, polycaprolactone (PCL), polydioxanone and polyorthoester. One of the most common polymers used as a biomaterial is the polyester copolymer poly(lactic acid-glycolic acid) (PLGA). PLGA is highly biocompatible, degrades into biocompatible monomers (e.g., if implanted) and has a wide range of mechanical properties making this copolymer and its homopolymers, PLA and PGA, useful as a substrate for cell deposition. The substrate can be porous or non-porous.

In some embodiments, other materials can be selected to be used as the substrate material, which can be selected from the group consisting of hydroxyapatite (HAP), tricalcium phosphate (TCP), tetracalcium phosphate (TTCP), dicalcium phosphate anhydrous (DCPA), dicalcium phosphate dihydrate (DCPD), octacalcium phosphate (OCP), calcium pyrophosphate (CPP), collagen, gelatin, hyaluronic acid, chitin, and poly(ethylene glycol). In alternative embodiments, the substrate can also comprise additional material, for example, but are not limited to calcium alginate, agarose, types I, II, IV or other collagen isoform, fibrin, hyaluronate derivatives or other materials (Perka C. et al. (2000) J. Biomed. Mater. Res. 49:305-311; Sechriest V F. et al. (2000) J. Biomed. Mater. Res. 49:534-541; Chu C R et al. (1995) J. Biomed. Mater. Res. 29:1147-1154; Hendrickson D A et al. (1994) Orthop. Res. 12:485-497).

In some embodiments, the ANP comprises a polymer substrate which is optically transparent.

In some embodiments, the ANP substrate can comprise a UV curable hydrogel polymer, a thermosensitive hydrogel polymer or a polymer produced by solvent evaporation. In some embodiments, the ANP substrate is composed of a biocompatible hydrogel compatible with capillary force lithography.

In some embodiments, the ANP will be configured using a polymer construction which mimics the rigidity of the tissue, e.g., a normal heart or other muscle of interest. The rigidity of a normal heart is typically varies from 5 kPa to 40 kPa. In some embodiments, the ANP will be configured using a polymer construction which mimics a diseased or aged heart, which typically has a rigidity varying between 30 kPa to 200 kPa. Accordingly, the ANP comprises a polymer substrate that has a rigidity in the range of 5 to 200 kPa, for example, a rigidity of at least about 5 kPa, or at least about 10 kPa, or at least about 20 kPa, or at least about 30 kPa, or at least about 40 kPa, or at least about 50 kPa, or at least about 60 kPa, or at least about 70 kPa, or at least about 80 kPa, or at least about 90 kPa, or at least about 100 kPa, or at least about 120 kPa, or at least about 140 kPa, or at least about 160 kPa, or at least about 180 kPa, or at least about 200 kPa or more than 200 kPa, or any integer between 5-200 kPa.

In some embodiments, to model a normal heart, the ANP comprises a polymer substrate which has a rigidity of at least about 5 kPa, or at least about 10 kPa, or at least about 15 kPa, or at least about 20 kPa, or at least about 25 kPa, or at least about 30 kPa, or at least about 35 kPa, or at least about 40 kPa. In alternative embodiments, to model a diseased or aged heart, the ANP comprises a polymer scaffold which has a rigidity of at least about 30 kPa, or at least about 40 kPa, or at least about 50 kPa, or at least about 60 kPa, or at least about 70 kPa, or at least about 80 kPa, or at least about 90 kPa, or at least about 100 kPa, or at least about 120 kPa, or at least about 140 kPa, or at least about 160 kPa, or at least about 180 kPa, or at least about 200 kPa or more than 200 kPa, or any integer between 5-200 kPa.

In some embodiments, the ANP comprises a polymer substrate which comprises one or more of gelatin, collagen type I, collagen type IV, fibronectin, fibronectin domains, laminin and engineered extracellular matrix proteins and peptides. These can be incorporated within the polymer, or alternatively, coated on the surface of the ANP as discussed below.

In some embodiments, the ANP can comprise within or upon the substrate, additional components selected from the group including extracellular matrix proteins, growth factors, lipids, fatty acids, steroids, sugars and other biologically active carbohydrates, biologically derived homopolymers, nucleic acids, hormones, enzymes, pharmaceuticals, cell surface ligands and receptors, cytoskeletal filaments, motor proteins, and combinations thereof. Alternatively or in addition, the structure can comprise at least one conducting polymer selected from poly(pyrrole)s, poly(acetylene)s, poly(thiophene)s, poly(aniline)s, poly(fluorene)s, Poly(3-hexylthiophene), polynaphthalenes, poly(p-phenylene sulfide), poly(N-Isopropylacrylamide) (PIPAAm), and poly (para-phenylene vinylene)s. In some cases, the polymer structure comprises an integral pattern of the polymer and molecular remnant traces of poly(N-Isopropylacrylamide).

In some embodiments, the polymer structure composed of or comprising at least one biological hydrogel selected from fibrin, collagen, gelatin, elastin and other protein and/or carbohydrate derived gels or synthetic hydrogel selected from polyethylene glycol, polyvinyl alcohol, polyacrylamide, poly(N-isopropylacrylamide), poly(hydroxyethyl methacrylate) and other synthetic hydrogels, and combinations thereof.

The ANP polymer substrate for use in the compositions and methods to generate tissue engineered myocardium as disclosed herein, can be spatially organized from the nanometer to centimeter length scales and can be generated via methods described herein. The polymers, including, for example, biopolymer (e.g., protein, carbohydrate, glycoprotein etc.,) can be deposited onto a transitional polymer surface using patterning techniques that allow for nanometer scale spatial positioning of the deposited polymers. These patterning techniques include but are not limited to soft-lithography, self-assembly, vapor deposition and photolithography. Once on the surface, inter-polymer interactions attract the polymers together such that they become bound together. These interactions may be hydrophilic, hydrophobic, ionic, covalent, Van der Waals, hydrogen bonding or physical entanglement depending on the specific polymers involved. In the appropriate solvent, dissolution or a change in the surface energy of the transitional polymer releases the patterned polymer structure from the surface into solution as an integral, free-standing structure.

Further, in some embodiments, the substrate can be transparent, so as to facilitate observation of the cells cultured on the ANP substrate. Optical transparency can be achieved for many substrate materials by making the structure sufficiently thin as to permit light to transmit.

In some embodiments, the substrate is bioresorbable and/or biodegradable. Further, in some embodiments the substrate is biocompatible and bioreplaceable.

In some embodiments, a ANP polymer substrate useful in the methods as disclosed herein is a decellularized tissue sheet, such as a decellularized pericardial tissue which is disclosed in U.S. Patent Application 2008/0195229 and International Patent Application WO/2003/050266 which are incorporated herein in their entirety by reference, or other sheet such as a perfusion-decellularized matrix as disclosed in Ott et al., 2008, Nature Medicine 14, 213-221 which is incorporated herein by reference. In another embodiment, a substrate useful in the methods and compositions as disclosed herein is a commercially available scaffold, such as INTEGRA® Dermal Regeneration Template, which is bilayer membrane system comprising a 2 layers: (1) a first layer of a porous matrix of fibers of cross-linked bovine tendon collagen and a glycosaminoglycan (chondroitin-6-sulfate) that is manufactured with a controlled porosity and defined degradation rate. A second layer (2) comprising a temporary epidermal substitute layer is made of synthetic polysiloxane polymer (silicone) and functions to control moisture loss from the wound. The first (1) layer serves as a matrix for the infiltration of fibroblasts, macrophages, lymphocytes, and capillaries derived from the wound bed. As healing progresses an endogenous collagen matrix is deposited by fibroblasts; simultaneously, this first layer of INTEGRA® Dermal Regeneration Template is degraded. Upon adequate vascularization of the dermal layer and availability of donor autograft tissue, the temporary silicone (2) layer can optionally be removed and a thin, meshed layer of epidermal autograft is placed over the "neodermis."

In one embodiment, a bioreplaceable material for use as a ANP polymer substrate in the methods and compositions as disclosed herein is submucosal tissue. In some embodiments, the submucosal tissue useful in as a polymer substrate in the methods and compositions as disclosed herein can also be in a fluidized form. Submucosal tissue can be fluidized by comminuting the tissue and optionally subjecting it to enzymatic digestion to form a substantially homogenous solution. The preparation of fluidized forms of submucosa tissue is described in U.S. Pat. No. 5,275,826, the disclosure of which is expressly incorporated herein in its entirety by reference.

In one embodiment, the submucosa tissue suitable in accordance with the invention comprises natural collagenous matrices that include highly conserved collagens, matrix proteins, glycoproteins, proteoglycans, and glycosaminoglycans in their natural configuration and natural concentrations, and other factors. In some embodiments, the submucosal tissue is a commercially available material, such as SURGISIS® (SIS) which is available from Cook Biotech Incorporated (Bloomington, Ind.).

The preparation of SIS from a segment of small intestine is disclosed in U.S. Pat. No. 4,902,508 which is incorporated herein by reference. A segment of intestine is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use. Details of the characteristics and properties of intestinal submucosa (SIS) which one can use in the methods and compositions as disclosed herein are described in U.S. Pat. No. 4,352,463, U.S. Pat. No. 4,902,508, U.S. Pat. No. 4,956,178, U.S. Pat. No. 5,281,422, U.S. Pat. No. 5,372,821, U.S. Pat. No. 5,445,833, U.S. Pat. No. 5,516,533, U.S. Pat. No. 5,573,784, U.S. Pat. No. 5,641,518, U.S. Pat. No. 5,645,860, U.S. Pat. No. 5,668,288, U.S. Pat. No. 5,695,998, U.S. Pat. No. 5,711,969, U.S. Pat. No. 5,730,933, U.S. Pat. No. 5,733,868, U.S. Pat. No. 5,753,267, U.S. Pat. No. 5,755,791, U.S. Pat. No. 5,762,966, U.S. Pat. No. 5,788,625, U.S. Pat. No. 5,866,414, U.S. Pat. No. 5,885,619, U.S. Pat. No. 5,922,028, U.S. Pat. No. 6,056,777 and WO-97/37613, which are incorporated herein in their entirety by reference.

In some embodiments, the ANP polymer substrate useful in the compositions for the methods described herein can be sterilized using conventional disinfection/sterilization techniques including glutaraldehyde tanning, formaldehyde tanning at acidic pH, propylene oxide treatment, ethylene oxide treatment, gas plasma sterilization, gamma irradiation or electron beam treatment, and peracetic acid (PAA) disinfection. Sterilization techniques which do not adversely affect the mechanical strength, structure, and biotropic properties of the polymer substrate are preferred. For instance, strong gamma irradiation can cause loss of strength of the sheets of polymer substrates. Preferred sterilization techniques include exposing the polymer substrate to peracetic acid, 1-4 Mrads gamma irradiation (more preferably 1-2.5 Mrads of gamma irradiation) or gas plasma sterilization. Typically, a polymer substrate can be subjected to two or more sterilization processes. After the polymer substrate is treated in an initial disinfection step, for example by treatment with peracetic acid, the polymer substrate can be wrapped in a plastic or foil wrap and sterilized again using electron beam or gamma irradiation sterilization techniques.

In some embodiments, a ANP polymer substrate has a substantially planar surface. In further embodiments, the substrate is mechanically strong and also malleable. In some embodiments, the ANP polymer substrate is malleable under non-physiological conditions, including, but not limited to exposure to temperature above body temperature, and for example by pressures exceeding normal physiological pressures, for example, by mechanical manipulation or mechanical shaping or by an altered surrounding environment, for example heat, pressure or acidic or alkaline conditions to mold the substrate prior to seeding of the cells.

In one embodiment, the ANP polymer substrate is biocompatible, and biodegrades or autocatalytically degrades in vivo into biocompatible byproducts. Not to be bound by theory, but prevailing mechanism for polymer degradation is chemical hydrolysis of the hydrolytically unstable backbone of the PLGA polymers. Polymers of varying copolymer ratios including PLA, PLGA75:25, and PLGA50:50 have different degradation rates, with PLGA50:50 degrading the quickest, followed by PLGA 75:25 then PLA. Therefore, with increasing percentage of PGA and concurrent decrease in percentage of PLA in a co-polymer of PLGA increases the rate of degradation compared to PLA alone, and thus the rate of degradation can be tailored to the desired use. Any ration of PLA:PGA copolymer is encompassed for use in the technology described herein.

Coatings and Modifications to the Surface of the ANP Polymer Substrate

The surface of the nanotextured ANP can be modified with one or more bioactive agent, deposited or adsorbed on the polymer surface, to promote cardiomyocyte attachment, differentiation and maturation, adhesion-dependent cell signaling and electroconductivity of the substrate. According, in some embodiments, the ANP comprises within its polymer matrix, or on its surface, a bioactive agent that enhances maturation of cardiomyocytes, enhances survival of cardiomyocytes in response to toxic stimuli, enhances cardiomyocyte adherence to the polymer substrate, or enhances action potential wave propagation across said cardiomyocytes. In some embodiments, the ANP polymer may comprise a substrate layer, and optionally, a surface layer.

In some embodiments, the ANP substrate for use in the methods and compositions as disclosed herein can additionally provide controlled release of bioactive factors to the cardiomyocytes, for example, growth factors and other agents to sustain or control subsequent cell growth and proliferation of the cells coated on the ANP substrate of the technology described herein. In such a way, the cardiomyocytes or cardiomyocyte-derived cells are supplied with a constant source of growth factors and other agents for the duration of the lifetime of the cell coated scaffold. In some embodiments, the growth factors and other agents are cardiotrophic factors commonly known in the art.

In some embodiments, any agent or differentiation factor can be deposited on the surface of the ANP to promote further maturation and/or adhesion of the cardiomyocytes.

In some embodiments, the ANP comprises within its polymer matrix, or on its surface, an agent that promotes differentiation of said stem cells to cardiomyocytes. In some embodiments, the ANP polymer substrate comprises, either coated on its surface or within its polymer matrix, one or more agents selected from the group consisting of sphingosine phosphate or an analog thereof, fluric acid, zFAD-vmk, cardiotropin, or a growth factor selected from the group consisting of FGF, HGF, IGF1, SDF1a, EGF, angiopoietin, BMP, erthyropoietin (EPO), GDNG, c-GSF, GDF9, HDNF, GDF, thrombopoietin, TGFα, TGFβ, TNFα, PIGF, PDGF, interleukins IL1-IL17 and VEGF. In some embodiments, one or more agents can be selected from the group consisting of an antibody, antigen, glycoprotein, lipoprotein, DNA, RNA, polysaccharide, lipid, growth hormone, organic compound, and inorganic compound.

Additionally, in some embodiments, the surface of the ANP polymer substrate can be modified to include, at least one of the agents selected from following group: (a) extracellular matrix proteins to direct cell adhesion and function (e.g., collagen, fibronectin, laminin, etc.); (b) growth factors to direct cell function specific to cell type (e.g., nerve growth factor, bone morphogenic proteins, vascular endothelial growth factor, etc.); (c) lipids, fatty acids and steroids (e.g., glycerides, non-glycerides, saturated and unsaturated fatty acids, cholesterol, corticosteroids, sex steroids, etc.); (d) sugars and other biologically active carbohydrates (e.g., monosaccharides, oligosaccharides, sucrose, glucose, glycogen, etc.); (e) combinations of carbohydrates, lipids and/or proteins, such as proteoglycans (protein cores with attached side chains of chondroitin sulfate, dermatan sulfate, heparin, heparan sulfate, and/or keratan sulfate); glycoproteins [e.g., selectins, immunoglobulins, hormones such as human chorionic gonadotropin, Alpha-fetoprotein and Erythropoietin (EPO), etc.]; proteolipids (e.g., N-myristoylated, palmitoylated and prenylated proteins); and glycolipids (e.g., glycoglycerolipids, glycosphingolipids, glycophosphatidylinositols, etc.); (f) biologically derived homopolymers, such as polylactic and polyglycolic acids and poly-L-lysine; (g) nucleic acids (e.g., DNA, RNA, etc.); (h) hormones (e.g., anabolic steroids, sex hormones, insulin, angiotensin, etc.); (i) enzymes (types: oxidoreductases, transferases, hydrolases, lyases, isomerases, ligases; examples: trypsin, collagenases, matrix metalloproteinases, etc.); (j) pharmaceuticals (e.g., beta blockers, vasodilators, vasoconstrictors, pain relievers, gene therapy, viral vectors, anti-inflammatories, etc.); (k) cell surface ligands and receptors (e.g., integrins, selectins, cadherins, etc.); and (l) cytoskeletal filaments and/or motor proteins (e.g., intermediate filaments, microtubules, actin filaments, dynein, kinesin, myosin, etc.).

In some embodiments, in addition to the cardiomyocytes, a polymer substrate for use in the tissue engineered myocardium as disclosed herein can also be seeded with functional elements, including drugs or any type of cardiotrophic growth factor as disclosed herein. Accordingly, in the ANP polymer substrate, ECM type, growth factors and/or other cardiotrophic factors which assist in directing differentiation of cardiomyocytes into a more mature and differentiated phenotype, e.g., ventricular cardiomyocytes, can be used to aid in the production of a functional, tissue engineered myocardium construct as disclosed herein.

In some embodiments, the ANP can be coated with materials that promote electroconductivity. In some embodiments, such material can be selected from the group consisting of charcoal, graphene, graphene oxide, reduced graphene oxide, nanotubes, titanium (Ti) and gold (Au), whereby electrical conductivity, or other physico-chemical property is modulated in a manner that influences the phenotype of the cardiac cells. In some embodiments, the ANP comprises electroactive polymer fibers, that yield fibers that exhibit crystalline structures in polar form due to strong electromagnetic fields. Exemplary systems and methods for aligning the fibers are disclosed in US Application 2009/0108503, which is incorporated herein in its entirety by reference.

Depending on the substrate employed, examples of surface layers can include electroconductive materials, including for example, but not limited to, a thin metallic or conducting surface deposit, e.g. graphene, graphene oxide and reduced graphene oxide (rGO), tantalum, titanium, Ti—Al—V alloys, gold, chromium, metal oxides, semiconductor oxides, metal nitrides, semiconductor nitrides, polymers, biopolymers, or other alloys. Preferred surface compositions for implants include graphene and graphene oxide as disclosed in the Examples, tantalum, titanium, platinum or an oxide thereof.

In some embodiments, the nanotextured platform is coated with, or comprises within its polymercapillary force lithography matrix, either biocompatible extracellular matrix polypeptides, engineered matrix polypeptides, or engineered polypeptides.

In some embodiments, the ANP can comprise a layer of thermoresponsive material. A thermoresponsive material is one which shrinks uniformly without substantial distortion when the temperature is changed. In some embodiments, a thermoplastic material can be used to remove a substantial monolayer of mature cardiomyocytes from the ANP. The removed monolayer can be used as is, or as a tissue mimetic in the in vitro assays, or for example, multiple monolayers of mature cardiomyocytes can be stacked to form a 3D-tissue engineered myocardium tissue as disclosed herein.

A "thermoresponsive material" is intended to mean a plastic material which shrinks upon heating. In one aspect, the thermoplastic materials are those which shrink uniformly without distortion. The shrinking can be either bi-axially (isotropic) or uni-axial (anisotropic). Suitable thermoplastic materials for inclusion in the compositions and methods as described herein include, for example, high molecular weight polymers such as acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), Poly(methyl methacrylate) (PMMA), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyal kanoates (PHAs), polyketone (PK), polyester polyethylene (PE), polyetheretherketone (PEEK), polyetherimide (PEI), polyethersulfone (PES), polysulfone polyethylenechlormates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC), polyolefin, and spectralon.

In some embodiments, a transitional polymer can be coated onto a ANP polymer substrate. In one embodiment, the transitional polymer is a thermally sensitive polymer that can be dissolved to cause the release of the ANP polymer scaffold. An example of such a polymer is linear, non-cross-linked poly(N-Isopropylacrylamide), which is a solid when dehydrated, and which is a solid at 37° C. (wherein the polymer is hydrated but relatively hydrophobic). However, when the temperature is dropped to less than 32° C. (where the polymer is hydrated but relatively hydrophilic), the polymer becomes a liquid, thereby releasing the polymer scaffold.

In another embodiment, the transitional polymer is a thermally sensitive polymer that becomes hydrophilic, thereby releasing a hydrophobic scaffold coated thereon. An example of such a polymer is cross-linked poly(N-Isopropylacrylamide), which is hydrophobic at 37° C. and which is hydrophilic at 32° C.

In yet another embodiment, the transitional polymer is an electrically actuated polymer that becomes hydrophilic upon application of an electric potential to thereby release a hydrophobic (or less hydrophilic) structure coated thereon. Examples of such a polymer include poly(pyrrole)s, which are hydrophobic when oxidized and hydrophilic when reduced. Other examples of polymers that can be electrically actuated include poly(acetylene)s, poly(thiophene)s, poly(aniline)s, poly(fluorene)s, poly(3-hexylthiophene), polynaphthalenes, poly(p-phenylene sulfide), and poly(para-phenylene vinylene)s, etc.

In still another embodiment, the transitional polymer is a degradable polymer that can be dissolved to release the ANP polymer scaffold. In one example, the polymer scaffold (e.g., polylactic acid, polyglycolic acid, poly(lactic-glycolic) acid copolymers, nylons, etc.) undergoes time-dependent degradation by hydrolysis. In another example, the polymer undergoes time-dependent degradation by enzymatic action (e.g., fibrin degradation by plasmin, collagen degradation by collagenase, fibronectin degradation by matrix metalloproteinases, etc.). It will be understood by those skilled in the art that the foregoing list of optional substances is not intended to be exhaustive and that other materials can be admixed with substrate within the practice of the technology described herein.

Any of a variety of medically and/or surgically useful optional substances can be incorporated in, or associated with, the scaffold substrate either before, during, or after preparation of the tissue engineered myocardial composition as disclosed herein. Thus, for example, one or more of such substances can be introduced into the scaffold, e.g., by soaking or immersing the substrate in a solution or dispersion of the desired substance(s), by adding the substance(s) to the carrier component of the cell coated substrate or by adding the substance(s) directly to cell coated substrate. Medically/surgically useful substances include physiologically or pharmacologically active substances that act locally or systemically in the host subject.

Techniques for covalently bonding peptides to the surface of substrates such as polymers can be performed by a variety of conventional methods using known coupling agents and known derivatization methods which are well known to those of skill in the art. This invention also relates to the covalent coupling of such peptides to the nanotextured surface of the substrate either directly or via an appropriate linking or spacer group. U.S. Pat. No. 4,789,601, incorporated by reference in its entirety, describes a polyorganosiloxane composition having a biocompatible surface. The surface of the composition is treated with a primary amine or a peptide. This patent is incorporated herein by reference as teaching methods of modifying polymer surfaces.

U.S. Pat. No. 5,733,538, incorporated herein by reference, describes surface-modifying copolymers having cell adhesion properties. The surface modification techniques and polymers described therein also may be useful in conjunction with the substrates derived herein. More particularly, the patent discusses a hemocompatible surface-modifying additive for modifying polyurethane or polyurethane urea substrates. The additive has a polyurethane or polyurethane urea hard block or an alternative block which is miscible with the poly(urethane) or poly(urethane-urea) base polymer, a polysiloxane hydrophobic soft block, an optional hydrophilic spacer and a peptide selected from the group consisting of Arg-Gly-Asp. X-Arg-Gly-Asp, Arg-Gly-Asp-X and X-Arg-Gly-Asp-X', wherein X and X' are amino acids.

In some embodiments, the peptides GRGDSP (Fibronectin Receptor Ligand, SEQ ID NO: 1) and/or the YIGSRC (Laminin Receptor Ligand; SEQ ID NO: 2) can be covalently bound to the surface of the ANP polymer substrate to increase cell attachment. Cell attachment efficiency can be analyzed as previously described (Samarel and Engelmann, Am J Physiol 261, H1067-77, 1991). Briefly, plating efficiency is analyzed as the amount of recovered DNA from adherent cells 4 h after plating compared to the amount of DNA in the plating suspension. In the case of Type I collagen-coated plastic dishes, plating efficiency of freshly isolated neonatal rat ventricular myocytes was 68°±4% (Samarel and Engelmann, Am J Physiol 261, H1067-77, 1991). It is expected that plating efficiency will vary between flat and microtextured surfaces, and with the two peptides (whether used alone or in combination).

Fabrication of an Anisotropically Nanotextured Platform (ANP).

In some embodiments, the nanotextured array of parallel grooves and ridges is generated using a process selected from the group consisting of capillary force lithography, nanoindentation, e-beam lithography, and electrospinning.

In some embodiments, the array of parallel grooves and ridges is formed by capillary force lithography and/or thermal and UV based curing methods. In some embodiments, the array of parallel grooves and ridges on the ANP polymer substrate can be patterned with spatial control spanning the nanometer-length scales. This level of spatial control can be achieved via patterning techniques including but not limited to soft lithography, self-assembly, vapor deposition and photolithography. Each of these techniques is discussed, in turn, below.

Capillary Force Lithography.

Poly(urethane acrylate) (PUA) or other polymers can be used as mold material and poly(dimethylsiloxane) (PDMS) as a solvent absorbent. PUA molds are generated by drop-dispensing a PUA precursor onto a patterned silicon master wafer fabricated by standard photolithography. Next, a poly (ethylene terephthalate) (PET) film (thickness: 75 µm) is pressed lightly against the liquid drop in order to be used as a supporting backplane. Polymer replicas are fabricated by exposing the PUA to UV for a few tens of seconds and then peeling away the PET film with the polymer from the silicon master. To complete polymer curing, the replicas are exposed to UV for several hours overnight. PDMS solvent absorbers are made by mixing the PDMS precursor with the curing agent in a 10:1 mixing ratio and curing it at 60° C. for 10 hrs. The cured PDMS molds are manually removed and cut prior to use. These molds are now available for capillary force lithography. ANPs are prepared using nanoimprint lithography. In brief, glass coverslips are washed with isopropyl alcohol for 30 min in a water sonicator and dried under a nitrogen stream. Polymer or hydrogel solution is prepared in the relevant solvent, e.g. chloroform and drop-dispensed onto the glass coverslip. A flat PDMS mold is placed on the dispensed solution to absorb the solvent and obtain a smooth, flat polymer layer. A light pressure (~10 kPa) is applied to evenly disperse the polymer on the PDMS mold for 5 min. Coverslips are placed on a preheated plate (120° C.) for 5 min to remove residual solvent and increase adhesion between the polymer and the cover glass. Next, a nanopatterned PUA mold is placed onto the polymer coated glass and the polymer is embossed with the nanopattern by applying constant pressure (~100 kPa) and heat (120° C.) for 15 min. After this thermal imprinting process, the assembled substrates are cooled to room temperature and the PUA mold carefully peeled off. Finally, the prepared ANPs are stored in a desiccator to remove residual solvent before cell seeding. For UV assisted CFL, we use UV instead of thermal curing to polymerize the polymer.

a) Soft Lithography:

In soft lithography, structures (particularly those with features measured on the scale of 1 nm to 1 µm) are fabricated or replicated using elastomeric stamps, molds, and conformable photomasks. One such soft lithography method is microcontact printing using a polydimethylsiloxane stamp. Microcontact printing has been realized with fibronectin, laminin, vitronectin and fibrinogen and can be extended to other extracellular matrix proteins including, but not limited to collagens, fibrin, etc. Other polymers can be used as well, as this soft lithography method is quite versatile. There are few, if any, limitations on the geometry of the polymer structure(s) beyond the types of patterns that can be created in the polydimethylsiloxane stamps used for microcontact printing. The range of patterns in the stamps, in turn, is presently limited only by the current microprocessing technology used in the manufacture of integrated circuits. As such, available designs encompass nearly anything that can be drafted in modern computer-aided-design software. Multiple layers of polymers can be printed on top of one another using the same or different stamps with the same or different proteins to form an integrated poly-protein (poly-polymer) layer that can subsequently be released and used.

b) Self Assembly:

Various polymers will spontaneously form self-assembled structures. Examples, without limitation, of self-assembly include assembly of collagen into fibrils, assembly of actin into filaments and assembly of DNA into double strands and other structures depending on base-pair sequence. The self-assembly can be directed to occur on the transitional layer to create a nanometer-scale spatially organized polymer layer. Further, self-assembly can be combined with soft lithography to create a self-assembled layer on top of a soft lithographically patterned polymer; alternatively, the processes can be carried out in the reverse order. The self-assembled polymer, depending on the strength and stability of intermolecular forces, may or may not be stabilized using a cross-linking agent (for example, glutaraldehyde, formaldehyde, paraformaldehyde, etc.) to maintain integrity of the polymer layer upon release from the transitional layer. Otherwise, existing intermolecular forces from covalent bonds, ionic bonds, Van der Waals interactions, hydrogen binding, hydrophobic/hydrophilic interactions, etc., may be strong enough to hold the polymer scaffold together.

c) Vapor Deposition:

Using a solid mask to selectively control access to the surface of the transitional polymer, polymers can be deposited in the accessible regions via condensation from a vapor phase. To drive polymers into a vapor phase, the deposition is performed in a controlled environmental chamber where the pressure can be decreased and the temperature increased such that the vapor pressure of the polymer approaches the pressure in the environmental chamber. Polymer surfaces produced via vapor deposition can be combined with polymer surfaces created by self-assembly and/or by soft lithography.

d) Patterned Photo-Cross-Linking:

Patterned light, x-rays, electrons or other electromagnetic radiation can be passed through a mask by photolithography; alternatively, the radiation can be applied in the form of a focused beam, as in stereolithography or e-beam lithography, to control where the transitional polymer polymers attach. Photolithography can be used with polymers that intrinsically photo-cross-link or that change reactivity via the release of a photoliable group or via a secondary photosensitive compound to promote cross-linking or breaking of the polymer chains so that the surface areas that are exposed to light are rendered either soluble or insoluble to a developing solution that is then applied to the exposed polymer to either leave only the desired pattern or remove only the desired pattern. The polymer is provided in an aqueous solution of polymer intrinsically photosensitive or containing an additional photosensitive compound(s).

2) Polymer Release and Scaffold Formation

The transitional polymer layer dissolves or switches states to release the polymer structure(s). For example, a transitional polymer layer formed of PIPAAm (non-cross-linked) will dissolve in an aqueous media at a temperature less than 32° C. In another example, a transitional polymer layer is formed of PIPAAm (cross-linked) will switch from a hydrophobic to hydrophilic state in an aqueous media at a temperature less than 32° C. The hydrophilic state will release the polymers. In yet another embodiment, the transitional polymer layer includes a conducting polymer, such as polypyrrole, that can be switched from a hydrophobic to hydrophilic state by applying a positive bias that switches the conducting polymer from a reduced to oxidized state. In additional embodiments, the transitional polymer layer can include a degradable polymer and/or polymer that undergoes time-dependent degradation by hydrolysis (as is the case, for example, for polylactic and polyglycolic acid) or by enzymatic action (for example, fibrin degradation by plasmin). These polymer structure(s) can then be further manipulated for the desired application.

The techniques of microfabrication and micromachining have been used to create precisely controlled biomaterial surfaces via photopatterning and etching (Desai et al., Biotechnol Bioeng 57:118-120, 1998; Bhatia et al, Biotech. Prog. 14:378-387, 1998; Chen et al., Biotech Prog. 14:356-363, 1998). Microfabricated substrates can provide unique advantages over traditional biomaterials due to their ability to control surface microarchitecture, topography, and feature size in the nanometer and micron size scale, and control of surface chemistry in a precise manner through biochemical coupling or photopatterning processes. With the capability to design components spanning from the millimeter down to the nanometer range, few other engineering technologies can so closely parallel the microdimensional scale of living cells and tissues.

Traditionally, microfabrication has only been applied to semiconductor materials due to their oxidation and etching properties, using expensive microfabrication equipment. However, techniques to translate micromachined structures from inorganic to organic polymeric materials have been introduced (Schmidt and von Recum, Biomaterials, 12: 385-389, 1991; Bucaro et al, IEEE Conference Transactions 0-7803-3869-3/97:217-219, 1997). This opens up unique opportunities in biological and tissue engineering applications.

The ability to spatially localize and control interactions of cell types on polymeric materials presents an opportunity to engineer hierarchically and more physiologically correct tissue analogs for mechanical, biochemical, and functional testing. The arrangement of cells in more complex two and three dimensional arrangements has beneficial effects on cell differentiation, maintenance, and functional longevity.

The substrates as described herein can provide a transparent biocompatible surface with specific nanoarchitectures upon which myocytes, e.g., cardiomyocytes can be grown. In an exemplary procedure, the nanotextured substrates are prepared using silicone membranes. Starting with a clean silicon wafer, a 5 μm conformal layer of light sensitive photoresist (Michrochem SU8-5, Michrochem Corp., Newton, Mass.) is spun onto the wafer at 1500 RPM for 30 seconds and soft baked at 90° C. for 6 minutes. A photomask is used to define the pattern on to the photoresist layer upon exposure to UV light. Arrays of ridges can be photolithographically defined. These dimensions correspond to cell dimension, as myocytes in culture are typically 50 microns in length and 10-15 microns in diameter. The resulting photoresist structure is developed and hard baked. Subsequently, the surface is spray coated or dipped into adhesion demoter and a thin layer of parylene is deposited on the photoresist/silicon substrate. The parylene deposition layer is approximately 25 microns in thickness. The parylene layer forms a flexible mold for the elastomeric silicone. Subsequently, silicone (polydimethysiloxane), which is prepared by mixing elastomer and catalyst (A103 Factor II Inc.) in a 10:1 ratio, is deposited on top of the parylene mold and allowed to cure at room temperature for 24-48 hours. The silicone can then be peeled off the parylene and cut to the desired shape and size.

The process for creating nanogrooves is similar except that a positive photoresist is used. Shipley 1818 photoresist is spun on the wafer at 500 RPM for 180 seconds. After a 5 minute soft bake the wafer is patterned with a mask aligner for 13 seconds at 20 mW. This can result in longitudinal grooves of 5 nm depth. The width and spacing of the grooves can be adjusted as desired according to the mask. The wafer is placed in developer (351 Shipley) for 0.9 minutes with continuous motion and rinsed with deionized water. The longitudinal grooves orient the myocytes and also to provide a greater surface area for lateral attachment.

It should be understood that given the teachings of the technology described herein it will be possible for those of skill in the art to produce arrays that correspond to dimensions smaller or larger than those exemplified here and still produce a surface useful for the arrangement and growth of cells.

As indicated elsewhere in the specification, most of the observations to date presented have come from two-dimensional cultured muscle. This is a limiting system in that the myofibrils can only make costameres (attachments) on the bottom surface of the dish and lack the fascia adherens at the ends of the cells. Cultured myocytes at present are (1) not oriented, (2) weakly adherent, and (3) not three-dimensional. The myocytes lack an important third dimension through which useful force is transmitted to the external world surrounding the cell. Early studies have shown that myocytes grow in more physiological arrangements (i.e. muscle-like configurations) when attached to perpendicular, rather than parallel, surfaces created by a pin impaled in a soft dish (Yeoh and Holtzer, Experimental Cell Research, 104(1):63-78, 1977) or by Vandenburgh's less well known horizontal device (Vandenburgh et al., FASEB J. 5; 2860-2867, 1991). The methods for introducing nanotopography into the membrane surfaces as presented herein will overcome these architectural defects in cardiac cell anatomy and physiology.

These platforms will provide a transparent biocompatible surface with specific nanoarchitectures upon which cells will exhibit enhanced differentiation and maturity. The nanotopography as disclosed herein provides anisotropic or directional growth for cells and thus, can recreate tissue architecture at the cellular and subcellular level in a reproducible fashion.

The nanotopograpy image forming material can be applied to the polymer substrate by a variety of methods known to one skilled in the art, such as printing, sputtering and evaporating. The term "evaporating" is intended to mean thermal evaporation, which is a physical vapor deposition method to deposit, for example, a thin film of metal on the surface of a substrate. By heating a metal in a vacuum chamber to a hot enough temperature, the vapor pressure of the metal becomes significant and the metal or deposited composition (e.g., graphene) evaporates. It recondenses on the target substrate. As used herein, the term "sputtering" is intended to mean a physical vapor deposition method where atoms in the target material are ejected into the gas phase by high energy ions and then land on the substrate to create the thin film on the surface of the substrate. Such methods are well known in the art (Bowden et al. (1998) Nature (London) 393: 146-149; Bowden et al. (1999) Appl. Phys. Lett. 75: 2557-2559; Yoo et al. (2002) Adv. Mater. 14: 1383-1387; Huck et al. (2000) Langmuir 16: 3497-3501; Watanabe et al. (2004) J. Polym. Sci. Part 6: Polym. Phys. 42: 2460-2466; Volynskii et al. (2000) J. Mater. Sci. 35: 547-554; Stafford et al. (2004) Nature Mater. 3:545-550; Watanabe et al. (2005) J. Polym. Sci. Part 6: Polym. Phys. 43: 1532-1537; Lacour et al. (2003) Appl. Phys. Lett. 82: 2404-2406).

In addition, the image forming material can be applied to thermoplastic material using "pattern transfer." The term "pattern transfer" refers to the process of contacting an image-forming device, such as a mold or stamp, containing the desired pattern, with the thermoplastic material. After releasing the mold, the pattern is transferred to the thermoplastic material. In general, high aspect ratio pattern and sub-nanometer patterns have been demonstrated. Such methods are well known in the art (Sakurai, et al, U.S. Pat. No. 7,412,926; Peterman, et al, U.S. Pat. No. 7,382,449; Nakamura, et al, U.S. Pat. No. 7,362,524; Tamada, U.S. Pat. No. 6,869,735).

Another method for applying the image forming material includes, for example "nano-contact printing." The term "nano-contact printing" refers to the use of the relief patterns on a PDMS stamp to form patterns of self-assembled monolayers (SAMs) of an image-forming material on the surface of a thermoplastic material through conformal contact. Nano-contact printing differs from other printing methods, like inkjet printing or 3D printing, in the use of self-assembly (especially, the use of SAMs) to form nanopatterns and nanostructures of various image-forming materials. Such methods are well known in the art (Cracauer et al, U.S. Pat. No. 6,981,445; Fujihira et al, U.S. Pat. No. 6,868,786; Hall et al, U.S. Pat. No. 6,792,856; Maracas et al, U.S. Pat. No. 5,937,758).

"Soft-lithography" is intended to refer to a technique commonly known in the art. Soft-lithography uses a patterning device, such as a stamp, a mold or mask, having a transfer surface comprising a well defined pattern in conjunction with a receptive or conformable material to receive the transferred pattern. Microsized and nanosized structures are formed by material processing involving conformal contact on a molecular scale between the substrate and the transfer surface of the patterning device.

A "patterning device" is intended to be broadly interpreted as referring to a device that can be used to convey a patterned cross-section, corresponding to a pattern that is to be created in a target portion of the substrate.

A "pattern" is intended to mean a pre-determined mark or design, generally a substantially nanoscale design of repeating parallel grooves and ridges in a surface as described herein.

In some embodiments, the exact spatial structure of the nanotextured array of parallel grooves and ridges can be changed by altering the features of a polydimethylsiloxane (PDMS) stamp used for microcontact printing and/or by printing multiple times at different angles.

In Vitro-Differentiated Cardiomyocytes.

The myocytes applied to the ANP polymer substrates as disclosed herein can be any myocytes, e.g., cardiomyocytes, skeletal muscle myocytes, smooth muscle myocytes and the like. In some embodiments, the myocytes cells can be derived from any mammal, e.g., human cardiomyocytes. Importantly, in some embodiments the myocytes, e.g., cardiomyocytes are differentiated in vitro prior to seeding on the ANP polymer substrates as disclosed herein.

In some embodiments, the cardiomyocytes can be differentiated from stem cell, or a cardiovascular precursor into an immature cardiomyocyte, which are then seeded onto the ANP polymer substrates as disclosed herein, where they undergo organization in an anisotropic manner and are further matured into a more differentiated phenotype.

In some embodiments, the cardiomyocytes are derived from stem cells, such as embryonic stem (ES) cells, adult stem cells, or induced pluripotent stem cells (iPSCs). In some embodiments, the differentiation of iPSC or ESCs into immature cardiomyocytes can be done prior to coating the cells on the nanotextured platform substrate, or can be done while they are coated on, or present on, the nanotextured platform. In some embodiments, the iPSCs are cells which have been reprogrammed from somatic cells obtained from a subject, e.g., a human subject. In some embodiments, the human subject is a healthy subject, and in some embodiments, the subject has a cardiovascular condition, disease or disorder as disclosed herein, or the subject has, for example, arrhythmia.

In some embodiments, the cardiomyocytes cultured on the ANP polymer substrate for a pre-determined time differentiate into a more mature phenotype and express at least one marker from the group consisting of Nkx2.5, GATA4, connexin-43, α-myosin heavy chain, cTNT, sarcomere expression, sarcomere length, contractility, beat rate, or electrical propagation in a manner more similar to adult or mature cardiomyocytes as compared to in vitro-differentiated cardiomyocytes which are not cultured on the ANP polymer substrate or cardiomyocytes which are cultured on a polymer substrate of the same composition but substantially lacking the nanotextured array of parallel grooves and ridges.

Sources of Cardiomyocytes

As discussed above, one embodiment of the technology described herein is a tissue engineered myocardial composition comprising a substantially pure population of in vitro-differentiated cardiomyocytes seeded on an ANP polymer substrate. In another embodiment, described herein are methods for the generation of functional tissue engineered myocardium.

As disclosed herein in the Examples, the inventors have demonstrated the use of ESC, and iPSC derived-cardiomyocytes to generate functional tissue engineered myocardium. Accordingly, one can use cardiomyocyte cells derived from tissues, such as embryonic cardiac tissue and/or ESC cell sources for use in the generation of functional tissue engineered myocardium as disclosed herein. Alternatively, one can use cardiomyocytes derived from any number of cell sources known to a person of ordinary skill in the art, such as for example, but not limited to, stem cells, such as cardiac progenitor cells, adult stem cells (ASC), and embryoid bodies (EB). In some embodiments, an iPS cell produced by any method known in the art can be used, for example virally-induced or chemically induced generation of iPS cells as disclose in EP1970446, US2009/0047263, US2009/0068742, and 2009/0227032, which are incorporated herein in their entirety by reference. In some embodiments cardiomyocytes are derived from human embryonic stem cell lines.

In some embodiments, the cardiomyocytes are derived from the reprogramming of cells. For example, a population of cardiomyocytes for use in the methods and tissue engineered myocardium as disclosed herein can be from an induced pluripotent stem cell (iPS), by method known by a person of ordinary skill in the art. For example, methods to produce skin derived iPS cell derived-cardiomyocytes have been described in Mauritz et al., *Circulation.* 2008; 118: 507-517, and disclosed in International Application WO2008/088882 which is incorporated herein by reference. In some embodiments, an iPS cell used to derive a cardiomyocytes can be produced by any method known in the art can be used, for example virally-induced or chemically induced generation of iPS cells as disclose in EP1970446, US2009/0047263, US2009/0068742, and 2009/0227032, which are incorporated herein in their entirety by reference.

The term "induced pluripotent stem cell" (or "iPS cell"), as used herein, refers to a pluripotent stem cell induced from a somatic cell, e.g., a differentiated somatic cell. iPS cells are capable of self-renewal and differentiation into cell fate-committed stem cells, including neural stem cells, as well as various types of mature cells.

Non-cardiomyocyte cells that are suitable for generating iPS-derived cardiomyocytes cells for use in the methods and tissue engineered myocardium as disclosed herein include stem cells, progenitor cells, and somatic cells. Suitable cells include, but are not limited to, embryonic stem cells; adult stem cells; induced pluripotent stem (iPS) cells; skin fibroblasts; skin stem cells; cardiac fibroblasts; bone marrow-derived cells; skeletal myoblasts; neural crest cells; and the like. In some embodiments, a iPS cell for use in generating a iPS-derived cardiomyocytes is derived from a stem cell, a non-cardiomyocyte somatic cell, or a progenitor cell is a human stem cell, a human non-cardiomyocyte somatic cell, or human progenitor cell. In other embodiments, a iPS cell for use in generating a iPS-derived cardiomyocytes derived from a stem cell, non-cardiomyocyte somatic cell, or progenitor cell is a non-human primate stem cell, a non-human primate non-cardiomyocyte somatic cell, or non-human primate progenitor cell. In other embodiments, a iPS cell for use in generating a iPS-derived cardiomyocytes is derived from a stem cell, non-cardiomyocyte somatic cell, or progenitor cell is a rodent stem cell, a rodent non-cardiomyocyte somatic cell, or a rodent progenitor cell. In some embodiments, a iPS cell for use in generating a iPS-derived cardiomyocytes is derived from a stem cells, non-cardiomyocyte somatic cells, and progenitor cells from other mammals (e.g., ungulate cells, e.g., porcine cells) are also contemplated.

Human induced pluripotent stem cells (hiPSCs) are generated by reprogramming adult somatic cells (e.g. dermal fibroblasts), and they can be subsequently expanded and differentiated into cardiomyocytes, making them a potentially inexhaustible supply of genetically diverse human cardiomyocytes for use in both cardiac therapies and in vitro drug screening assays. However, pluripotent stem-cell derived cardiomyocytes have been functionally and phenotypically immature. They are smaller than adult cardiomyocytes, with disorganized myofibrils, no anisotropy or physiological organization, and smaller force generation. In order to use pluripotent stem cells for accurate modeling of the myocardium or for therapeutic interventions, these cells need to be matured or conditioned into a more adult-like phenotype. As mentioned above, cardiomyocytes have been found to be responsive to extracellular matrix-like cues, as well as electrical and mechanical stimulation. However, these cues have not yet been investigated in synergy on stem cell-derived cardiomyocytes. As mentioned above, biomimetic alignment and organization of cardiomyocytes is important in generating confluent monolayers of cells which can mimic the physiological function of heart tissue.

In some embodiments, a cardiomyocyte is derived from an induced pluripotent stem (iPS) cell. iPS cells are generated from somatic cells, including skin fibroblasts, using, e.g., known methods. iPS cells produce and express on their cell surface one or more of the following cell surface antigens: SSEA-3, SSEA-4, TRA-1-60, TRA-1-81, TRA-2-49/6E, and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPP A2, DPPA4, and hTERT. In some embodiments, an iPS cell expresses Oct-3/4, Sox2, Nanog, GDF3, REX1, FGF4, ESG1, DPPA2, DPPA4, and hTERT. Methods of generating iPS are known in the art, and any such method can be used to generate iPS. See, e.g., Takahashi and Yamanaka (2006) Cell 126:663-676; Yamanaka et. al. (2007) Nature 448:313-7; Wernig et. al. (2007) Nature 448:318-24; Maherali (2007) Cell Stem Cell 1:55-70.

iPS cells can be generated from somatic cells (e.g., skin fibroblasts) by genetically modifying the somatic cells with one or more expression constructs encoding Oct-3/4 and Sox2. In some embodiments, somatic cells are genetically modified with one or more expression constructs comprising nucleotide sequences encoding Oct-3/4, Sox2, c-myc, and Klf4. In some embodiments, somatic cells are genetically modified with one or more expression constructs comprising nucleotide sequences encoding Oct-4, Sox2, Nanog, and LIN28.

In some embodiments, cardiomyocytes as disclosed herein can be derived from Isl1+ multipotent progenitor cells such as those disclosed in U.S. Provisional Application 60/856,490 and 60/860,354 and in International Application PCT/US07/23155, which is incorporated herein in its entirety by reference.

Accordingly, in addition to derivation from in vitro differentiation of an ES cell or ES cell line, cardiomyocytes for use in the methods and compositions as disclosed herein can be derived from any kind of tissue or cell line amenable to reprogramming to an iPS cell. Where ES cells are used, they can be provided in the form of an established cell line, or they may be obtained directly from primary embryonic tissue and used immediately for differentiation. Included are human embryonic stem cell lines, such as those listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13 and H14 (Wisconsin Alumni Research Foundation (WiCell Research Institute)). In some embodiments, cardiomyocytes use in the methods and compositions as disclosed herein are derived from a stem cell source where the embryo is not destroyed.

Stem cells for generation of in vitro-differentiated myocytes, e.g., cardiomyocytes can include stem cells from umbilical cord blood, placenta, bone marrow, or chondral villi. Also of interest are lineage committed stem cells, such as mesodermal stem cells and other early cardiogenic cells (see Reyes et al. (2001) Blood 98:2615-2625; Eisenberg & Bader (1996) Circ Res. 78(2):205-16; etc.)

In some embodiments, cardiomyocytes for use in the methods and tissue engineered myocardium as disclosed herein can be derived from tissues or stem cells obtained from any mammalian species, e.g. human, equine, bovine, porcine, canine, feline, rodent, e.g. mice, rats, hamster, primate, etc. In some embodiments, the cardiomyocytes for use in the methods and compositions as disclosed herein are human cardiomyocytes.

In some embodiments, cardiomyocytes can be derived from hematopoietic stem cells, or from a suitable source of endothelial, muscle, and/or neural stem cells which are harvested from a mammalian donor by methods known by one of ordinary skill in the art. A suitable source is the hematopoietic microenvironment. For example, circulating peripheral blood, preferably mobilized (e.g., recruited) as described below, may be removed from a subject. Alternatively, bone marrow may be obtained from a mammal, such as a human patient, undergoing an autologous transplant.

In alternative embodiments, cardiomyocytes for use in the methods, compositions and tissue engineered myocardium as disclosed herein can be derived from human umbilical cord blood cells (HUCBC) have recently been recognized as a rich source of hematopoietic and mesenchymal progenitor cells (Broxmeyer et al., 1992 Proc. Natl. Acad. Sci. USA 89:4109-4113). Previously, umbilical cord and placental blood were considered a waste product normally discarded at the birth of an infant. Cord blood cells are used as a source of transplantable stem and progenitor cells and as a source of marrow repopulating cells for the treatment of malignant diseases (e.g. acute lymphoid leukemia, acute myeloid leukemia, chronic myeloid leukemia, myelodysplastic syndrome, and neuroblastoma) and non-malignant diseases such as Fanconi's anemia and aplastic anemia (Kohli-Kumar et al., 1993 Br. J. Haematol. 85:419-422; Wagner et al., 1992 Blood 79; 1874-1881; Lu et al., 1996 Crit. Rev. Oncol. Hematol 22:61-78; Lu et al., 1995 Cell Transplantation 4:493-503). A distinct advantage of HUCBC is the immature immunity of these cells that is very similar to fetal cells, which significantly reduces the risk for rejection by the host (Taylor & Bryson, 1985 J. Immunol. 134:1493-1497).

In an alternative embodiment, a population of cardiomyocytes for use in the methods and tissue engineered myocardium as disclosed herein can be de-differentiated stem cells, such as stem cells derived from differentiated cells. In such an embodiment, the de-differentiated stem cells can be for example, but not limited to, neoplastic cells, tumor cells and cancer cells.

In some embodiments, the de-differentiated cells are from a subject, such as a human subject. In some embodiments, the subject such as a human subject has, or is at risk of developing a cardiovascular disease or condition, or the subject has a cardiac pathology or cardiomyopathy. In some embodiments, the subject is a human subject in need of a cardiac treatment and the subject derived-cardiomyocytes are used to generate a tissue engineered myocardium as disclosed herein which is transplanted into the same subject in which the cells were obtained to derive the cardiomyocytes. In some embodiments, the de-differentiated stem cells are obtained from a biopsy.

Methods to Differentiate Cells to Cardiomyocytes

Methods to differentiate cells, e.g., stem cells into cardiomyocytes, such as immature cardiomyocytes are known in the art. In some embodiments, non-genetic techniques can be used, including, but not limited to a FACs based method using on mitochondrial dye uptake, as disclosed in Hattori et al., Nat. Methods., 2010, 7, 61-66.

In some embodiments, the dye tetramethylrhodamine methyl ester perchlorate, a florescent dye, can be used to selectively labels embryonic and neonatal cardiomyocytes derived from human PSCs and iPSC. Such methods can enrich a population of cardiomyocytes from stem cells to a >99% purity, as disclosed in Hattori et al., Nat. Methods, 2010, 7; 61-66.

In some embodiments, pluripotent stem cells (PSCs) and iPSC cultured can be cultured in a glucose-depleted and lactate abundant culture to differentiate into cardiomyocytes, where only cardiomyocytes survive and can be isolated, as described in the methods of Tohama et al., Cell Stem cell, 2013; 12; 127-137.

In some embodiments, cardiomyocytes for use in the compositions and methods as disclosed herein can be obtained after stable transfection of stem cells with aminoglycoside phosphotransferase under the alpha-cardiac myosin heavy chain promoter, which has reported to produce a stable form of cardiomyocytes. (Klug et al., J Clin Invest, (1996), 98(1); 216-224).

Cardiovascular stem cell differentiation agents for use in the technology described herein are well known to those of ordinary skill in the art. Examples of such agents include, but are not limited to, cardiotrophic agents, creatine, carnitine, taurine, cardiotropic factors as disclosed in U.S. Patent Application Serial No. 2003/0022367 which is incorporated herein by reference, TGF-beta ligands, such as activin A and activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway.

Methods to Identify and Isolate In-Vitro Differentiated Cardiomyocytes

In some embodiments, cardiomyocytes can be identified and isolated by using agents reactive to markers typical of the cardiomyocytes lineage, including but without limitation, the positive expression of Mef2c, Nxk2.5, Tbx20, Isl1, GATA4, GATA6; Tropinin T (TnT), Troponin C (TnI), BMP7, BMP4, BMP2, miR-208, miR-143, miR-133a, miR-133b, miR-1, miR-143, miR-689 and smooth muscle actin (smActin), or homologues or variants thereof. Alternatively, cardiomyocytes in a population of cells can be selected based on the positive expression of Mef2c and Nxk2.5. To be more precise, cardiomyocytes in a population of cells can be selected or identified based on the positive expression of Mef2c and Nxk2.5 and the lack of or low level expression of at least one of the following markers: Tbx5; Snai2; miR-200a; miR-200b; miR-199a; miR-199b; miR-126-3p; miR-322 and CD31 or homologues or variants thereof.

Typically, conventional methods to isolate cardiomyocytes involves positive and negative selection using markers of interest. For example, agents can be used to recognize markers present on the cardiomyocytes, for instance labeled antibodies that recognize and bind to cell-surface markers or antigens on cardiomyocyte can be used to separate and isolate a cardiomyocytes from a population of non-cardiomyocytes using fluorescent activated cell sorting (FACS), panning methods, magnetic particle selection, particle sorter selection and other methods known to persons skilled in the art, including density separation (Xu et al. (2002) Circ. Res. 91:501; U.S. patent application Ser. No. 20030022367) and separation based on other physical properties (Doevendans et al. (2000) J. Mol. Cell. Cardiol. 32:839-851). Alternatively, genetic selection methods can be used, where cardiomyocytes can be genetically engineered to express a reporter protein operatively linked to a tissue-specific promoter and/or a specific gene promoter, therefore the expression of the reporter can be used for positive selection methods to isolate and enrich for a population of cardiomyocytes. For example, a fluorescent reporter protein can be expressed in the desired stem cell by genetic engineering methods to operatively link the marker protein to the promoter expressed in a desired differentiated cell product (Klug et al. (1996) J. Clin. Invest. 98:216-224; U.S. Pat. No. 6,737,054). Other means of positive selection include drug selection, for instance such as described by Klug et al, supra, involving enrichment of desired cells by density gradient centrifugation. Negative selection can be performed, selecting and removing cells with undesired markers or characteristics, for example fibroblast markers, epithelial cell markers etc.

In some embodiments, isolation of cardiomyocytes comprises a separation step involving contacting a heterologous population of cells (e.g. cardiomyocytes and non-cardiomyocytes) with an antibody specific for at least one, or at least two or at least three cardiomyocyte-specific markers.

Separation can be carried out using any of a number of well-known methods, including, e.g., any of a variety of sorting methods, e.g., fluorescence activated cell sorting (FACS), negative selection methods, etc. The selected cells are separated from non-selected cells, generating a population of selected ("sorted") cells. A selected cell population can be at least about 75%, at least about 80%, at least about 85%, at least about 90%, at least about 95%, at least about 98%, at least about 99%, or greater than 99% cardiomyocytes.

Cell sorting (separation) methods are well known in the art. Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide [PI], LDS). Any technique may be employed which is not unduly detrimental to the viability of the selected cells. Where the selection involves use of one or more antibodies, the antibodies can be conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry.

In some embodiments, the cell marker, SIRPA (signal-regulatory protein alpha), which is specifically expressed in cardiomyocytes derived from hESCs and hiPSCs can be used to identify a population of cardiomyocytes differentiated from stem cells and permits, for example, the isolation of a population that is 98% cardiac troponin T positive (Dubois et al., Nat. Biotech, (2011) 29; 1011-1018). In the methods described by Dubois et al., negative selection of stem cells for PECAM, THY1, PDGFRB and ITGA1 can be used to remove the non-myocyte population.

Uosaki et al. (PLOS One, 2011, 6(8): e23657) describes methods for in vitro differentiation of human iPS cells to cardiomyocytes. The authors describe the use of the cell marker VCAM1 (vascular cell adhesion molecule 1) for the enrichment of cardiomyocytes, providing a 95-98% enrichment for TNNT2 (cardiac troponin-T) positive cardiomyocytes from a stem cell population. In some embodiments, the combination of markers VCAM1 and CD144, CD140b and TRA-1 can be used to isolate a population of cardiomyocytes from undifferentiated hESCs and hiPSCs, as disclosed in the methods discussed in the Uosaki et al. publication.

In some embodiments, cardiomyocytes as disclosed herein can differentiate into mature cardiomyocytes, e.g., ventricular cardiomyocytes by organization in an ansiotrophic manner by being cultured on the surface of the ANP polymer substrate as disclosed herein, and can develop into functional ventricular tissue which comprises spontaneous periodic contractile activity. In some embodiments, the functional ventricular tissue can be evoked to contract upon appropriate stimulation. Spontaneous contraction generally means that, when cultured in a suitable tissue culture environment with an appropriate $Ca^{2+}$ concentration and electrolyte balance, the cells can be observed to contract in a periodic fashion along one axis of the cell, and then release from contraction, without having to add any additional components to the culture medium. Non-spontaneous contraction may be observed, for example, in the presence of pacemaker cells, or other stimulus.

Methods to determine the expression, for example the expression of RNA or protein expression of markers of cardiomyocytes as disclosed herein, such as Mef2c and Nkx2.5 expression are well known in the art, and are encompassed for use in the methods described herein. Such methods of measuring gene expression are well known in the art, and are commonly performed on using DNA or RNA collected from a biological sample of the cells, and can be performed by a variety of techniques known in the art, including but not limited to, PCR, RT-PCR, quantitative RT-PCR (qRT-PCR), hybridization with probes, northern blot analysis, in situ hybridization, microarray analysis, RNAse protection assay, SAGE or MPSS. In some embodiments, the probes used detect the nucleic acid expression of the marker genes can be nucleic acids (such as DNA or RNA) or nucleic acid analogues, for example peptide-nucleic acid (PNA), pseudocomplementary PNA (pcPNA), locked nucleic acid (LNA) or analogues or variants thereof.

In other embodiments, the expression of the markers can be detected at the level of protein expression. The detection of the presence of nucleotide gene expression of the markers, or detection of protein expression can be similarity analyzed using well known techniques in the art, for example but not limited to immunoblotting analysis, western blot analysis, immunohistochemical analysis, ELISA, and mass spectrometry. Determining the activity of the markers, and hence the presence of the markers can be also be done, typically by in vitro assays known in by a person skilled in the art, for example Northern blot, RNAse protection assay, microarray assay etc of downstream signaling pathways of Mef2c and Nkx2.5. In particular embodiments, qRT-PCR can be conducted as ordinary qRT-PCR or as multiplex qRT-PCR assay where the assay enables the detection of multiple markers simultaneously, for example Mef2c and/or Nkx2.5, either together or separately, from the same reaction sample.

The methods of RNA isolation, RNA reverse transcription (RT) to cDNA (copy DNA) and cDNA or nucleic acid amplification and analysis are routine for one skilled in the art and examples of protocols can be found, for example, in the Molecular Cloning: A Laboratory Manual (3-Volume Set) Ed. Joseph Sambrook, David W. Russel, and Joe Sambrook, Cold Spring Harbor Laboratory; 3rd edition (Jan. 15, 2001), ISBN: 0879695773. Particularly useful protocol source for methods used in PCR amplification is PCR (Basics: From Background to Bench) by M. J. McPherson, S. G. Møller, R. Beynon, C. Howe, Springer Verlag; 1st edition (Oct. 15, 2000), ISBN: 0387916008. Other methods for detecting expression of the marker genes by analyzing RNA expression comprise methods, for example but not limited to, Northern blot, RNA protection assay, hybridization methodology and microarray assay etc. Such methods are well known in the art and are encompassed for use in this invention.

Primers specific for PCR application can be designed to recognize nucleic acid sequence encoding Mef2c and Nkx2.5, are well known in the art. For purposes of an example only, the nucleic acid sequence encoding human Mef2c can be identified by accession number: AL833268 or NM_002397. For purposes of an example, the nucleic acid sequence encoding human Nkx2.5 can be identified by GenBank Accession No: AB021133 or NM_004387.

Nkx2-5 is a cardiac transcription factor that binds the atrial natriuretic factor promoter. Durocher et al. (1997) EMBO J. 16:5687. Amino acid sequences of Nkx2-5 polypeptides are known in the art. See, e.g., Turbay et al. (1996) MoI. Med. 2:86; GenBank Accession No. NP_004378 {*Homo sapiens* Nkx2-5); GenBank Accession No. AAC97934; *Mus musculus* Nkx2-5); and GenBank Accession No. AAB62696 (*Rattus norvegicus* Nkx2-5).

Nucleotide sequences encoding Nkx2-5 polypeptides are known in the art. See, e.g., GenBank Accession No.

NM_004387 (encoding a *Homo sapiens* Nkx2-5 polypeptide); GenBank Accession No. AF091351 (encoding a *Mus musculus* Nkx2-5 polypeptide); and GenBank Accession No. AF006664 (encoding a *Rattus norvegicus* Nkx2-5 polypeptide).

Any suitable immunoassay format known in the art and as described herein can be used to detect the presence of and/or quantify the amount of marker, for example Mef2c or Nkx2.5, expressed by the cardiomyocytes.

Immunohistochemical assays are well known to those of skill in the art (e.g., see Jalkanen, et al., J. Cell. Biol. 101:976-985 (1985); Jalkanen, et al., J. Cell. Biol. 105:3087-3096 (1987). Antibodies, polyclonal or monoclonal, can be purchased from a variety of commercial suppliers, or may be manufactured using well-known methods, e. g., as described in Harlow et al., Antibodies: A Laboratory Manual, 2nd Ed; Cold. Spring Harbor Laboratory Press, Cold Spring Harbor, N.Y. (1988).

Commercially available antibodies can be purchased from companies such as Cell Signalling, ABI, Sigma, Stressgen, SantaCruz Biotechnology, AbCam, Ad Serotec, Invitrogen and the like.

Where it is desired to confirm that cells have been differentiated to cardiomyocytes, it can be helpful to permeabilize a sample of the cells for staining of cytoplasmic or nuclear markers. In general, antibodies that specifically bind a differentially expressed polypeptide are added to a sample, and incubated for a period of time sufficient to allow binding to the epitope, usually at least about 10 minutes. The antibody can be detectably labeled for direct detection (e.g., using radioisotopes, enzymes, fluorophores, chemiluminescent labels, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods of qualitative or quantitative detection of levels or amounts of differentially expressed polypeptide can be used, for example ELISA, western blot, immunoprecipitation, radioimmunoassay, etc.

In addition to protein markers detectable by immunological methods, structural or morphological methods can also be used to confirm cardiomyocyte differentiation. If such a marker is a morphological and/or functional trait or characteristic, suitable methods including visual inspection using, for example, the unaided eye, a stereomicroscope, a dissecting microscope, a confocal microscope, or an electron microscope are encompassed for use in the invention. Also contemplated are methods of analyzing the progressive or terminal differentiation of a cell employing a single marker, as well as any combination of molecular and/or non-molecular markers.

Also encompassed for use in the methods and compositions described herein are in vitro-differentiated cardiomyocytes selected using an introduced reporter gene that aids with the identification and selection of cardiomyocytes from a mixed population comprising cardiomyocytes and non-cardiomyocytes. For example, stem cells or cardiomyocyte precursors can be genetically engineered to express a construct comprising a reporter gene which can be used for selection and identification purposes. For example, cardiomyocytes or population of cardiomyocytes can be genetically engineered to comprise a reporter gene including, but not limited to, a fluorescent protein, enzyme or resistance gene, which is operatively linked to a particular promoter (including, but not limited to Mef2c and/or Nkx2.5) active only in cardiomyocytes. In such an embodiment, when the cell expresses the gene to which the reporter of interest is operatively linked, it also expresses the reporter gene, for example the enzyme, fluorescent protein or resistance gene. That is, only cells that have differentiated to cardiomyocytes will express the reporter. Cells that express the reporter gene can be readily detected and in some embodiments positively selected for. Other reporter genes that can be used include fluorescent proteins, luciferase, alkaline phosphatase, lacZ, or CAT.

In some embodiments, a reporter gene is a resistance gene. The resistance gene can include, for example, genes for resistance to puromycin, G418, blasticidin and variants and fragments thereof, which can be used as a functional positive selection marker to select for a population of cardiomyocytes, where the non-cardiomyocytes do not express the resistance gene. In other embodiments, the reporter gene can be a fluorescent protein, including, but not limited to: green fluorescent protein (GFP); green fluorescent-like protein (GFP-like); yellow fluorescent protein (YFP); blue fluorescent protein (BFP); enhanced green fluorescent protein (EGFP); enhanced blue fluorescent protein (EBFP); cyan fluorescent protein (CFP); enhanced cyan fluorescent protein (ECFP); red fluorescent protein (dsRED); and modifications and fluorescent fragments thereof.

In some embodiments, methods to remove unwanted cells are encompassed, by removing unwanted cells by negative selection. For example, unwanted antibody-labeled cells are removed by methods known in the art, such as labeling a cell population with an antibody or a cocktail of antibodies, to a cell surface protein and separation by FACS or magnetic colloids. In an alternative embodiment, the reporter gene may be used to negatively select non-desired cells, for example a reporter gene encodes a cytotoxic protein in cells that are not desired. In such an embodiment, the reporter gene is operatively linked to a regulatory sequence of a gene normally expressed in the cells with undesirable phenotype.

Once cardiomyocytes have been differentiated in vitro, e.g., from an appropriate stem cell population, they can be applied to a nanotextured substrate as described herein. The cells can be of mammalian origin, and in some embodiments the cardiomyocytes are of human origin. In other embodiments, a population of cardiomyocytes are or rodent origin, for example mouse, rat or hamster. In another embodiment, a population of cardiomyocytes includes genetically engineered cardiomyocytes, for example where a population of cardiomyocytes have been genetically modified to carry a pathological gene which causes, or increases the risk of a cardiovascular disease. Alternatively, cardiomyocytes can be genetically modified to have a functional characteristic of a cardiovascular disease or arrhythmia, for instance the cardiomyocytes exhibit a functional phenotype of a cardiovascular disease, or abnormal action potential. By way of a non-limiting example, cardiomyocytes which have a characteristic or phenotype of a cardiovascular disease or arrhythmia can exhibit, for example, a decrease in spontaneous contraction, or decrease or increase in contractile force, etc.

Seeding the In Vitro-Differentiated Cardiomyocytes on the ANP Polymer

After the preparation of in vitro-differentiated cardiomyocytes as described herein above, in the Examples herein, or as known in the art, the cells can be seeded onto nanotextured substrates as described herein. This is generally accomplished by simply adding as suspension of the cells to a dish or wells of a multiwell plate comprising the nanotextured substrate, generally with an appropriate tissue culture medium. In some embodiments, the ANP which is coated with immature cardiomyocytes can be in any geometric conformation, for example, a flat sheet (e.g., substantially planar), a spiral, a cone, a v-like structure and the like. In some embodiments, after culturing the immature cardiomyocytes on the ANP, the ANP is removed (e.g. bioabsorbed or physically removed), and the layers of mature cardiomyocytes maintain substantially the same conformation as the scaffold, such that, for example, if the scaffold was spiral shaped, the mature cardiomyocytes form a 2D- and 3D-engineered myocardium tissue which is spiral shaped. In some embodiments, the shape of the scaffold is a V, such that the 3D engineered myocardium is in a V-like shape such that when contraction occurs it forms a pincher like action.

In some embodiments, the construction of the tissue engineered myocardium composition can be carried out by assembling multiple ANPs and then seeding them with in vitro differentiated cardiomyocytes. Each assembly is cultured, and the cells align and mature due to the nanotexture. Alternatively, a layered tissue engineered myocardium composition can be assembled in an iterative manner in which an ANP is seeded with immature cardiomyocytes and cultured for a predetermined time to allow maturation of the cardiomyocytes, and then the monolayer of mature cardiomyoctes can be removed and stacked upon other monolayers of mature cardiomyocytes. This seed/stack process is repeated to construct the structure. In some embodiments, any number of monolayers of matured cardiomyocytes can be removed from the ANPs and stacked, for example at least 2, or at least 3, or at least 4, or a least 5, or at least 6 or a least 7 or more monolayers of cardiomyocyte cells.

In some cases a second cell type other than immature cardiomyocytes cells can be seeded together or sequentially, e.g., for construction of muscle tissue with blood vessels where an ANP layer is seeded with immature cardiomyocytes and then a layer of ANP is seeded with a different population of cells which make up blood vessels, neural tissue, cartilage, tendons, ligaments and the like. The predetermined pattern of the ANP as well as the combination of use of immature cardiomyocytes with other populations of cells will determine the desired functionality of the myocardial tissue. For example, ventricular myocardium with a pacemaker functionality will comprise immature cardiomyocytes in combination with a pacemaker cell type, and a ventricular myocardium with ligament or tendon structures will comprise immature cardiomyocytes in combination with cell types which generate tendon and ligament structures. It is contemplated that different texturing of substrate can enhance the functional characteristics or differentiation of the other cell types seeded on such substrates.

Maturation and Measurement of Maturation of In Vitro-Differentiated Myocytes and Cardiomyocytes on the ANP Polymer Substrate.

As disclosed herein, the ANP substrate as disclosed herein can be used in methods to mature in vitro-differentiated cardiomyocytes to a more mature, or differentiated phenotype as compared to cardiomyocytes not cultured on a substrate, or cardiomyocytes cultured on a similar polymer substrate which does not comprise nanotexture as described (e.g., a non-ANP substrate). In some embodiments, the cardiomyocytes are any known subpopulation of cardiomyocytes, including, but not limited to atrial cardiomyocytes, ventricular cardiomyocytes, outflow tract cardiomyocytes, conduction system cardiomyocytes, and coronary arterial tree differentiation.

In some embodiments, the myocytes are any known subpopulation of myocytes, for example, but not limited to cardiomyocytes, skeletal muscle myocytes, and smooth muscle myocytes.

In some embodiments, the in-vitro differentiated cardiomyocytes are immature cardiomyocytes, e.g., less mature than isolated cardiomyocytes. In particular, in vitro-differentiated cardiomyocytes derived from stem cells, e.g., ESC and/or iPSC-derived cardiomyocytes have a more fetal phenotype. Culturing the ESC and/or iPSC-derived cardiomyocytes on the ANP allows further maturation of the cells in a multi-cellular format mimicking cardiac like ansiotrophic structure and expressing markers, and having functional properties which are more characteristic of adult cardiomyocyte phenotypes.

Accordingly, in some embodiments, the ANP can be used to enhance the maturation of in vitro-differentiated cardiomyocytes to a more mature, differentiated phenotype which have similar functional, electrophysiological, morphological, and marker expression characteristic of the phenotype of mature adult cardiomyocytes.

In some embodiments, the cardiomyocytes spontaneously organize in an anisotropic manner on the ANP substrate to become more differentiated and display a mature, adult-like phenotype. Cardiomyocytes can be identified as having a mature phenotype by an increased expression of cardiac specific transcription factors, cardiac specific proteins expressed in adult human heart, expression of ion and voltage channels, as compared to an immature cardiomyocyte. In some embodiments, the ANP substrate enhances the maturation of cardiomyocytes so they are anisotropically organized similar to adult heart tissue patterns as compared to cardiomyocytes cultured on control textures (e.g., non-ANP substrates). In some embodiments, the ANP substrate enhances the maturation of cardiomyocytes such that they have increased hypertrophy and/or increase in the size of cells as compared to such immature cardiomyocytes, or cardiomyocytes cultured on non-ANP substrates. In some embodiments, the ANP substrate enhances the maturity of the cardiomyocytes such that they have increased Z-disk and a higher expression of gap junction proteins.

In some embodiments, cardiomyocytes which have differentiated to a more mature phenotype by culturing on the surface of the ANP substrate have increased cell-cell connections, increased cell-contraction, an anisotropic arrangement of cells, as well as anisotropic/directional propagation of an induced electrical impulse across the cultured tissue on nanotextured platform, as compared to cardiomyocytes cultured on a non-nanotextured polymer substrate lacking the array of parallel grooves and ridges.

In some embodiments, an ANP can be used to enhance the maturation of in vitro-differentiated cardiomyocytes into a more mature, differentiated phenotype, where the more mature cardiomyocytes have increased expression of markers characteristic of mature cardiomyocytes. In some embodiments, the cardiomyocytes have an increased expression of cardiomyocyte markers α-actinin, c-TnT, β-MHC expression. In some embodiments, the culturing of the in vitro-differentiated cardiomyocytes on the ANP substrate increases the expression of these cardiomyocyte markers by at least about 10%, or at least about 20% or at least about 30% or at least about 40% or more than 40% as compared to cardiomyocytes which have been cultured on non-nanotextured polymer substrate lacking the array of parallel grooves and ridges.

In some embodiments, cardiomyocytes which have differentiated to a more mature phenotype by culturing on the surface of the ANP substrate can have any one of the following characteristics of mature cardiomyocytes: an increased anisotropy, and increased cellular alignment, as well as an anisotropic arrangement of gap junctions & cadherins between cells, increased T-tubule formation and caveolin expression, as compared to cardiomyocytes which have been cultured on a non-nanotextured polymer substrate lacking the array of parallel grooves and ridges. In some embodiments, the cardiomyocytes which have been matured on the ANP substrate increases anisotropy, cellular alignment, and anisotropic arrangement of gap junctions & cadherins between cells, and increases the T-tubule formation and caveolin expression, by at least about 10%, or at least about 20% or at least about 30% or at least about 40% or more than 40% as compared to cardiomyocytes which have been cultured on non-nanotextured polymer substrate lacking the array of parallel grooves and ridges.

In some embodiments, cardiomyocytes which have differentiated to a more mature phenotype by culturing on the surface of the ANP substrate can have any one of the following characteristics of mature cardiomyocytes: an increased conversion of ssTnI to ctTnI (cardiac tissue troponin I), conversion or switching of titin isoform N2BA to N2B, similar expression of voltage gated K+ channels, Na+ channels, voltage dependent Ca2+ channels, cyclic nucleotide dependent K+ channels, and other ion channels which are characteristic of adult mature cardiomyocytes. Expression of ion or voltage channels can be any method commonly known by persons of ordinary skill, e.g., RT-PCR and other methods.

In some embodiments, cardiomyocytes which have differentiated to a more mature phenotype by culturing on the surface of the ANP substrate can have an increased contraction at single cell and/or multi-cellular level, (which can be determined by, for example, contraction mapping aided by microscopy) and/or increased contractile strength (e.g., strength of contraction). In some embodiments, the cardiomyocytes which have been matured on the ANP substrate have an increased contraction at single cell and/or multi-cellular level, and/or increased contractile strength by at least about 10%, or at least about 20% or at least about 30% or at least about 40% or more than 40% as compared to cardiomyocytes which have been cultured on non-nanotextured polymer substrate lacking the array of parallel grooves and ridges.

In some embodiments, cardiomyocytes which have differentiated to a more mature phenotype by culturing on the surface of the ANP substrate can have the electrophysical characteristics of adult mature cardiomyocytes, e.g., increased cell-cell electrical conductivity, increased syncytial nature of 2D in vitro culture in large area (cm$^2$) allowing electrical action potential to propagate from one point to another, increased wave speed and decreased excitation threshold, increased Ca2+ transient current. In some embodiments, the cardiomyocytes which have been matured on the ANP substrate have an increased cell-cell electrical conductivity, and/or increased electrical action potential to propagate from one point to another, and/or increased wave speed and/or decreased excitation threshold, and/or increased Ca2+ transient current by at least about 10%, or at least about 20% or at least about 30% or at least about 40% or more than 40% as compared to cardiomyocytes which have been cultured on non-nanotextured polymer substrate lacking the array of parallel grooves and ridges.

In some embodiments, the matured cardiomyocytes have the characteristics of adult mature cardiomyocytes, for example, they have an increased expression of cardiac specific transcription factors, cardiac specific proteins expressed in adult human heart, expression of ion and voltage channels more similar to adult heart tissue pattern as compared to cardiomyocytes cultured on control textures, hypertrophy or increased size of cells, increased Z-disk, higher expression of gap junction proteins, increased cell-cell connection, increased cell-contraction, anisotropic arrangement of cells, anisotropic/directional propagation of an induced electrical impulse across the cultured tissue on nanotextured platform, as compared to immature cardiomyocytes, or cardiomyocytes which have not been cultured on the nanotextured platform. In some embodiments, increased size of cells and/or increase in Z-disc can be detected using microscope analysis after staining with F-actin. In some embodiments, an increase in cell-cell connection can be assessed by microscope analysis after immunostaining for connexin-43 and electrical propagation using optical mapping. In some embodiments, increased cell contraction can be assessed by contractile analysis using video microscopy, and mathematical analysis. In some embodiments, the anisotropic arrangement of cells can be assessed by microscopy and mathematical analysis after immunostaining with analysis F-actin and a-actinin. In some embodiments, anisotropic/directional propagation of induced electrical impulse, and/or increased cell-cell electrical conductivity can be assessed by optical mapping. In some embodiments, an increased syncytial nature of cells can be assessed by optical mapping using voltage sensitive dye after point stimulation by electrodes. In some embodiments, increased wave speed and/or decreased excitation threshold can be assessed by optical mapping, and/or patch clamping.

Uses of the ANP Polymer Substrate Comprising Cardiomyocytes

In some embodiments, a composition comprising the ANP polymer substrate and cardiomyocytes and/or tissue engineered myocardium composition and method of their generation as disclosed herein are useful for various research applications, treatment methods, and screening methods.

Accordingly, the ANP polymer substrate as disclosed herein can be used as a cell culture platform with tunable parameters, such as variable polymer composition, rigidity and topography type and dimension. More specifically, an ANP polymer substrate can be seeded with human pluripotent stem-cell derived cardiomyocytes to create anisotropic, confluent monolayers of cardiomyocytes which more closely mimic native cardiac tissue. Additionally, the pairing of electrical pacing systems in parallel with the gratings will further condition and mature the cardiomyocytes.

Research Applications

One of the most frequent side effects of new or investigational drugs resulting in the drug being deemed unsafe is cardiac toxicity or functional disturbance. The in vitro-differentiated cell/substrate compositions derived herein provide an assay system, readily scaled for high throughput analyses, that permits evaluation or prediction of cardiac effects of test agents. The platform described herein can be used to screen for such off-target effects, or, alternatively, to identify agents with a desired effect on cardiac muscle, e.g., maintaining or setting proper rhythm or enhancing contraction strength, etc. For example, a ANP and cardiomyocyte population generated herein using a subject method can be contacted with a test agent, and the effect, if any, of the test agent on a biological activity of cardiomyocyte cell population present on the ANP, or the function contractibility of a cardiomyocyte cell population can be assessed, where a test agent that has an effect on a biological activity of a cardiomyocyte cell population or the contractibility of the tissue engineered myocardium is a candidate agent for treating a cardiac disorder. Alternatively, one can use introduction of the tissue engineered myocardium into a non-human animal model of a disease (e.g., a cardiac disease, or arrhythmia) to determine efficacy of the tissue engineered myocardium in the treatment of the disease.

By way of an example only, a 24 well plate (4×6) can be used with 4 rows of different scaffold rigidities and 6 columns of varying nanotexture dimensions. hiPSC-CMs can be seeded to each well and cultured. During cell culture, the impact of variable rigidity and topography on cell morphology and alignment can be monitored, e.g. certain nanotopography dimensions induce more cell anisotropy or certain rigidities increase cell spreading. These wells can also be individually analyzed in a number of cell characterization techniques, such as biochemical analysis, to characterize scaffold parameters in affecting cardiomyocyte maturity and protein expression. This experiment could answer basic science questions about the role of the cardiac microenvironment in regulating cell function or development.

In some embodiments, the ANP polymer substrate can also be useful in modeling diseases. For example, as differing cardiac disease states can be characterized through changes in ECM architecture or changes in tissue stiffness, these disease states can be modeled and replicated through the ANP substrate. A researcher could characterize and compare the function of the cardiomyocytes in defined disease states. This more accurate modeling of cardiac pathology could allow for insight into the development of such disease states and the differing effects of pharmaceuticals on healthy cardiac tissue versus diseased cardiac tissue.

Screening Methods

As noted above, a ANP and cardiomyocyte population or tissue engineered myocardium composition as disclosed herein can be used in a screening method to identify candidate agents for treating a cardiac disorder. For example, a composition comprising an ANP and cardiomyocyte population can be contacted with a test agent; and the effect, if any, of the test agent on a parameter associated with normal or abnormal cardiomyocyte function, such as contractibility, including frequency and force of contraction is determined. Such parameters can also include: expression of a cardiomyocyte-specific marker; propagation of electrical signals associated with heart beating; and the like. The cells can be derived from a patient with a known cardiac defect or functional anomaly. In that instance, the methods permit screening to identify agents or procedures that will correct or ameliorate the defect or anomalous function.

By way of example only, a drug screening method could be as follows: A 96 (8×12) well plate can be used with one set nanotopography dimension and rigidity which will model healthy cardiac tissue. 8 different patient iPSC-CMs can be used (each row has a different patient cardiac model). 12 drugs can be tested on each patient's healthy cardiac model, and the effects of these drugs on cardiomyocyte function as well as phenotype and protein expression can be analyzed in tandem. As each person is different, not all drugs will have the same effects on cardiac function. Such a platform will allow the screening of drugs in a diverse patient population.

The development of a novel "off-the-shelf" engineered heart tissue platform, e.g., the ANP comprising cardiomyocytes for high throughput drug screening would have wide applicability both for safety testing and the identification of new therapeutic compounds. Indeed, many promising compounds are found to have unanticipated cardiotoxic effects, with pro-arrhythmic interference cardiac ion channels being the most common reason that otherwise efficacious drugs are removed from the market. Regulatory agencies require preclinical safety screens in heterologous systems (e.g. cultured cells genetically modified to overexpress a particularly susceptible ion channel, such as the HERG channel) and animal models, but both have important limitations. Heterologous systems lack the full constellation of ion channels and signaling pathways present in intact cardiomyocytes, while animal studies are very expensive, low-throughput and often limited to relatively short time-points. There are also important differences between human and non-human cardiomyocytes in terms of their electrophysiological properties and neurohormonal responsiveness.

Another aspect of the technology described herein relates to a use of a composition comprising an ANP and cardiomyocyte population as disclosed herein, in assays to identify agents which affect (e.g. increase or decrease) the contractile force and/or contractibility of the tissue engineered myocardium in the presence of the agent as compared to a control agent, or the absence of an agent. Such an assay is useful to identify an agent which has a cardiotoxic effect, such as an agent which decreases contractile force, and/or cardiomyocyte atrophy, and/or results in another dysregulation of contractibility, such as arrhythmia or abnormal contraction rate. In another embodiment, such an assay is useful to identify an agent which has a cardiotoxic effect by increasing contractile force and/or other types of dysregulation such as an increase in contraction rate and could lead to the development of cardiac muscle hypertrophy.

In another embodiment, a composition comprising an ANP and cardiomyocyte population as disclosed herein can be used in an assay to study a cardiovascular disease. By way of an example only, a composition comprising an ANP and cardiomyocyte population can comprise genetically modified cardiomyocytes, for example cardiomyogenic progenitors or cardiomyocytes carrying a mutation, polymorphism or other variant of a gene (e.g. increased or decreased expression of a heterologous gene) which can be assessed to see the effects of such a gene variant on the contractile force and contractile ability of the composition comprising an ANP and cardiomyocyte population. Such a composition comprising an ANP and cardiomyocyte population comprising genetically modified cardiomyogenic progenitors, or immature cardiomyocytes can also be used to identify an agent which attenuates (e.g. decreases) any dysfunction in contractibility or contraction force as a result of the genetically modified cardiomyogenic progenitors or cardiomyocytes, or alternatively can be used to identify an agent which augments (e.g. increases) any dysfunction in contractibility or contraction force as a result of the genetically modified cardiomyogenic progenitors or cardiomyocytes.

Another aspect of the technology described herein relates to methods to screen for agents, for example any entity or chemical molecule or gene product which affects (e.g. increase or decrease) the functionality of a composition comprising an ANP and cardiomyocyte population as disclosed herein, such as an agent which increases or decreases the contractile force, and/or frequency of contraction and/or contractibility of the composition comprising an ANP and cardiomyocyte population in the presence of the agent as compared to a control agent, or the absence of an agent. In such an embodiment, an agent which increases or decreases the contractile force, and/or frequency of contraction and/or contractibility of the composition comprising an ANP and cardiomyocyte population can affect the function of a cardiomyocyte, for example but not limited to, an agent which promotes differentiation, proliferation, survival, regeneration, or maintenance of a population of cardiomyocytes, or an agent which prevent the differentiation of cardiomyocytes into mature cardiomyocytes, e.g., mature ventricular cardiomyocytes, and/or inhibits or negatively affects the cardiomyocytes, e.g., ventricular cardiomyocyte function.

Parameters are quantifiable components of cells, particularly components that can be accurately measured, desirably in a high throughput system. A useful parameter can be any measurable parameter related to the action potentials and/or other electrical function and/or functional contraction of a composition comprising an ANP and cardiomyocyte population and/or the tissue engineered myocardium as disclosed herein. Such parameters include, but are not limited to, action potential frequency, duration and threshold of activation, contractile force, peak systolic stress, frequency of contraction and the like. Other parameters include changes in characteristics and markers of the cardiomyocytes, and/or a change in the cardiomyocyte phenotype, including but not limited to changes in cardiomyocyte markers, cell surface determinant, receptor, protein or conformational or post-translational modification thereof, lipid, carbohydrate, organic or inorganic molecule, nucleic acid, e.g. mRNA, DNA, etc. or a portion derived from such a cell component or combinations thereof. While most parameters related to functionality of the composition comprising an ANP and cardiomyocyte population provide a quantitative readout, in some instances a semi-quantitative or qualitative result will also be acceptable. Readouts can include a single determined value, or may include mean, median value or the variance, etc. Characteristically a range of parameter readout values will be obtained for each parameter from a multiplicity of the same assays. Variability is expected and a range of values for each of the set of test parameters can be obtained using standard statistical methods with a common statistical method used to provide single values.

As discussed, an agent which effects or modulates (e.g. increase or decrease) the functionality of a composition comprising an ANP and cardiomyocyte population and/or the tissue engineered myocardium as disclosed herein, can be screened for. Such an agent, for example, can increase or decrease the contractile force, and/or frequency of contraction and/or contractibility of the composition comprising an ANP and cardiomyocyte population and/or tissue engineered myocardium in the presence of the agent as compared to a control agent, or the absence of an agent. Thus, in some embodiments, any agent which increases or decreases the end diastole to peak diastole and back by a statistically significant amount, or by at least about 10% as compared to the end to diastole to peal diastole and back in the absence of an agent, or from a reference value 500 ms, is identified to have modulated the function of the tissue engineered myocardium. If an agent increases or decreases the end diastole to peak diastole and back by at least about 10% or by at least about 15% or at least about 20% or at least about 30%, or least about 40% or at least about 50% or more than 50% as compared to a reference end diastole to peak diastole value (e.g. 500 ms) it is identified to have modulated the function of the composition comprising an ANP and cardiomyocyte population and/or tissue engineered myocardium construct.

In some embodiments, any agent which increases or decreases the Vmax of an action potential generated by cardiomyocytes present on the ANP by a statistically significant amount, or by at least about 10% as compared to the Vmax of an action potential generated by cardiomyocytes present on the ANP in the absence of an agent, or from the reference value of ~10V/ms, is identified to have modulated the function of the cardiomyocytes present on the ANP and/or tissue engineered myocardium. If an agent increases or decreases the Vmax by at least about 10% or by at least about 15% or at least about 20% or at least about 30%, or least about 40% or at least about 50% or more than 50% as compared to a reference Vmax (e.g. 10 V/ms) it is identified to have modulated the function of the cardiomyocytes present on the ANP polymer substrate.

In some embodiments, any agent which increases or decreases the action potential duration (ADP) 50 of an action potential generated by cardiomyocytes present on the ANP by a statistically significant amount, or by at least about 10% as compared the ADP 50 of an action potential generated a cardiomyocyte present on the ANP in the absence of an agent, or from the reference value of 165 ms, is identified to have modulated the function of the cardiomyocytes present on the ANP. If an agent increases or decreases the ADP 50 by at least about 10% or by at least about 15% or at least about 20% or at least about 30%, or least about 40% or at least about 50% or more than 50% as compared to a reference ADP 50 (e.g. 165 ms) it is identified to have modulated the function of the cardiomyocytes present on the ANP.

In some embodiments, any agent which increases or decreases the ADP 90 of an action potential generated by cardiomyocytes present on the ANP a statistically significant amount, or by at least about 10% as compared the ADP 90 of an action potential generated cardiomyocytes present on the ANP in the absence of an agent, or from the reference value of 100 ms, is identified to have modulated the function of the tissue engineered myocardium. If an agent increases or decreases the ADP 90 by at least about 10% or by at least about 15% or at least about 20% or at least about 30%, or least about 40% or at least about 50% or more than 50% as compared to a reference ADP 90 (e.g. 100 ms) it is identified to have modulated the function of the cardiomyocytes present on the ANP.

In some embodiments, any agent which increases or decreases the amplitude (Amp) of an action potential generated by cardiomyocytes present on the ANP by a statistically significant amount, or by at least about 10% as compared to the amplitude of an action potential generated by cardiomyocytes present on the ANP in the absence of an agent, or from the reference value of 58 mV, is identified to have modulated the function of the tissue engineered myocardium. If an agent increases or decreases the amplitude by at least about 10% or by at least about 15% or at least about 20% or at least about 30%, or least about 40% or at least about 50% or more than 50% as compared to a reference amplitude (e.g. 58 mV) it is identified to have modulated the function of cardiomyocytes present on the ANP.

A cardiomyocyte present on the ANP as disclosed herein can also spontaneously beat about 20 beats/min. Thus, in some embodiments, any agent which increases or decreases the frequency of beats/min of cardiomyocytes present on the ANP by a statistically significant amount, or by at least about 10% as compared the frequency of beat by cardiomyocytes present on the ANP in the absence of an agent, or from the reference value of 20 beats/min, is identified to have modulated the function of the cardiomyocytes present on the ANP.

If an agent increases or decreases the frequency of beats by at least about 10% or by at least about 15% or at least about 20% or at least about 30%, or least about 40% or at least about 50% or more than 50% as compared to a reference number of beats (e.g. 20 beats/min), the agent is identified to have modulated the function of the cardiomyocytes present on the ANP.

In another embodiment, the methods described herein provide a screen for agents which have cardiovascular toxicity. In some embodiments, an agent (such as a drug or compound) can be an existing agent, and in other embodiments, an agent can be new agent or modified version of an existing agent (e.g. a modified drug or compound or variant thereof). In another embodiment, a composition comprising the ANP and a cardiomyocyte population as disclosed herein can be used for screening methods of an agent which affects cardiomyocytes and/or stem cell-derived, e.g., iPSC or ESC-derived cardiomyocytes present on the ANP polymer substrate, and in some embodiments, the cardiomyocytes present on the ANP are a variant cardiomyocyte, for example but not limited to a genetic variant and/or a genetically modified cardiomyocyte as disclosed herein.

A composition comprising the ANP comprising cardiomyocytes as disclosed herein is also useful for in vitro assays and screening to detect agents that are active on cardiomyocytes present on the ANP, for example, to screen for agents that affect the differentiation and/or maturation of cardiomyocytes present on the ANP, including differentiation of the immature cardiomyocytes into a more mature and more differentiated cardiomyocyte, and differentiation of immature cardiomyocytes along the cardiomyocyte lineage, for example ventricular cardiomyocyte lineages. Of particular interest are screening assays for agents that are active on human cardiomyocyte cells. In such embodiments, the cardiomyocyte cells can be ES derived or iPS derived-cardiomyocytes.

In some embodiments, the composition comprising the ANP comprising cardiomyocytes for use in screening purposes can comprise cardiomyocytes with a desired pathological characteristic. For example, the desired pathological characteristic can include a mutation and/or polymorphism which contributes to disease pathology, such as a cardiovascular disease or arrhythmia. In such an embodiment, the cardiomyocytes can be derived from a stem cell, e.g., iPSC originally obtained from a subject with such a pathology, and/or alternatively, genetically modified to have a mutation or polymorphism that is characteristic of a particular disease pathology. In such embodiments, a composition comprising the ANP comprising cardiomyocytes which have a desired pathological characteristic can be used to screen for agents which alleviate at least one symptom of the pathology, e.g., alleviate the characteristic of the action potentials from the cardiomyocytes back to a more normal phenotype.

In alternative embodiments, a composition comprising the ANP comprising a population of genetic variant cardiomyocytes, e.g., cardiomyocytes which endogenously, or genetically have been modified to have a particular mutation and/or polymorphism, can be used to identify agents that specifically alter the function cardiomyocytes present on the ANP substrate as compared to the effect of the agent on the function of normal cardiomyocytes present on the ANP substrate (e.g. cardiomyocytes without the mutation and/or polymorphism). Accordingly, a composition comprising the ANP comprising a population of a genetic variant cardiomyocytes can be used to assess the effect of an agent in defined subpopulations of people and/or cardiomyocytes which carry the modification. Therefore, the technology described herein permits high-throughput screening of agents for personalized medicine and/or pharmacogenetics. The manner in which a composition comprising the ANP comprising a population of genetic variant cardiomyocytes responds to an agent, particularly a pharmacologic agent, including the timing of responses, is an important reflection of the physiologic state of the cell.

The agent used in the screening method using a composition comprising the ANP comprising cardiomyocytes as disclosed herein can be selected from a chemical, small molecule, nucleic acid, nucleic acid analog, aptamer, protein or polypeptide or analogue or fragment thereof. In some embodiments, the nucleic acid is DNA or RNA, and nucleic acid analogues, for example can be PNA, pcPNA and LNA. A nucleic acid may be single- or double-stranded, and can be selected from a group comprising a nucleic acid encoding a protein of interest, oligonucleotides, PNA, etc. Such nucleic acid sequences include, but are not limited to, nucleic acid sequence encoding proteins that act as transcriptional repressors, antisense molecules, ribozymes, and small inhibitory nucleic acid sequences, including, but not limited to RNAi, shRNAi, siRNA, micro RNAi (mRNAi), antisense oligonucleotides etc. A protein and/or peptide agent or fragment thereof, can be any protein of interest, including, but not limited to: mutated proteins; therapeutic proteins; truncated proteins, wherein the protein is normally absent or expressed at lower levels in the cell. Proteins of interest can be selected from a group comprising: mutated proteins; genetically engineered proteins; peptides; synthetic peptides; recombinant proteins; chimeric proteins; antibodies; humanized proteins; humanized antibodies; chimeric antibodies; modified proteins and fragments thereof. An agent can contact the surface of the composition comprising the ANP comprising cardiomyocytes (e.g. contact the population of cardiomyocytes) such as by applying the agent to a medium surrounding the composition comprising the ANP comprising cardiomyocytes, where it contacts the cardiomyocytes and induces its effects. Alternatively, an agent can be intracellular within the cardiomyocytes as a result of introduction of a nucleic acid sequence into cardiomyocytes and its transcription to result in the expression of a nucleic acid and/or protein agent within the cardiomyocyte. An agent as used herein also encompasses any action and/or event or environmental stimuli that a tissue composition comprising the ANP comprising cardiomyocytes is subjected to. As non-limiting example, an action can comprise any action that triggers a physiological change in the cardiomyocytes present on the ANP substrate, including, but not limited to heat-shock, ionizing irradiation, cold-shock, electrical impulse (including increase or decrease in stimuli frequency and/or stimuli intensity), mechanical stretch, hypoxic conditions, light and/or wavelength exposure, UV exposure, pressure, stretching action, increased and/or decreased oxygen exposure, exposure to reactive oxygen species (ROS), ischemic conditions, fluorescence exposure etc. Environmental stimuli also include intrinsic environmental stimuli.

The exposure (e.g. contacting) of a composition comprising the ANP and cardiomyocytes to agent may be continuous or non-continuous. In some embodiments, where the exposure (e.g. contacting) of a composition comprising the ANP and cardiomyocytes to agent is a non-continuous exposure, the exposure to one agent can be followed with the exposure to a second agent, or alternatively, by a control agent (e.g. a washing step). In some embodiments, a composition comprising the ANP and cardiomyocytes can be exposed to at least one agent, or at least 2, or at least 3, or at least 4, or at least 5, or more than 5 agents at any one time, and this exposure can be continuous or non-continuous, as discussed above.

In some embodiments, the agent is an agent of interest including known and unknown compounds that encompass numerous chemical classes, primarily organic molecules, which may include organometallic molecules, inorganic molecules, genetic sequences, etc. An important aspect of the technology described herein is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, e.g. drug candidates.

Agents such as chemical compounds, including candidate agents or candidate drugs, can be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for effect on a composition comprising the ANP and cardiomyocytes by adding the agent to at least one and usually a plurality of ANP substrates comprising cardiomyocytes. A change in a parameter (e.g. a change in a parameter to indicate a change in the contraction functionality) of a composition comprising the ANP and cardiomyocytes in response to the agent is measured, and the result is evaluated by comparison to a reference composition comprising the ANP and cardiomyocytes. A reference composition comprising the ANP and cardiomyocytes can include, but is not limited to, a composition comprising the ANP and cardiomyocytes in the absence of the same agent, or a composition comprising the ANP and cardiomyocytes in the presence of a positive control agent, where the agent is known to cause an increase or decrease in at least one parameter being assessed, e.g., such as a property of an action potential. In alternative embodiments, a reference composition comprising the ANP and cardiomyocytes is a negative control, e.g. where composition comprising the ANP and cardiomyocytes is not exposed to an agent (e.g. there is an absence of an agent), or is exposed to an agent which is known not to gave an effect on at least one parameter being assessed, e.g., does not have an effect on a property of the action potentials.

In some embodiments, the agents can be conveniently added in solution, or readily soluble form, to the tissue engineered myocardium as disclosed herein. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over a composition comprising the ANP and cardiomyocytes followed by the second. In a single solution method, a bolus of the test compound is added to the volume of medium surrounding a composition comprising the ANP and cardiomyocytes. The overall concentrations of the components of the culture medium surrounding the composition comprising the ANP and cardiomyocytes should not change significantly with the addition of the bolus, or between the two solutions in a flow through method. In some embodiments, agent formulations do not include additional components, such as preservatives, that have a significant effect on the overall formulation. Thus, preferred formulations consist essentially of a biologically active agent and a physiologically acceptable carrier, e.g. water, ethanol, DMSO, etc. However, if an agent is a liquid without a solvent, the formulation may consist essentially of the compound itself.

A plurality of assays comprising compositions of ANP and cardiomyocytes can be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, e.g. at zero concentration or below the level of detection of the agent or at or below the concentration of agent that does not give a detectable change in the phenotype, change in an action potential characteristic or contractibility of a composition comprising the ANP and cardiomyocytes.

Optionally, a composition comprising the ANP and cardiomyocytes used in a screen as disclosed herein can comprise cardiomyocytes which have been manipulated to express a desired gene product. Gene therapy and genetic modification can be used to either modify a cardiomyocyte to replace a gene product or add a heterologous gene product, or alternatively knockdown a gene product endogenous to the cardiomyocyte.

In some embodiments the genetic engineering of cardiomyocytes present on an ANP substrate can be done to facilitate the maturation and/or differentiation into a more mature phenotype, e.g., into ventricular cardiomyocytes, or for the regeneration of tissue, to treat disease, or to improve survival of the cardiomyocytes, either while they are present as a component of the ANP, or if they are removed from the ANP and used to form a 3D-tissue engineered myocardium construct as disclosed herein, to promote survival following implantation into a subject (e.g. to prevent rejection by the recipient subject). Techniques for genetically altering and transfecting cells, including cardiomyocytes are known by one of ordinary skill in the art.

A skilled artisan could envision a multitude of genes which would convey beneficial properties to a cardiomyocyte. Furthermore, cardiomyocytes can also be modified to convey an indirect beneficial property, such as the survival of the cardiomyocytes following transplantation of a tissue engineered myocardium into a subject (discussed in more detail below). An added gene can ultimately remain in the recipient cardiomyocyte and all its progeny, or alternatively can remain transiently, depending on the embodiment. As a non-limiting example, a gene encoding an angiogenic factor could be transfected into cardiomyocytes prior to seeding onto the ANP support and/or prior to generation of the composition comprising the ANP and cardiomyocytes, or alternatively a cardiomyocyte can be transfected with a desired gene product when it is part of the tissue engineered myocardium composition as disclosed herein. Use of such genes, such as genes which encode an angiogenic factor may be useful for inducing collateral blood vessel formation as the ventricular myocardium is generated, particularly if the tissue engineered myocardium is used for transplantation purposes into a subject in need of treatment, such as a subject with a cardiovascular disease or disorder. It some situations, it may be desirable to transfect cardiomyocytes with more than one gene, for instance, a gene which promotes survival and/or a gene which promotes angiogenesis, and/or a gene which inhibits or prevents rejection by the recipient subject following transplantation of a tissue engineered myocardium into a subject.

In some instances, it is desirable to have the gene product from the cardiomyocytes present on the ANP and/or in the tissue engineered myocardium secreted. In such cases, a nucleic acid which encodes the protein preferably contains a secretory signal sequence that facilitates secretion of the protein. For example, if the desired gene product is an angiogenic protein, a skilled artisan could either select an angiogenic protein with a native signal sequence, e.g. VEGF, or can modify the gene product to contain such a sequence using routine genetic manipulation (See Nabel et al., 1993).

The desired gene for use in modification of cardiomyocytes for use in a composition disclosed herein can be transfected into the cell using any of a variety of techniques. Preferably, the gene is transfected into the cell using an expression vector. Suitable expression vectors include plasmid vectors, viral vectors (such as replication defective retroviral vectors, herpes virus, adenovirus, adenovirus associated virus, and lentivirus), and non-viral delivery agents (such as liposomes or receptor ligands).

A desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used in transgenic "knockout" mice (U.S. Pat. Nos. 5,616, 491; 5,614,396). These techniques take advantage of the ability of mouse embryonic stem cells to promote homologous recombination, an event that is rare in differentiated mammalian cells. Recent advances in human embryonic stem cell culture may provide a needed component to applying the technology to human systems (Thomson; 1998). Furthermore, the methods of the technology described herein can be used to isolate and enrich for stem cells or progenitor cells that are capable of homologous recombination and, therefore, subject to gene targeting technology. Indeed, the ability to isolate and grow somatic stem cells and progenitor cells has been viewed as impeding progress in human gene targeting (Yanez & Porter, 1998).

Disease Modeling:

In some embodiments, the nanotextured substrates can be used in a method for analyzing the function of a myocyte on a nanotextured platform, comprising analysis of at least one functional parameter of the myocytes on the platform. In some embodiments, a least one functional parameter analysed is an electrical parameter, for example, but not limited to, action potential duration (ADP), wave propagation, action potential frequency, beat frequency, action potential transmission, Vmax of the acton potential, contraction force, end diastole to peak diastole rate. Such disease modeling can be used to assess the effect of an agent which restores a phenotype of the functional parameter back to a more normal phenotype. For example, in some embodiments, at least one functional parameter is analysed in the presence of an agent as compared to in the absence of an agent.

Nanotextured substrates can comprise myocytes, e.g., cardiomyocytes, skeletal muscle myocytes, smooth muscle myocytes and the like. In some embodiments, the myocytes are human, e.g., differentiated from stem cells and/or induced pluripotent stem cells (iPSC). In some embodiments, the human has a cardiovascular disease or a disorder or arrhythmia, as discussed herein. In alternative embodiments, the human, whom the iPSC-derived myocyte was derived from has a myogenic or muscle degenerative disorder, for example, but not limited to muscular dystrophy, amylateral sclerosis (ALS) and other muscle wasting disorders. Such a disease model is useful to see the effects of the muscle degenerative disorder or myogenic disorder on other muscle types, e.g., to assess their effect on cardiac cells and cardiomyocytes.

Therapeutic Uses of the ANP Comprising Cardiomyocytes and/or Tissue Engineered Myocardium Constructs.

In some embodiments, the nanotextured platform as disclosed herein can be used to generate the functional muscle tissue, e.g., functional engineered myocardium, as the nanotextured platform is patterned so that the cellular environment at multiple spatial scales (nanometer to meter) directs the maturation of in vitro differentiated myocytes, e.g., cardiomyocytes, and to subsequently organize the in vitro differentiated myocytes into two-dimensional (2D) and three-dimensional (3D) myocardial tissue structures. In some embodiments, the nanotextured platform can be coated with agents, such as differentiation factors, which further promote the differentiation of the myocytes, e.g., cardiomyocytes along a more differentiated phenotype, and/or the culture media can also comprise similar differentiating factors.

In some embodiments, an engineered myocardium construct comprises the cells and the ANP substrate, and in alternative embodiments, an engineered myocardium construct comprises the matured cells without the ANP (e.g., the cells removed in 2D-monolayers alone, or stacked together with other 2D-monolayers to form a 3D-engineered myocardium construct). Typically, a tissue engineered myocardial structure as disclosed herein is used in methods for therapeutic use or for screening agents, as disclosed herein.

In some embodiments, monolayers of cardiomyocytes are removed from an ANP substrate by altering the hydrophobicity and/or adhesiveness of the substrate. In some embodiments the ANP is coated with a thermosensitive polymer, such as PNIPAM-grafted ANP as disclosed in the Examples, allowing removal of substantially monolayers of cardiomyocytes from the ANP substrate by a change in temperature, where the substantial monolayer of cardiomyocytes can be stacked on other similar monolayers to generate the tissue engineered myocardium constructs as disclosed herein. In some embodiments, there can be non-cardiomyocyte cells between the layers of cardiomyocytes, such as fibroblasts or any epithelial cell type for vascularization of the tissue engineered myocardium as disclosed herein.

In another embodiment, the tissue engineered myocardium as disclosed herein can be used for prophylactic and therapeutic treatment of a cardiovascular condition or disease and/or a subject with arrhythmia. By way of an example only, in such an embodiment, a tissue engineered myocardium construct as disclosed herein can be administered to a subject, such as a human subject by way of transplantation, where the subject is in need of such treatment, for example, the subject has, or has an increased risk of developing a cardiovascular condition or disorder.

In some embodiments, a composition comprising the ANP and cardiomyocytes and/or tissue engineered myocardium composition as disclosed herein can be introduced into a subject in need thereof, e.g., a composition comprising the ANP and cardiomyocytes or tissue engineered myocardium composition as disclosed herein can be introduced on or adjacent to existing heart tissue in a subject. In one embodiment, a composition comprising the ANP and cardiomyocytes or tissue engineered myocardium composition as disclosed herein is useful for replacing or repairing damaged heart tissue (e.g., ischemic heart tissue), for example, where a composition comprising the ANP and cardiomyocytes or tissue engineered myocardium composition as disclosed herein is introduced or administered (e.g. implanted) into a subject. In some embodiments, the tissue engineered myocardium composition which is transplanted comprises cardiomyocytes originated and derived from the subject in which the tissue engineered myocardium is implanted. Accordingly, allogenic or autologous transplantation of the tissue engineered myocardium into a subject can be carried out.

Another aspect of the technology described herein provides methods of treating a cardiac disease or disorder in a subject, the method generally involving administering to a subject in need thereof a therapeutically effective amount of a composition comprising the ANP and cardiomyocytes or tissue engineered myocardium composition as disclosed herein. In some embodiments, the technology described herein also provides methods of treating a cardiac disorder in a subject, the method generally involving administering to a subject in need thereof a therapeutically effective amount of a substantially pure population of cardiomyocytes produced by maturation and/or differentiation on an ANP substrate as disclosed herein.

In some embodiments, a composition comprising the ANP and cardiomyocytes or tissue engineered myocardium composition as disclosed herein is useful for generating artificial heart tissue, e.g., for implanting into a mammalian subject. In some embodiments, the composition comprising the ANP and cardiomyocytes or tissue engineered myocardium composition as disclosed herein is useful for replacing damaged heart tissue (e.g., ischemic heart tissue) and/or damaged or degenerated muscle tissue (e.g., skeletal muscle in muscular dystrophy). Accordingly, one can use a composition comprising the ANP and cardiomyocytes or the tissue engineered myocardium composition as described herein to repair and/or reinforce the cardiac or heart tissue in a mammal, e.g., an injured or diseased human subject. For example, in some embodiments a composition comprising the ANP and cardiomyocytes or tissue engineered myocardium can be used, for example but not limited to, in tissue implants or as a patch or as reinforcement to a heart which is weak contraction or alternatively has been damaged due to a myocardial infarction, and/or as a wound dressing. Such wound dressing can offer improved cardiac function of a subject with a cardiac lesion such as myocardial infarction. The tissue engineered myocardial composition as disclosed herein is also useful to repair other tissue defects, e.g., for cardiac repair due to birth defects (congenic) or acquired cardiac defects, or to function as a splint for damaged or weakened muscle, for example in degenerative muscular disorders where muscle atrophy of the heart occurs, such as multiple sclerosis (MS), ALS and muscular dystrophy and the like.

In some embodiments, a subject in need of treatment using a subject method includes, but is not limited to, an individual having a congenital heart defect, an individual suffering from a condition that results in ischemic heart tissue, e.g., an individuals with coronary artery disease, and the like. A subject method is useful to treat degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

Another aspect of the technology described relates to use of the nanotextured platform as disclosed herein to enhance the maturation of immature myocytes, e.g., cardiomyocytes in vitro to produce an engineered myocardial tissue. In some embodiments, after a predetermined time of culturing the myocytes on the nanotextured platform, the myocytes, e.g., cardiomyocytes are removed from the nanotextured platform and multiple layers of two-dimensional myocyte monolayers or sheets can be stacked upon each other to generate a three-dimensional engineered tissue muscle tissue, e.g., engineered tissue myocardium. Such engineered tissue muscle tissue, e.g., engineered tissue myocardium can be used in methods for the treatment of subject, for example, as "muscle patches" for repair of skeletal muscle and/or cardiac muscle in subject in need thereof.

For example, another embodiment relates to use for the nanotextured substrate to align, elongate and mature skeletal muscle cells derived from animals and humans, for example, cells differentiated from stem cells (e.g., iPSC), or muscle cell lines (e.g. C2C12). In some embodiments, the nanotextured substrate comprises additional features, e.g., components of the extracellular matrix fibers found in a given muscle tissue, which can increase cell maturation, and allow more effective transplantation and integration with the host tissue.

In some embodiments, any number of maturation markers can be used to identify the enhanced maturity of myocytes into skeletal muscle myocytes, for example, including, but not limited to an increase in any number of the following as compared to myocytes cultured on a non-textured substrate: (a) Higher metabolic output, (b) More elongated and anisotropic morphology, (b) Higher expression of Pax7, Myf5, MyoG, MyoD, and dystrophin genes. In some embodiments, a higher or increased level of any one of these parameters is an increase of at least 10% as compared to the same parameter of myocytes cultured on non-textured substrates.

In some embodiments, nanotextured substrates which are used to culture skeletal muscle cells can be made from any polymer that is biocompatible, for example, a biodegradable material, and can be conjugated with a multitudes of factors that are known to promote angiogenesis, myogenesis, and nerve cell migration, including but not limited to, S1P, growth factors, laminin and other factors known to persons of ordinary skill in the art In some embodiments, the nanotextured substrates with skeletal muscle cells can be transplanted into a subject at the site of muscle injury, or diseased muscle and promote cell maturation, cell integration when the direction of patch is parallel to the host muscle fibers. In some embodiments, the subject has a muscle injury, or other wound (e.g., burn). In some embodiments, the subject has a myogenic disease or muscle wasting disease or disorder, for example, but not limited to muscular dystrophy, amylolateral sclerosis (ALS) and other such diseases.

In some embodiments, the nanotextured substrates can be coated with a thermoresponsive polymers (e.g. NIPAAm) as discussed herein, which can be used to create detachable skeletal muscle sheets that can be stacked to form 3D muscle grafts with anisotropy maintained at individual sheet level. Monolayer or multiple layer muscle patches with or without scaffold when transplanted promote cell integration, and maturation as defined by increased calcium transient, increased force generation, increase metabolic activity, increased expression of muscle-specific markers. These characteristics can be measured by of immunostaining, or live cell imaging of a reporter gene (e.g. calcium reporter in transplanted cells). Force generation can be measured by myography, and animal motor control measurements.

For administration to a mammalian host, a composition comprising ANP and cardiomyocytes or tissue engineered myocardium as disclosed herein can be formulated as a pharmaceutical composition. Any suitable carrier known to those of ordinary skill in the art may be employed in a subject pharmaceutical composition. The selection of a carrier will depend, in part, on the nature of the substance (here, an artificial tissue preparation or a substrate with an artificial tissue preparation) being administered. Representative carriers include physiological saline solutions, gelatin, water, glycols or other materials that maintain the structure, hydration and/or viability of the tissue preparation, or a combination of such materials. Optionally, a pharmaceutical composition may additionally contain preservatives and/or other additives such as, for example, antimicrobial agents, anti-oxidants, chelating agents and/or inert gases, and/or other active ingredients.

In some embodiments, where a composition comprising ANP and cardiomyocytes or tissue engineered myocardium are administered to a subject in need thereof, the population of cardiomyocytes can be encapsulated, according to known encapsulation technologies, including microencapsulation (see, e.g., U.S. Pat. Nos. 4,352,883; 4,353,888; and 5,084,350, which are incorporated herein by reference). Where the cardiomyocytes are encapsulated, in some embodiments the cardiomyocytes are encapsulated by macroencapsulation, as described in U.S. Pat. Nos. 5,284,761; 5,158,881; 4,976,859; 4,968,733; 5,800,828 and published PCT patent application WO 95/05452 which are incorporated herein by reference. A unit dosage form of a cardiomyocyte tissue preparation can contain from about $10^3$ cells to about $10^9$ cells, e.g., from about $10^3$ cells to about $10^4$ cells, from about $10^4$ cells to about $10^5$ cells, from about $10^5$ cells to about $10^6$ cells, from about $10^6$ cells to about $10^7$ cells, from about $10^7$ cells to about $10^8$ cells, or from about $10^8$ cells to about $10^9$ cells.

A composition comprising ANP and cardiomyocytes or tissue engineered myocardium as disclosed herein can be cryopreserved according to routine procedures. For example, cryopreservation can be carried out on from about one to ten million cells in "freeze" medium which can include a suitable proliferation medium, 10% BSA and 7.5% dimethylsulfoxide. Growth medium is aspirated and replaced with freeze medium. Cell preparations are slowly frozen, and then stored at −80° C. Preparations are thawed, for example, by swirling in a 37° C. bath, provided fresh proliferation medium, and grown as described above.

As discussed above, a composition comprising ANP and cardiomyocytes or tissue engineered myocardium as disclosed herein can be used as a pharmaceutical composition to the treatment of a subject in need thereof, for example for the treatment of a subject with a cardiomyopathy or a cardiovascular condition or disease. In some embodiments, a composition comprising ANP and cardiomyocytes or tissue engineered myocardium as disclosed herein may further comprise a cardiomyocyte differentiation agent, which promotes the differentiation of cardiomyocytes into a more mature phenotype, e.g., into ventricular cardiomyocytes. Cardiovascular stem cell differentiation agents for use in the technology described herein are well known to those of ordinary skill in the art. Examples of such agents include, but are not limited to, cardiotrophic agents, creatine, carnitine, taurine, cardiotropic factors as disclosed in U.S. Patent Application Serial No. 2003/0022367 which is incorporated herein by reference, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway. The pharmaceutical compositions may further comprise a pharmaceutically acceptable carrier.

A composition comprising ANP and cardiomyocytes or tissue engineered myocardium composition as disclosed herein can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. As noted above, the composition comprising ANP and cardiomyocytes or tissue engineered myocardium composition as disclosed herein may also be modified by insertion of DNA to modify the function of the cells for structural and/or therapeutic purpose.

In another aspect, a composition comprising ANP and cardiomyocytes or tissue engineered myocardium composition as disclosed herein for transplantation can be modified to comprise a gene encoding pro-angiogenic and/or cardiomyogenic growth factor(s) which would allow the cardiomyocytes to act as their own source of growth factor during cardiac repair or regeneration following transplantation into a subject. Genes encoding anti-apoptotic factors or agents could also be applied. Addition of the gene (or combination of genes) could be by any technology known in the art, including but not limited to adenoviral transduction, "gene guns," liposome-mediated transduction, and retrovirus or lentivirus-mediated transduction, plasmid' adeno-associated virus. Cardiomyocytes could be genetically manipulated to release and/or express gene products for a defined period of time (such that gene expression could be induced and/or controlled, so expression can be continued and/or be initiated. Particularly, when a composition comprising ANP and cardiomyocytes or tissue engineered myocardium composition as disclosed herein is administered to a subject other than the subject from whom the cells and/or tissue were obtained, one or more immunosuppressive agents may be administered to the subject receiving a composition comprising ANP and cardiomyocytes or tissue engineered myocardium composition as disclosed herein in order to reduce, and preferably prevent, rejection of the transplant by the recipient subject. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 20020182211. In one embodiment, a immunosuppressive agent is cyclosporine A. Other examples include myophenylate mofetil, rapamicin, and anti-thymocyte globulin. In one embodiment, an immunosuppressive drug is administered with at least one other therapeutic agent. An immunosuppressive agent can be administered to a subject in a formulation which is compatible with the route of administration and is administered to a subject at a dosage sufficient to achieve the desired therapeutic effect. In another embodiment, an immunosuppressive agent is administered transiently for a sufficient time to induce tolerance of the composition comprising ANP and cardiomyocytes or tissue engineered myocardium composition as disclosed herein.

In some embodiments, a composition comprising ANP and cardiomyocytes or tissue engineered myocardium composition as disclosed herein can be administered to a subject with one or more cellular differentiation agents, such as cytokines and growth factors, as disclosed herein. Examples of various cell differentiation agents are disclosed in U.S. Patent Application Serial No. 2003/0022367 which is incorporated herein by reference, or Gimble et al., 1995; Lennon et al., 1995; Majumdar et al., 1998; Caplan and Goldberg, 1999; Ohgushi and Caplan, 1999; Pittenger et al., 1999; Caplan and Bruder, 2001; Fukuda, 2001; Worster et al., 2001; Zuk et al., 2001. Other examples of cytokines and growth factors include, but are not limited to those noted above, i.e., cardiotrophic agents, creatine, carnitine, taurine, TGF-beta ligands, such as activin A, activin B, insulin-like growth factors, bone morphogenic proteins, fibroblast growth factors, platelet-derived growth factor natriuretic factors, insulin, leukemia inhibitory factor (LIF), epidermal growth factor (EGF), TGFalpha, and products of the BMP or cripto pathway.

A composition comprising ANP and cardiomyocytes or tissue engineered myocardium composition as disclosed herein can be administered to a subject in need of a transplant. In other aspects of the technology described herein, a composition comprising ANP and cardiomyocytes or tissue engineered myocardium composition as disclosed herein is directly administered at the site of or in proximity to the diseased and/or damaged tissue. A composition comprising ANP and cardiomyocytes or tissue engineered myocardium composition as disclosed herein for therapeutic transplantation purposes can optionally be packaged in a suitable container with written instructions for a desired purpose, such as the use of a composition comprising ANP and cardiomyocytes or tissue engineered myocardium composition as disclosed herein to improve some abnormality of the cardiac muscle, for example, in the right ventricle of the heart.

In one embodiment, a subject can be administered a composition comprising ANP and cardiomyocytes or tissue engineered myocardium composition as disclosed herein and also administered, either in conjunction or temporally separated, a differentiation agent. In one embodiment, a composition comprising ANP and cardiomyocytes or tissue engineered myocardium composition as disclosed herein is administered separately to the subject from the differentiation agent. Optionally, if a composition comprising ANP and cardiomyocytes or tissue engineered myocardium composition as disclosed herein is administered separately from the differentiation agent, there is a temporal separation in the administration of the a tissue engineered myocardium composition and the differentiation agent. The temporal separation may range from about less than a minute in time, to about hours or days in time. The determination of the optimal timing and order of administration is readily and routinely determined by one of ordinary skill in the art.

The composition comprising ANP and cardiomyocytes or tissue engineered myocardium composition as disclosed herein can be used for allogenic or autologous transplantation into a subject in need thereof.

Pharmaceutical Compositions

Described herein are tissue engineered myocardium compositions generated using in vitro-differentiated cardiomyocytes and a suitable nanotextured substrate. In some embodiments, the tissue engineered myocardium composition is muscle thin film (MTF) tissue. In alternative embodiments, the tissue engineered myocardium composition is artificial heart tissue.

In some embodiments, a tissue engineered myocardium is present in a liquid medium together with one or more components. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

The tissue engineered myocardium as disclosed herein can be used for allogenic or autologous transplantation into an individual in need thereof.

The technology described herein is further illustrated by the following examples which in no way should be construed as being further limiting, The contents of all cited references, including literature references, issued patents, published patent applications, and co-pending patent applications, cited throughout this application are hereby expressly incorporated by reference.

The technology described herein has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

In Some Embodiments, the Present Invention May be Defined in any of the Following Numbered Paragraphs:

1. A nanotextured platform composition comprising a polymer substrate comprising:
   a. a nanotextured array of parallel grooves and ridges that organizes cultured cardiomyocytes in an anisotropic manner; and
   b. in vitro-differentiated cardiomyocytes cultured on said nanotextured array, wherein said cardiomyocytes have a more differentiated phenotype on said nanotextured array than said in vitro-differentiated cardiomyocytes when cultured on a polymer substrate of the same composition but substantially lacking said array of parallel grooves and ridges.
2. A nanotextured platform composition comprising a polymer substrate comprising:
   a. a nanotextured array of parallel grooves and ridges that organizes cultured cardiomyocytes in an anisotropic manner; and
   b. and embryonic or induced pluripotent stem cells cultured on said nanotextured array.
3. The nanotextured platform of paragraph 2, wherein said stem cells differentiate to cardiomyocytes with a more differentiated phenotype on said nanotextured array than said stem cells when cultured on a polymer substrate of the same composition but substantially lacking said array of parallel grooves and ridges.
4. The nanotextured platform of paragraph 1, wherein said in vitro-differentiated cardiomyocytes are human.
5. The nanotextured platform of paragraph 2, wherein said stem cells are human stem cells.
6. The nanotextured platform of paragraph 1 or paragraph 2 wherein said cardiomyocytes or stem cells are derived from a patient diagnosed with a cardiac disease.
7. The nanotextured platform of paragraph 2, further comprising an agent that promotes differentiation of said stem cells to cardiomyocytes.
8. The nanotextured platform of paragraph 1 or paragraph 2, wherein said grooves have a depth of 10 nm-10 μm and width of 50 nm-10 μm, and said ridges, between said grooves, have a width of 50 nm-10 μm.
9. The nanotextured platform of paragraph 1 or paragraph 2, wherein said grooves have a depth of 1-1000 nm and width of 5-1000 nm, and said ridges, between said grooves, have a width of 5-1000 nm.
10. The nanotextured platform of paragraph 1 or paragraph 2, wherein said grooves have a depth of 50-500 nm and width of 200-1000 nm, and said ridges, between said grooves, have a width of 200-1000 nm.
11. The nanotextured platform of paragraph 9, wherein said grooves have a depth of 20-100 nm and width of 200-800 nm, and said ridges, between said grooves, have a width of 200-800 nm.
12. The nanotextured platform of paragraph 1 or paragraph 2 wherein said cardiomyocytes form a monolayer on said substrate with anisotropic and polarized cell arrangement in the direction of the nanotextures.
13. The nanotextured platform of paragraph 1 or paragraph 2, wherein said nanotextured array of parallel grooves and ridges covers a surface area >1 $cm^2$.
14. The nanotextured platform of paragraph 1 or paragraph 2, wherein said array of parallel grooves and ridges has a precision of texture of at least 90% fidelity, as determined by atomic force microscopy or electron microscopy.
15. The nanotextured platform of paragraph 1 or paragraph 2, wherein said array of parallel grooves and ridges is generated using a process selected from the group consisting of capillary force lithography, nanoindentation, e-beam lithography, and electrospinning
16. The nanotextured platform of paragraph 1 or paragraph 2, wherein said array of parallel grooves and ridges is formed by capillary force lithography.
17. The nanotextured platform of paragraph 1 or paragraph 2, wherein the nanotextured platform is coated with or wherein the substrate comprises within its polymer matrix, either biocompatible extracellular matrix polypeptides, engineered matrix polypeptides, or engineered polypeptides.
18. The nanotextured platform of paragraph 1 or paragraph 2, wherein the nanotextured platform further comprises a coating with a materials selected from the group consisting of charcoal, graphene, graphene oxide, reduced graphene oxide, nanotubes, and gold, whereby one or more functional parameters of the substrate, selected from adsorption of proteins to surface, or electrical conductivity, or other physico-chemical property is modulated in a manner that influences the phenotype of said cardiac cells.
19. The nanotextured platform of paragraph 1 or paragraph 2, wherein said substrate comprises a polymer hydrogel comprising, within the matrix of said polymer substrate, a biocompatible extracellular matrix protein, a synthetic or engineered matrix polypeptide, or engineered polypeptides.
20. The nanotextured platform of paragraph 1 or paragraph 2, wherein said substrate comprises, within the substrate polymer, one or more of gelatin, collagen type I, collagen type IV, fibronectin, fibronectin domains, laminin, and an engineered extracellular matrix protein or peptide.
21. The nanotextured platform of paragraph 1 or paragraph 2, wherein said substrate polymer comprises a surface coating of one or more of gelatin, collagen type I, collagen type IV, fibronectin, fibronectin domains, laminin, and an engineered extracellular matrix protein or peptide.
22. The nanotextured platform of paragraph 1 or paragraph 3, wherein said cardiomyocytes cultured on said nanotextured polymer substrate express at least one marker from the group consisting of Nkx2.5, GATA4, connexin-43, a-myosin heavy chain, cTNT, sarcomere expression, sarcomere length, contractility, beat rate, or electrical propagation in a manner more similar to adult cardiomyocytes than in vitro-differentiated cardiomyocytes cultured on a polymer of the same composition but substantially lacking said nanotextured array.
23. The nanotextured platform of paragraph 1 or paragraph 2, wherein said polymer comprises, either coated on its surface or within its polymer matrix, one or more agents selected from the group consisting of sphingosine phosphate or an analog thereof, fluric acid, zFADvmk, cardiotropin, or a growth factor selected from the group consisting of FGF, HGF, IGF1, SDF1a, EGF, VEGF, AM, HGF, Angiopoietin, BMPs, BDNF, Erythropoietin, GDNF, G-CSF, GDF9, HDNF, GDF, Thrombopoietin, TGF-alpha, TGF-beta, TNF-alpha, PIGF, PDGF, and interleukins IL1-7.
24. The nanotextured platform of paragraph 1 or paragraph 2, wherein said agent enhances maturation of cardiomyocytes on said platform, enhances cardiomyocyte adherence to said substrate, or enhances action potential wave propagation across said cardiomyocytes.
25. The nanotextured platform of paragraph 1 or paragraph 2, wherein said polymer substrate is optically transparent.
26. The nanotextured platform of paragraph 1 or paragraph 2, wherein said polymer substrate has rigidity in the range of 5 to 200 kPa.
27. The nanotextured platform of paragraph 1 or paragraph 2, wherein said polymer substrate has rigidity in the range of 5 to 40 kPa.
28. The nanotextured platform of paragraph 1 or paragraph 2, wherein said polymer substrate has rigidity in the range of 30 to 200 kPa.
29. The nanotextured platform of paragraph 1 or paragraph 2, wherein said polymer substrate is composed of a biocompatible hydrogel compatible with thermal or UV based curing methods to fabricate.
30. The nanotextured platform of paragraph 1 or paragraph 2, wherein said polymer substrate is composed of PEG or a chemical variant thereof, PUA, PLGA, PMMA, and chemical variant thereof.
31. The nanotextured platform of paragraph 1 or paragraph 2 wherein said polymer substrate comprises a UV curable hydrogel polymer, a thermosensitive hydrogel polymer or a polymer produced by solvent evaporation.
32. The nanotextured platform of paragraph 1 or paragraph 2, wherein said polymer substrate comprises a nanotextured array of parallel grooves and ridges that organizes cultured cardiomyocytes on one or both sides of a substantially planar substrate.
33. The nanotextured platform of paragraph 32, comprising cardiomyocytes or stem cells on one or both sides of said substantially planar substrate.
34. The nanotextured platform of paragraph 1 or paragraph 2, wherein said polymer substrate comprises a nanotextured array of parallel grooves and ridges that organizes cultured cardiomyocytes on one or both sides of a substantially planar substrate.
35. The nanotextured platform of paragraph 1 or paragraph 2, wherein the cardiomyocytes are differentiated from stem cells or induced pluripotent stem cells.
36. The nanotextured platform of paragraph 35, wherein the cardiomyocytes are differentiated from human stem cells or induced pluripotent stem cells.
37. The nanotextured platform of paragraph 36, wherein the human has a cardiovascular condition or disorder or arrthymthia.
38. The nanotextured platform of paragraph 36, wherein the human has a myogenic or muscle degenerative disorder.
39. The nanotextured platform of any of paragraphs 1-38, wherein the nanotextured substrate comprises an electroconductive coating.
40. The nanotextured platform of paragraph 39, wherein the electroconductive coating is selected from the group of graphene, graphene-oxide, titanium, gold and alloys or variants thereof.
41. The nanotextured platform of any of paragraphs 1-40, wherein the nanotextured substrate comprises an additional cell population.
42. The nanotextured platform of paragraphs 41, wherein the additional cell population is selected from the group consisting of: fibroblasts, endothelial cells, mesenchymal cells.
43. The nanotextured platform of paragraphs 42, wherein the fibroblasts, endothelial cells or mesenchymal cells are cardiac fibroblasts, endothelial cells or mesenchymal cells.
44. A multiwell culture plate comprising a plurality of polymer substrate compositions, each substrate in a separate well of said multiwell plate and comprising a nanotextured array of parallel grooves and ridges that organizes cultured cardiomyocytes in an anisotropic manner, wherein individual members of said plurality have different rigidities.
45. A multiwell culture plate comprising a plurality of polymer substrate compositions, each substrate in a separate well of said multiwell plate and comprising a nanotextured array of parallel grooves and ridges that organizes cultured cardiomyocytes in an anisotropic manner, wherein individual members of said plurality have different topographies.
46. A multiwell culture plate comprising a plurality of polymer substrate compositions, each substrate in a separate well of said multiwell plate and comprising a nanotextured array of parallel grooves and ridges that organizes cultured cardiomyocytes in an anisotropic manner, wherein individual members of said plurality have different coatings.
47. A multiwell culture plate comprising a plurality of polymer substrate compositions, each substrate in a separate well of said multiwell plate and comprising a nanotextured array of parallel grooves and ridges that organizes cultured cardiomyocytes in an anisotropic manner, wherein individual members of said plurality independently have different rigidities, topographies and/or coatings.

48. The multiwell culture plate of paragraphs 44-47, wherein said different rigidities range from 5 to 200 kPA.
49. The multiwell culture plate of paragraphs 44-47, further comprising cardiomyocytes cultured on said nanotextured arrays.
50. The multiwell culture plate of paragraphs 44-47, wherein said cardiomyocytes are human.
51. The multiwell culture plate of paragraphs 44-47, wherein said cardiomyocytes were differentiated in vitro from a stem cell.
52. The multiwall plate of paragraph 47, wherein, within the respective substrates in respective wells, said grooves have a uniform depth of 1-1000 nm and uniform width of 5-1000 nm, and said ridges, between said grooves, have a uniform width of 5-1000 nm.
53. The multiwall plate of paragraph 52, wherein said grooves have a depth of 1-1000 nm and width of 5-1000 nm, and said ridges, between said grooves, have a width of 5-1000 nm.
54. The multiwall plate of paragraph 52, wherein said grooves have a depth of 50-500 nm and width of 200-1000 nm, and said ridges, between said grooves, have a width of 200-1000 nm.
55. The multiwall plate of paragraph 52, wherein said grooves have a depth of 20-100 nm and width of 200-800 nm, and said ridges, between said grooves, have a width of 200-800 nm.
56. The multiwell culture plate of paragraph 44, wherein rigidity is varied by varying polymer substrate curing time, UV intensity, or relative co-polymer concentration.
57. A nanotextured platform composition comprising a polymer substrate comprising:
    a. a nanotextured array of parallel grooves and ridges that organizes cultured skeletal muscle cells in an anisotropic manner; and
    b. in vitro-differentiated skeletal muscle cells cultured on said nanotextured array, wherein said skeletal muscle cells have a more differentiated phenotype on said nanotextured array than said in vitro-differentiated skeletal muscle cells when cultured on a polymer substrate of the same composition but substantially lacking said array of parallel grooves and ridges.
58. The nanotextured platform composition of paragraph 57, within the respective substrates in respective wells, said grooves have a uniform depth of 1-1000 nm and uniform width of 5-1000 nm, and said ridges, between said grooves, have a uniform width of 5-1000 nm.
59. The nanotextured platform composition of paragraph 57, wherein, within said array of parallel grooves and ridges, said grooves have a depth of 1-1000 nm and width of 5-1000 nm, and said ridges, between said grooves, have a width of 5-1000 nm.
60. The nanotextured platform composition of paragraph 57, wherein, within said array of parallel grooves and ridges, said grooves have a depth of 50-500 nm and width of 200-1000 nm, and said ridges, between said grooves, have a width of 200-1000 nm.
61. The nanotextured platform composition of paragraph 57, wherein, within said array of parallel grooves and ridges, said grooves have a depth of 20-100 nm and width of 200-800 nm, and said ridges, between said grooves, have a width of 200-800 nm.
62. The nanotextured platform composition of paragraph 57, wherein, within said array of parallel grooves and ridges, said grooves have a depth of 10 nm-10 μm and width of 50-10 μm and said ridges, between said grooves, have a width of 50 nm-10 μm
63. The nanotextured platform of paragraph 57, wherein the skeletal muscle cells are differentiated from stem cells or induced pluripotent stem cells.
64. The nanotextured platform of paragraph 57, wherein the skeletal muscle cells are differentiated from human stem cells or induced pluripotent stem cells.
65. The nanotextured platform of paragraph 64, wherein the human has a myogenic or muscle degenerative disorder.
66. The nanotextured platform of any of paragraphs 57-65, wherein the nanotextured substrate comprises an electroconductive coating.
67. The nanotextured platform of paragraph 66, wherein the electroconductive coating is selected from the group of graphene, graphene-oxide, titanium, gold and alloys or variants thereof.
68. The nanotextured platform of any of paragraphs 57-67, wherein the nanotextured substrate comprises an additional cell population.
69. The nanotextured platform of paragraphs 68, wherein the additional cell population is selected from the group consisting of: fibroblasts, endothelial cells, mesenchymal cells.
70. The nanotextured platform of paragraphs 69, wherein the fibroblasts, endothelial cells or mesenchymal cells are cardiac fibroblasts, cardiac endothelial cells or cardiac mesenchymal cells.
71. A method of making a tissue composition, the method comprising:
    a. contacting a plurality of polymer substrates, each comprising a nanotextured array of parallel grooves and ridges that organizes cultured myocytes in an anisotropic manner, with cultured myocytes to generate on each of said plurality of polymer substrates, a layer of anisotropically arranged myocytes;
    b. removing a plurality of said layers from their respective substrates; and
    c. contacting said plurality of layers of anisotropically arranged myocytes with each other such that they are stacked one upon the other, and culturing the stacked layers such that a tissue composition is formed with desired anisotropy at individual layer levels.
72. The method of paragraph 71, wherein the cardiomyocytes in each layer are arranged substantially parallel to cardiomyocytes in the other layers, such that the direction of contraction of the cells is substantially the same in each layer.
73. The method of paragraph 71, wherein the myocytes are cardiomyocytes.
74. The method of paragraph 71, wherein the myocytes are skeletal muscle myocytes.
75. The method of paragraph 71, wherein the myocytes are smooth muscle myocytes.
76. The method of paragraph 71, wherein the anisotropic arrangement of the cardiomyocytes in each layer are arranged at an angle relative to cardiomyocytes in the other layers.
77. The method of paragraph 76, wherein said cardiomyocytes are differentiated in culture prior to contacting the cardiomyocytes with said polymer substrates.
78. The method of paragraph 71, wherein said myocytes are human.

79. The method of paragraph 76, wherein the myocytes are differentiated from stem cells or induced pluripotent stem cells.
80. The method of paragraph 76, wherein the human has a cardiovascular disease or a disorder or arrhythmia.
81. The method of paragraph 76, wherein the human has a myogenic or muscle degenerative disorder.
82. The method of paragraph 76, wherein the nanotextured substrate comprises an additional cell population.
83. The method of paragraphs 68, wherein the additional cell population is selected from the group consisting of: fibroblasts, endothelial cells, mesenchymal cells.
84. The method of paragraphs 69, wherein the fibroblasts, endothelial cells or mesenchymal cells are cardiac fibroblasts, cardiac endothelial cells or cardiac mesenchymal cells.
85. A tissue composition formed in the manner of paragraph 71-84.
86. A method of making a tissue composition, the method comprising:
   a. contacting in vitro-differentiated myocytes with a polymer substrate comprising a nanotextured array of parallel grooves and ridges that organizes cultured myocytes in an anisotropic manner; and
   b. culturing said myocytes on said substrate, wherein said myocytes arrange anisotropically on said substrate and have a more differentiated myocyte phenotype than said myocytes prior to said contacting and culturing steps.
87. The method of paragraph 86, further comprising, prior to said contacting step, differentiating a stem cell to a cardiomyocyte phenotype.
88. The method of paragraph 86, wherein the myocytes are cardiomyocytes.
89. The method of paragraph 86, wherein the myocytes are skeletal muscle myocytes.
90. The method of paragraph 86, wherein the myocytes are smooth muscle myocytes.
91. The method of paragraph 86, wherein said myocytes are human.
92. The method of paragraph 86, wherein the myocytes are differentiated from stem cells or induced pluripotent stem cells (iPSC).
93. The method of paragraph 91, wherein the human has a cardiovascular disease or a disorder or arrhythmia.
94. The method of paragraph 91, wherein the human has a myogenic or muscle degenerative disorder.
95. The method of paragraph 86, wherein the polymer substrate comprises an additional cell population.
96. The method of paragraph 95, wherein the additional cell population is selected from the group consisting of: fibroblasts, endothelial cells, mesenchymal cells.
97. The method of paragraph 96, wherein the fibroblasts, endothelial cells or mesenchymal cells are cardiac fibroblasts, cardiac endothelial cells or cardiac mesenchymal cells.
98. The method of paragraph 92, wherein said stem cell is an embryonic stem cell.
99. The method of paragraph 92, wherein said stem cell is a human stem cell.
100. The method of paragraph 86, within said grooves have a uniform depth of 1-1000 nm and uniform width of 5-1000 nm, and said ridges, between said grooves, have a uniform width of 5-1000 nm.
101. The method of paragraph 86, within said grooves have a depth of 1-1000 nm and width of 5-1000 nm, and said ridges, between said grooves, have a width of 5-1000 nm.
102. The method of paragraph 86, within said grooves have a depth of 50-500 nm and width of 200-1000 nm, and said ridges, between said grooves, have a width of 200-1000 nm.
103. The method of paragraph 86, within said grooves and ridges, said grooves have a depth of 20-100 nm and width of 200-800 nm, and said ridges, between said grooves, have a width of 200-800 nm.
104. The method of paragraph 86, wherein said nanotextured array of parallel grooves and ridges can cover a surface area greater than 1 $cm^2$.
105. The method of paragraph 86, wherein the nanotextured platform is coated with or wherein the substrate comprises within its polymer matrix, either biocompatible extracellular matrix polypeptides, engineered matrix polypeptides, or engineered polypeptides.
106. The method of paragraph 86, wherein said cardiomyocytes cultured on said nanotextured polymer substrate express at least one marker from the group consisting of Nkx2.5, GATA4, connexin-43, a-myosin heavy chain, cTNT, sarcomere expression, sarcomere length, contractility, beat rate, or electrical propagation, in a manner more similar to adult cardiomyocytes than in vitro-differentiated cardiomyocytes cultured on a polymer of the same composition but substantially lacking said nanotextured array.
107. The method of paragraph 86, wherein said polymer substrate is optically transparent.
108. The method of paragraph 86, wherein said polymer substrate has rigidity in the range of 5 to 200 kPa.
109. The method of paragraph 86, wherein said polymer substrate is composed of a biocompatible hydrogel compatible with capillary force lithography.
110. The method of paragraph 86, wherein said polymer substrate is composed of PEG, PUA, PLGA, PMMA or a chemical variant thereof.
111. The method of paragraph 86, wherein said polymer substrate comprises a UV curable hydrogel polymer, a thermosensitive hydrogel polymer or a polymer produced by solvent evaporation.
112. The method of paragraph 86, wherein said polymer substrate comprises a nanotextured array of parallel grooves and ridges that organizes cultured cardiomyocytes on both sides of a substantially planar substrate.
113. The method of paragraph 86, wherein cardiomyocytes or stem cells are present on both sides of said substantially planar substrate.
114. The method of paragraph 86, wherein the polymer substrate comprises an electroconductive coating.
115. The method of paragraph 114, wherein the electroconductive coating is selected from the group of graphene, graphene-oxide, titanium, gold and alloys or variants thereof.
116. A method of making a tissue composition, the method comprising:
   a. contacting a stem cell with a polymer substrate comprising a nanotextured array of parallel grooves and ridges that organizes cultured cardiomyocytes in an anisotropic manner; and
   b. culturing said stem cell on said substrate in the presence of one or more agents that induces cardiomyocyte differentiation, wherein said culturing generates cardiomyocytes arranged anisotropically on said substrate, and wherein said cardiomyocytes have a more mature cardiomyocyte phenotype than cardiomyocytes differentiated from said stem cells with the same one or more agents but in the absence of said polymer substrate.

117. The method of paragraph 116, wherein said stem cell is an iPS cell or an embryonic stem cell.

118. The method of paragraph 117, wherein said stem cell is a human stem cell.

119. A method of enhancing the maturity of in vitro differentiated cardiomyocytes, the method comprising contacting in vitro-differentiated cardiomyocytes with a polymer substrate comprising a nanotextured array of parallel grooves and ridges that organizes cultured cardiomyocytes in an anisotropic manner, wherein said contacting results in anisotropic arrangement and enhanced maturity of said cardiomyocytes.

120. The method of paragraph 119, within said grooves have a uniform depth of 1-1000 nm and uniform width of 5-1000 nm, and said ridges, between said grooves, have a uniform width of 5-1000 nm.

121. The method of paragraph 119, within said grooves have a depth of 1-1000 nm and width of 5-1000 nm, and said ridges, between said grooves, have a width of 5-1000 nm.

122. The method of paragraph 119, within said grooves have a depth of 50-500 nm and width of 200-1000 nm, and said ridges, between said grooves, have a width of 200-1000 nm.

123. The method of paragraph 119, within said grooves and ridges, said grooves have a depth of 20-100 nm and width of 200-800 nm, and said ridges, between said grooves, have a width of 200-800 nm.

124. The method of paragraph 119, wherein said cardiomyocytes are human cardiomyocytes.

125. The method of paragraph 119, wherein said anisotropically-arranged cardiomyocytes express one or more of the following markers of cardiomyocyte maturity in a manner more similar to cardiomyocytes in cardiac tissue than said in vitro differentiated cardiomyocytes prior to contacting with said polymer substrate.

126. The method of paragraph 119, wherein said polymer substrate is composed of PEG, PUA, PLGA, PMMA or a chemical variant thereof.

127. The method of paragraph 119, wherein cells arranged on said nanotextured array cover an area at least 1 cm$^2$ in size.

128. The method of paragraph 119, wherein said polymer substrate has rigidity in the range of 5 to 200 kPa.

129. The method of paragraph 119, wherein said polymer substrate has rigidity in the range of 5 to 40 kPa.

130. The method of paragraph 119, wherein said polymer substrate has rigidity in the range of 30 to 200 kPa.

131. A method of differentiating stem cells to cardiomyocytes, the method comprising:
   a. contacting a population of stem cells with a polymer substrate comprising a nanotextured array of parallel grooves and ridges that organizes cultured cardiomyocytes in an anisotropic manner; and
   b. contacting said population of stem cells with an agent that promotes cardiomyocyte differentiation
   c. wherein said stem cells differentiate to a cardiomyocyte phenotype.

132. The method of paragraph 131, wherein said stem cells are human stem cells.

133. The method of paragraph 131, wherein said method results in cardiomyocytes with a more mature phenotype than the differentiation of said stem cells achieved by contacting said stem cells with said agent that promotes cardiomyocyte differentiation on a polymer substrate of the same composition but substantially lacking said nanotextured array of parallel grooves and ridges.

134. A method of screening for agents that cause cardiac arrhythmia or irregularity in action potential generation and/or propagation, the method comprising:
   a. contacting cardiomyocytes differentiated in vitro with a polymer substrate comprising a nanotextured array of parallel grooves and ridges that organizes cultured cardiomyocytes in an anisotropic manner, such that a monolayer of cardiomyocytes is arranged anisotropically on said substrate;
   b. measuring one or more parameters indicative of cardiac rhythm, and/or action potential generation or propagation in said monolayer;
   c. contacting said cardiomyocytes with a test agent; and
   d. measuring said one or more parameters after test agent contacting, wherein a difference in said one or more parameters is indicative that said agent may cause cardiac arrhythmia or irregularity in action potential generation and/or propagation.

135. The method of paragraph 134, wherein said measuring one or more parameters comprises use of a calcium-sensitive or voltage-sensitive dye, confocal microscopy, optical mapping, or other fluorescent detection system.

136. A method of screening for anti-arrythmogenic agents, the method comprising:
   a. contacting cardiomyocytes differentiated in vitro with a polymer substrate comprising a nanotextured array of parallel grooves and ridges that organizes cultured cardiomyocytes in an anisotropic manner, such that a monolayer of cardiomyocytes is arranged anisotropically on said substrate;
   b. contacting said monolayer with an arrythmogenic agent such that one or more parameters indicative of cardiac rhythm and/or action potential is perturbed relative to a parallel culture lacking said arrythmogenic agent;
   c. contacting said cardiomyocytes with a test agent; and
   d. measuring said one or more parameters after test agent contacting, wherein detection of a shift in said one or more parameters to a value more closely similar to the value for that parameter in the absence of the arrythmogenic agent is indicative that said test agent is a candidate anti-arrythmogenic agent.

137. A method of screening for anti-arrythmogenic agents, the method comprising:
   a. contacting cardiomyocytes differentiated in vitro from a stem cell derived from an individual with cardiomyopathy with a polymer substrate comprising a nanotextured array of parallel grooves and ridges that organizes cultured cardiomyocytes in an anisotropic manner, such that a monolayer of cardiomyocytes is arranged anisotropically on said substrate;
   b. measuring one or more parameters indicative of cardiac rhythm, and/or action potential generation or propagation in said monolayer, wherein at least one of said parameters indicates an abnormal cardiac cell rhythm;
   c. contacting said cardiomyocytes with a test agent; and d. measuring said one or more parameters after test agent contacting, wherein detection of a shift in said one or more parameters to a value more closely similar to the value for that parameter in cells derived from an individual with normal cardiac rhythm is indicative that said test agent is a candidate anti-arrythmogenic agent.

138. A method for analyzing the function of a myocyte on a nanotextured platform of paragraphs 1-43, comprising analysis of at least one functional parameter of the myocytes on the platform.

139. The method of paragraph 138, wherein the at least one functional parameter is an electrical parameter.

140. The method of paragraph 139, wherein the at least functional parameter is action potential duration (ADP), wave propagation, action potential frequency, beat frequency, action potential transmission, Vmax of the acton potential, contraction force, end diastole to peak diastole rate.

141. The method of paragraph 139, wherein the at least one functional parameter is analysed in the presence of an agent as compared to in the absence of an agent.

142. The method of paragraph 139, wherein the myocytes are cardiomyocytes.

143. The method of paragraph 139, wherein the myocytes are skeletal muscle myocytes.

144. The method of paragraph 139, wherein the myocytes are smooth muscle myocytes.

145. The method of paragraph 139, wherein said myocytes are human.

146. The method of paragraph 139, wherein the myocytes are differentiated from stem cells or induced pluripotent stem cells (iPSC).

147. The method of paragraph 145, wherein the human has a cardiovascular disease or a disorder or arrhythmia.

148. The method of paragraph 145, wherein the human has a myogenic or muscle degenerative disorder.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods & Characterization:

Fabrication of Nanotextured Substrates

Ultrastructural analysis of the myocardial ECM shows aligned fibrils approximately 100 nm in diameter, consistent with previous reports of collagen fibrils varying in diameter in the 30-120-nm range (Perumal, S. et al., PNAS, 2008. 105(8): p. 2824-9). To account for possible variability, the widths of the grooves and ridges can be varied in the designed patterns (e.g., substantially parallel) from 150-50 nm ridge width and 800-800 nm groove width) and from 200 nm to 500 nm in height. Nanoscale features can be extended to tissue dimension (>3 $cm^2$) to facilitate functional analyses at tissue-level (e.g. macroscopic contraction, optical mapping etc.), while also allowing large coverage of infarct (>10 $cm^2$).

To fabricate various nanotextured features of PEG, PUA, PLGA, or any other polymer that can be cured with UV or temperature, any of the following techniques can be employed: capillary force lithography, nanoindentation, ebeam lithography. For UV assisted capillary force lithography, see references as previously described (Kim, et al., Langmuir, 2006. 22(12): p. 5419-5426; Kim, D. H., et al., Integr Biol (Camb), 2012. 4(9): p. 1019-3; Kim, et al., PNAS, 2010. 107(2): p. 565-570; Kim, D. H., et al., Advanced Functional Materials, 2009. 19(10): p. 1579-1586; You, M. H., et al., Biomacromolecules, 2010. 11(7): p. 1856-1862). Briefly, the cover glass is washed with isopropyl alcohol (IPA) for 1 min, cleaned using distilled water and dried in N2. PEG-GelMA prepolymer solution (100 µL) is be drop-dispensed on the glass and kept at 40° C. to prevent premature gelation. Nanopatterned polyurethane acrylate (PUA) mold is placed on the coated polymer layer and embossed into the prepolymer, and prepolymer capillarity fills the nanofeatures of the PUA master. The polymer is then exposed to UV light (360-480 nm) for ~50 sec. to polymerize and assume the nanotextures.

For thermal assisted capillary force lithography, cover glass (25 mm typically) is washed with isopropyl alcohol for 30 min in a water sonication and dried in nitrogen stream. The prepared 100 µl of polymeric solution (15%, w/v) in chloroform is dropped on the cover glass. A flat PDMS is placed on the dispensed polymeric solution to remove solvent and obtain a smooth flat layer. A metal mass is placed to evenly press on PDMS mold for 5 min. The cover glass is placed on preheated plate (120° C.) to remove residual solvent and increase adhesion between polymer and cover glass for 5 min. Then, a nanopatterned PUA mold is placed on the polymer coated glass and embossed with constant pressure using metal mass (1,500 g) at preheated plate (120° C.) for 15 min. After thermal imprinting process, the assembly substrates is cooled to room temperature, and the PUA mold is carefully peeled off from the polymer coated glass. Finally, the prepared nano-patterned substrate stored at desiccator for removing residual solvent.

Characterization:

High pattern fidelity and physical integrity of nanofabricated polymeric biomaterials is accessed by SEM and AFM measurements. Elastic modulus and hardness of the resulting cured nanotextured substrates are measured by using nanoindentation (Nano Indenter XP, MTS).

PUA Mold Fabrication

In order to generate high-fidelity nanoscale grooved substrates, polyurethane acrylate (PUA) molds were fabricated from a silicon master for subsequent replications. PUA precursor (MINS 201RM, Minuta Tech.) was drop-dispensed onto a silicon master which was fabricated using standard lithography techniques. Transparent poly(ethylene terephthalate) (PET) film (Skyrol®, SKC Company) was pressed gently into the PUA precursor and silicon master for use as a supporting backplane. The PUA was then cured by exposure to UV light (2=250-400 nm) for 50 sec. After curing, the PET film and attached PUA, in the form of the negative of the silicon master, were peeled from the silicon master and exposed to UV light for an additional 12 hours to complete curing.

Cover Glass Nanofabrication

Figure 1B:
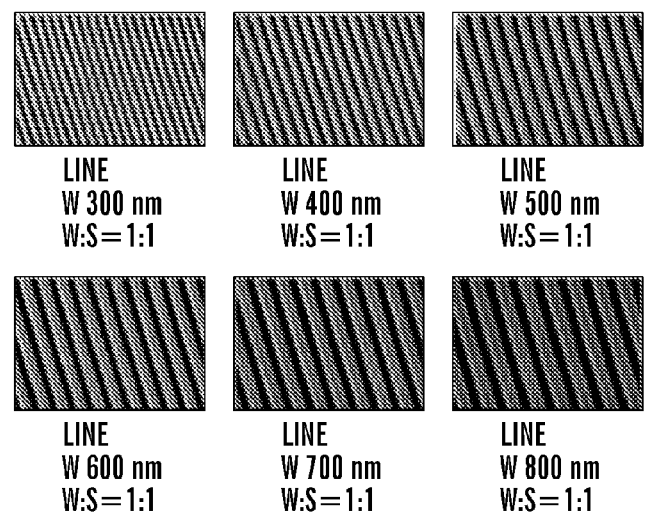
Figure 2A:
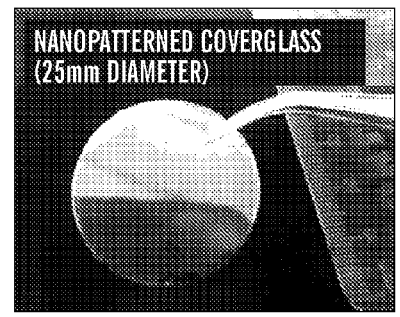
FIG. 2A-2B shows an image of the PLGA substrate in the culture dish and SEM images for each substrate.
Figure 2B:
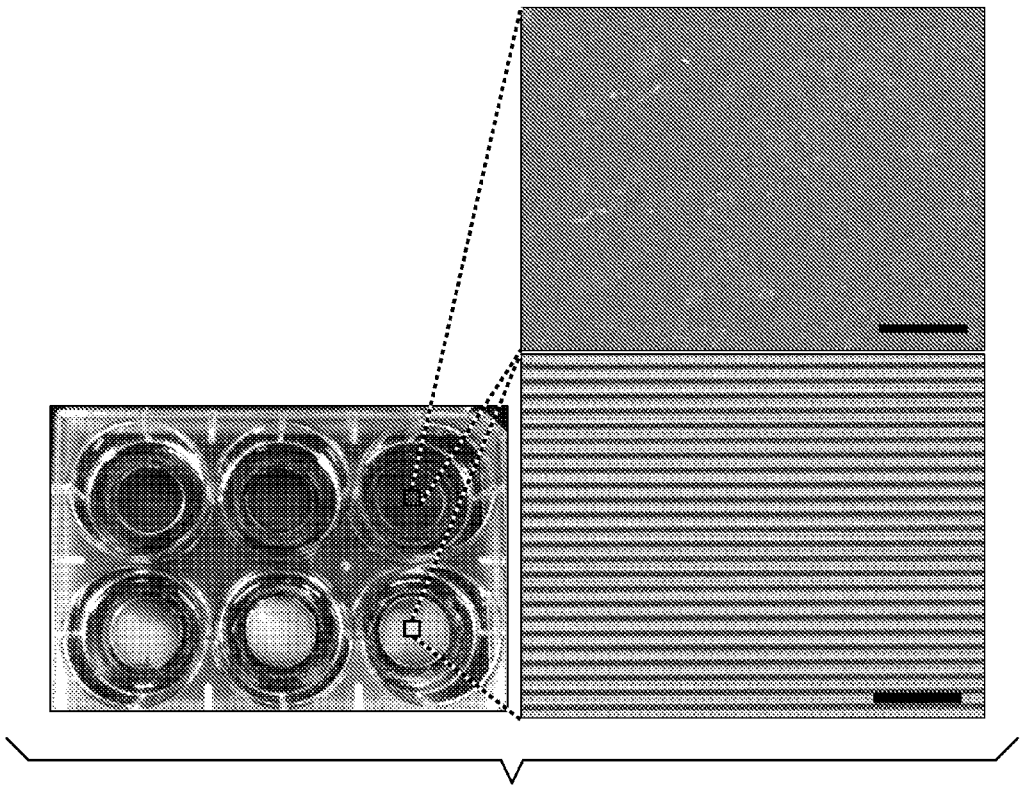

To prepare glass surfaces for fabrication, 25 mm diameter circular cover glass slides (Fisher) were placed in isopropyl alcohol for 30 min in a water sonicator and then dried under a nitrogen stream. Capillary force lithography was used to fabricate the anisotropic nanogrooved substrates from the PUA master. Briefly, a thioester prepolymer (NOA 83H, Norland Products, Inc.) was drop-dispensed onto the center of a glass slide and the PUA mold was placed pattern-face-down on top. A rubber roller was then used to evenly spread the prepolymer across the surface of the glass slide. The thioester polymer was then cured by exposure to UV light for 60 sec. After curing, the PUA mold was carefully peeled off the glass slide, leaving behind the nanopatterned substrate with 800 nm wide ridges and grooves with a ridge height of 500 nm (FIG. 1). The cover glass slides could then be placed into the well of a multi-well dish for cell culture.

Flat control substrates were created using a similar method as described above. However, instead of placing the PUA nanopatterned mold onto the thioester prepolymer on the glass slide, a piece of PET film was gently placed on top. A rubber roller was again used to evenly disperse the prepolymer over the glass slide before UV curing.

Cell Culture

Isolation and Culture of aGPFs and aGPVMs

The perfusion and isolation of adult guinea-pig myocytes will be performed according to published protocols (O'Rourke et al, 1999). For long-term culture, we used a method modified from Joshi-Mukherjee et al (manuscript in prep). The dissociated adult guinea-pig cardiomyocytes are suspended in M199 medium (Gibco) supplemented by 20% fetal bovine serum (Gibco), 2 mM L-Glutamine (Gibco) and MEM non-essential amino acids (Gibco). Accordingly, cells are plated as shown in the timeline.

aGPFs Culture

The supernatant from freshly dissociated cardiomyocytes isolation as discussed above was centrifuged at ~800 rpm for 5 min. The pellet contains mainly fibroblast and some myocytes. The pellet was suspended in 10% M199 media and plated in 10 cm tissue culture dish and incubated at 37° C. with 5% CO2. The following day the cells are replaced with fresh media to boost cell growth and to discard cell debris. Fibroblasts have limited lifespan in culture (1-5 passages) therefore it is important to keep them in proliferating state to produce ECM and growth factors support for cardiomyocyte growth. Every other day the media is changed until confluency which is between 5-7 days since day 0 (the day of isolation). This fibroblast culture is passage 0 ($P_0$). At 90% confluence fibroblast are subcultured for healthy fibroblast growth using 0.25% trypsin and replated in 10 cm dish for further proliferation (P1). Subculturing is repeated so as to obtain 90% confluent 5-7 10 cm tissue culture dishes of healthy proliferating fibroblast (P2). Fibroblasts can be frozen in the freezing media (70% FBS, 20% media and 10% DMSO) at $2 \times 10^5$ cell/ml.

Mitotic Inactivation of Fibroblast and Culture:

Fibroblast was inactivated by mitomycin C (Sigma cat no. M4287). Mitomycin C is a mutagen so extreme care was taken when handling. Also all the solutions and material that contained this solution was disposed according to the manufacturer's recommendation. To 80-90% confluent fibroblasts 10 ug/ml mitomycin C is added and incubated for 2.5 to 3 hrs at 37° C. in the incubator with 5% CO2. Aspirate and store the media with MitoC in designated waste for proper disposal. The culture dish is washed with PBS thrice. Trypsinize the cells (0.25% trypsin-EDTA) and incubate for 1-3 min and observed under the microscope. Add 10 ml of media to the dishes and transfer the cells to fresh conical and centrifuge at 270×g for 5 min and discard the supernatant. Wash the cells with media once more and centrifuge. Gently pipette up and down to break the cell clump and count the cells. The final concentration of the cells 1×106 cells/ml/vial. Freezing media is added accordingly (70% FBS, 20% media and 10% DMSO) and stored in liquid nitrogen for long term storage. Arrested fibroblast media needs to be changed with fresh 1% M199 every other day until cardiomyocytes plating and then changed every third day thereafter for 3-5 weeks.

aGPVM Plating and Culture

For aGPVM culture, the dissociated adult guinea-pig cardiomyocytes are suspended in M199 medium (Gibco) supplemented by 20% fetal bovine serum (Gibco), 2 mM L-Glutamine (Gibco) and MEM non-essential amino acids (Gibco). The key to making a monolayer of synchronously beating cells is to use a high density ($2 \times 10^5$ cells/ml/12 well tissue culture dish) of high-quality cells. Arrested fibroblast-myocyte contact affects the de-differentiated phenotype of the adult cardiomyocyte, and aids in cell survival. Accordingly, the guinea pig cardiomyocytes are plated on the arrested fibroblast culture. The cells are allowed to attach to fibroblast overnight at 37° C. in an atmosphere of 5% CO2. The following day they are washed and cultured for 24 h in media M199 plus 5% FBS. Subsequently, the medium is changed every third day with M199 plus 1% FBS for a period of up to 3-5 weeks.

Cytoskeletal Staining and Analysis

F-Actin Immunostaining

Immunocytochemistry of cultured aGPVM monolayers was performed according to protocol described in Joshi-Mukherjee et al, 2007. Primary sarcomeric actinin antibody was diluted in 10% nonfat milk plus PBS and incubated overnight, then incubated with Alexa fluorochrome-conjugated secondary antibody (1:200) and actin phalloidin (1:40), and DAPI (1:1000) for 1 hour at room temperature and washed with $Ca^{2+}$-free PBS. Cells were mounted in ProLong Gold and visualized under confocal microscope.

Fiber Orientation Analysis

The fluorescent images of the cells in each group were analyzed and the F-actin fiber orientations were measured using a custom MATLAB script. To detect edges and changes in fluorescent intensity, a 2D convolution was performed on each image and a Sobel edge-emphasizing filter was applied. These edges were them combined to calculate the gradient at each pixel in the image and a threshold was applied to select only the major F-actin fibers. The angle that each fiber made with the x-axis (between −90° to +90°) was then determined by calculating the angle orthogonal to the intensity gradient at each pixel. A probability density histogram of the fiber angle distribution was calculated for each image and averaged per condition.

Optical Mapping

Optical mapping studies were performed on aGPVM monolayers 21-28 days post-plating using 5 µM di-4-ANEPPS according to Sekar et al, 2009. Cells were point stimulated from near the center at 1.1 times threshold amplitude in order to minimize the area of instantaneous activation. A 2000 ms recording was taken after a twenty beat drive train. Action potentials were recorded from 253 sites using a custom built contact fluorescence imaging system. Conduction velocity, APD values and their spatio-temporal characteristics were analyzed from the optical maps using MATLAB data analysis scripts developed in the laboratory.

Coating of Proteins/Peptides Matrix Molecules on Nanotextured Substrates

The nanotextured substrates can be coated with a variety of proteins, peptides and matrix molecules by applying aqueous solution of the desired molecules on the surface of nanotextured platform, and coating for 1-24 hours at multiples of concentrations. In multi-well nanotextured platforms, conditions can be varied by varying multiples of concentration of the desired molecule in each well. The extent of coating and evenness of coating can be measured using fluorescent labeled molecules to coat (when available), or by immunostaining.

Coating of Lipid Molecules on Nanotextured Substrates

To immobilize biolipid molecules, e.g. sphingosine 1-phosphate (S1P) to nanotextured substrates, various amounts of S1P dissolved in sterile phosphate buffered saline is placed on substrates and dried for 1 hour at 4° C. The efficiency of S1P complexation to various nanopatterned substrates is determined using enzyme-linked immunosorbant assay (ELISA), or X-ray photoelectron spectroscopy (XPS). Since S1P-nanotextured polymeric platform is non-conducting, aS-probe spectrophotometer containing monochromatized Al Kα X-ray and a low energy electron flood gun for charge neutralization can be used. The amount of nitrogen and phosphate are expected to be significantly higher in comparison to the control unconjugated substrates. Further analysis of C1s line shape should indicate that peaks assigned to COOH decrease after S1P coating.

Few-Layer Graphene Oxide and Reduced Graphene Oxide Coating on Nanotextured Substrates GO consists of single atomic layer of carbon atoms arranged in honeycombs, bonded to oxygen atoms in the form of carboxyl, hydroxyl, or epoxy groups[7-9]. Reduced GO can be prepared from GO via chemical, thermal, hydrothermal and electrical reduction, thereby removing the oxygen functional groups (refs). For fabrication of few-layered graphene coating on the PEG ANP, graphene oxide (GO) suspension is first prepared using well established Hummus method from graphite (refs). The prepared GO suspension was then rinsed in deionized water three times and the resulting GO suspension had a concentration of 5 mg/ml. The few-layerd GO was coated on previously prepared PEG nanostructure by chemically adsorbing the GO flakes to PEG overnight via covalent and non-covalent interactions. The electrical and chemical properties, including electrical conductivity, oxygen functional group species and density can be modulated by changing the duration of chemical reduction, concentration of reducing chemical agents, changing temperature in thermal and hydrothermal reduction and changing applied current in electrical reduction. The GO can be characterized using raman spectroscopy, 4-point probe, scanning electron microscopy (SEM), atomic force microscopy (AFM) and conductive atomic force microscopy (cAFM) are used to measure the nanoscale topology, surface chemistry and electrical conductivity of the samples.

Single-Layer Graphene Coating and Controlled Oxidation for Tunable Chemical Functionality and Electrical Properties Single-layer Graphene was grown on copper (Cu) foil by chemical vapor deposition (CVD) at 990° C. using methane as precursor. Following deposition, a thin film of poly (methyl methacrylate) (PMMA) was spin-coated on the graphene. The Cu foil was then be etched away in dilute HNO3, and graphene/PMMA was rinsed twice in deionized water. In order to avoid graphene/PMMA film from folding up, the transfer of graphene took place at an air-water interface, where surface tension of water will keep graphene flat. The transfer of graphene onto patterned PEG substrates was done while floating graphene/PMMA flat at air-water interface with the graphene side facing down. The PEG substrate will then be placed in water with the patterned PEG side facing up underneath the graphene/PMMA, and brought up through the air-water interface at an angle to make a confluent contact with graphene. Once the graphene/PMMA is transferred on top of the PEG ANP, the PEG/graphene/PMMA was left in the hood to dry. During the drying process, capillary force allowed graphene film to fill in the grooves and make the desired patterned graphene. Finally, the PMMA was removed in acetone and isopropanol alcohol in order and the resulting graphene/PEG nanostructure was rinsed in de-ionized water twice.

The surface composition of oxygen functional groups and resulting electrical conductivity of prepared single-layer graphene coated PEG nanopattern was controlled by introducing oxygen defects onto graphene surface. The defects could be successfully introduced by oxygen, argon and carbon dioxide plasma treatment. A single-layer of graphene or GO can be characterized and analysed using raman spectroscopy, 4-point probe, scanning electron microscopy (SEM), atomic force microscopy (AFM) and conductive atomic force microscopy (cAFM) are used to measure the nanoscale topology, surface chemistry and electrical conductivity of the samples.

Graphene (G) and Graphene-Oxide (GO) Coating on Nanotextured Substrates

Graphene-oxide (GO) consists of carbon atoms bound in a single-atom-thick sheet as honeycombs, bonded to oxygen atoms in the form of carboxyl, hydroxyl, or epoxy groups (Yang, K., et al., Biomaterials, 2012. 33(7): p. 2206-14; Dreyer, D. R., et al., Chem Soc Rev, 2010. 39(1): p. 228-40; Andre Mkhoyan, K., et al., Nano Lett, 2009. 9(3): p. 1058-63). Nanogrooves are cleaned with 10 mM APTES-toluene solution, followed by a toluene+ethanol wash. GO-water solution is dispersed through ultra-sonication, and substrates submerged in the solution to facilitate GO self-assembly coating process, washed with ethanol and dried in N2. Raman spectroscopy and atomic force microscopy (AFM) is used to measure the extent and evenness of coating. The characterization of conductivity of the scaffold is done using conductive AFM, scanning electron microscopy, in addition to measuring resistance to current flow.

Combination of Nanotextured Substrates with hES/hiPSC-Derived Cardiomyocytes

Nanotextured substrates are coated with fibronectin, or other relevant molecules for 1-24 hours. The optimal plating density to form confluent monolayers or aligned hESC/hiPSC-derived cardiomyocytes is dependent on the type of polymer used as well as the coating. For PEG patterns, as an example, $5 \times 10^5$ cells/cm$^2$ (initial plating density) iPSC-derived cardiomyocytes form the confluent monolayer on 21-mm diameter nanopatterned (800 nm×800 nm×500 nm, corresponding to ridge width×groove width×height) substrates in 1 week. Cultures are incubated for 1-2 weeks to allow them to spontaneously beat as a confluent monolayer.

For cardiomyocytes derived from hiPSCs obtained from diseased patients, the plating density must vary in accordance to the average size of cells on nanopatterns to allow complete coverage of the susbtrata.

Creating 3D Stacks of Nanopatterned Mature hESC/hiPSC-Derived Cardiomyocytes with Arbitrary Anisotropy in Each Sheet First, hESC/hiPSC-derived cardiomyocytes are cultured on the nanopatterned substratum with NIPAAM deposited using iCVD. A gelatin coated plunger system is then used to attach the cell sheet while it detaches from the NIPAAM coated surface at room temperature. The confluent cell sheet attached to gelatin and is stacked on top of other sheets at 37° C. The optimization data indicate that aligned cell sheets are easily detached from nanopatterned NIPAAm substrates (NIPAAm thickness: 50 nm; 800 nm×800 nm×500 nm, corresponding to ridge width×groove width×height).

Biological Endpoints to Measure Cardiac Maturity on Nanotextured Substrates

Maturity of the hES/hiPSC-derived cardiomyocytes is measured using a combination of multiple endpoints, that can be broadly divided as biochemical, structural, and functional.

Evaluation of Cell Phenotypes:

Cell adhesion (live cell imaging in continuous trypsin flow at 96 nL/min in a µfluidic single channel (Kim, D. H., et al., Integr Biol (Camb), 2012. 4(9): p. 1019-33), proliferation (Ki67, EdU staining, BrdU staining), and migration speed (live cell imaging for 12 h).

Evaluation of Cardiac Maturation:

No single endpoint defines cardiac maturation conclusively, so the inventors used a comprehensive analysis of nanopatterned hESC/hiPSC-CM patch to test if, and how significantly, cardiac maturation occurred. In some embodiments, maturation can be judged relative to cardiomyocytes isolated from adult heart grown on the same substrates. In alternative embodiments, maturation of cardiomyocytes can be compared to cardiac cells cultured on non-textured surfaces, where at least about 25% increased directional organization of sarcomere and myofibrils, measured by immunostaning and high resolution microscopy is detected on the cardiomyocytes cultured on the nanotextured substrates as compared to identical cardiomyocytes cultured on non-textured or non-nanotextured substrates.

In some embodiments, an increase in contractile strength, or increase in troponin I to titin switch (e.g., change in phenotype to troponin I to titin), an increase in the rate of Ca2+ release and uptake by cardiomyocytes cultured on the nanotextures can be compared to identical cardiomyocytes cultured on non-textured or non-nanotextured substrates is a measure of increased maturity of the cardiomyocytes. In some embodiments, at least a 10% or more increase in the switch from troponin I to titin positive cardiomyocytes as measured by immuostaning, and/or western blot indicates an increased maturity of the cardiomyocytes. Similarly, an increase in at least about 10% of the calcium uptake of cardiomyocytes cultured on a nanostructured substrate as compared to cardiomyocytes cultured on a non-textured surface, or non-nanotextured platform indicates an increased maturity of the cardiomyocytes.

In some embodiments, an increase hypertrophy and/or increase in formation of intercalated disks and/or an increased contractile force generation by cardiomyocytes is a measure of increased maturity of cardiomyocytes. Cardiomyocytes cultured on the nanotextures can be compared to identical cardiomyocytes cultured on non-textured or non-nanotextured substrates to determine the level of increased maturity of the cardiomyocytes. For example, in some embodiments, at least a 10% or more increase hypertrophy and/or increase in formation of intercalated disks and/or an increased contractile force generation by cardiomyocytes of cardiomyocytes cultured on the nanotextures as compared to identical cardiomyocytes cultured on non-textured or non-nanotextured substrates indicates an increased maturity of the cardiomyocytes. The specific endpoints to be tested are summarized in Table 1. Sarcomere maturation is assessed by immunostaining, and confocal microscopy, and electron microscopy. Troponin I switch (slow skeletal to cardiac), and titin switch (N2BA to N2B) is used to evaluate maturity and purity of cardiomyocytes. Atrial natriuretic factor (ANF) reduction is measured to assess maturation of ventricular cardiomyocytes.

TABLE 1

Maturation of engineered human myocardium
Table 1. Maturation of Engineered Human Myocardium

| Category | Technique | Analyzed Parameter | Details |
|---|---|---|---|
| Structure | Immunocytochemistry | Hypertrophy | β-MHC area/nuclei |
| | | Sarcomere maturation | α-actinin, cTnT, β-MHC |
| | | Cellular Alignment | β-MHC, F-actin |
| | | Anisotropy | β-MHC, F-actin, length/width |
| | | Intercellular Junctions | Connexin43, N-cadherin |
| | | T-tubules | Caveolin3 |
| | Electron Microscopy | Ultrastructure Organization | Z-disk formation, myofibril alignment, junctions polarized to intercalated disks |
| Molecular Markers | qRT-PCR | Isoform switching | ssTnl→ctTnl: N2BA→N2B |
| | | Myocyte maturation | Decreased atrial natriuretic factor |
| | Western Blot | Isoform switching | ssTnl→ctTnl: N2BA→N2B |
| | | Cell junctions | Connexin43. N-cadherin |
| Physiology | Confocal Microscopy | Conduction Velocity | Line scan with Fluo-4 $Ca^{2+}$ dye Computational Vector Mapping of Phase-contrast |
| | Myocyte $Ca^{2+}$ & contractility | Excitation | Excitation threshold, maximum capture rate, $Ca^{2+}$ transient |

Functional Evaluation of Cardiac Maturation:

Mechanical contraction is measured using force gauge. Spatial contraction is characterized by tracking fluorescent bead motion on contracting hiPSC-CMs/hESC-CMs, allowing average direction and speed of local contraction. Electrophysiological function is measured by Ca2+ sensing fluorescent Dyes and multi-site optical mapping of cell membrane potential. With a pacing system generating stimulation frequencies of 1 Hz and upwards, one can characterize beating frequencies of patches. Lower capture threshold indicates maturity.

Example 1

The development of a novel "off-the-shelf" engineered heart tissue platform for high throughput drug screening would have wide applicability both for safety testing and the identification of new therapeutic compounds. Many promising compounds are found to have unanticipated cardiotoxic effects (e.g. pro-arrhythmic interference cardiac ion channels), and this remains the most common reason that otherwise efficacious drugs are removed from the market. Regulatory agencies require preclinical safety screens in heterologous systems (e.g. cultured cells genetically modified to overexpress a particularly susceptible ion channel, such as the HERG channel) and animal models, but both have important limitations. Heterologous systems lack the full constellation of ion channels and signaling pathways present in intact cardiomyocytes, while animal studies are very expensive, low-throughput and often limited to relatively short time-points. There are also important differences between human and non-human cardiomyocytes in terms of their electrophysiological properties and neurohormonal responsiveness.

Human induced pluripotent stem cells (hiPSCs) are generated by reprogramming adult somatic cells (e.g. dermal fibroblasts), and they can be subsequently expanded and differentiated into cardiomyocytes, making them a potentially inexhaustible supply of genetically diverse human cardiomyocytes. While others have contemplated the use of hiPSC-derived cardiomyocytes (hiPSC-CMs) in drug screens, an advantage of the technology described herein is the use of large-scale, nanotextured surfaces that provide biomimetic cues for the arrangement and differentiation of the cells, which in turn provide for enhanced function and greater similarity to adult cardiac tissue. The nanotextured substrates are preferably optically transparent. Methods are described herein to separately tune nanopatterned texture and mechanical stiffness, thereby mimicking native myocardial conditions and conferring tissue-like anisotropy to sheets of hiPSC-CMs. Diseased hearts also accumulate interstitial fibrosis over time, resulting in increased stiffness and patchy loss of the usual anisotropic architecture (so-called "cardiomyocyte disarray"). Thus, the described methods permit modeling of both normal and diseased myocardium by culturing patient-derived cardiomyocytes on substrates of varying anisotropy and rigidities. This provides an ideal model for drug screening, using available high-throughput optical methods.

The nanotextured platform as disclosed herein includes a nanofabricated polymer cell culture scaffold with tunable topographies, topographical dimensions and scaffold rigidities. These scaffolds are scalable and can be used individually in a dish or incorporated into a multiwell format for multiplex analysis. More specific to the application of mature anisotropic cardiac tissue, the nanotexture (e.g., groove width and depth) of the ANP can be modified to varying dimensions to mimic the extracellular matrix (ECM) of heart tissue. In some embodiments, the ANP polymer substrate as disclosed herein is unique in its ability to independently vary the scaffold topography and rigidity in a scalable and high throughput format.

Topography.

The nanotextures on the ANP have four independently tunable parameters: ridge width, groove width, ridge height and periodicity. These parameters can be easily tuned by the use of differing masters using capillary force lithography, and these masters can be custom generated through conventional nanofabrication techniques such as electron-beam lithography. By being able to vary these dimensions independently, cell function, morphology and alignment can be altered. These effects may also additionally impact cell maturity. This precise level of nanotopographical tuning allows the inventors to faithfully recreate the topographical cues of the heart ECM, as well as alter the cardiac monolayer model as needed.

Rigidity.

Additionally, the ANP substrates can be independently modified to alter scaffold/substrate rigidity in addition to the tunability of the scaffold topography. Scaffold rigidity can be altered in several ways, most notably through polymer concentration, crosslinker concentration, and polymer composition/type. For example, the concentration of the polymer can be varied (such as weight percent in an aqueous or solvated solution), and these varying concentrations of polymer can be nanofabricated to incorporate the same topographical cues (such as linear nanogratings with fixed dimensions in the case of cardiac tissue engineering) but will also have varying rigidities. This makes it possible to separately characterize the effects of scaffold rigidity on cell function. Rigidity tuning also allows the ANP substrate to model differing cardiac states, such as healthy cardiac tissue or cardiac scar tissue, which have variable stiffness and profoundly impact cell function.

Scalability.

Capillary force lithography or nano-imprinting techniques can be used by one of ordinary skill in the art to fabricate highly uniform nanopatterned substrates on a large area for large scale tissue generation; this robust technique can be used on a number of polymers with various chemical, physical and electrical properties. This technique is scalable, and the ANP substrate size (surface area) can vary from extremely small for smaller or individual cell analyses, to large (e.g., 1-10 $cm^2$ or greater) for creation of macroscopic tissue constructs to examine tissue-level characteristics.

High Throughput Format.

Additionally, the ANP supports can be incorporated into a multiwell format for multiplex analysis, due to the ability to change the scale of individual scaffolds. This multiwell format will enable the examination or analysis of multiple scaffold parameters at once, and thus will be able to generate multiple cardiac models and analysis them in tandem. For example, a 24 well plate (4×6) could be used to examine the effects of varying rigidity and varying topography dimension on cardiomyocyte function by having 4 rows of different scaffold rigidities and 6 columns of varying scaffold topographical dimension (see supplemental figures). This multiwell format will be extremely helpful in rapidly characterizing the independent effects of nanotopography and rigidity on cardiomyocyte function. Additionally, a multiwell format could be used in patient specific modeling by utilizing one patient's own iPSC-CMs in different cardiac models or using different patients' iPSC-CMs to examine the same cardiac model. Accordingly, the ANP support can be used in mid and high-throughput screens and analysis systems.

Example 2

Development of a High Throughput and Patient-Specific Tissue Culture Platform with Different Nanotopographical Patterns and Stiffnesses.

Development of ANP Cell Culture Substrates with Tunable Topography and Stiffness.

Using a PEG-based materials, the inventors have generated an ANP using well-established biocompatible hydrogel polymer whose mechanical and topographic properties can be modulated by UV-assisted capillary force lithography. In particular, the inventors synthesized polyethylene glycol-gelatin methacrylate (PEG-GelMA) composite prepolymers and then fabricated nanogroove structures on large areas (>10 cm2). Modulation of the concentration of PEG and GelMA allows for control of the Young's modulus of the material to match the rigidity of myocardium. The gelatin component of the composite biomaterial helps promote cell attachment. To account for the scale of the ECM cues and possible variability in the diameter of the ECM fibrils in the heart tissue, the widths of the grooves and ridges and height/depth of the grooves are modulated in a defined manner.

Integration of Large Area Nanotopographic Substrates in a Multi-Well Platform (FIG. 1).

The effect of substrate stiffness on individual cardiomyocytes has been well studied, but less is known about its effects at the multicellular level. Furthermore, little is known about the combined influence of nanotopography and stiffness on adult cardiomyocyte function, so different combinations are tested in a multi-well platform. Large area nanotopographical substrates are adapted to a multi-well plate format and the substrate is designed with varying pattern feature size and/or substrate stiffness to permit screening of different topographic parameters and stiffness in each well. Such methods provide a platform for rapid, quantitative assessments of adult myocardial tissue function over time.

Example 3

Maintenance of Human iPSC Derived Cardiomyocytes in Long Term Culture on Substrates with Different Nanotopographical Patterns and Stiffnesses Sustains Cellular and Tissue-Level Electrophysiological and Contractile Function Optimization of Cellular Function.

The inventors have identified an optimal combination of nanotopography and substrate stiffness that maximizes cell survival and maintains cellular function at both the single cell and monolayer level. Multi-well plates can be used for studies of confluent monolayers. As an additional biomimetic cue, electrical pacing can be applied to the cell culture for up to 3 months. Optical mapping is performed using voltage- and calcium sensitive dyes, thereby measuring action potential duration (APD), calcium transient amplitude (CaT), spontaneous beat rate, average conduction velocity (av CV), conduction anisotropy ratio (AR), maximum capture rate (MCR), and heterogeneity index of action potential duration (HI) for comparison to healthy human cardiac function. The size of the cells can be assayed in terms of cell perimeter and area, and cell shape is analyzed using methods developed in computer vision for unbiased quantification of the shape parameters, eccentricity (E) and rectangularity (R). Biochemical assays by Western blots of structural and contractile proteins such as cardiac troponin I, α-myosin heavy chain, and α-actinin can identify the maturation and differentiation of the cardiomyocytes. To assess mechanical contraction, fluorescent bead motion immobilized on the contracting hiPSC-derived cardiomyocytes can be tracked on both flat and engineered substrates.

Validation of the ANP in High-Throughput Assays Using Pharmacological Interventions Having Known or Putative Effects.

The platform can be assessed using drugs known to interfere with cardiomyocyte function (e.g. drugs causing acquired long QT syndrome). Such drugs can include, for example, epinephrine (α-adrenergic agonist), E-4031 ($I_{Kr}$-blocker), chromanol ($I_{Ks}$ blocker), and quinidine (use-dependent $I_{Na}$ blocker). Drugs with putative cardiotoxic effects, including erythromycin and doxorubicin, can be tested for their influence on cellular and tissue-level parameters.

Compared to control cultures, the inventors discovered significantly improved tissue characteristics of the cardiomyocytes in monolayers grown on nanopatterned substrates or substrates with medium-soft stiffness, and demonstrated conditions closer to those in native myocardium. This was demonstrated by increased sarcomeric organization and alignment, increased force generation, reduced automaticity, higher propagation speeds, higher maximum capture rates, and lower overall heterogeneity. The inventors also demonstrated that the opposite is true for hiPSC-derived cardiomyocytes (e.g., derived from subjects with a cardiovascular disease) cultured under conditions deliberately mimicking those in diseased myocardium.

In some embodiments, because the platform and system as used herein can be seeded with patient-derived cardiomyocytes, it can facilitate the development of personalized medicine.

Example 4

Nanotextured Substrates for Enhanced Myogenesis and Regeneration of Skeletal Muscle Tissue and Generation of Muscular Tissue in Mdx Dystrophic Mice.

Skeletal muscle displays a robust capacity for regeneration following injury. However, few effective therapeutic methods are available for muscle regeneration. Recent advances in biomimetic tissue engineered systems have resulted in an increase in tissue regeneration. One possible solution is cell-based and tissue-engineered biomimetic muscle cell therapies.

Herein, the inventors have demonstrated a simple method to create transplantable, uni-directionally aligned skeletal muscle cell patches which contains a mixture of muscle mononuclear cells, including the progeny of satellite cells and other potential resident myogenic cells. Furthermore, the inventors have demonstrated that biodegradable nanopatterned PLGA patches not only directed uniform alignment in vitro, but also enhanced myogenic contribution in vivo compared to flat patches after 4 weeks of transplantation. The increase of dystrophin positive myofibers with nanopatterned patch as compared to flat patches demonstrates that the transplantable muscle cell patch can be utilized for treating chronic and acute muscle diseases or injuries.

Skeletal muscle consists of highly striated cells packed into longitudinally oriented extracellular matrix (ECM) fibers, with features on the sub-micrometer scale extending for various length scales. The inventors have established a nanotopography-guided tissue engineering platform for the delivery of muscle mononuclear cells into the muscular tissue in mdx dystrophic mice by a nanopatterned polymeric scaffolds that mimic ECM fibers. Specifically, the inventors have developed scalable, nanopatterned muscle cell patches mimicking the in vivo muscular tissue, and characterized their structure and function in vitro and dystrophin expression post-implantation into mdx dystrophic mice. Using solvent-assisted capillary force lithography, we fabricated biodegradable, PLGA-based scaffolds with precisely controlled nanoscale topography and cultured a mixture of muscle mononuclear cells on the nanopatterned PLGA substrates. From in vitro characterization of nanotopographically-stimulated muscle patches, we found that nanotopographical cues not only enhanced cell alignment and elongation, but also promoted myogenic differentiation and maturation. Interestingly, we also found the increase of dystrophin positive myofibers at 4 weeks post transplantation of nanopatterned patch (vs. unpatterned patches) into mdx mouse quadriceps muscle. These tissue-engineered biomimic muscle cell therapies transplantable muscle cell patch can be suitably utilized for treating chronic and acute muscle diseases or injuries.

Recent advances in nanofabrication techniques enable the design and fabrication of scalable scaffolding materials mimicking the structural properties of complex ECM structures. Engineered skeletal muscles require the parallel alignment of muscle fibers, thus transplanted muscle tissue should integrate with the host muscle tissue in a coordinated orientation. Extracellular matrix (ECM) fibers, with features on the nanometer scale, connect these cells and extend for various length scales with high fidelity. These extracellular topographies provide guidance cues for cell alignment, satellite cell migration, myotube fusion, and muscle fiber formation.

Functional skeletal muscle requires the parallel alignment of muscle fibers, thus transplanted muscle tissue should integrate with the host muscle tissue in a coordinated orientation 3. Further, the anisotropic muscle scaffold must degrade slowly to be replaced by endogenous extracellular matrix 4. In this proposal, we propose to use Poly(lactic-co-glycolic acid), PLGA, a biocompatible and biodegradable material, to create nanopatterned scaffolds that mimic the ECM within the muscle tissue, allowing the cultured cells to align unidirectionally, enhance migration, and mature the tissue As disclosed herein, inspired by ultrastructural analysis of the native tissue, the inventors used a scalable, nanotopographically controlled model of myocardium mimicking the in vivo ventricular organization. Guided by nanoscale mechanical cues provided by the underlying hydrogel, the tissue constructs displayed anisotropic action potential propagation and contractility characteristic of the native tissue. Surprisingly, cell geometry, action potential conduction velocity, and the expression of a cell-cell coupling protein were exquisitely sensitive to differences in the substratum nanoscale features of the surrounding extracellular matrix. The inventors have demonstrated that controlling cell-material interactions on the nanoscale can stipulate structure and function on the tissue level and yield novel insights into in vivo tissue physiology, while providing materials for tissue repair.

Duchenne muscular dystrophy (DMD) is the most common type of muscular dystrophy, affecting one in every 3500 males within the US.5, 6 DMD is caused by a mutation in the dystrophin gene, which encodes for the dystrophin protein, an essential structural component within skeletal muscle cells. There is no cure available for DMD, and treatment is largely limited to palliative and supportive efforts to extend expectancy of life (rarely extends beyond teenage or early adulthood). Though muscle is a highly regenerative tissue, since DMD is a genetic disorder, the innate regenerative capacity of the tissue cannot improve DMD condition. DMD is primarily a disease of loss of functional skeletal muscle tissue. Consequently, there is a significant effort towards development of stem cell based therapies to address cell attrition and loss of tissue function. However, intramuscular transplantation of stem cells from various sources have resulted only in limited success in regaining muscle function.9 A successful stem cell therapy for DMD requires a readily available source of stem cells that can be expanded in sufficient numbers and can engraft in muscle fibers capable of replacing dystrophin expression robustly while also repopulating the satellite cell niche to provide long-lasting and continuous regeneration to the muscle. One of the significant and unaddressed causes is that transplanted cells fail to integrate into an organized tissue like skeletal muscle.

Skeletal muscle is a complex tissue, consisting of highly striated cells arranged in the highly anisotropic manner, attached to an extracellular matrix composed of many fibers in the nanometer size range, extending for various length scales with high fidelity. These extracellular matrix topographies provide guidance cues for cell alignment, satellite cell migration, myotube fusion, and muscle fiber formation. Skeletal muscles exert force by uni-directional contraction of muscle fibers in a synchronized manner. Force propagation within a cell is along the myofibers. Therefore a parallel and additive alignment of small force-generating myofibers in transplanted cells, in the direction of the existing force vector, is critically important to restore muscle function.

Recent studies have strongly underlined the importance of extracellular matrix nanotopography as a potent cue defining cell shape, orientation, alignment, migration, and regulation of tissue level functions in other organized tissues such as cardiac tissue, ligament/tendon, and neuronal tissues. However, the role of nanotopography in regulating muscle cell phenotypes, differentiation, and maturation, and its effect on tissue level function have not been investigated. Here, a nanoengineered nanotextured substrate to generate a biodegradable muscle patch constituted of primary muscle mononuclear cells, can be transplanted intramuscularly to enhance biochemical and structural maturation of cells, and functional improvement in a mdx mouse model of DMD. Inspired by the highly organized structure of the skeletal muscle, the transplantable tissue scaffold is engineered to mimic the native extracellular matrix structure of the collagen fibers present in skeletal muscle at nanometer level. The transplantable patch can be composed of biocompatible poly(lactic-co-glycolic acid) (PLGA) facilitating controlled degradation and gradual replacement of the scaffold by endogenous extracellular matrix post transplantation.

The nanotextured PLGA substrate cell alignment, proliferation, migration, biochemical and structural maturation of primary mononuclear muscle cells in vitro and enhanced engraftment in a mdx mouse model in vivo.

Fabrication of Biodegradable Nanopatterned PLGA Substrates

Figure 35A:
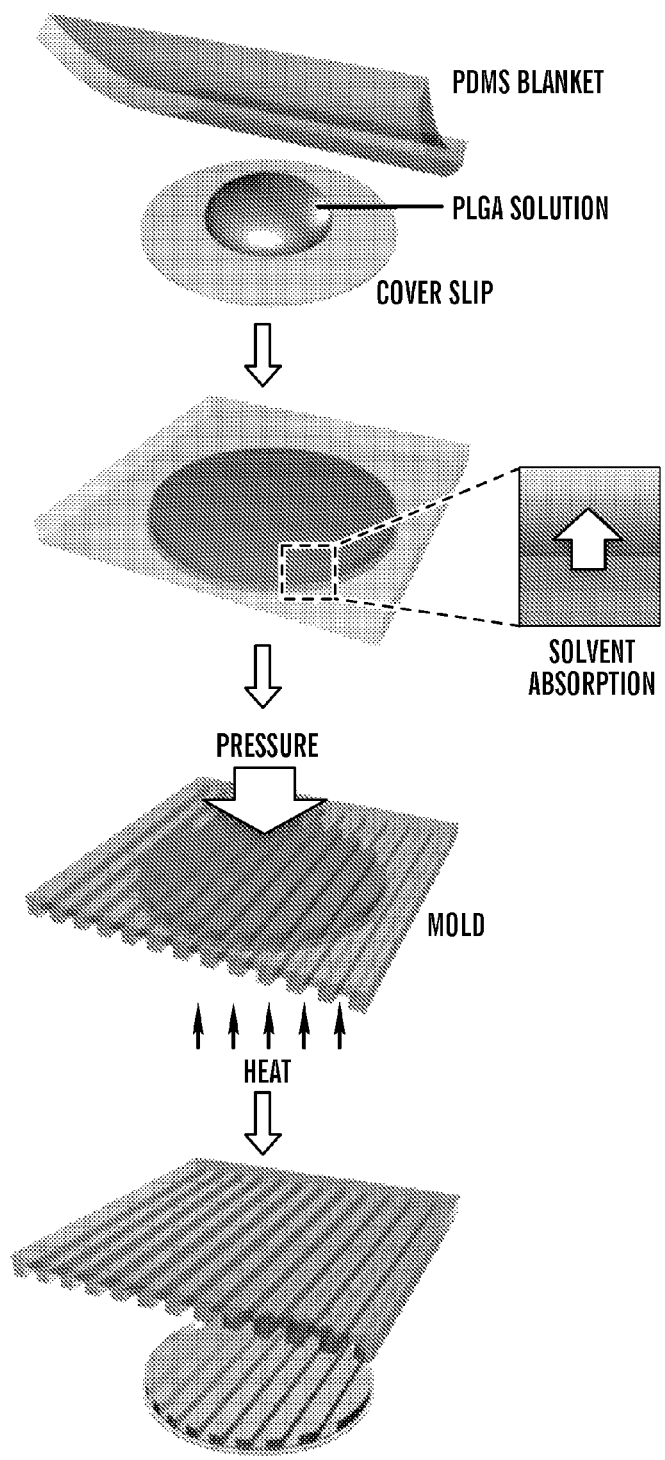
FIGS. 35A-35D depict a schematic diagram of fabrication and concept of muscle cell patch transplantation.
Figure 35C:
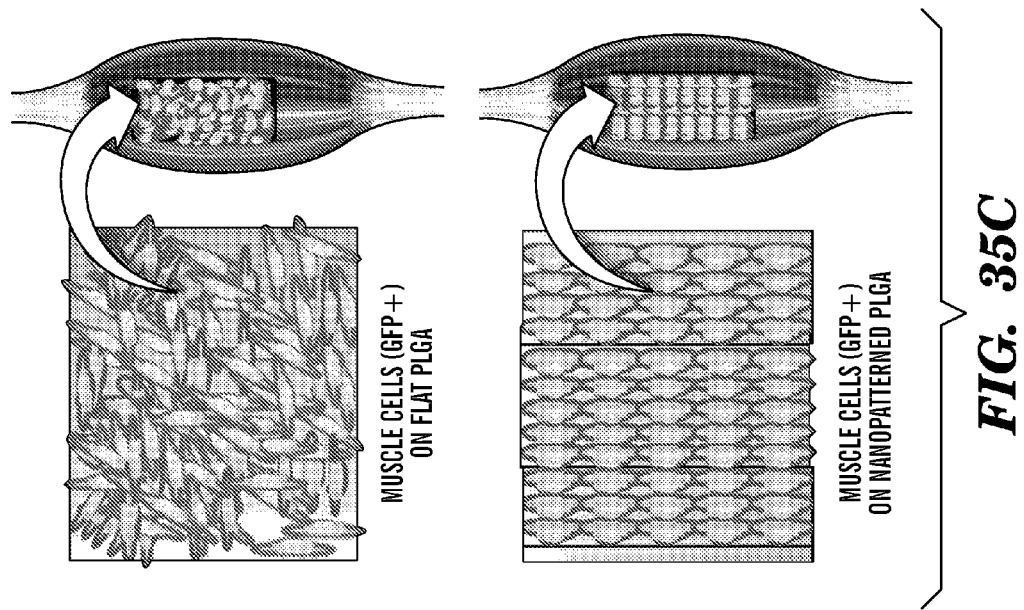
Figure 35B:
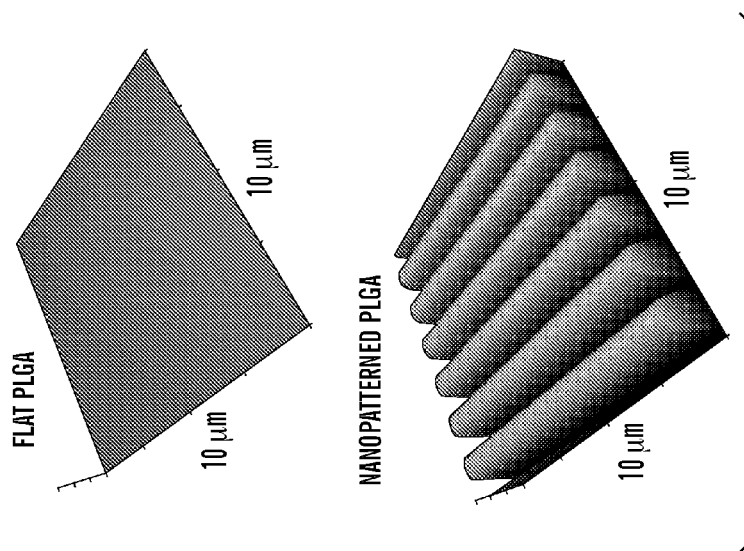

FIG. 35A shows a schematic illustration of the capillary molding process used in this study for preparing nanopatterned PLGA substrates. Since PLGA has relatively low glass transition temperature ($T_g$, 40~60°),[19] a thin PLGA film can be easily molded with pressure while heated above $T_g$. This fabrication technique utilizes direct solvent-absorption capability of polydimethylsiloxane (PDMS, Sylgard 184, Dow Corning) mold.[25] In brief, as shown in FIG. 35A, a flat PLGA layer was prepared by placing a PDMS blanket (3×3 cm) onto a drop-dispensed PLGA solution (15%, w/v) on cover glass (ø25 mm) and subsequently pressed with a slight pressure (~10 kPa). The solution then spreads and forms a uniform film to ~20-μm thickness. In this step, the solvent (typically chloroform or toluene) is absorbed into the PDMS mold and evaporates within 10 min. The topographical modification was made by bringing a nanopatterned polyurethane acrylate (PUA) mold into uniform contact with the PLGA film while applying heat (~120° C.) under a slight pressure (~100 kPa) for 15 min. After removal of the mold, a nanopatterned PLGA scaffold was left behind over a large area (ø25 mm) with good structural fidelity as shown in FIG. 35B. The fabricated nanogrooves had an 800-nm equal line-and-space pattern with a height of 800 nm as visualized by atomic force microscopy (FIG. 35C). As illustrated in the schematic in FIG. 35D, the nanopatterned PLGA scaffold was used to induce contact-guided alignment along the direction of the grooves and mimic the uni-directionally organized in vivo muscle fibers as compared to randomly oriented cells on flat substrate.

Figure 35D:
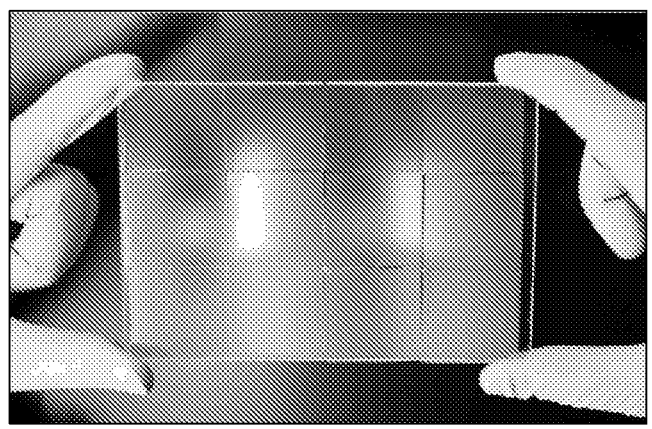

Our micromolding method has several distinct advantages over previous methods (e.g., electrospinning and self assembly) to make nanopatterned scaffolds. First, nanopatterns of variable topographic density, thickness, and geometry can be readily formed over a large area, as dictated by the merits of top-down based approaches. As shown in FIG. 35D, the nanopatterns show high physical integrity and uniformity over ø25 mm, which is useful to study the effect of topographical cues in myogenesis and generation of muscle cells. Although not shown, a gradient pattern with a range of pattern widths and spaces can be easily incorporated on a single culture platform, which is not simply accessible by other methods.[26, 27] Second, the method is highly reproducible and generates the topographically identical patterns each time, which minimizes run-to-run variations and other experimental factors. Third, other polymer materials like thermoplastic and UV-curable polymers are equally used to make nanopatterns without significant modifications of the experimental protocol.[28]

To date, the biocompatible and biodegradable properties of PLGA material have been utilized for in vitro culture and in vivo transplantation and engraftment in the heart tissue.[29, 30] PLGA is a FDA-approved biocompatible polymer due to its comparatively smaller cytotoxicity and longer-term safety upon transplantation. For this reason, PLGA material has extensively been used in clinical tools such as absorbable sutures and fixation units for medical surgeries.[31] Although some side effects such as production of acids (lactic and glycolic acids) or release of small particles upon degradation have been reported, such side effects emerge only when excessive volumes are introduced.[19]

In addition to the biocompatibility, biodegradability is one of key factors for transplantable tissue engineering. Biodegradability of material is described as the time required for the loss of total mass. As previously reported,[32] the degradation of PLGA polymer within human tissues can be tuned by adjusting relative ratio of lactide and glycolide (50:50, 65:35, 75:25 and 85:15 are commercially available). Several experiments have demonstrated that the shortest degradation time of 1~2 months was achieved with 50:50 (lactide: glycolide) ratio, while the longest time of 5~6 months being with a ratio of 85:15.[19] To decide the suitable degradation time of tissue patch, tissue regeneration speed has to be carefully examined. If the degradation time is too short, the tissue cannot be fully reconstructed during the degradation of the scaffold. In this study, the 50:50 ratio of PLGA was chosen in light of the rapid regeneration capability of the muscles.

In Vitro Characterization of Nanopatterned Muscle Cell Patches

For in vivo transplantation, cell seeded scaffolds should promote cell proliferation, self-renewal, myogenesis, engraftment, and function. To date, a number of potential myogenic cells with therapeutic potential have been identified.[33-35] An obvious source of myogenic cells is from skeletal muscle satellite cells that reside in between the plasma membrane and basement membrane of individual muscle fibers.[36, 37] However, satellite cells comprise <10% of total muscle nuclei, and can be technically challenging to purify.[37, 38] For this reason, we used a mixture of primary muscle mononuclear cells including the progeny of satellite cells and other potential resident myogenic cells. To induce proliferation and differentiation, cells were cultured with 15% horse serum and 20 ng/ml bFGF. Within five days in culture, differentiation was observed by the presence of multinucleated myotubes generated from the fusion of myoblasts.[39]

Figure 36B:
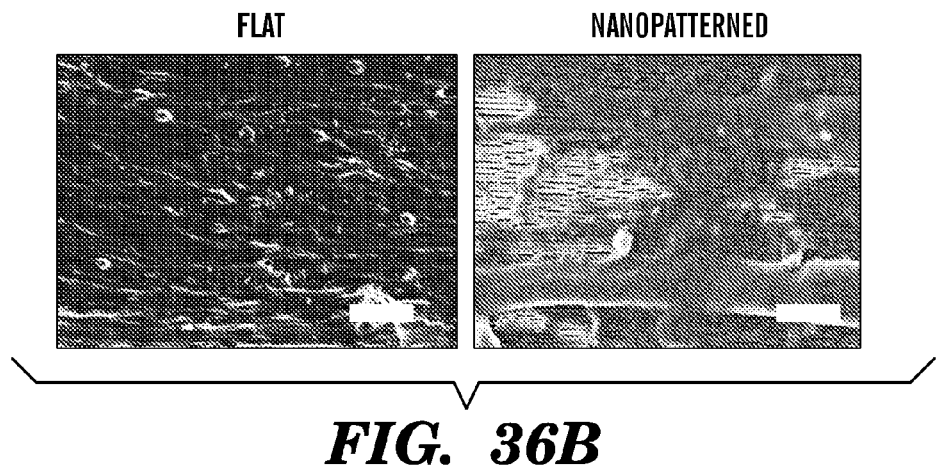

On flat and nanopatterned PLGA substrates coated with gelatin, GFP positive muscle cells isolated from chicken actin promoter driven EGFP reporter mice were cultured for 3, 6, and 10 days and their cellular behavior was investigated (FIG. 36A-36B). Up to day 3, the nanopatterned surfaces had not induced distinctive cell adhesion and proliferation, presenting similar apparent population to cells seeded on the flat (non-patterned) substrate (FIG. 36A, first column). However, at day 6, cells cultured on both flat and nanopatterned surfaces showed dramatic differences in terms of, e.g., myotube formation and cellular elongation, which was barely observed with the flat substrate (FIG. 36A, second column). At day 10, cells grew to high confluence on both flat and nanopatterned substrates (FIG. 36Aa, third column); however, their organizations were different. Muscle cells grown on the nanogroove patterned substrate were organized and uniformly oriented. In contrast, cells grown on the flat substrate were randomly organized and oriented. Typical cellular morphology at day 10 on two substrates was measured with scanning electron microscope (FEI Sirion SEM) (FIG. 36B). As shown, cells on the flat PLGA surface were relatively randomly oriented and less elongated compared to those on the nanogrooved substrate.

Figure 36C:
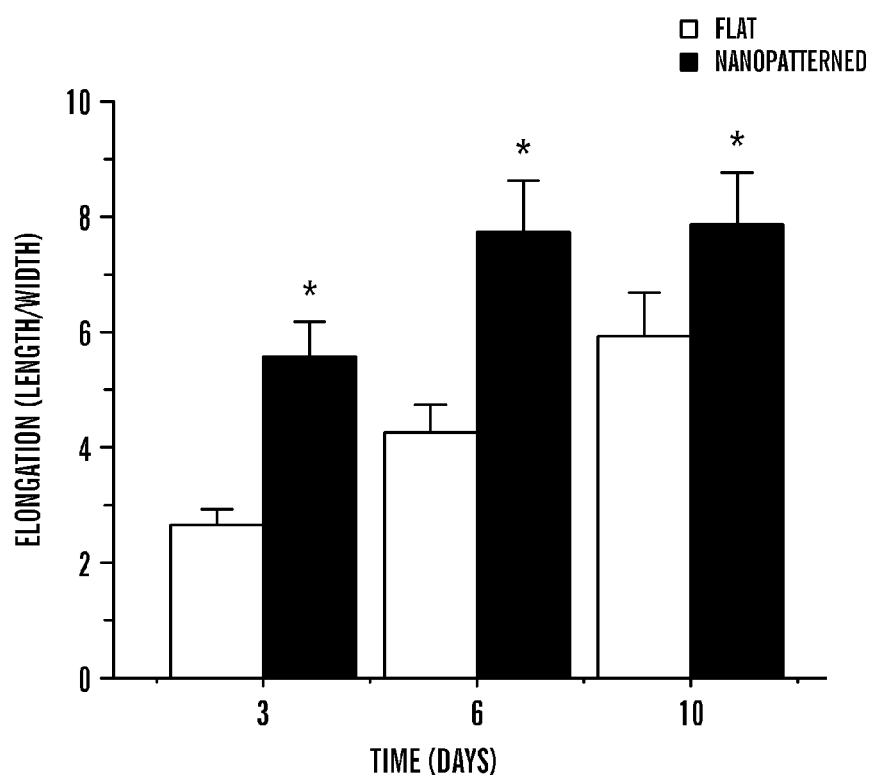
Figure 36D:
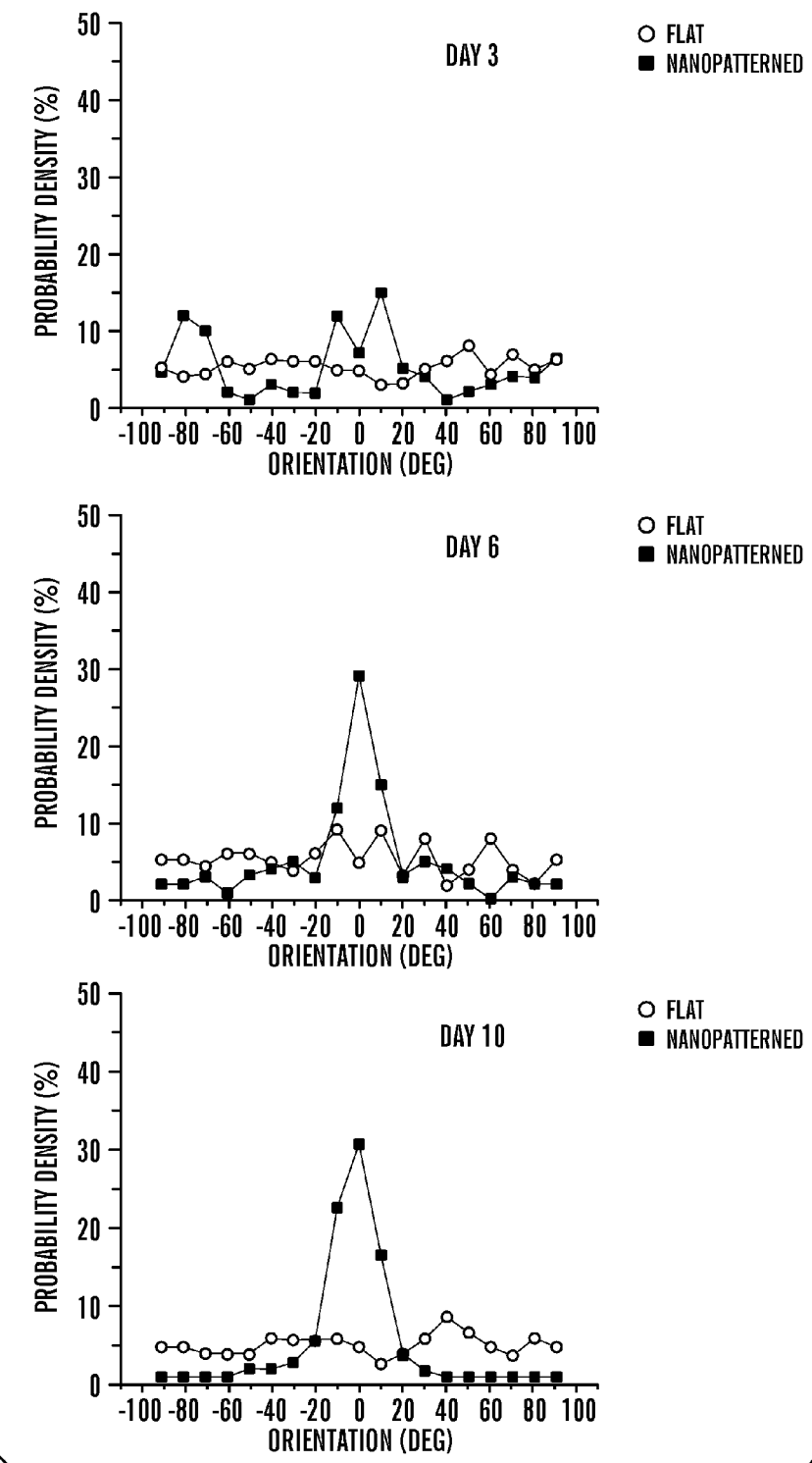

In a more detailed analysis, the elongation (FIG. 36C) and alignment (FIG. 36D) were quantified. The spindle-shaped morphology is an indicator of the degree of adhesion. At high adhesion, the cells were more elongated as compared to a more rounded shape at low adhesion. Here the cells cultured on nanotopography tended to be more spindle-shaped than on flat substrate throughout the entire culture time. However, there was less of a difference at day 10 (FIG. 36Cc). Furthermore, cells were gradually elongated with culture time, suggesting that a long-term culture can present further morphological similarity to in vivo tissues. The reduced gap of elongation between the flat and nanopatterned surfaces appears to be induced by two factors: sufficient adhesion and myotube formation in a longer culture period. Since at day 10, the cells on nanogrooves were already fully adhered onto substrate and/or fused into myotubes, the elongation was saturated between day 6 and 10.

Figure 26A:
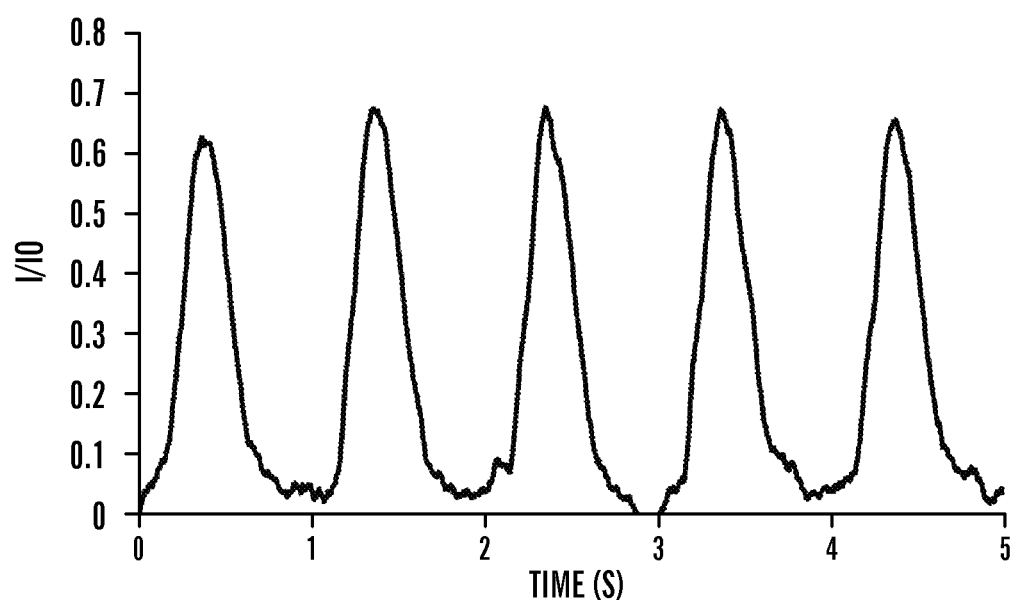
Figure 26B:
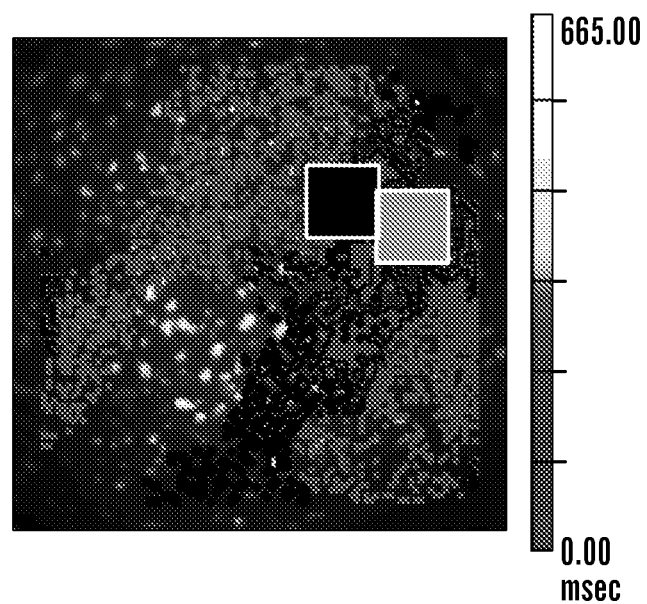
FIG. 26B shows an action potential map of the hESC-derived cardiac tissue on day 10, showing long-range electrical coupling of the mature cardiomyocyte cells on graphene PEG nanopatterned substrate.
Figure 27A:
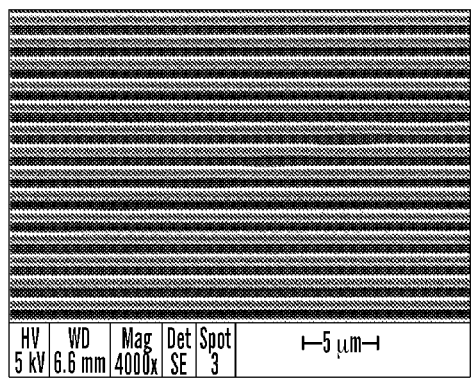
FIGS. 27A-27D show the ANP can be combined with thermoresponsive polymers including NIPAAM for anisotropic mature sheet formation of cells, and scaffolds retain nanopattern fidelity and successfully incorporate PNIPAm.
Figure 27B:
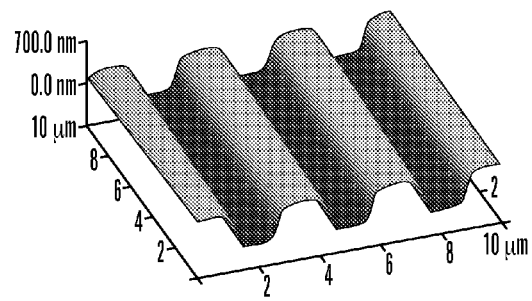
Figure 27C:
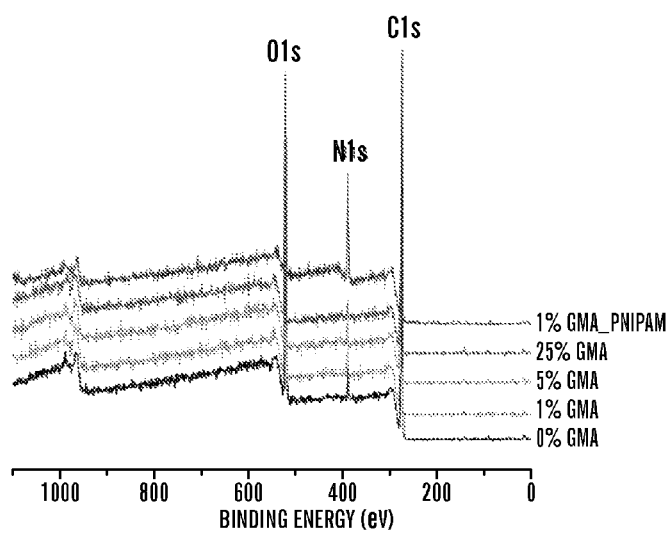
Figure 27D:
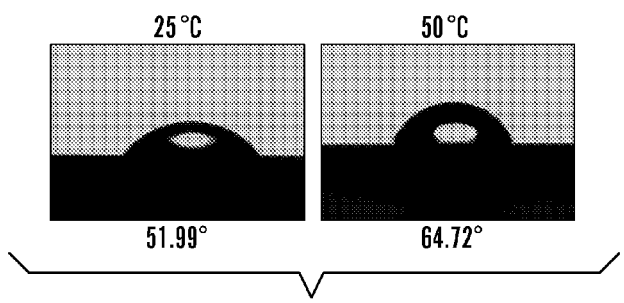
Figure 28A:
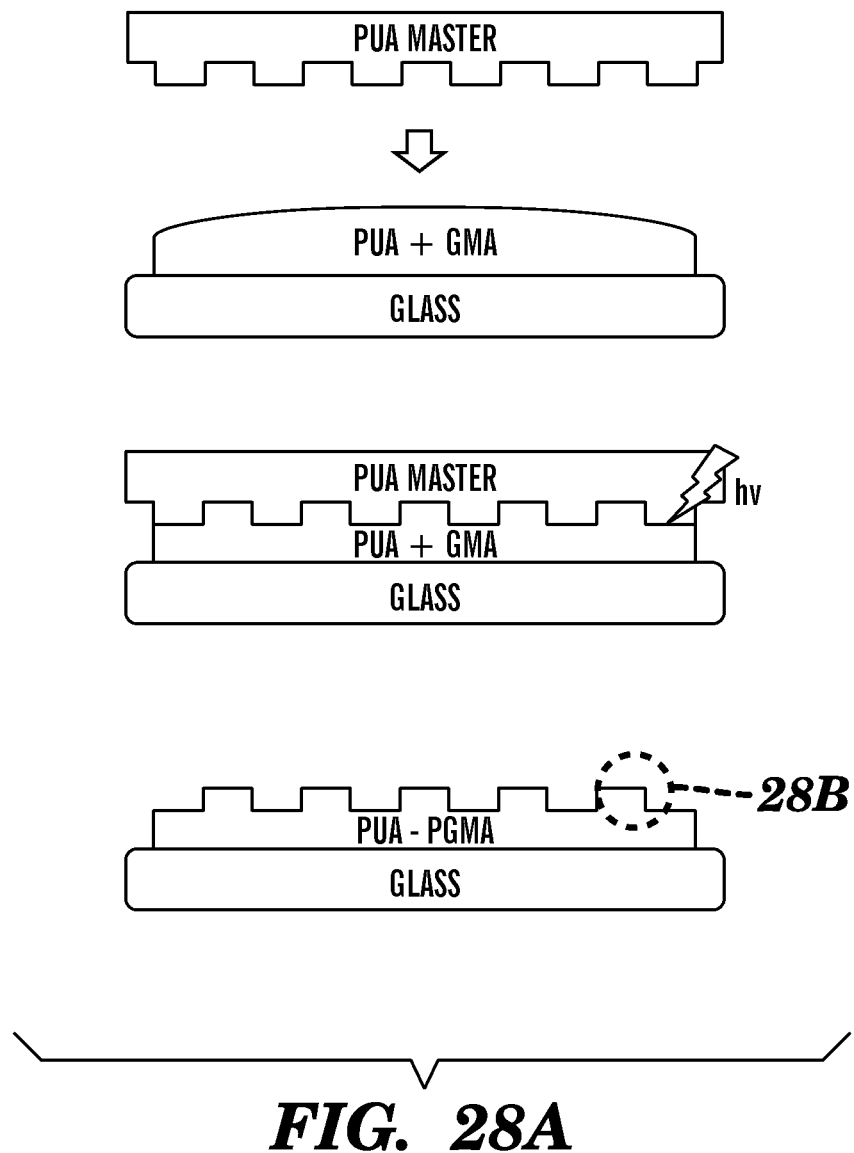
FIGS. 28A-28B shows one embodiment of a method to incorporate a thermoresponsive polymer, e.g. NIPAAM on the nanopatterned substrate, using capillary force lithography fabrication of PUA-PGMA scaffolds and PNIPAM dip coating.
Figure 28B:
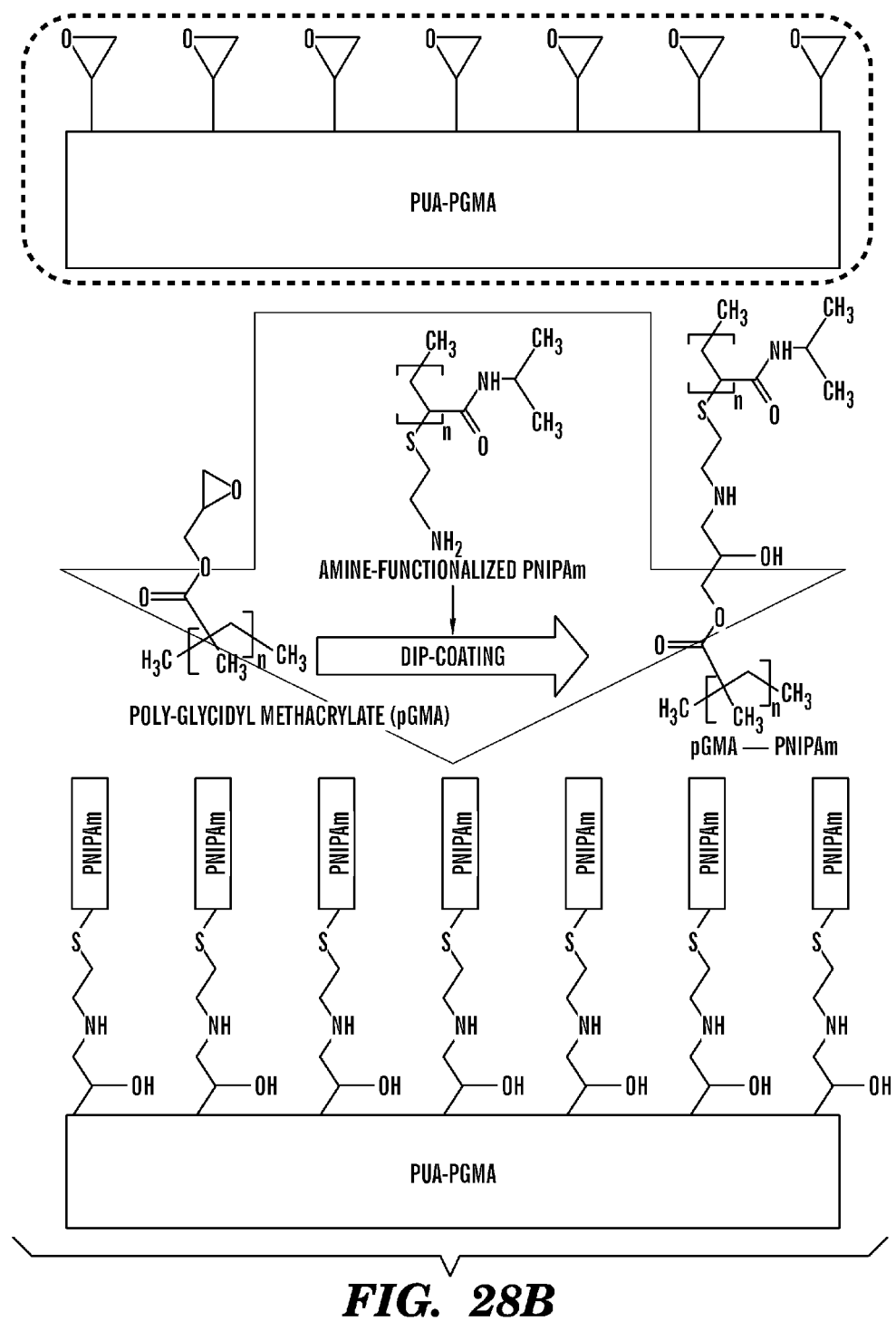
Figure 29A:
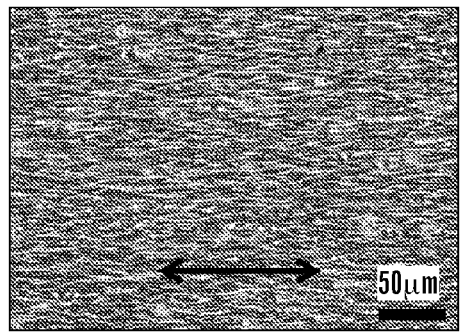
FIGS. 29A-29D show the cell viability and alignment is well maintained on thermoresponsive polymers coated Spriha Nanopatterns as cells attach well and align on PNIPAM-grafted PUA-PGMA nanofabricated scaffolds.
Figure 29B:
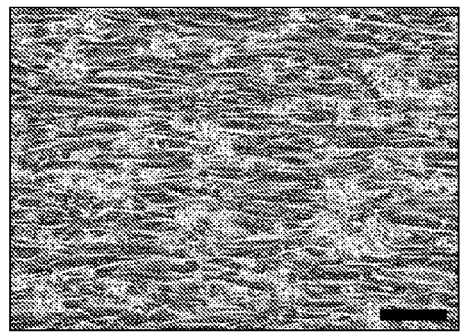
Figure 29C:
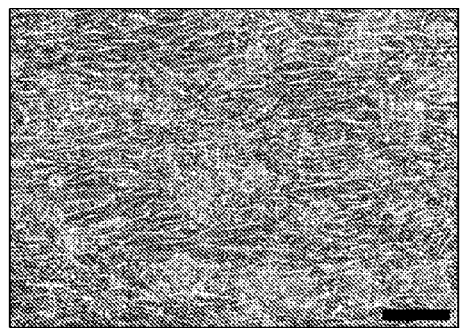
Figure 29D:
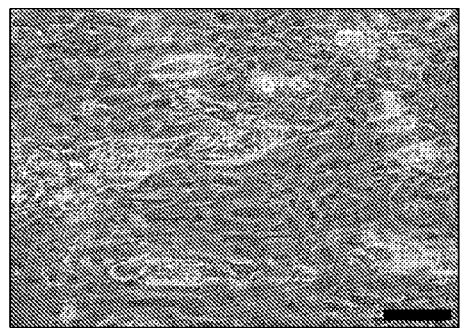
Figure 30C:
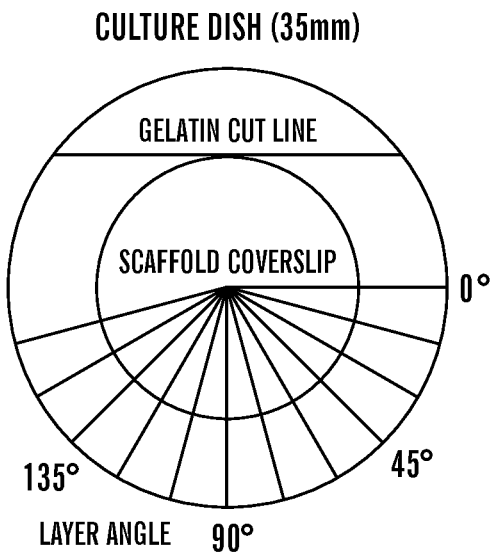
Figure 30D:
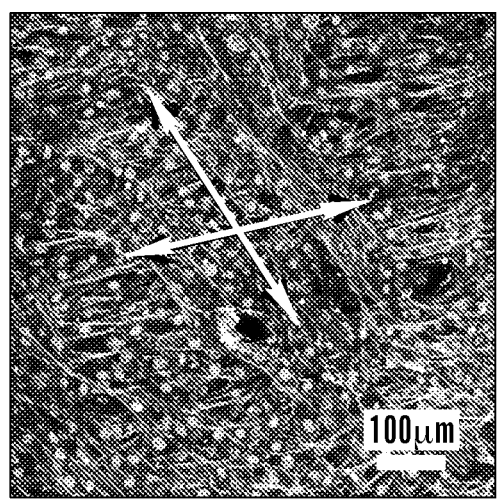
Figure 31A:
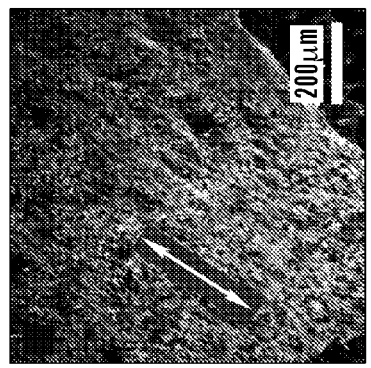
FIGS. 31A-31F show the generation of multiple layers of aligned and mature cardiac sheets using the nanotextured substrates combined with thermoresponsive polymer, followed by scaffold-free sheet engineering. Transferred anisotropic cardiac sheets retain morphological alignment and beating. Cardiomyocytes cultured on thermoresponsive nanopatterned scaffolds detach during room temperature media incubation and can be transferred while retaining anisotropy of the cardiomyocytes.
Figure 31B:
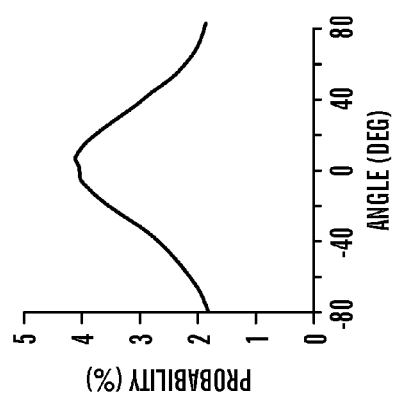
Figure 31C:
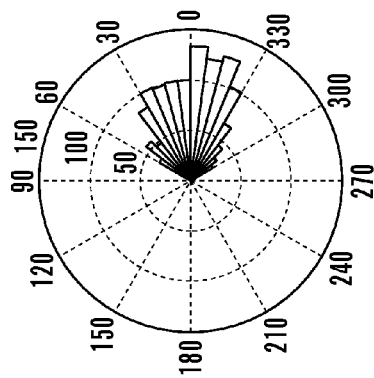
Figure 31D:
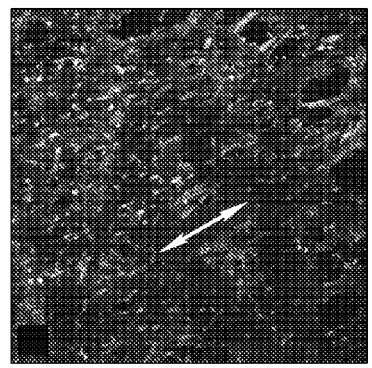
Figure 31E:
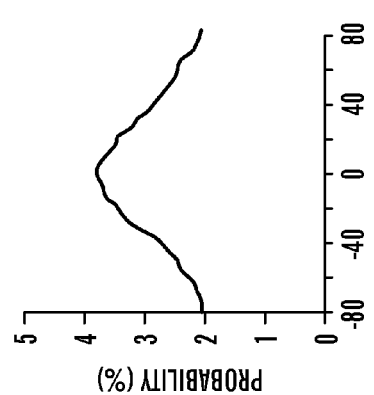
Figure 31F:
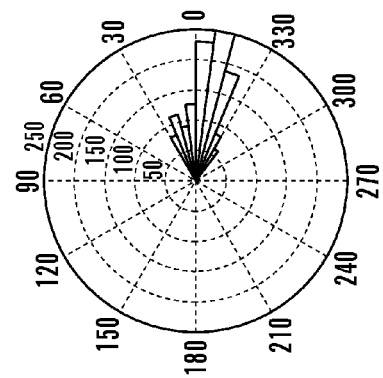
Figure 32A:
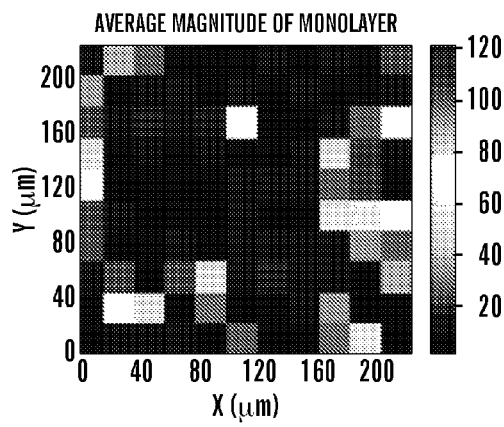
FIGS. 32A-32C show stacked nanopatterned cell sheets exhibit enhanced contractile function.
Figure 32B:
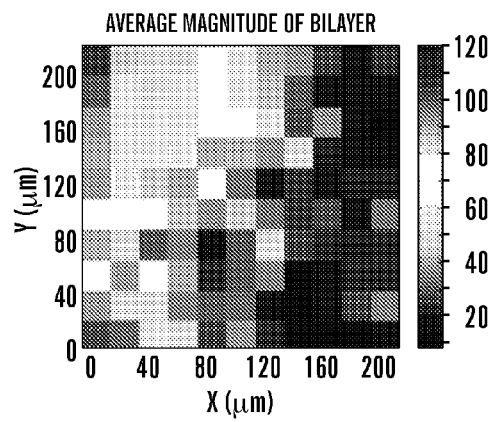
Figure 32C:
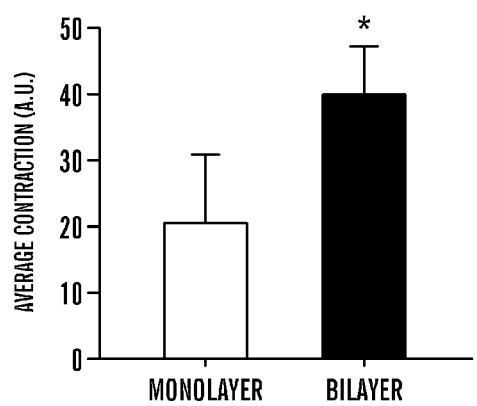

Next, muscle cell alignment was quantified by measuring the angle between the cells and an arbitrary axis on the substrate from a series of immunofluorescence images (n≥100). The minimum alignment of 0° denotes parallel alignment of cells along with the axis, while maximum 90° represents perpendicular alignment. The cells on nanogrooves preferred orientation along the groove line which was not observed with the flat substrate. Statistical analysis showed that the elongations of muscle cells on flat PLGA substrate were 2.6±0.2, 4.2±0.4 and 5.9±0.7 (length/width) at 3, 6, and 10 days, respectively. In sharp contrast, the elongations of muscle cells on nanopatterned PLGA substrate were 5.6±0.5, 7.7±0.8 and 7.9±0.8 (length/width) at 3, 6, and 10 days, respectively (P<0.05, FIG. 26D). The average of cellular orientation on flat PLGA substrate showed around 26.6% from −20 to 20 degree range, suggesting no preferred orientation. On the other hand, the average orientation on nanopatterned PLGA substrate showed a preferred orientation along the direction of pattern, 60.6% from −20 to 20 degree range. Furthermore, the alignment on the nanogrooves progressed with time between 3 to 10 days in culture (shown from the peak rise from day 3 to 10 in FIG. 26D). The tendency toward cellular alignment on nanopatterned substrate was described by re-organization of cytoskeleton following the aspect of surface features.[40] These findings are in accordance with previously reported results, indicating that this behavior may be defined as contact-mediated elongation and orientation.[26,41,42]

Figure 37A:
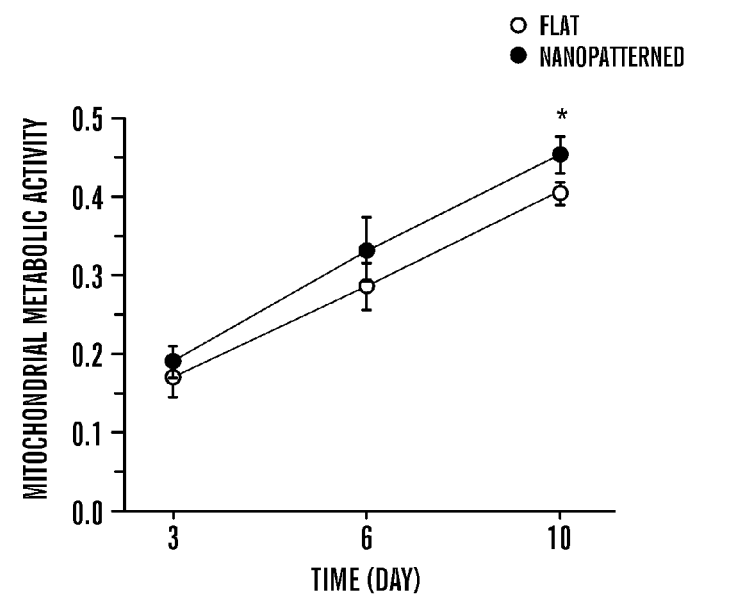
FIGS. 37A-37D demonstrate muscle cell growth and maturation on flat and nano-patterned PLGA.

Cellular adhesion on each substrate can be quantified indirectly by assessing the metabolic (lactate dehydrogenase) activity of cells. Since the proliferation was influenced by adhesion, the cell proliferation on nanopatterned PLGA was evaluated by mitochondrial metabolic activity (MTT) assay (P<0.05, FIG. 37A), which was observed by measuring light absorption with 540 nm wavelength. The MTT showed that muscle cells cultured on nanogrooves demonstrated higher activities compared to flat substrate throughout the experiment, implying the nanotopographical cues induce greater cellular metabolism. It is believed that this high activity was induced by increased cell-biomaterial interactions based on penetration into spaces between nanogrooves.[10]

Figure 33A:
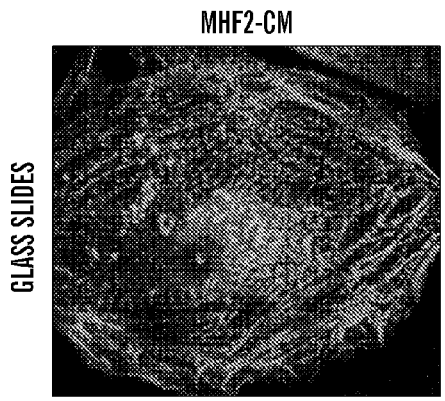
FIG. 33A-33D show nanotextured substrates as disease modeling platforms for cardiomyopathies, showing nanotextured platforms facilitate maturation of hiPSC-derived cardiomyocytes allowing them to be used as effective disease models for drug testing against cardiomyopathies, and as in vitro cardiac disease models.
Figure 33B:
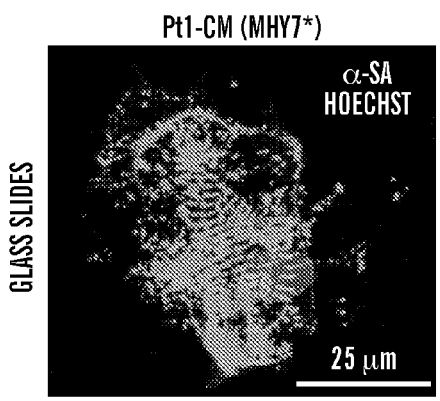
Figure 33C:
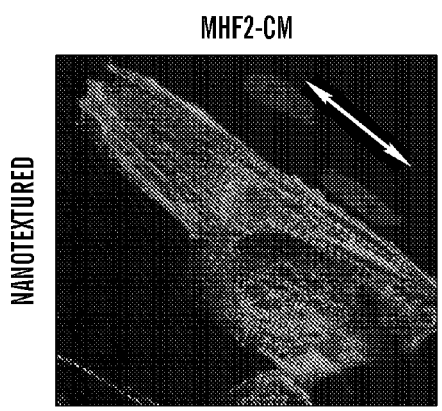
Figure 33D:
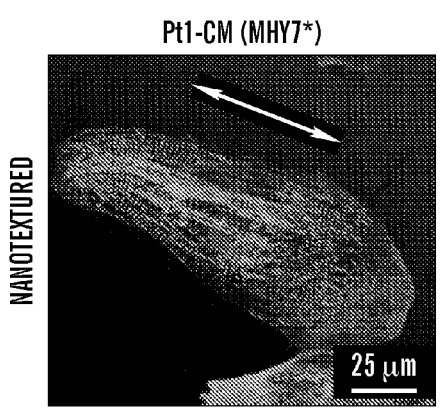
Figures 34A, 34C:
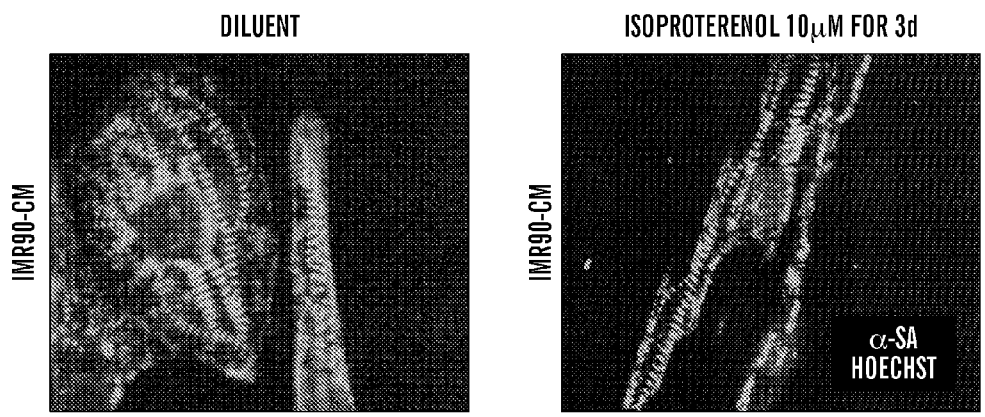
FIG. 34A-34D show nanotextured platforms facilitate maturation of hiPSC-derived cardiomyocytes allowing them to be used as effective disease models for drug testing against cardiomyopathies, and as in vitro cardiac disease models.
Figures 34B, 34D:
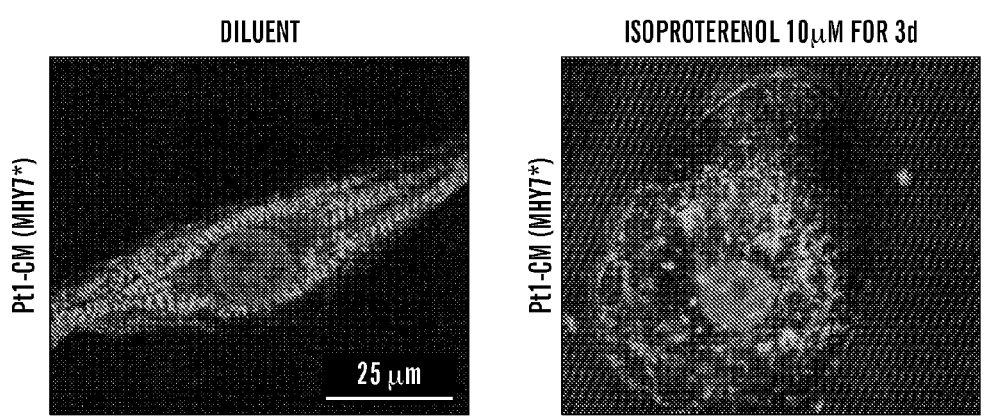

X-gal in isotonic buffer is routinely used to identify whether a cell expresses the β-galactosidase enzyme decoded by lacZ gene. When X-gal is divided into galactose and 5-bromo-4-chloro-3-hydroxyindole from β-galactosidase, the latter is then oxidized into 5,5'-dibromo-4,4'-dichloro-indigo, resulting in an insoluble blue product.[43] With this blue color, functional lacZ gene can be easily distinguished to identify donor cells that contain the reporter construct. In our experiment we utilized the MLC3F-nLacZ transgene, a marker of myonuclei which encodes nuclear localized β-galactosidase expressed by the nuclei in differentiated myotubes in vitro and muscle fibers in vivo.[23] The X-gal staining results showed a higher number of myonuclei in myotubes formed on nanogrooved substrate compared to the flat controls (FIG. 33B).[23] The quantification of X-gal positive nucleus staining showed significantly higher nucleus number in nanopatterned PLGA cultures compared to flat PLGA (P<0.05, FIG. 37C). From FIG. 37A to 37C, it can be judged that the cell growth and metabolic activity in pattern PLGA was significantly increased compared to flat PLGA by day 10 in culture.

To assay myogenic progression, quantitative reverse-transcription PCR (q-RT-PCR) was performed at day 6 (FIG. 37D) for myogenic regulatory factors; Myf5, MyoD and myogenin (MyoG). The q-RT-PCR results for myogenic regulatory factors revealed that higher levels of the Myf5 were expressed on the nanopatterned PLGA surface by most myogenic cells including quiescent satellite cells and committed myoblasts excepting mature myotubes.[44] In addition, MyoD and MyoG genes expressed during the intermediate and late phases of myogenic differentiation were also up-regulated in nanopatterned PLGA.[45] These results suggest that nanotopographical cues promote myogenic differentiation and maturation of primary muscle cells.

In Vivo Transplantation into Mdx Mouse Quadriceps Muscle

For decades, researchers have utilized animal models to assay the effectiveness and efficacy of therapies and drugs. Currently, the most utilized model for the muscle wasting disease Duchenne Muscular Dystrophy, is the mdx mouse which lacks functional expression of dystrophin.[16] Due to the absence of the dystrophin protein, mdx mice display chronic rounds of skeletal muscle degeneration and regeneration beginning 2-3 weeks post birth, with progressing muscle weakness and fibrosis accumulating with age.[46-49] In turn, the effectiveness of therapies or drugs can be determined by dystrophin replacement in mdx mice.[50,51] In this study, we transplanted cultured muscle cell patches into the quadriceps muscle of mdx mouse model in order to quantify engraftment not only from the presence of genetic reporters, but also from dystrophin protein.

Figure 37B:
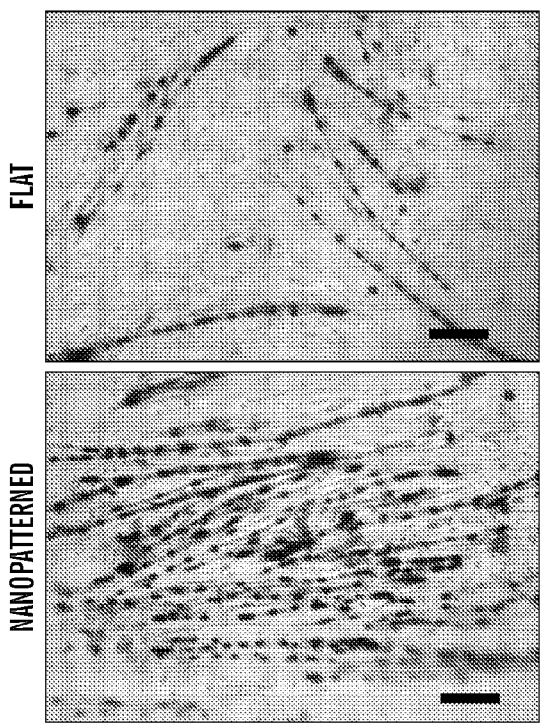
Figure 37C:
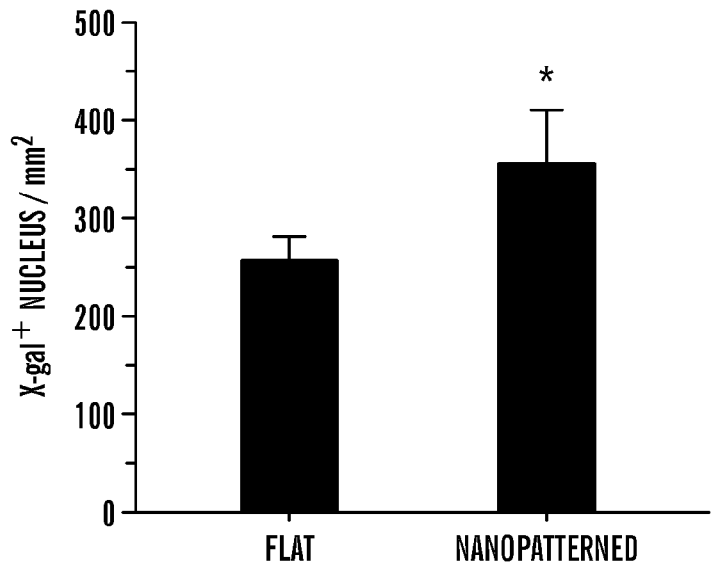
Figure 37D:
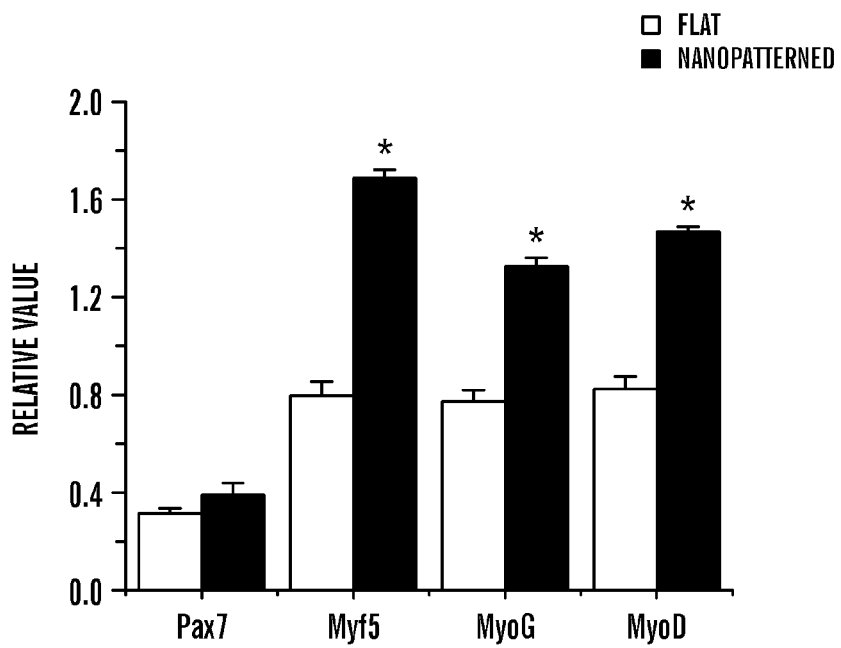
Figure 38A:
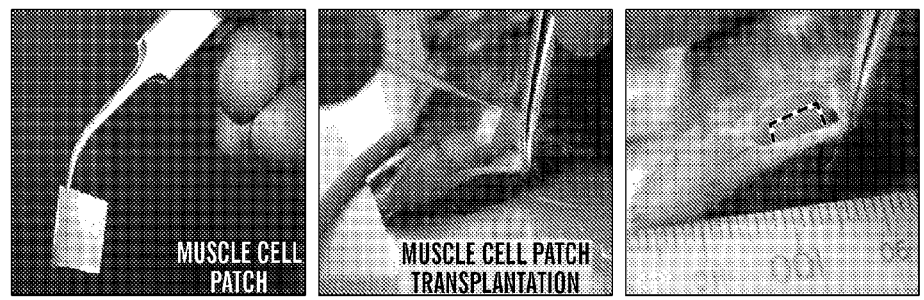
FIGS. 38A-38D demonstrate in vivo muscle cell patch transplantation on mdx mouse and immunohistology.
Figure 38B:
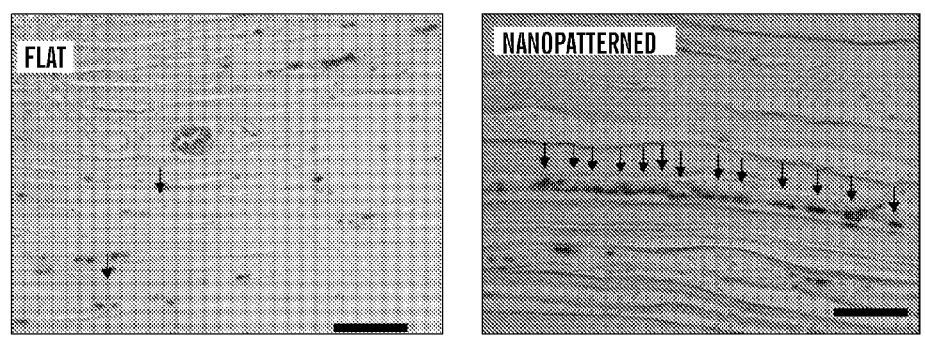
Figure 38C:
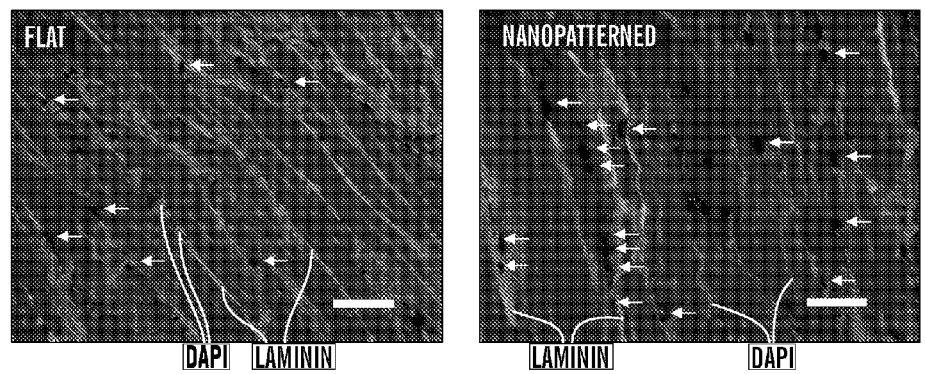

First, to identify whether the enhanced in vitro cell functions are maintained in vivo, muscle cell patch was transplanted into the quadriceps muscle in mouse. The 2 mm by 4 mm sized muscle cell patch supported by PLGA nanogroove scaffold was transplanted parallel to the muscle fibers in vivo. The photograph and transplantation procedures are illustrated in FIG. 38A. The muscle cell patch was successfully integrated into mouse muscle tissues causing no notable deleterious problems within the timeframes examined. To assess engraftment, mice were euthanized and muscles were harvested at 2 and 4 weeks post transplantation. In turn, muscle sections stained with X-gal displayed a higher number of β-galactosidase positive myonuclei from nanopatterned PLGA patches as compared to flat patches (FIG. 38B), which was similarly observed in vitro (FIG. 37B). X-gal positive myonuclei were distinguished by laminin staining and the quenching of DAPI fluorescence as previously reported.[52] As shown in FIG. 37C, the number of X-gal positive/DAPI-negative cells compared to DAPI-positive cells demonstrates the relative portion of active cells. After transplantation, muscle cells on nanopatterns showed a higher portion of X-gal-positive/DAPI-negative, i.e., a greater number of engrafted cells, implying even in vivo cells are influenced by nanotopographical effects.

In order to determine whether the transplanted muscles are fully developed, the expression of dystrophin by staining was imaged and quantified. Dystrophin is a vital part of the protein complex that connects the cytoskeleton of a muscle fiber to the surrounding extracellular matrix through the cell membrane.[53] As in humans with DMD, the absence of dystrophin in mdx mice leads to chronic muscle wasting to include myofiber necrosis, progressive muscle weakness and fatigability.[54-57] For this reason, determining the presence of dystrophin is necessary for assaying successfully engraftment and beneficial incorporation of transplanted cells.

Figure 38D:
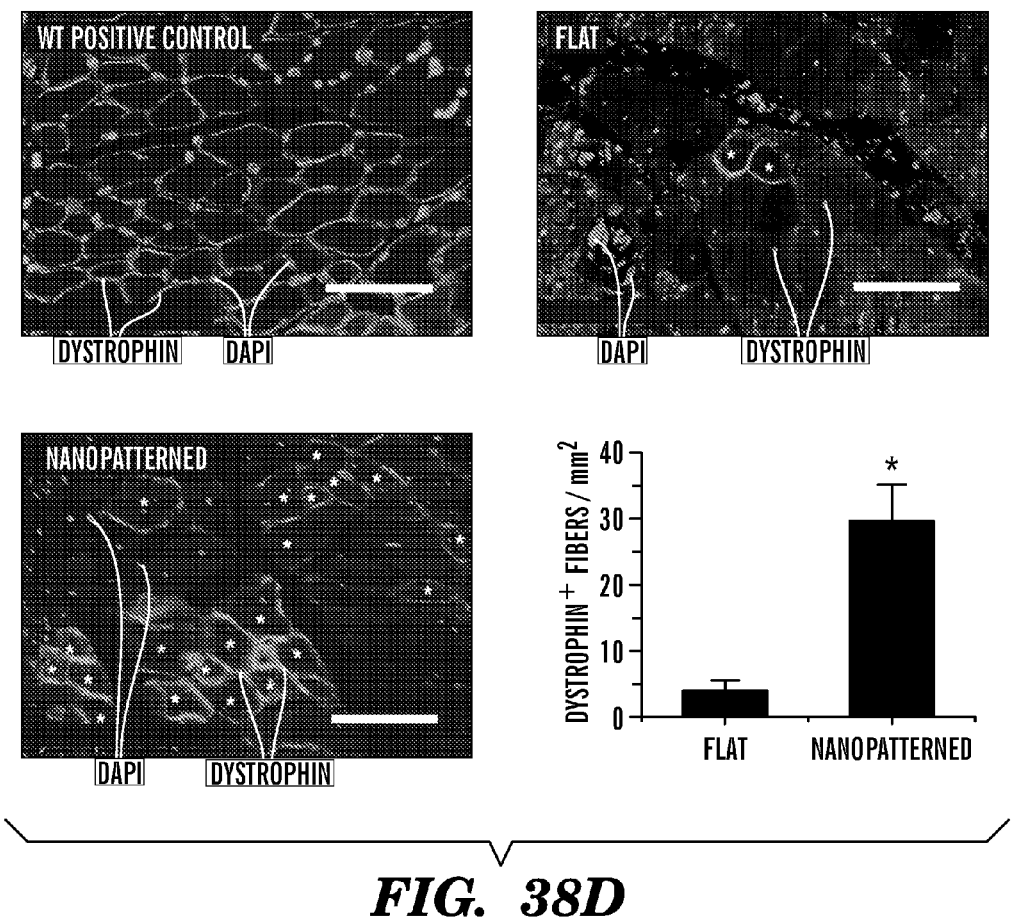

Despite the appearance of X-gal positive myonuclei in all transplants indicating myogenic contribution to the mdx muscle under both conditions, fewer dystrophin positive fibers were observed in muscles with flat versus nanopatterned PLGA patch (FIG. 38D). The quantification analysis revealed significantly greater number of dystrophin+ muscle fibers in nanopatterned transplanted muscles. These results indicate that although muscle cells from both patches may contribute to myonuclei generation, nanopatterned PLGA patches promoted functional myogenesis over flat patches as indicated by the increased contribution of dystrophin positive myofibers in mdx mice. Therefore, in vivo nanopatterns can solely promote tissue regeneration without any assistance of chemical or soluble factors. It is believed that this long-term transplantation without noticeable problems was possible because of the biocompatibility and biodegradability of PLGA material.

Skeletal muscle is a highly organized tissue, and anisotropic alignment of cells is essential to the fundamental function of the muscle, i.e. directional generation of force. To date, myogenic cells have been predominantly delivered by direct injection into muscles. This method has several limitations including poor cell survival, migration, engraftment and immune rejection.[9] However, the most significant disadvantage of direct injection of cells or transplantation of disorganized tissue is that cells do not engraft in the native tissue in an organized manner resulting in suboptimal functional improvement.[58-61] DMD is a disease of loss of muscle function, resulting in skeletal muscle being incapable of generating directional force to support many essential physiological functions. Functional skeletal muscle requires the parallel alignment of muscle fibers, thus transplanted muscle tissue should integrate with the host muscle tissue in a coordinated orientation.[3] To achieve this, tissue engineering scaffolds should enable single cells to distribute and adhere, to proliferate (if necessary), to differentiate and mature to a functional state. Ideally, the transplanted tissue engineered scaffold should be degraded slowly and replaced by an endogenous extracellular matrix.[4]

Here, the inventors developed a method to create aligned mixture of muscle mononuclear cells including the progeny of satellite cells and other potential resident myogenic cells using biodegradable nanopatterned PLGA. It turned out that the nanopatterned PLGA patch provided biomimetic muscle fiber with the architecture to support the seeded mixture muscle cell development and maturation. Primary mononucleated muscle cells cultured on nanogrooves were metabolically more active, and showed enhanced myogenesis compared to flat substrate without the introduction of chemical reagents, or soluble factors. This suggests that nanotopography can play a significant role in defining cellular and tissue-level phenotypes in organized tissues like skeletal muscle. Furthermore, we have demonstrated that biodegradable nanopatterned PLGA patches not only directed uniform alignment in vitro, but also enhanced myogenic contribution in vivo compared to flat patches after 4 weeks of transplantation. The increase of dystrophin positive myofibers with nanopatterned patches as compared to flat cellular patches demonstrated that the transplantable muscle cell patch can be utilized for treating chronic and acute muscle diseases or injuries. This novel approach of cell delivery holds potential for functional stem cell delivery not only in muscle wasting diseases, but also for the treatment of chronic and acute muscle injuries.

The following material and methods are relevant to Example 4:

Preparation of PUA Mold and PDMS Blanket

Polyurethane acrylate (PUA, MINS 301 RM, Minuta Tech.), and PDMS were used as the mold and solvent absorbing blanket materials, respectively. PUA molds were fabricated by dispensing the PUA precursor onto the patterned silicon wafer which had been made by standard photolithography, and a polyethylene terephthalate (PET, Skyrol®, SKC company) film (thickness: 75 µm) was slightly pressed against the liquid drop for it to be used as a supporting backplane. After preparation of polymer replica by UV exposure for few tens of seconds and mold removal, the PUA replica was additionally exposed to UV for several hours for complete curing. We used the PDMS precursor with a mixing ratio of 10:1 (precursor: curing agent) and cured it at 60° C. for 10 hrs. The cured PDMS molds were manually removed and cut prior to use.

Preparation of PLGA Nanopatterns

PLGA nanopatterns were prepared by using solvent-assisted capillary force lithography (CFL) as reported earlier.[20] In brief, a cover glass (ø 25 mm, Fisher) was washed with isopropyl alcohol for 30 min in a water sonicator and dried in nitrogen stream. A 100 µl of PLGA solution (15%, w/v) dissolved in chloroform or toluene was drop-dispensed on the cover glass. A flat PDMS was placed on the dispensed PLGA solution to absorb solvent and obtain a smooth flat PLGA layer. A slight pressure (~10 kPa) was applied to evenly press on PDMS blanket for 5 min. The cover glass was placed on a preheated hot plate (120° C.) to remove residual solvent and increase adhesion between PLGA and cover glass for 5 min. After that, a nanopatterned PUA mold was brought into contact with the PLGA coated glass and embossed with a constant pressure (~100 kPa) at preheated plate (120° C.) for 15 min. After this molding process, the sample was cooled to room temperature, and the PUA mold was carefully peeled off from the PLGA coated glass, leaving behind a nanopatterned PLGA substrate over a large area (ø25 mm) with good structural fidelity. The patterned PLAG substrate was stored at a desiccator to remove residual solvent.

Muscle Cells Isolation & Culture on PLGA Patches

Prior to cell seeding, the PLGA patches were coated with 0.67% gelatin. Flat PLGA and nanopatterned PLGA patches were then seeded with mononuclear muscle cells digested from a pool of right and left limb Tibialis Anterior, EDL, Quadriceps, and Gastrocnemius muscles by collagenase and dispase, as previously reported by our group.[21, 22] For cell transplantation and reporter characterization, muscle cells were isolated from an 8 month old male mouse on a C57BL/6 background, heterozygous for the ubiquitously expressed EGFP driven by the chicken β-actin promoter and the MLC3F-nLacZtransgene expressed by myonuclei and differentiating myoblasts.[23, 24] Cells seeded for MRF Q-RT-PCR were isolated using the same protocol from a male wt C57BL/6 mouse. Both flat and nanopatterned patches were used for cell culture on a 6 well plate (Corning). First, the two types of patches were rehydrated in phosphate-buffered saline (PBS, Sigma) for 2 h at room temperature, sterilized by series ethyl alcohol from 50% to 100%, and washed with culture medium. GFP+muscle cells ($1 \times 10^6$ cells/ml) were seeded on the two types of patches and cultured under the controlled environment of 37° C., 5% $O_2$, and 5% $CO_2$ and in F10 supplemented with 15% v/v horse serum, 2 mM $CaCl_2$, 100 units/ml of penicillin, and 100 µg/ml streptomycin, and 20 ng/ml bFGF.

In Vitro Characterization of Nanopatterned Muscle Tissue Constructs

The morphology of GFP+muscle cells cultured on two types of patches was observed using a monochromatic camera, Zeiss Axiovert 200, and SEM. Samples were fixed in 2.5% glutaraldehyde for 3 hrs, washed with PBS, dehydrated in ascending grades of ethyl alcohol, dried, and mounted on an aluminum stub using double-side carbon tape. The specimens were coated with palladium and gold using an SPI-module Sputter Coater (Structure Probe Inc.) and examined at an acceleration voltage of 18 kV for 90 sec. In addition, mitochondrial metabolic activity (n=3) was determined by 3-(4,5-dimethylthiazol-2-yl)-2,5-diphenyltetrazolium bromide (MTT) assay, respectively. For the MTT assay, 100 µl of MTT stock solution in PBS was added to cells cultured in glass bottomed dish (LiveAssay Inc.) containing 1 ml of cell culture medium. After incubation at 37° C. in 5% $CO_2$ for 4 hrs, the medium was removed and 100 µl dimethyl sulfoxide was added to dissolve the formazan crystals. The absorbance at 540 nm was spectrophotometrically detected with an enzyme-linked immunosorbent assay plate reader (VICTOR³V, PerkinElmer Inc.).

Transplantation to the Mdx Mouse Hind Limb Muscle

Figure 3A:
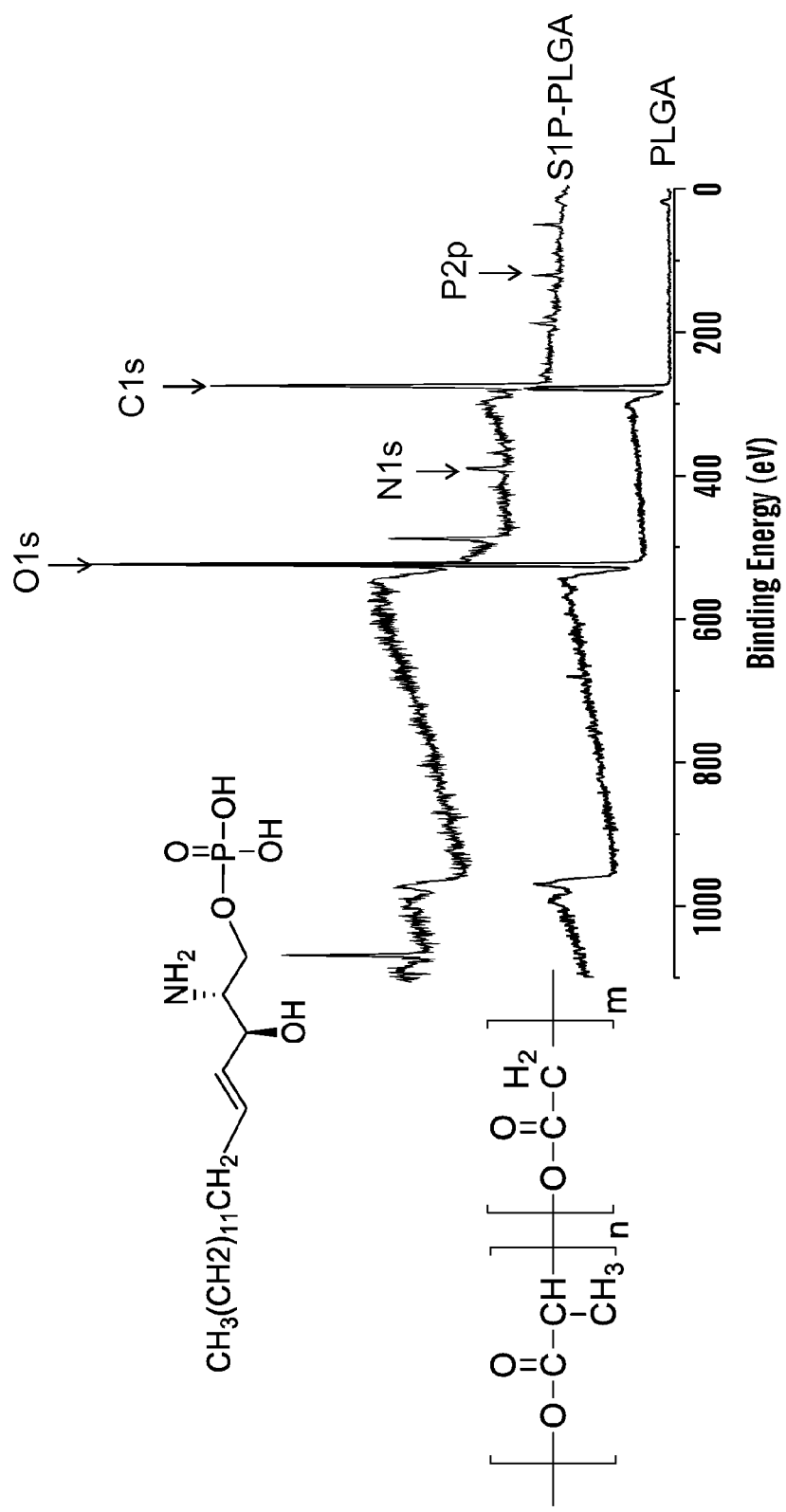
FIG. 3A-3B shows the X-ray photoelectron spectroscopy (XPS) analysis of surface composition of S1P-PLGA substrates, showing that the nanotextured substrate can be conjugated with a variety of growth factors, peptides, lipids and matrix molecules.
Figure 3B:
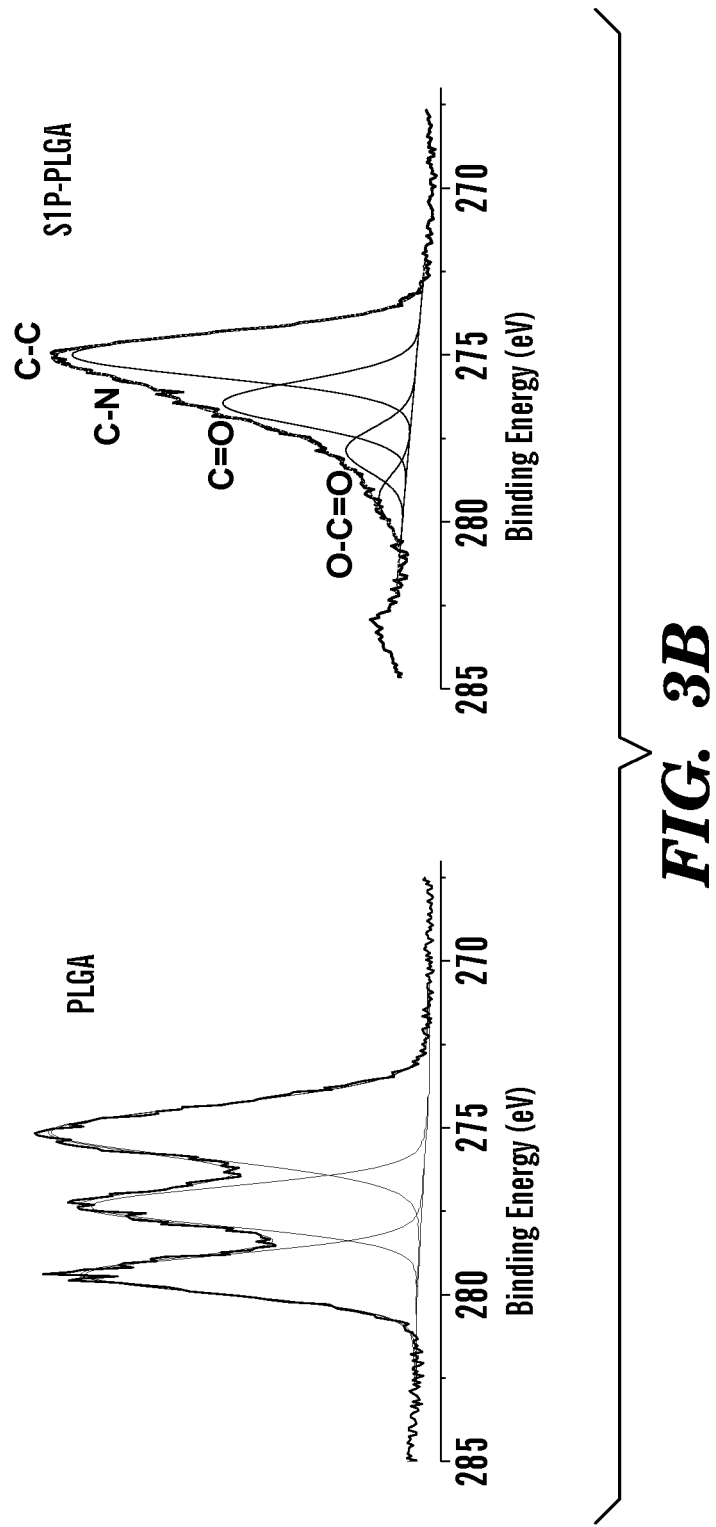
Figure 4A:
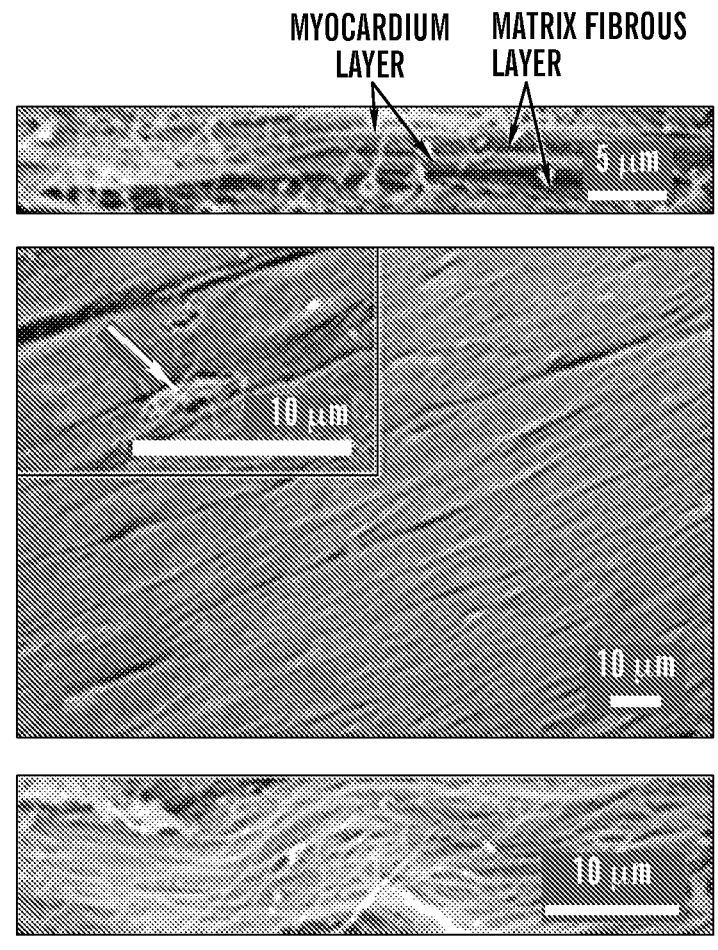
FIGS. 4A-4D show examples of nanotopographically-controlled cardiac tissue constructs can be fabricated to mimic the nanostructure of heart tissue matrix, and action potential propagation is anistropic on the nanotextured substrate when measured using rat ventricular myocytes.
Figure 4B:
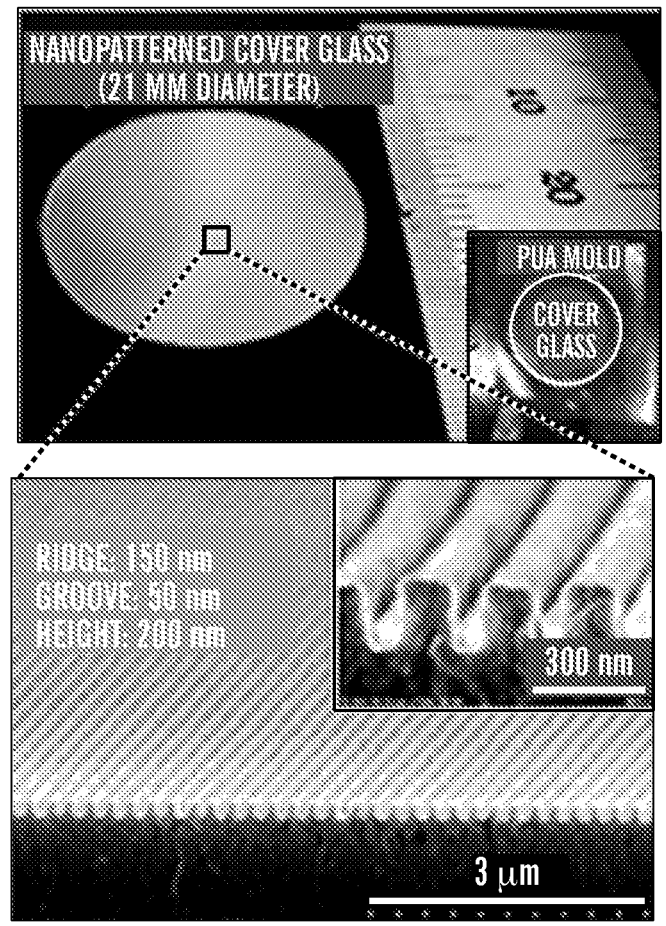
Figure 4C:
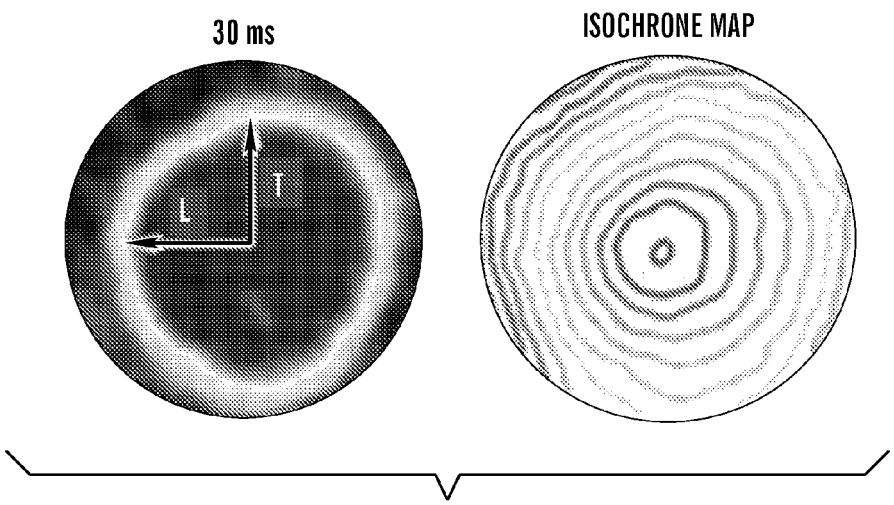
Figure 4D:
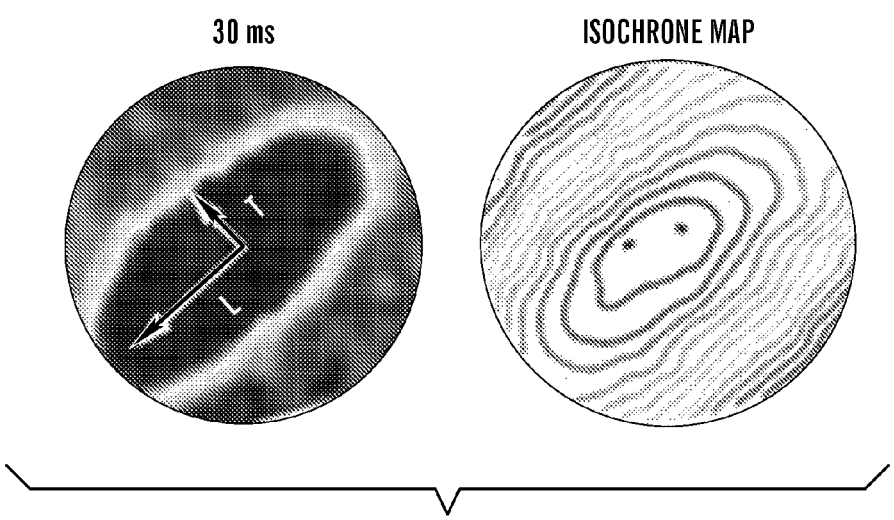
Figure 5:
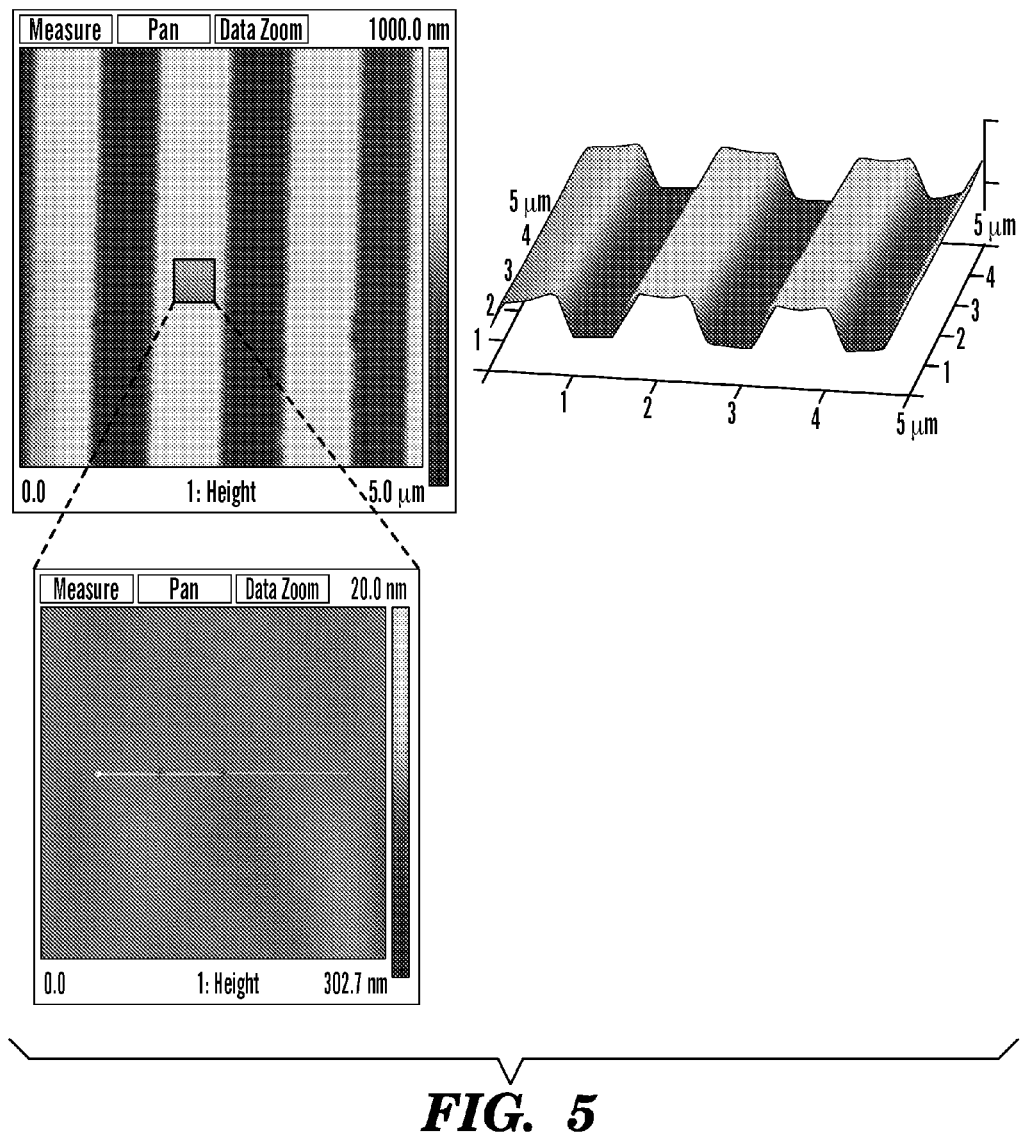
FIG. 5 shows a schematic of the nanostructure platform created using PEG polymer as measured by atomic force microscopy (AFM). AFM analysis shows that the nanostructured platform is highly regular over many ridges, and is very smooth and uniform.
Figure 6A:
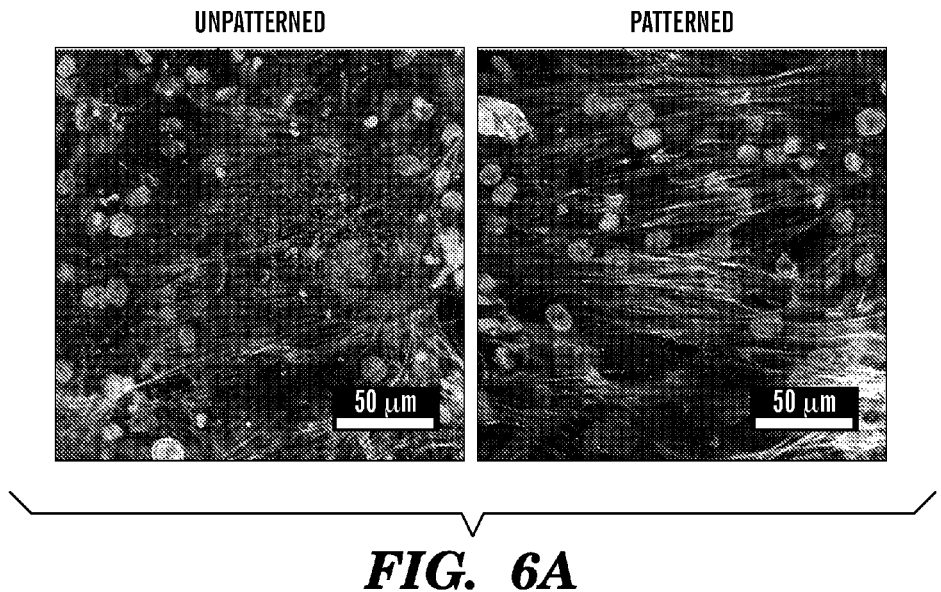
FIG. 6A-6C shows the formation of an aligned monolayer of hiPSC-CM or hESC-CM on ANP.
Figure 6B:
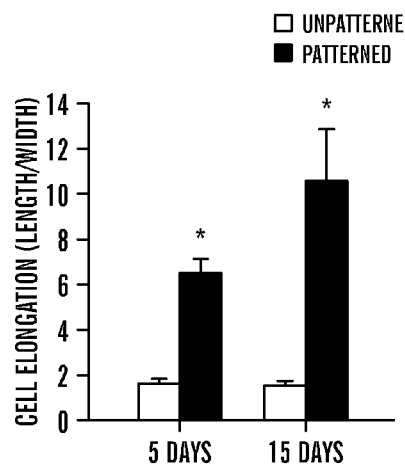
Figure 6C:
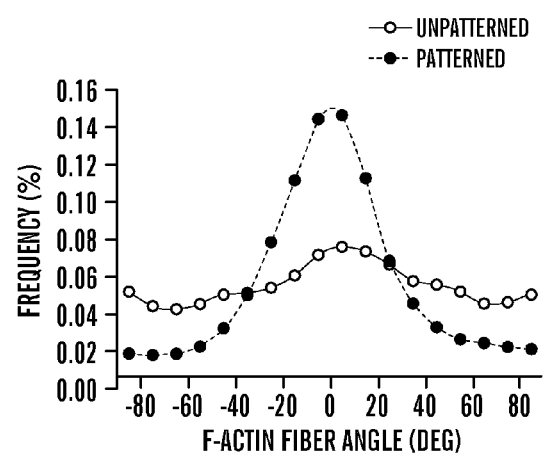
Figure 7A:
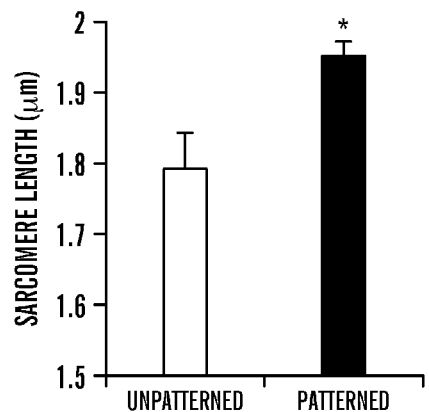
FIGS. 7A-7D show the identification of the extent of cardiac maturation of hiPSC-CM cultured on the nanotextured polymer substrate, showing the nanotextured polymer substrate causes greater cardiac maturation of hESC-CM/hiPSC-CMs both at cellular level, and tissue level.
Figure 7B:
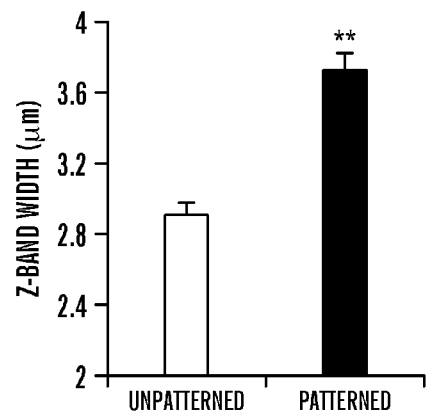
Figure 7C:
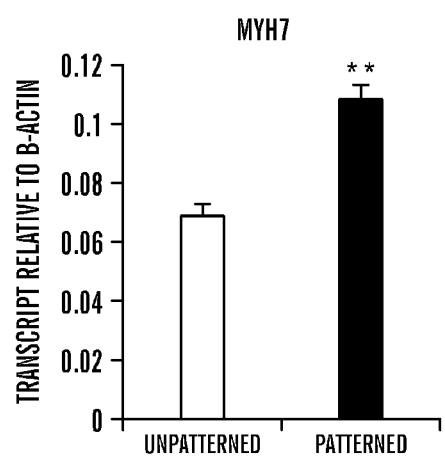
Figure 7D:
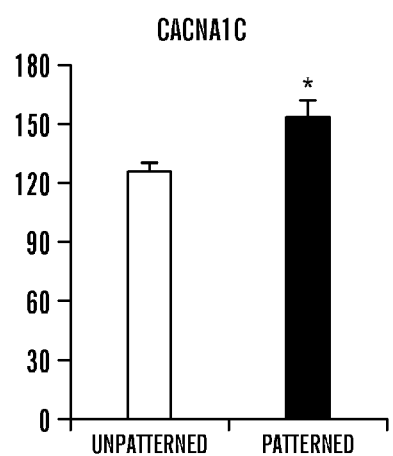
Figure 8A:
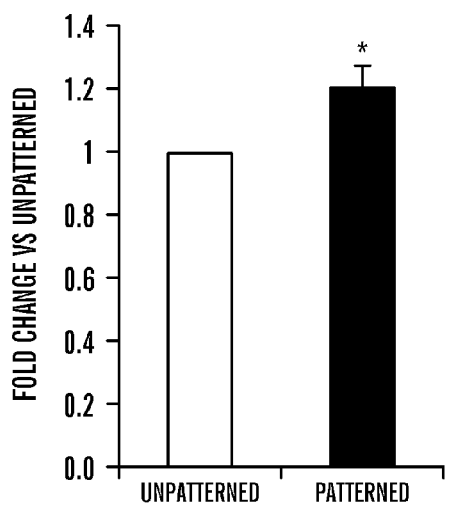
FIG. 8A-8C shows the hypertrophy related gene expression and binucleation rate in the hESC-derived cardiomyocytes (hESC-CMs) on each substrate. The results from quantitative RT-PCR performed on hESC-CMs on unpatterned substrate or patterned substrate at 1 week after cell seeding to determine the mRNA transcript levels of the contractile and hypertrophy related genes.
Figure 8B:
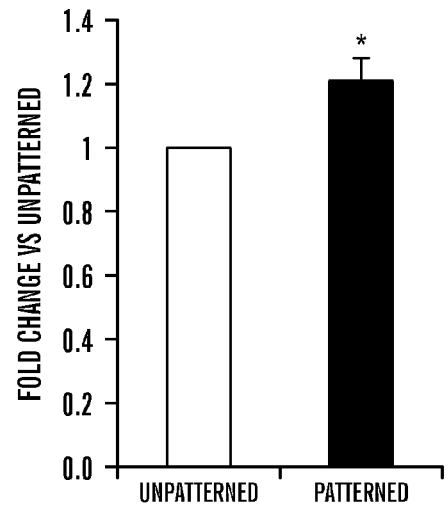
Figure 8C:
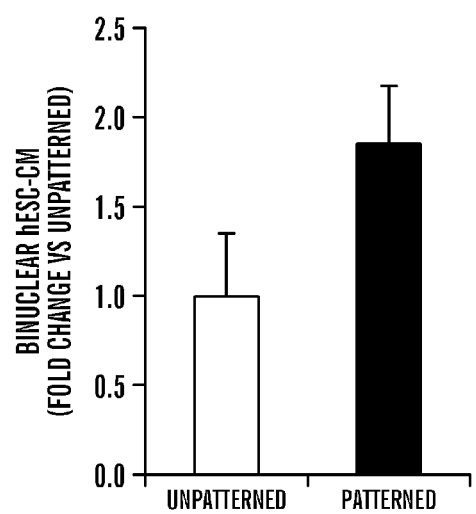
Figure 9A:
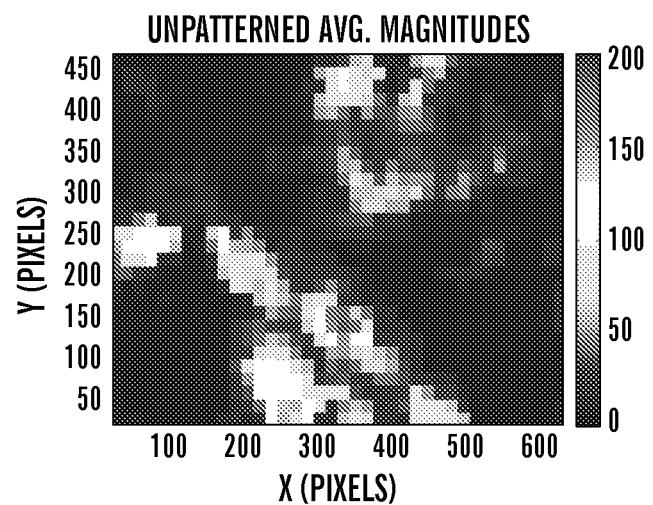
FIG. 9A-9C shows the contraction Mapping of hESC-CMs. Movies of beating hESC-CM monolayers were taken and analyzed to measure the magnitude to contraction of the cells.
Figure 9B:
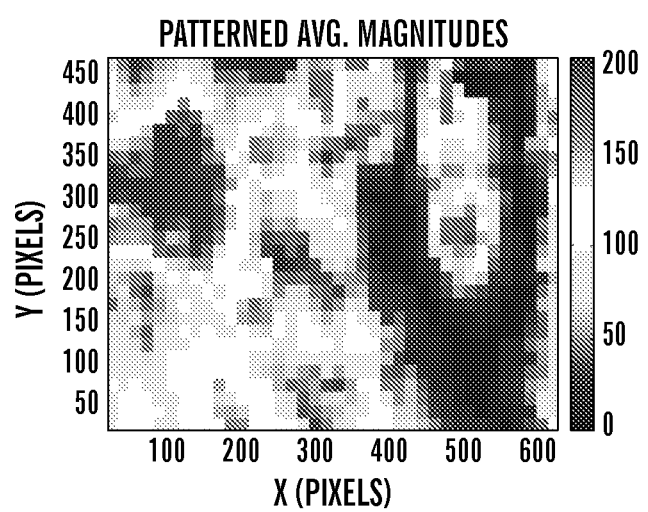
Figure 9C:
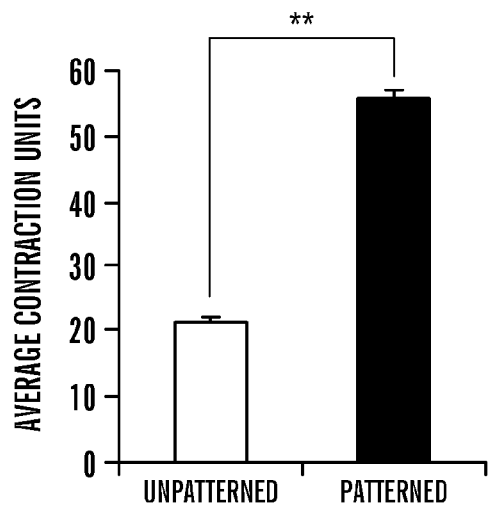
Figure 10:
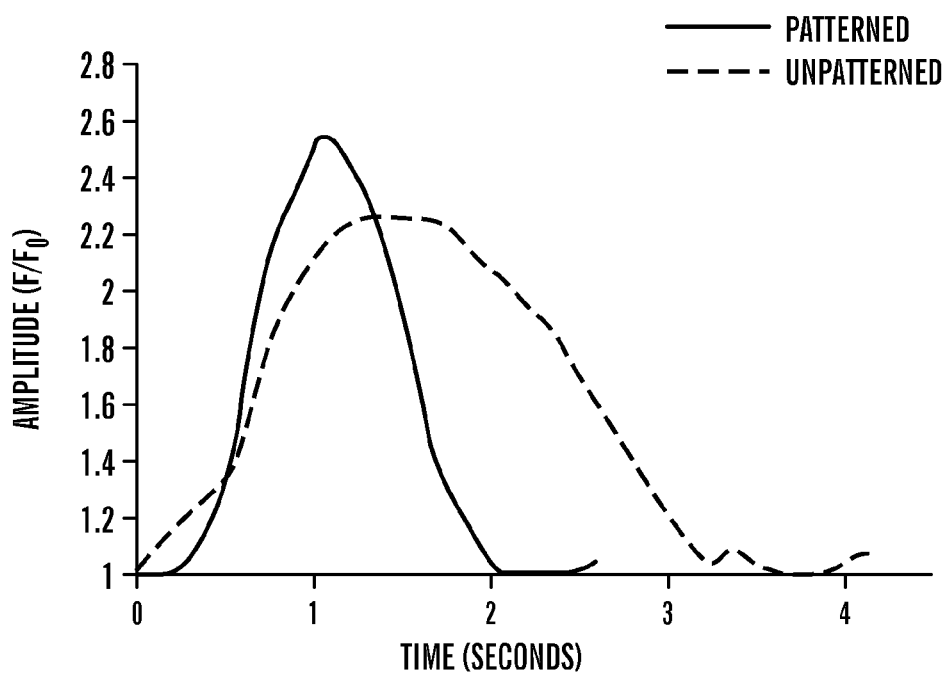
FIG. 10 shows a representative of the Ca2+ fluorescence transient for cells on unpatterned flat and patterned substrates.
Figure 11A:
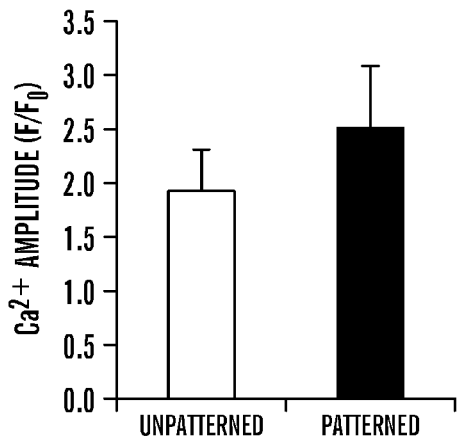
FIG. 11A-11D show Ca2+ Transient Analysis of hESC-CMs showing the magnitude of Ca2+ signal is greater for hESC-CMs on nanopatterned substrates as compared to non-textured substrates, but the transient dynamics of hESC-CMs on nanotextured substrates are faster.
Figure 11B:
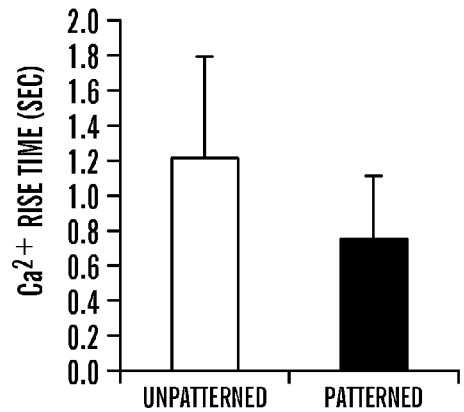
Figure 11C:
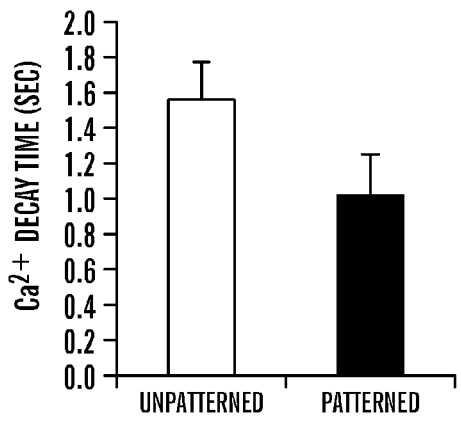
Figure 11D:
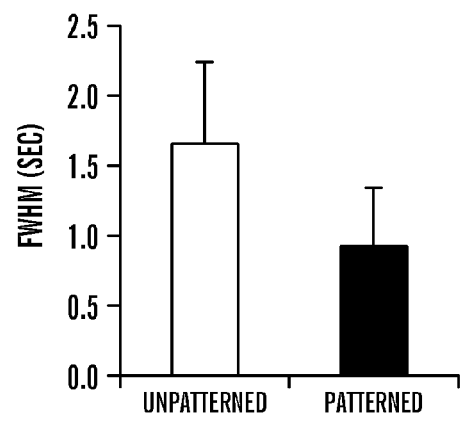
Figure 12A:
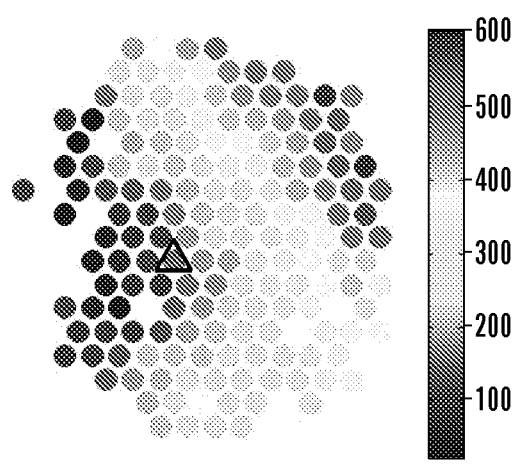
FIGS. 12A-12B show the nanogrooved substrata of the ANP induce increased synchronocity in action potential propagation in hESC/hiPSC-CM cultures.
Figure 12B:
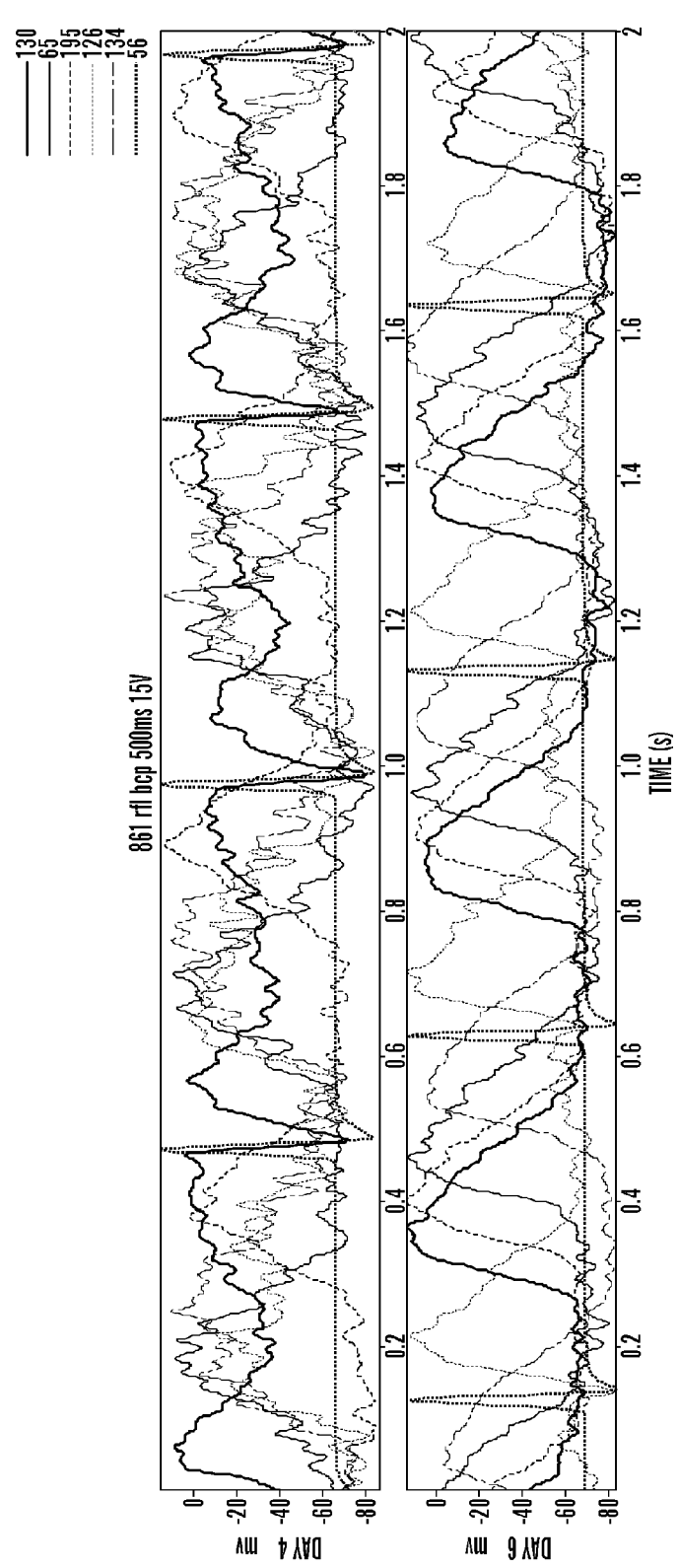
Figure 13A:
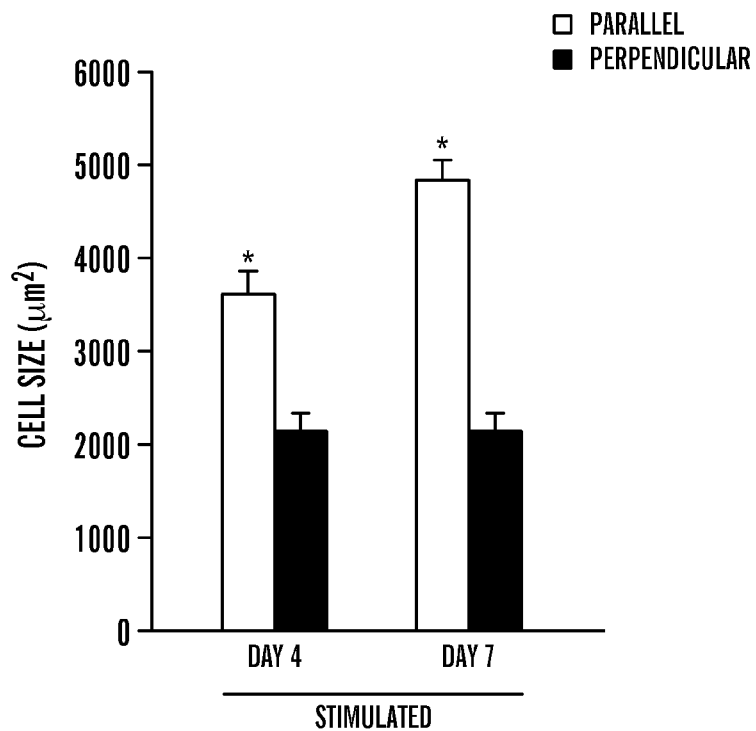
FIG. 13A-13B show the maturation of cardiac phenotype is achieved further by combining nanocue stimulation by the nanotextured substrate in combination with pulsatile electrical stimulation.
Figure 13B:
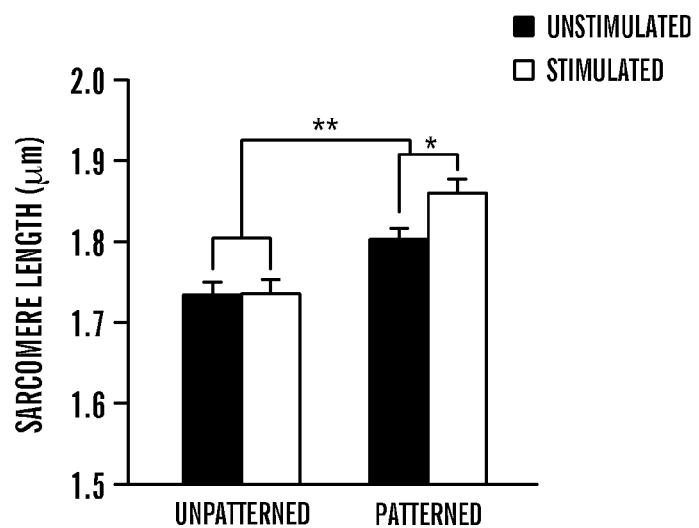
Figure 14A:
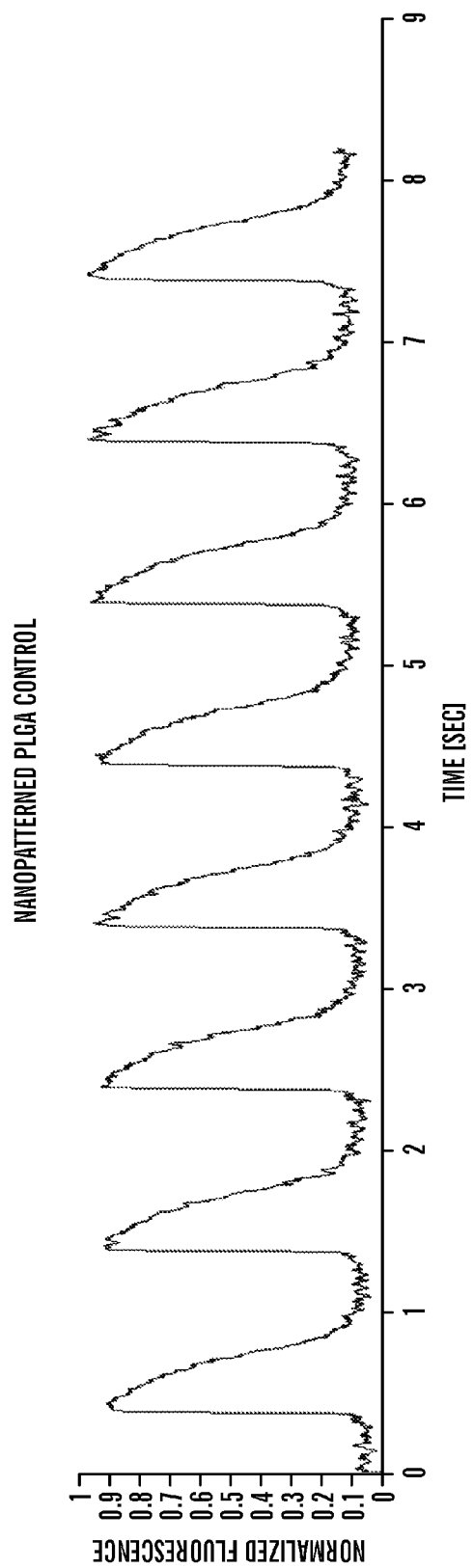
FIG. 14A-14B show the electrical responsiveness in monolayers of human cardiomyocytes on the nanotextured substrate.
Figure 14B:
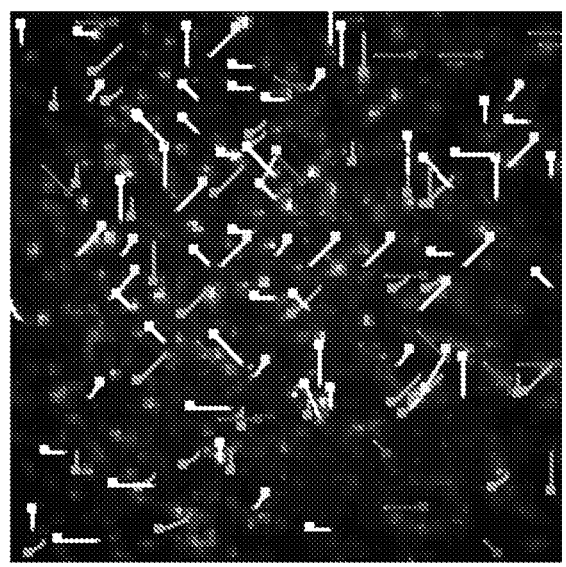
Figure 15A:
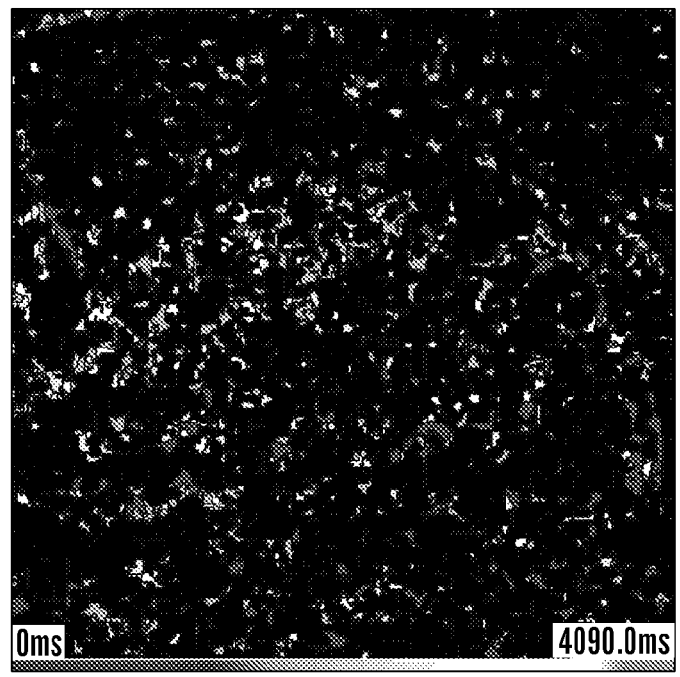
FIG. 15A-15B show that the nanotextured substrate can be used as a multi-throughput platform to induce syncytial electrical connectivity in hES/hiPSC-derived cardiomyocytes resulting in an in vitro cardiac tissue mimetic that is organized anisotropically and also electrically functional similar to normal human cardiac tissue, as detected by syncytial electrical activity on human in vitro differentiated cardiomyocytes on the nanotextured polymer substrate.
Figure 15B:
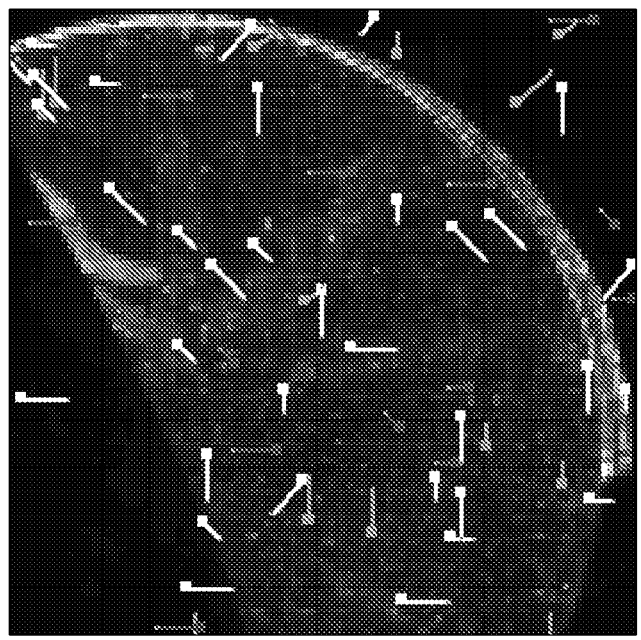
Figure 16A:
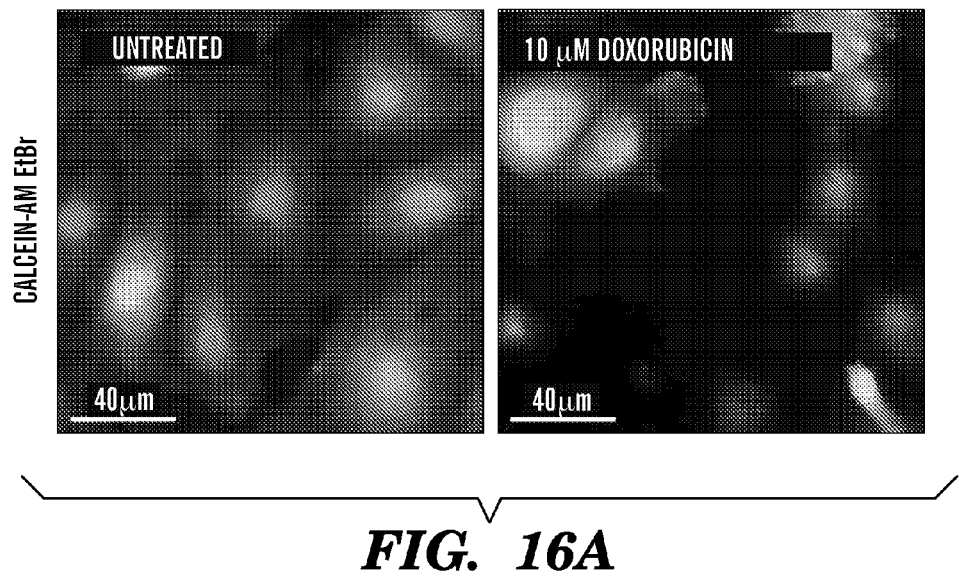
FIGS. 16A-16B show high throughput cardiotoxicity profiling. To test the capacity of the ANP and system to identify cardiotoxic drugs, hESC-derived cardiomyocytes (hESC-CMs) were treated with doxorubicin for 24 hrs and then imaged using the high-throughput Applied Precision DeltaVision system.
Figure 16B:
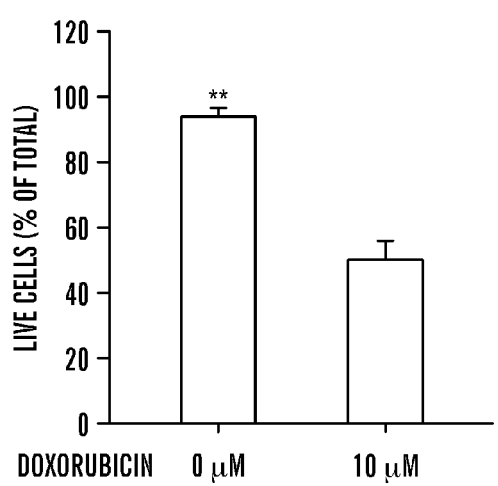
Figure 17A:
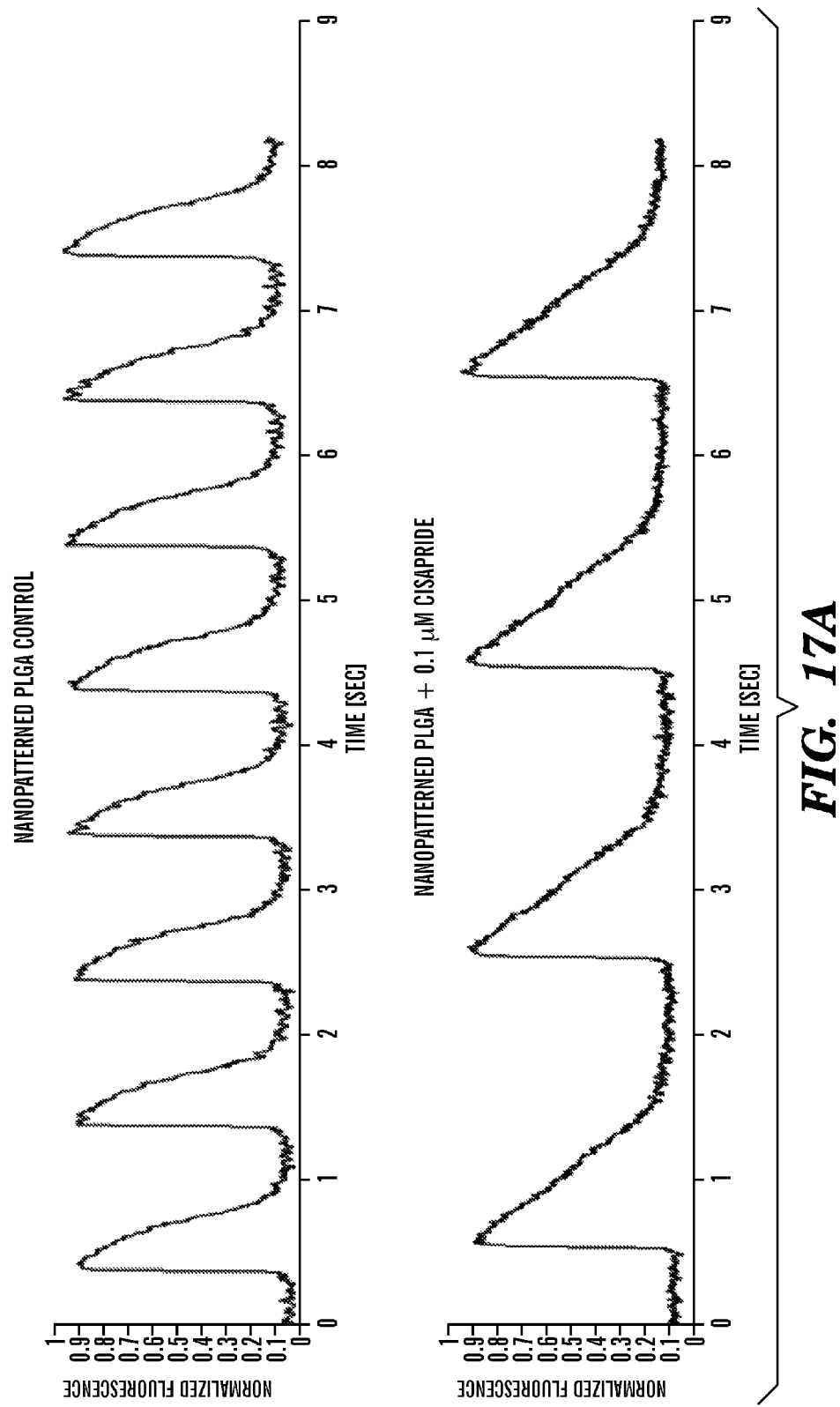
FIG. 17A-17D show that the ANP polymer substrate successfully detects effect of K+ channel inhibitor in hES-CM monolayers and demonstrates elongation of action potentials (AP), and distortions in AP profile.
Figure 17B:
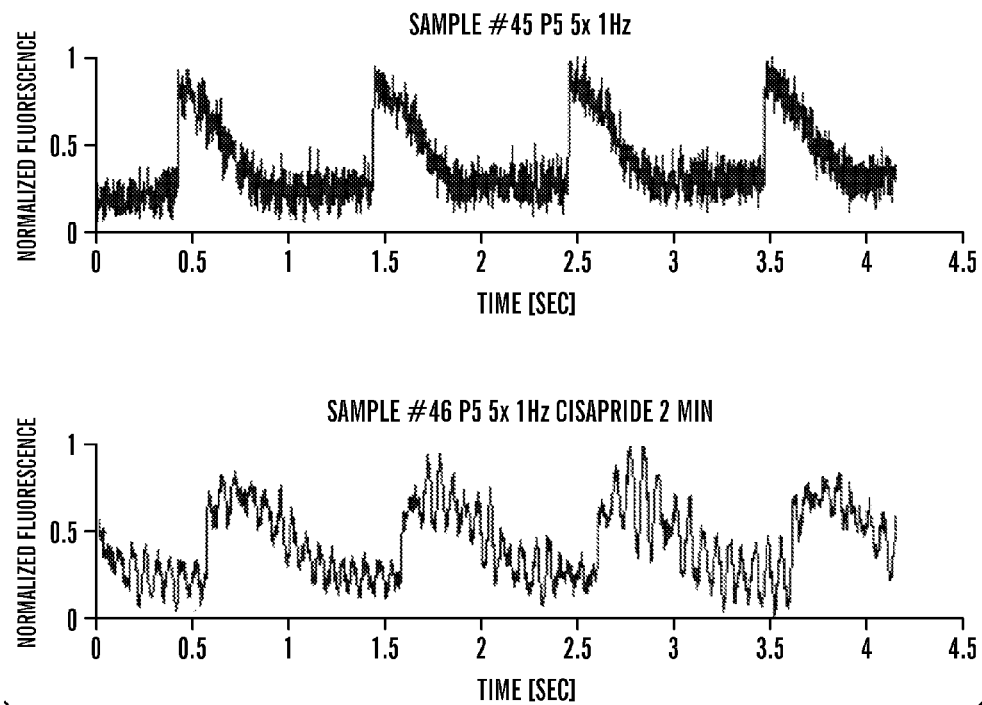
Figure 17C:
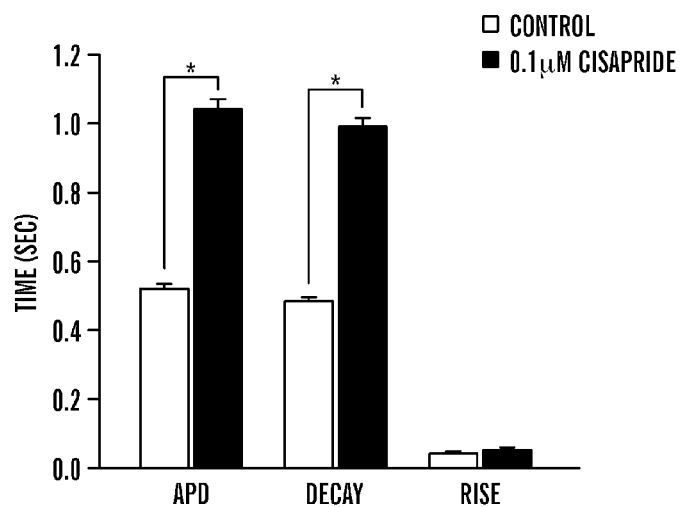
Figure 17D:
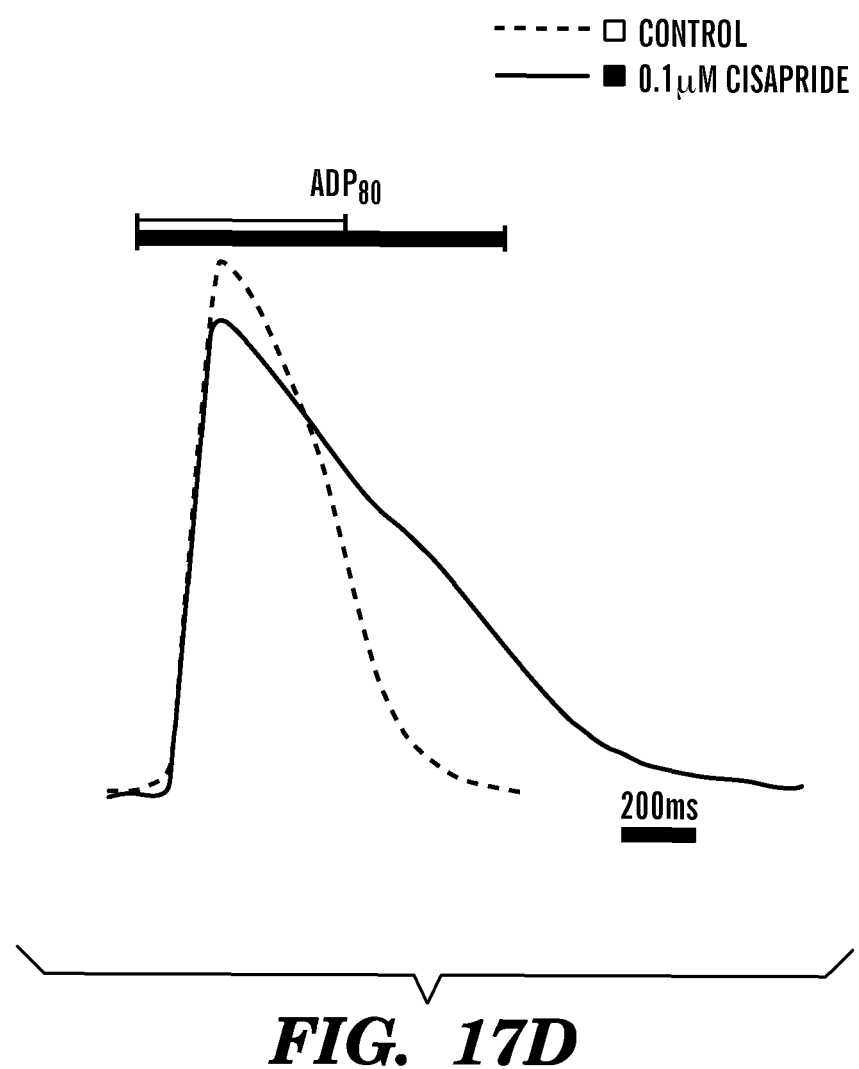
Figure 18:
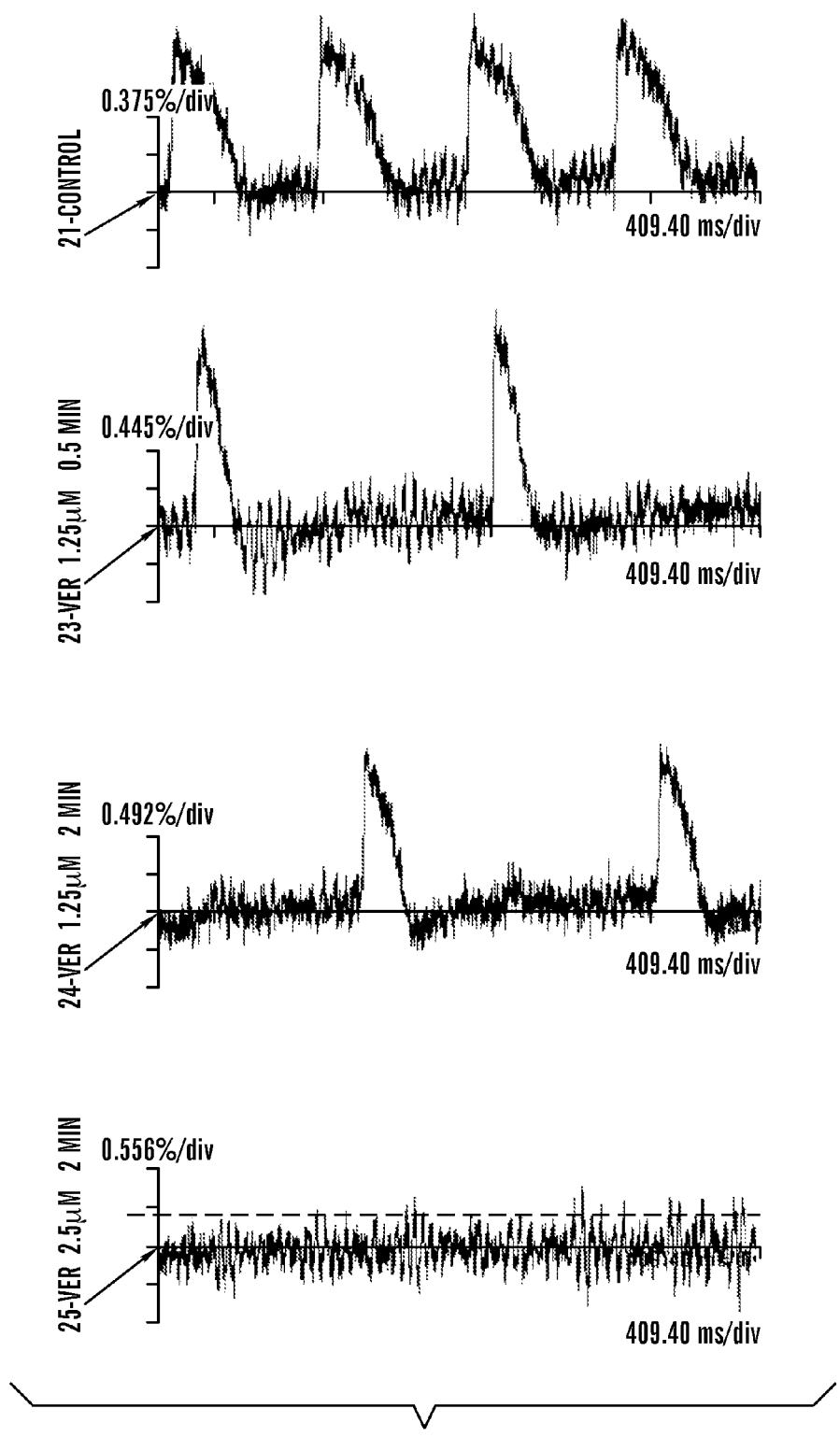
FIG. 18 shows that ANP can be used for drug testing, and testing for maturation of cardiomyocytes derived from healthy, and diseased hiPSC cells.
Figure 19A:
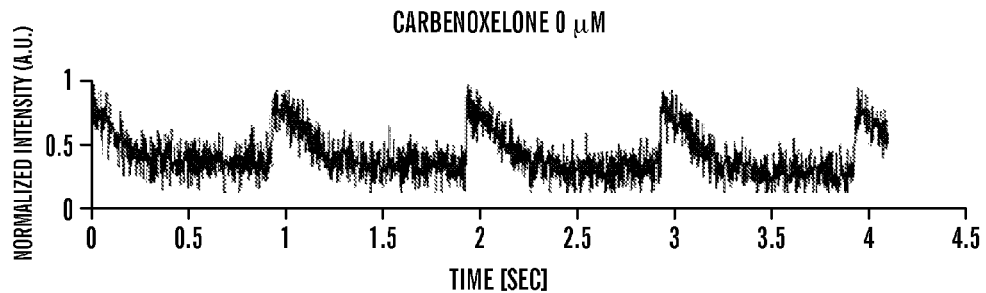
FIG. 19A-19C show the effect of GAP junction inhibitor on hESC-derived cardiomyocyte cultures on the nanotextured substrate in a dose dependent fashion. Representative action potential time course traces for 4 seconds in the presence of 1 Hz pacing in the presence of carboxelone, a GAP junction inhibitor at 0 μM (FIG. 19A), 20 μM (FIG. 19B), and 40 μM (FIG. 19C) are shown.
Figure 19B:
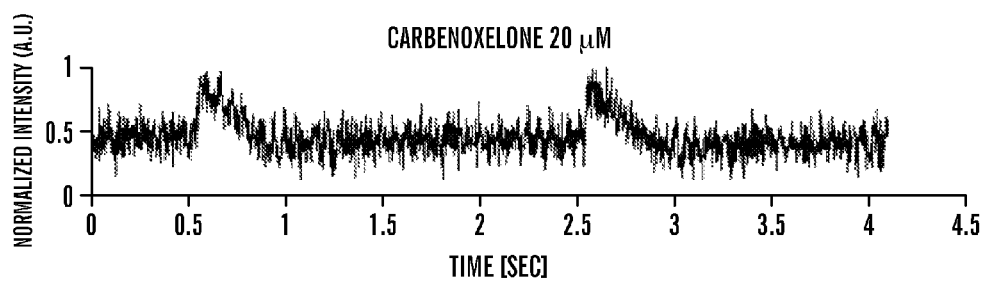
Figure 19C:
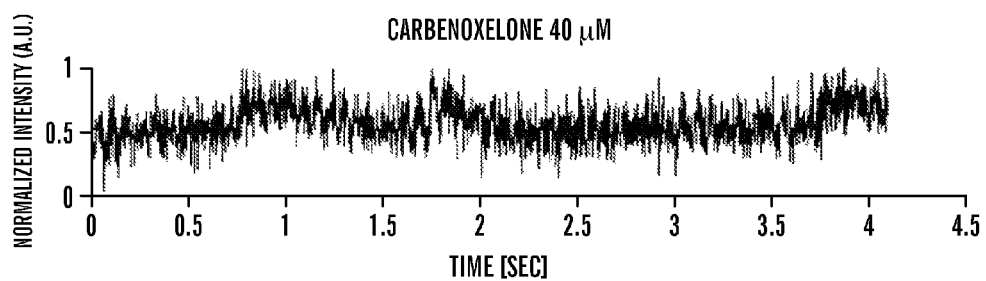
Figure 20A:
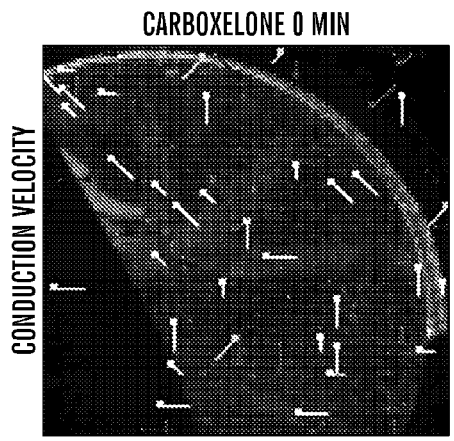
FIG. 20A-20D shows the nanotextured substrate can allow large area tissue-wide detection of electrical activity in hESC-derived cardiomyocytes.
Figure 20B:
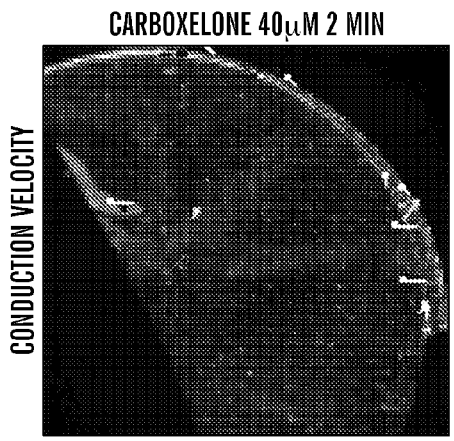
Figure 20C:
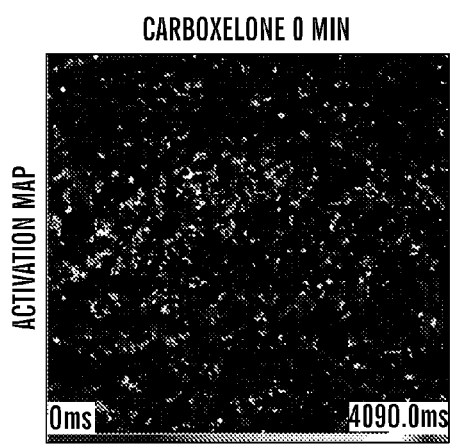
Figure 20D:
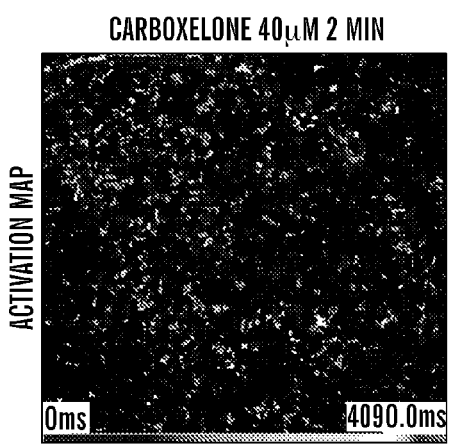
Figure 21:
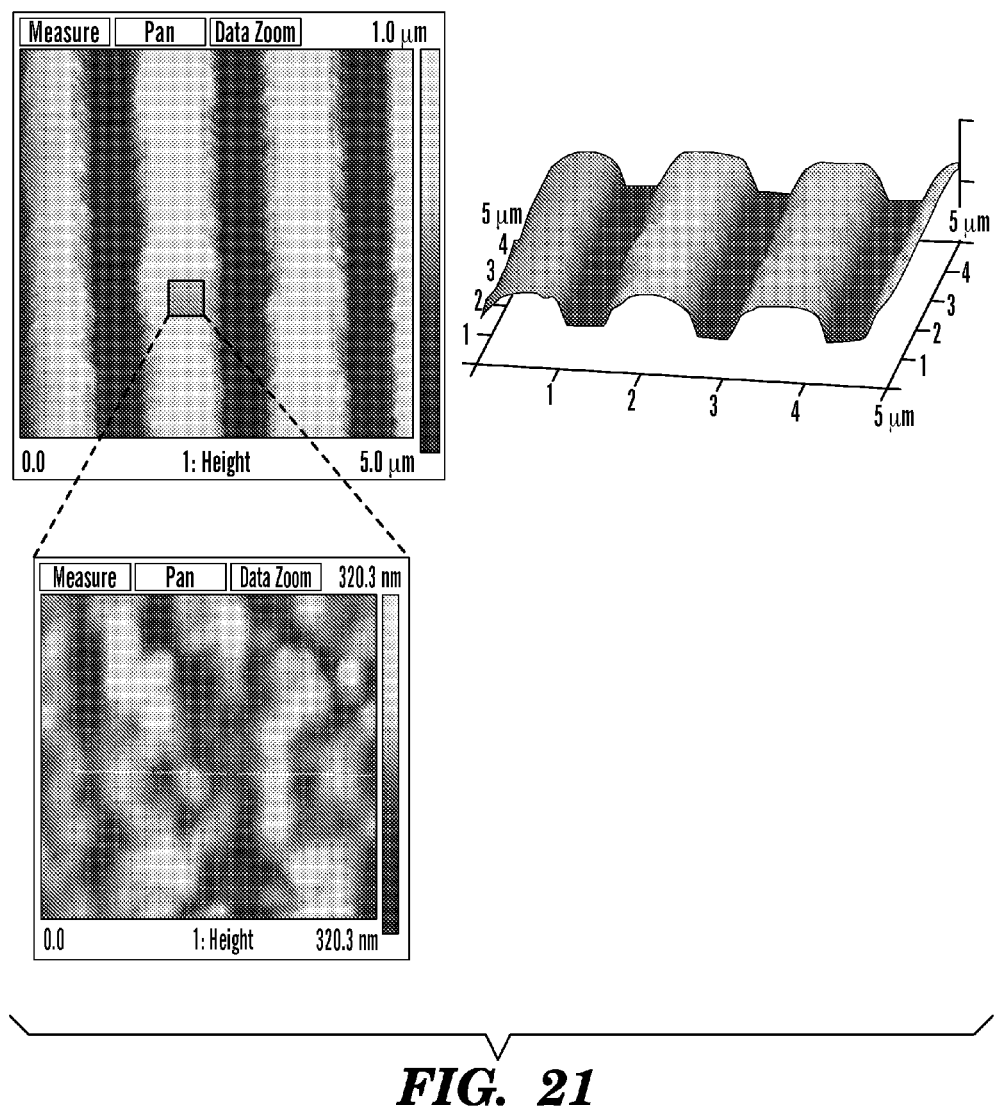
FIG. 21 shows the nano-scale topology of few-layer graphene coated nanotextured substrates.
Figure 22A:
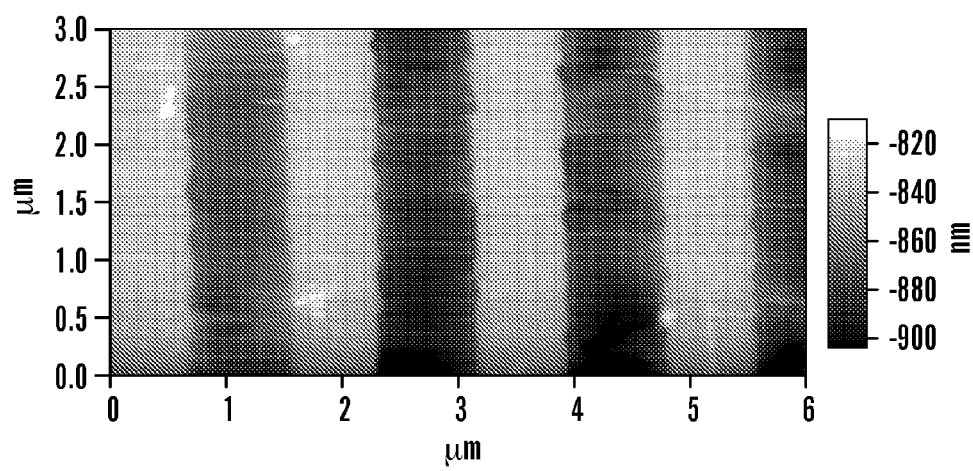
FIG. 22A-22B shows topology and conductivity maps of single-layer graphene coated ANP.
Figure 22B:
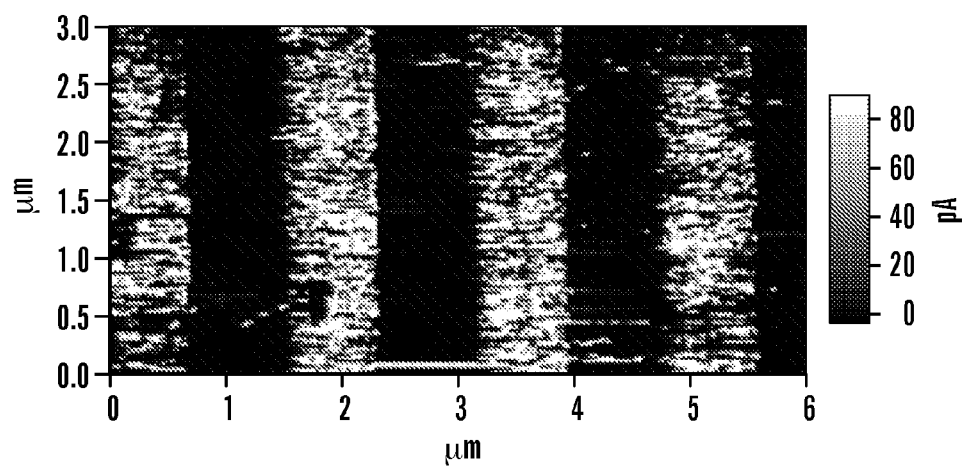
Figure 23A:
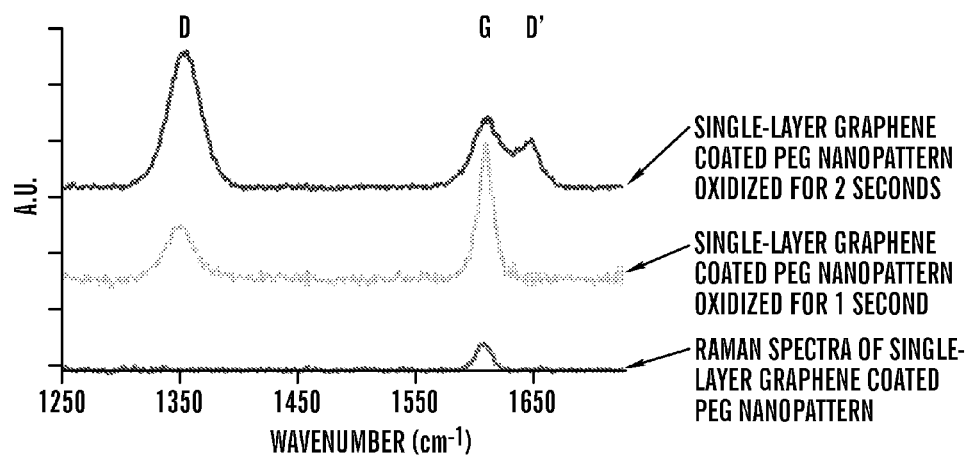
FIG. 23A-23B show the development of nanotextured substrates with controllable conductivity and surface chemistry using single-layer graphene coating and controlled oxidation.
Figure 23B:
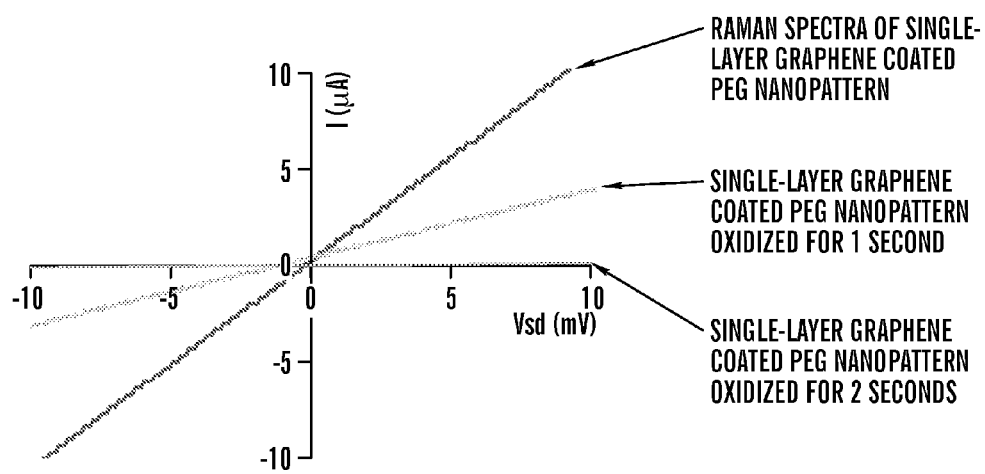
Figure 24A:
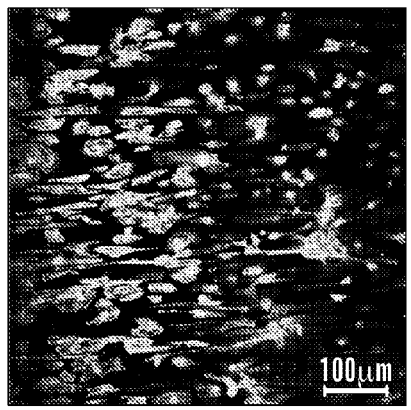
FIGS. 24A-24D show the graphene/graphene-oxide-coated nanotextured substrate promote maturation of hES/hiPSC-derived cardiomyocytes.
Figure 24C:
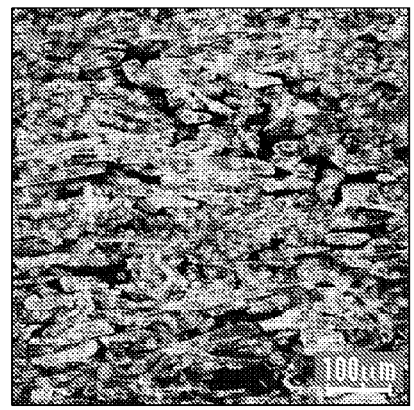
Figure 24B:
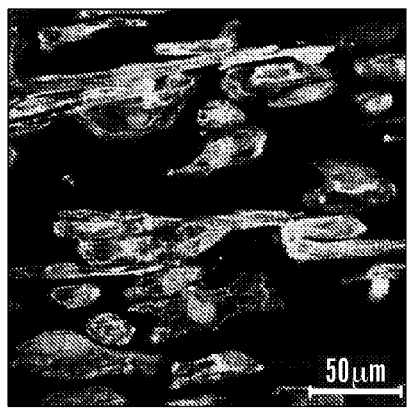
Figure 24D:
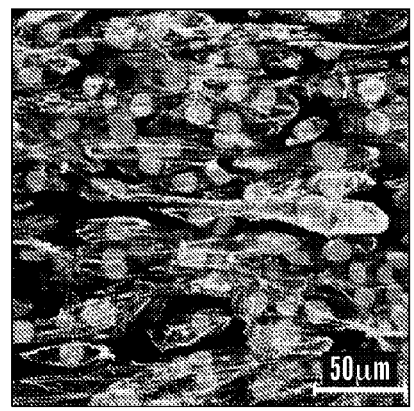
Figure 25:
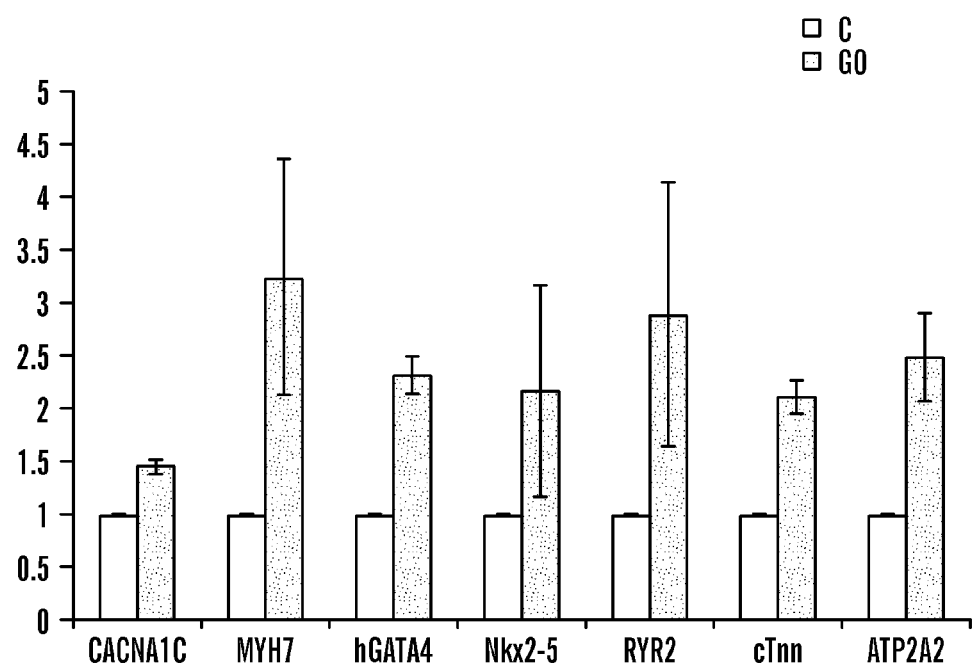
FIG. 25 shows graphene/graphene-oxide-coated nanotextured platforms promote maturation of hES/hiPSC-derived cardiomyocytes. Cardiac hypertrophy markers for RUES2 derived cardiomyocyte grown on control polystyrene nanotextured substrate (without the graphene or graphene-oxide) and few-layer graphene oxide film for 7 days show increased expression of adult cardiac specific markers in GO cultures.

These experiments were performed in 5.5 month old male mdx4cv mice (n=7). Before transplantation, muscle cell patches were manually cut 2 mm by 4 mm using blade and animals were anesthetized with Avertin. Muscle cell patches were transplanted parallel to the muscle fiber over quadriceps muscles as illustrated in FIG. 3a. Three animals were sacrificed at 2 weeks post-transplant (n=4 quadriceps with nanopatterned patch, n=2 with flat patch) and the remainder at 4 weeks post transplantation (n=6 quadriceps with nanopatterned patch, n=2 with flat patch). Muscles were harvested with patches and directly placed in PBS with 2% formaldehyde and 0.2% glutaraldehyde for 2 hrs at 4° C. Following fixation, tissues were transferred through a PBS sucrose gradient beginning with 10%, then transferred to 20%, and left in 30% sucrose overnight at 4° C. The next day tissues were frozen in optical cutting temperature compound (TISSUE-TEK® 4583; Sakura Finetek) with liquid nitrogen cooled isopentane and sectioned 8 μm thick for x-gal, laminin and dystrophin immunostaining. To reduce background fluorescence and non-specific binding from aldehyde groups produced by glutaraldehyde fixation, sections were incubating with PBS containing 1% bovine serum albumin (BSA) and 100 mM glycine prior to immunostaining. The slides were then stained with anti-laminin at 1:400 (Sigma, polyclonal rabbit) or anti-dystrophin at 1:200 (Abcam, polyclonal rabbit) in PBS containing 1% BSA for 1 hr at room temperature. Following primary antibody staining, goat anti-rabbit Fab fragments conjugated to Alexa Fluor 594 or 647 (Invitrogen) was applied at 1:1000 for 1 hr at room temperature. Sections were mounted with Vectashield+DAPI and photographs were captured with a monochromatic camera and Zeiss Axiovert 200. Individual fluorescent channels were colored and merged using Adobe Photoshop. Brightness and contrast levels were adjusted when necessary.

Example 5

Co-Culture of the Cardiomyocytes with Additional Cells on the Nanotextured Substrate.

The inventors have also recently developed a long term in-vitro adult guinea-pig cardiomyocyte (aGPVM) model who's β-adrenergic and calcium handling responses are closer to native tissue. This 2D aGPVM model is isotropic and doesn't resemble the native myocardium which is mechanically and electrically anisotropic. A number of studies have reported that fibroblast are crucial for maintaining ECM and collagen network for anisotropic microstructural pattern in myocardial tissue (Costa et al 2003; Baxter et al, 2008). Herein, the inventors have combined culturing of mitomycin C arrested adult fibroblast monolayer (aGPFm) on anisotropically nanofabricated substratum to closely mimic the myocardial ECM, with aGPVM. The inventors demonstrate that the nanoscale control of the nanotextured pattern of the substrates under the fibroblast-material interface still facilitates the creation of the maturation of cardiomyocytes abd also formation of a cardiac tissue construct that mimics in-vivo ventricular myocardial phenotype. The inventors assessed that the use of fibroblast-anisotropically nanotextured substrate as disclosed herein enhances the formation of anisotropic engineered adult guinea-pig cardiomyocyte monolayer constructs with structural and electrophysiological properties resembling their native myocardial tissue. Therefore, the fibroblast-anisotropically nanotextured substrate can be used to enhance the maturation of cardiomyocytes from any species, e.g., human species, for the development of mature human cardiomyocytes with the structural and electrophysiological properties resembling their native myocardial tissue.

Nanofabrication

The implementation of the soft lithographic technique of capillary force lithography, in combination with UV curable polymers, allows for straightforward, rapid production of nanopatterned cell culture substrates. The advantage of this type of fabrication method is that substrate dimensions are maintained over a large area with a high degree of fidelity. The nanotextured substrate can be on a standard large area nanopatterned cover glass (alone and in a 6 well plate format) as well as a scanning electron micrograph (SEM) of the nanopatterned surface. The iridescent appearance of the coverslips is due to the nanogrooved surface. The SEM image validates that the pattern dimensions are indeed being passed from silicon master, to the PUA mold, to the patterned glass cover glass without distortion and with a high degree of consistency.

Figure 39A:
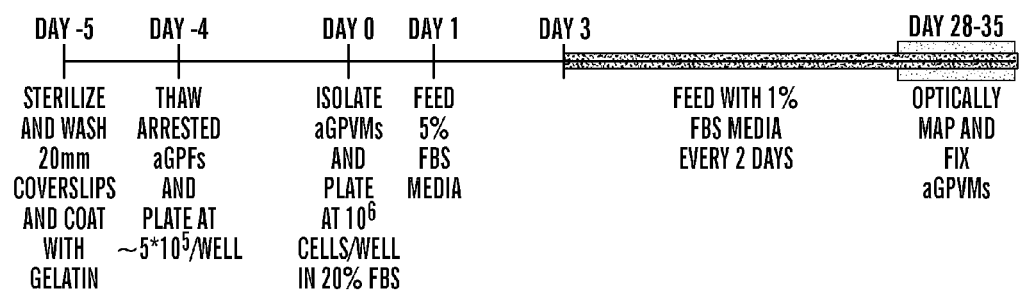
FIG. 39A-39B shows fibroblast aided alignment of aGPVMs on nanopatterned substrate FIG. 39B. Shows the timeline of aGPVM culture. on nanopatterned substrate pre-cultured with mitomycin-c arrested aGPFs.
Figure 39B:
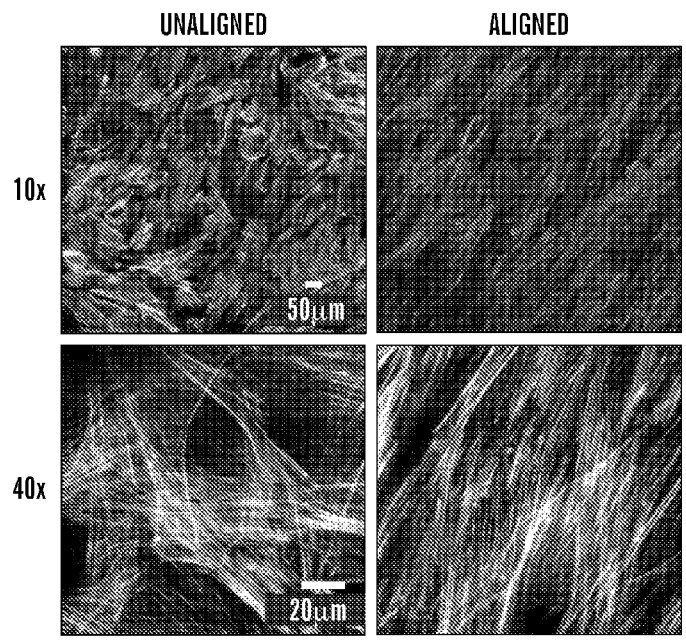
Figure 40A:
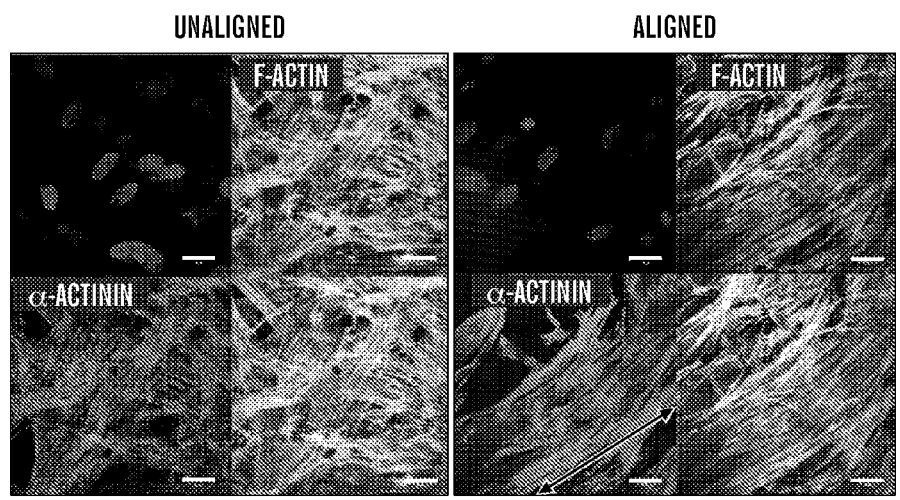
FIGS. 40A-40B show F-actin and Sarcomeric actinin immunostaining in aGPVM on nanopatterned substrate with fibroblast.
Figure 40B:
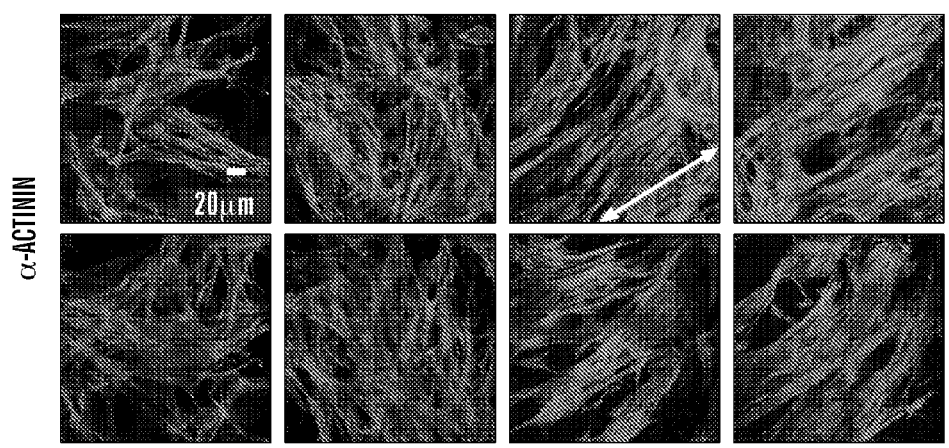

Structural Alignment of Arrested Adult Fibroblast (aGPFm) on Nanopatterned Substrate In the native myocardium the myocardial cell orientation is strongly correlated with the direction of alignment of the matrix fibers suggesting that the ECM organization in-vivo can provide nanotopographic cues guiding myocardial alignment (Kim et al, 2010). To test this hypothesis, we cultured aGPFm on nanopatterned substratum to form a monolayer to mimic mechanical and topographical features of native cardiac ECM. FIG. 39A shows the formation of confluent monolayer of aGPFm on nanopattern substrate. FIG. 39B shows the timeline of aGPVM culture on nanopatterned substrate. Confocal imaging of actin phalloidin was performed to show the fiber orientation in non-aligned and aligned nanopattern substrate at 10 and 40×. The aGPFm aligned with the ridge and groove of the nanopattern to form global anisotropic arrays, whereas on unpatterned substrata they were randomly orientated.

Structural Alignment of Adult Ventricular Myocytes on aGPFm-Nanopatterned Substrate The inventors examined the F-actin fiber orientation and sarcostructure organization in aGPVM cultures on aligned and non-aligned nanopatterned substrate. Immunocytochemical images of actin phalloidin and sarcomeric actinin in the aGPVM showed that they are aligned along the direction of the nanoridges/grooves and we found that aGPFm were crucial for aiding their alignment (FIG. 39A right). In contrast the unpatterned substrata resulted in mostly random distribution with some local alignment (FIG. 39A Left). FIG. 39B shows α-sarcomeric actinin images of different regions within one unaligned and aligned coverslip. Blue arrow shows the direction of grooves. Although there is some local alignment on the unaligned monolayer, images from different regions show no global alignment. However, on the aligned monolayer, there is global alignment in the direction of the grooves. Overall, these results suggest that anisotropic aGPFm-aGPVM interaction induced extensive geometrical alteration in cytoskeletal alignment.

Enhanced Electrophysiology of aGPVMs on Nanopatterned Substrates

Figure 41A:
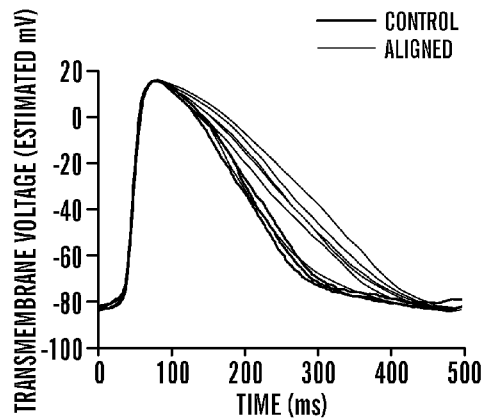
FIGS. 41A-41F show action potential morphology across several unaligned (blue) and aligned (green) aGPVM coverslips, showing an increase in action potential duration (APD) in aligned aGPVMs.
Figure 41B:
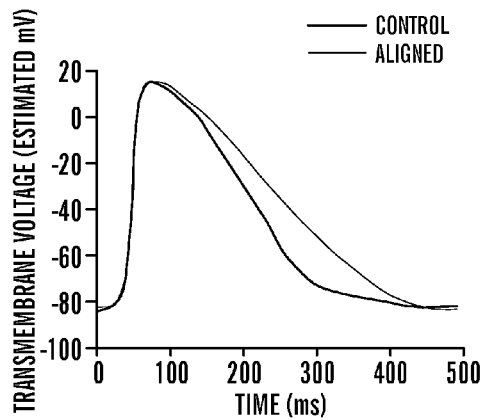
Figure 41D:
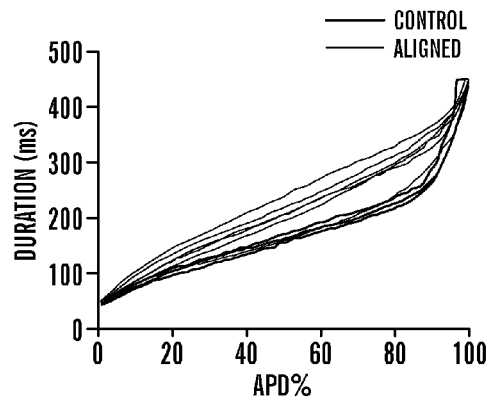
Figure 41E:
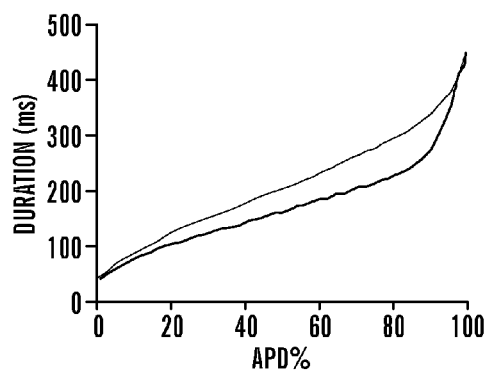
Figure 41C:
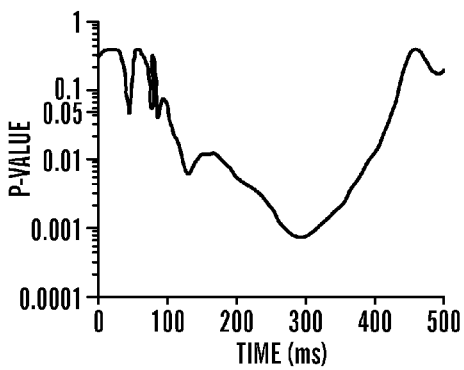
Figure 41F:
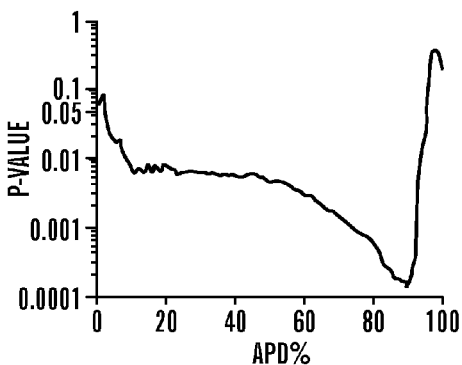

In the adult heart, ventricular APs have a long, depolarized plateau phase that corresponds to an inward Ca2+ current and the slow-developing K+ rectifier current. To assess the electrophysiologic function of the aGPVMs, optical mapping techniques were utilized to study the AP profile over time and through space. By plotting the voltage vs. time in the aGPVM monolayer, a classic AP curve with a rapid upstroke and slower repolarization phase is seen (FIG. 41A). Action potential morphology across several flat control and aligned aGPVM coverslips averaged over different waves were obtained. Compare to the flat control, aGPVMs cultured on aligned substrates had a (significantly) prolonged AP duration (APD) as shown in FIG. 41B. P-value of difference in voltage between aligned and unaligned monolayers over time shows that the APD significantly increases with time specially during later phase of repolarization (FIG. 41C). Significant difference in APD between aligned and unaligned monolayers over a wide range of repolarization levels was seen (FIGS. 41D and 41E). P-value of difference in APD between aligned and unaligned monolayers over levels of repolarization shows that aligned APDs are statistically significant at almost every stage of repolarization as compare to the flat controls (FIG. 41F)

Figure 42A:
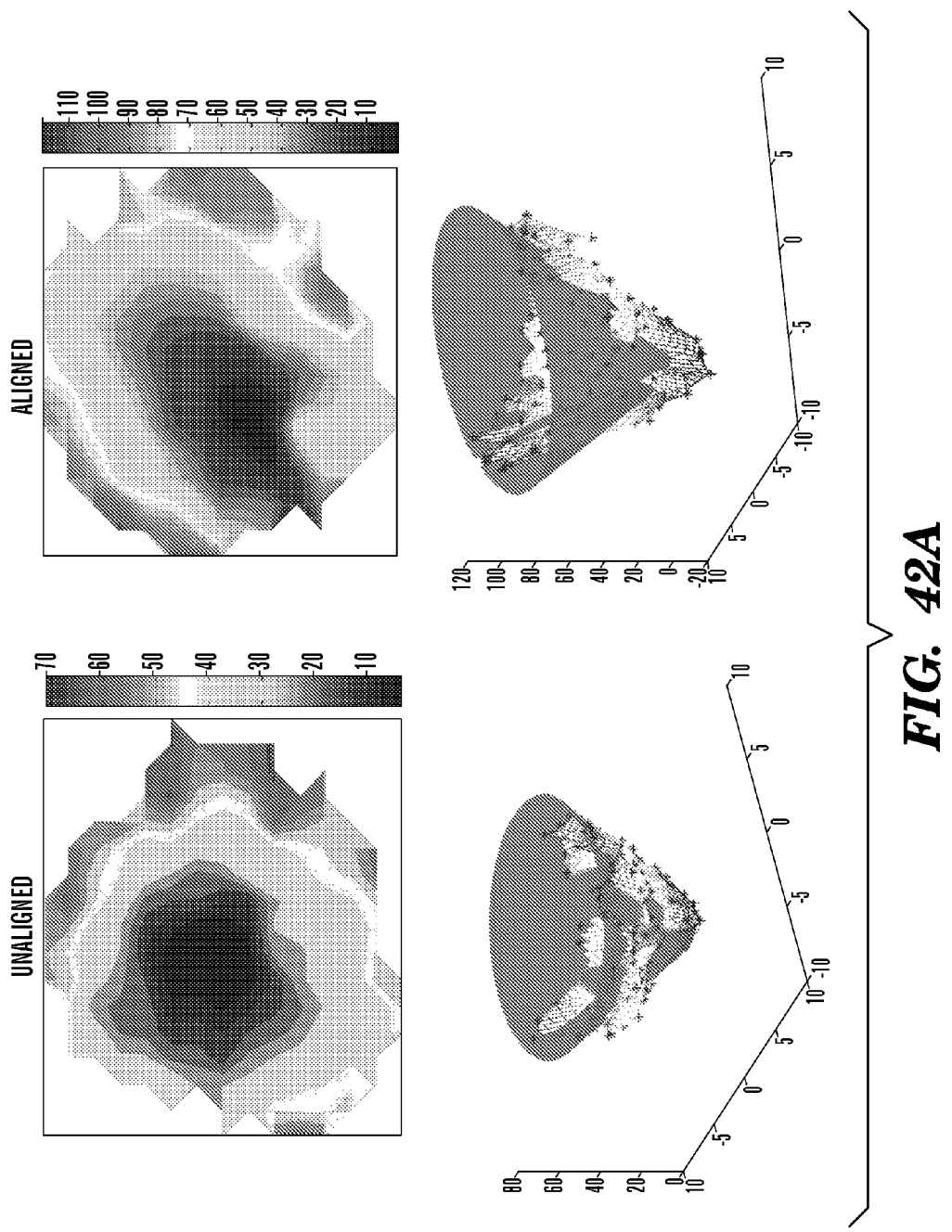
FIG. 42A-42B shows functional anisotropy of aGPVMs on nanopattern substrate. Custom built setup to optically map the activation pattern of the aGPVMs at 500 ms cycle length using di-4-ANEPPS. The resulting activation wavefronts were analyzed to calculate conduction anisotropy.
Figure 42B:
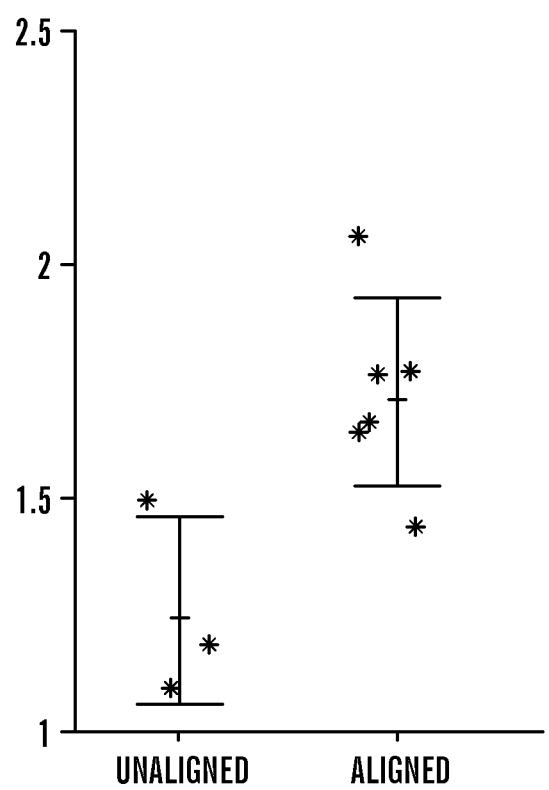

Cardiac muscle in the body propagates APs in an anisotropic manner, with higher cardiovascular myocytes in the direction of alignment compared to the transverse direction. The inventors assessed the two dimensional propagation of the AP of the aGPVM monolayer on flat controls and aligned substrate by optically mapping the activation pattern of the aGPVMs at 500 ms cycle length using di-4-ANEPPS. The resulting activation wavefronts were analyzed to calculate conduction anisotropy. The inventors discovered that the aligned monolayers had increased functional anisotropy over unaligned monolayers. Circular activation isochrones in the unaligned monolayer, indicating isotropic propagation, as opposed to the highly elliptical isochrones for the aligned monolayer, indicating anisotropic propagation (FIG. 42A, Top). Further, activation maps when mapped onto a surface in x,y,t space, fit to an elliptical cone in the case of aligned substrate (FIG. 42A, bottom).

By combining the exciting fields of nanotechnology and cardiac tissue engineering, the inventors have developed a unique cell culture method for obtaining more electrophysiologically mature muscle tissues that is possible in a scalable and practical manner. The inventors also demonstrate that simple, cellular alignment, induced by nanoscale anisotropic substrate cues and imparted onto the cardiomyocytes, via cell-cell interactions, as well as co-culturing with other cells such as fibroblasts, can elicit an enhanced electrophysiological response of the cells.

This anisotropic alignment cued by the nanotextured substrates, can by itself, influence the action potential (AP) propagation based on geometry alone. Cells conduct electrical impulse more rapidly through the cytosol than the cell membrane. Thus, since the cardiomyocytes are aligned in a common direction, the electrical impulse has less resistance in the direction of alignment compared to the transverse direction. This would lead to higher CVs in the longitudinal direction (i.e. the direction of cell alignment) compared to the transverse direction and larger anisotropic ratios.

What was more surprising was the finding that cellular alignment of cardiomyocytes can synergistically enhance the electrophysiology of the cells and induce prolonged action potential durations (APDs). By simply influencing the cellular structure by inducing alignment via simple nanofabrication methods, more mature cardiomyocyte function can be elicited.

In conclusion, with the advancements in stem cell biology and cardiac tissue engineering, stem cell-derived cardiomyocytes, e.g., iPSC-derived cardiomyocytes are useful as an in vitro surrogate for heart tissue. However, maturation and consistency hurdles remain to be addressed. To this end, adult cardiomyocytes can be used to get a baseline of how fully developed cardiomyocytes should behave in vitro. As disclosed herein, by combining nanofabrication of nanotextured substrates as disclosed herein and innovative cell culture techniques (e.g., culturing the myocytes, e.g., cardiomyocytes alone or in a combination with a fibroblast monolayer), could considerably aid in the development of detailed in vitro cardiac tissue screening platforms.

REFERENCES

All reference are cited in the specification and the Examples are incorporated in their entirety herein by reference.
1. Stevens M, et al., (2005) Exploring and engineering the cell surface interface. Science 310:1135-1138.
2. Mannix R J, et al. (2008) Nanomagnetic actuation of receptor-mediated signal transduction. Nat Nanotechnol 3:36-40.
3. Karuri N W, et al. (2004) Biological length scale topography enhances cell-substratum adhesion of human corneal epithelial cells. J Cell Sci 117:3153-3164.
4. Cavalcanti-Adam E A, et al. (2007) Cell spreading and focal adhesion dynamics are regulated by spacing of integrin ligands. Biophys J 92:2964-2974.
5. Koo L Y, et al., (2002) Co-regulation of cell adhesion by nanoscale RGD organization and mechanical stimulus. J Cell Sci 115:1423-1433.
6. Yim E K, et al. (2005) Nanopattern-induced changes in morphology and motility of smooth muscle cells. Biomaterials 26:5405-5413.
7. Dalby M J, et al. (2007) The control of human mesenchymal cell differentiation using nanoscale symmetry and disorder. Nat Mater 6:997-1003.
8. Park J, et al., (2007) Nanosize and vitality: TiO2 nanotube diameter directs cell fate. Nano Lett 7:1686-1691.
9. Geiger B, (2001) Transmembrane crosstalk between the extracellular matrix-Cytoskeleton crosstalk. Nat Rev Mol Cell Biol 2:793-805.
10. Abrams G A, (2003) Ultrastructural basement membrane topography of the bladder epithelium. Urol Res 31:341-346.
11. Park H, et al. (2007) Nanofabrication and microfabrication of functional materials for tissue engineering. Tissue Eng 13:1867-1877.
12. Fink C, et al. (2000) Chronic stretch of engineered heart tissue induces hypertrophy and functional improvement. FASEB J 14:669-679.
13. Bursac N, et al., (2002) Cardiomyocyte cultures with controlled macroscopic anisotropy: A model for functional electrophysiological studies of cardiac muscle. Circ Res 91:e45-54.
14. Radisic M, et al. (2004) Functional assembly of engineered myocardium by electrical stimulation of cardiac myocytes cultured on scaffolds. Proc Natl Acad Sci USA 101:18129-18134.
15. Fast V G, et al., (1996) Anisotropic activation spread in heart cell monolayers assessed by high-resolution optical mapping. Role of tissue discontinuities. Circ Res 79:115-127.
16. Bien H, et al., (2003) Cardiac cell networks on elastic microgrooved scaffolds. IEEE Eng Med Biol Mag 22:108-112.
17. McDevitt T C, et al. (2002) In vitro generation of differentiated cardiac myofibers on micropatterned laminin surfaces. J Biomed Mater Res 60:472-479.
18. Gopalan S M, et al. (2003) Anisotropic stretch-induced hypertrophy in neonatal ventricular myocytes micropatterned on deformable elastomers. Biotechnol Bioeng 81:578-587.
19. Watkins A W, Anseth K S (2005) Investigation of molecular transport and distributions in poly(ethylene glycol) hydrogels with confocal laser scanning microscopy. Macromolecules 38:1326-1334.
20. Kim P, et al. (2005) Fabrication of nanostructures of polyethylene glycol for applications to protein adsorption and cell adhesion. Nanotechnology 16:2420-2426.
21. Kim D H, et al. (2009) Guided cell migration on microtextured substrates with variable local density and anisotropy. Adv Funct Mater 19:1579-1586.

22. Perumal S, et al., (2008) Collagen fibril architecture, domain organization, and triple-helical conformation govern its proteolysis. Proc Natl Acad Sci USA 105:2824-2829.
23. Khademhosseini. A, et al. (2007) Microfluidic patterning for fabrication of contractile cardiac organoids. Biomed Microdevices 9:149-157.
24. Teunissen B E, et al., (2004) Regulation of myocardial connexins during hypertrophic remodelling. Eur Heart J 25:1979-1989.
25. Lim Z Y, et al., (2006) Spiral wave attachment to millimeter-sized obstacles. Circulation 114:2113-2121.
26. Bursac N, et al. (1999) Cardiac muscle tissue engineering: Toward an in vitro model for electrophysiological studies. Am J Physiol 277:H433-444.
27. Gibson J M (1997) Reading and writing with electron beams. Physics Today 50:56-61.
28. Silverman J P (1998) Challenges and progress in x-ray lithography. J Vac Sci Technol B 16:3137-3141.
29. Salaita K, et al., (2007) Applications of dip-pen nanolithography. Nat Nanotechnol 2:145-155.
30. Teixeira A I, et al., (2003) Epithelial contact guidance on well-defined micro- and nanostructured substrates. J Cell Sci 116:1881-1892.
31. Mandavi A, et al. (2008) A biodegradable and biocompatible gecko-inspired tissue adhesive. Proc Natl Acad Sci USA 105:2307-2312.
32. Jiang W, et al., (2008) Nanoparticle-mediated cellular response is size-dependent. Nat Nanotechnol 3:145-150.
33. Oh S, et al. (2009) Stem cell fate dictated solely by altered nanotube dimension. Proc Natl Acad Sci USA 106:2130-2135.
34. Ohashi K, et al. (2007) Engineering functional two- and three-dimensional liver systems in vivo using hepatic tissue sheets. Nat Med 13:880-885.
35. Perumal, S., O. Antipova, and J. P. Orgel, Collagen fibril architecture, domain organization, and triple-helical conformation govern its proteolysis. Proc Natl Acad Sci USA, 2008. 105(8): p. 2824-9.
36. Kim, D. H., et al., Guided three-dimensional growth of functional cardiomyocytes on polyethylene glycol nanostructures. Langmuir, 2006. 22(12): p. 5419-5426.
37. Kim, D. H., et al., Nanopatterned cardiac cell patches promote stem cell niche formation and myocardial regeneration. Integr Biol (Camb), 2012. 4(9): p. 1019-33.
38. Kim, D. H., et al., Nanoscale cues regulate the structure and function of macroscopic cardiac tissue constructs. Proceedings of the National Academy of Sciences of the United States of America, 2010. 107(2): p. 565-570.
39. Kim, D. H., et al., Guided Cell Migration on Microtextured Substrates with Variable Local Density and Anisotropy. Advanced Functional Materials, 2009. 19(10): p. 1579-1586.
40. You, M. H., et al., Synergistically Enhanced Osteogenic Differentiation of Human Mesenchymal Stem Cells by Culture on Nanostructured Surfaces with Induction Media. Biomacromolecules, 2010. 11(7): p. 1856-1862.
41. Yang, K., et al., The influence of surface chemistry and size of nanoscale graphene oxide on photothermal therapy of cancer using ultra-low laser power. Biomaterials, 2012. 33(7): p. 2206-14.
42. Dreyer, D. R., et al., The chemistry of graphene oxide. Chem Soc Rev, 2010. 39(1): p. 228-40.
43. Andre Mkhoyan, K., et al., Atomic and electronic structure of graphene-oxide. Nano Lett, 2009. 9(3): p. 1058-63.

The invention claimed is:
1. A nanotextured platform composition comprising a polymer substrate comprising:
  a. a nanotextured array of parallel grooves and ridges that organizes cultured human cardiomyocytes in an anisotropic manner, the grooves having a width of 200-1000 nm, and said ridges, between said grooves, having a width of 200-1000 nm, said nanotextured array providing nanotopographic cues guiding maturation of cells cultured on said nanotextured array; and
  b. in vitro-differentiated human cardiomyocytes cultured on said nanotextured array, said in vitro differentiated human cardiomyocytes being organized in an anisotropic manner in response to said nanotopographic cues wherein:
    (i) said in vitro-differentiated human cardiomyocytes are differentiated from human embryonic stem cells (ESCs) or from induced pluripotent stem cells (iPSCs) derived from an adult somatic cell of either a healthy individual or an individual diagnosed with a cardiac disease;
    (ii) said in vitro-differentiated human cardiomyocytes have at least one of the following characteristics of maturity:
      (a) express at least one marker from the group consisting of: Nkx2.5, GATA4, connexin-43, myosin heavy chain and cTNT, in a manner more similar to adult cardiomyocytes than in vitro differentiated cardiomyocytes cultured on a polymer substrate of the same composition but substantially lacking said nanotextured array;
      (b) isoform switching of ssTn1 to ctTn1 or N2Ba to N2B by at least 10%, as measured by Western Blot or qRT-PCR, to a profile more similar to adult cardiomyocytes than in vitro differentiated cardiomyocytes cultured on a polymer of the same composition but substantially lacking said nanotextured array; and
    (iii) said in vitro-differentiated human cardiomyocytes maintain the at least one characteristic noted in (ii) above for 10 days or more in culture.
2. The nanotextured platform of claim 1, further comprising an agent that promotes the differentiation of the human cardiomyocytes to a more mature phenotype.
3. The nanotextured platform of claim 1, wherein said grooves have a depth of 50-1000 nm.
4. The nanotextured platform of claim 1, wherein said grooves have a width of 200-800 nm, and said ridges, between said grooves, have a width of 200-800 nm.
5. The nanotextured platform of claim 1, wherein said cardiomyocytes form a monolayer on said substrate with anisotropic and polarized cell arrangement in the direction of the nanotextures.
6. The nanotextured platform of claim 1, wherein said array of parallel grooves and ridges has a precision of texture of at least 90% fidelity, as determined by atomic force microscopy or electron microscopy.
7. The nanotextured platform of claim 1, wherein said array of parallel grooves and ridges is generated using a process selected from the group consisting of capillary force lithography, nanoindentation, e-beam lithography, and electrospinning.
8. The nanotextured platform of claim 1, wherein said array of parallel grooves and ridges is formed by capillary force lithography.
9. The nanotextured platform of claim 1, wherein the nanotextured platform is coated with or wherein the sub- strate comprises within its polymer matrix, either biocompatible extracellular matrix polypeptides, engineered matrix polypeptides, or engineered polypeptides.

10. The nanotextured platform of claim 1, further comprising a coating with a materials selected from the group consisting of charcoal, graphene, graphene oxide, reduced graphene oxide, nanotubes, and gold, said coating effecting one or more functional parameters of the substrate selected from: adsorption of proteins to surface, electrical conductivity or other physico-chemical property in a manner that influences the phenotype of said cardiac cells.

11. The nanotextured platform of claim 1, wherein said substrate comprises a polymer hydrogel comprising, within the matrix of said polymer substrate, a biocompatible extracellular matrix protein, a synthetic or engineered matrix polypeptide, or engineered polypeptides.

12. The nanotextured platform of claim 1, wherein said polymer substrate comprises a UV curable hydrogel polymer, a thermosensitive hydrogel polymer or a polymer produced by solvent evaporation.

13. The nanotextured platform of claim 1, configured as a multi-well plate.

14. The nanotextured platform of claim 13, wherein the multi-well plate is a 24, 48 or 96 well plate.

* * * * *